US012570993B2

(12) United States Patent
Gocal et al.

(10) Patent No.: US 12,570,993 B2
(45) Date of Patent: Mar. 10, 2026

(54) MUTATED PROTOPORPHYRINOGEN IX OXIDASE (PPX) GENES

(71) Applicants: CIBUS US LLC, San Diego, CA (US); CIBUS EUROPE B.V., Ad Kapelle (NL)

(72) Inventors: Gregory F.W. Gocal, San Diego, CA (US); Peter R. Beetham, Carlsbad, CA (US); Aura Estela Gonzalez Schopke, San Diego, CA (US); Sarah Dumm, San Diego, CA (US); James Pearce, La Jolla, CA (US); Christian Schopke, San Diego, CA (US); Keith A. Walker, San Diego, CA (US)

(73) Assignees: CIBUS US LLC, San Diego, CA (US); CIBUS EUROPE B.V., Breda (NL)

( * ) Notice: Subject to any disclaimer, the term of this patent is extended or adjusted under 35 U.S.C. 154(b) by 167 days.

(21) Appl. No.: 17/468,335

(22) Filed: Sep. 7, 2021

(65) Prior Publication Data

US 2022/0298525 A1 Sep. 22, 2022

Related U.S. Application Data

(63) Continuation of application No. 16/042,985, filed on Jul. 23, 2018, now Pat. No. 11,111,500, which is a continuation of application No. 13/935,532, filed on Jul. 4, 2013, now abandoned, which is a continuation of application No. 13/247,954, filed on Sep. 28, 2011, now abandoned, which is a continuation of application No. PCT/US2011/049007, filed on Aug. 24, 2011, and a continuation of application No. PCT/US2011/046330, filed on Aug. 2, 2011.

(60) Provisional application No. 61/370,436, filed on Aug. 3, 2010.

(51) Int. Cl.
*C12N 15/82* (2006.01)
*C12N 9/02* (2006.01)

(52) U.S. Cl.
CPC ......... *C12N 15/8274* (2013.01); *C12N 9/001* (2013.01); *C12N 15/8213* (2013.01)

(58) Field of Classification Search
CPC ....................... C12N 15/8213; C12N 15/8274
See application file for complete search history.

(56) References Cited

U.S. PATENT DOCUMENTS

| | | | |
|---|---|---|---|
| 4,945,050 A | 7/1990 | Sanford et al. | |
| 5,100,792 A | 3/1992 | Sanford et al. | |
| 5,204,253 A | 4/1993 | Sanford et al. | |
| 5,268,463 A | 12/1993 | Jefferson | |
| 5,302,523 A | 4/1994 | Coffee et al. | |
| 5,334,711 A | 8/1994 | Sproat et al. | |
| 5,380,831 A | 1/1995 | Adang et al. | |
| 5,399,680 A | 3/1995 | Zhu et al. | |
| 5,424,412 A | 6/1995 | Brown et al. | |
| 5,436,391 A | 7/1995 | Fujimoto et al. | |
| 5,466,785 A | 11/1995 | De Framond | |
| 5,565,350 A | 10/1996 | Kmiec | |
| 5,569,597 A | 10/1996 | Grimsley et al. | |
| 5,593,874 A | 1/1997 | Brown et al. | |
| 5,604,121 A | 2/1997 | Hilder et al. | |
| 5,608,142 A | 3/1997 | Barton et al. | |
| 5,608,144 A | 3/1997 | Baden et al. | |
| 5,608,149 A | 3/1997 | Barry et al. | |
| 5,659,026 A | 8/1997 | Baszczynski et al. | |
| 5,731,181 A | 3/1998 | Kmiec | |
| 5,756,325 A | 5/1998 | Kmiec | |
| 5,760,012 A | 6/1998 | Kmiec et al. | |
| 5,767,373 A | 6/1998 | Ward et al. | |
| 5,780,296 A | 7/1998 | Holloman et al. | |
| 5,795,972 A | 8/1998 | Kmiec | |
| 5,871,984 A | 2/1999 | Kmiec | |
| 5,888,983 A | 3/1999 | Kmiec et al. | |
| 5,945,339 A | 8/1999 | Holloman et al. | |
| 6,004,804 A | 12/1999 | Kumar et al. | |
| 6,010,907 A | 1/2000 | Kmiec et al. | |
| 6,072,050 A | 6/2000 | Bowen et al. | |
| 6,177,611 B1 | 1/2001 | Rice | |
| 6,271,360 B1 | 8/2001 | Metz et al. | |
| 6,282,837 B1 | 9/2001 | Ward et al. | |
| 6,308,458 B1 | 10/2001 | Volrath et al. | |
| 6,479,292 B1 | 11/2002 | Metz et al. | |
| 6,753,458 B1 | 6/2004 | Filho et al. | |
| 6,808,904 B2 * | 10/2004 | Ward ................ C12N 15/8223 435/91.1 |

(Continued)

FOREIGN PATENT DOCUMENTS

| | | |
|---|---|---|
| AU | 2011285830 A1 | 3/2013 |
| CN | 103327809 B | 4/2017 |

(Continued)

OTHER PUBLICATIONS

An et al., Transformation of Tobacco, Tomato, Potato, and *Arabidopsis thaliana* Using a Binary Ti Vector System. Plant Physiol. May 1986;81(1):301-305.

(Continued)

*Primary Examiner* — David H Kruse

(74) *Attorney, Agent, or Firm* — Michael A. Whittaker

(57) ABSTRACT

Provided are compositions and methods relating to gene and/or protein mutations in transgenic or non-transgenic plants. In certain embodiments, the disclosure relates to mutations in the protoporphyrinogen IX (PPX) gene. In some embodiments the disclosure relates to plants that are herbicide resistant.

20 Claims, 14 Drawing Sheets

Specification includes a Sequence Listing.

(56)  References Cited

U.S. PATENT DOCUMENTS

| | | | |
|---|---|---|---|
| 6,905,852 | B1 | 6/2005 | Horikoshi et al. |
| 7,060,500 | B2 | 6/2006 | Metz et al. |
| 2001/0016956 | A1 | 8/2001 | Ward et al. |
| 2002/0073443 | A1 | 6/2002 | Heifetz et al. |
| 2002/0086395 | A1 | 7/2002 | Shimokawatoko et al. |
| 2003/0236208 | A1 | 12/2003 | Kmiec et al. |
| 2005/0081259 | A1 | 4/2005 | Heifetz et al. |
| 2009/0205064 | A1 | 8/2009 | Schopke et al. |
| 2010/0100988 | A1 | 4/2010 | Tranel et al. |
| 2014/0189906 | A1 | 7/2014 | Gocal et al. |

FOREIGN PATENT DOCUMENTS

| | | | |
|---|---|---|---|
| EP | 0629387 | A1 | 12/1994 |
| EP | 0679657 | A2 | 11/1995 |
| EP | 2600710 | B1 | 8/2018 |
| JP | 6058536 | B2 | 1/2017 |
| KR | 1920503 | B1 | 11/2018 |
| NZ | 607627 | A | 10/2015 |
| WO | 9849350 | A1 | 11/1998 |
| WO | 9907865 | A1 | 2/1999 |
| WO | 9940789 | A1 | 8/1999 |
| WO | 9943838 | A1 | 9/1999 |
| WO | 9958702 | A1 | 11/1999 |
| WO | 9958723 | A1 | 11/1999 |
| WO | 0112825 | A1 | 2/2001 |
| WO | 0115740 | A1 | 3/2001 |
| WO | 0168826 | A2 | 9/2001 |
| WO | 2009046334 | A1 | 4/2009 |
| WO | 2012018862 | A2 | 2/2012 |
| WO | 2013028188 | A1 | 2/2013 |
| WO | 0112969 | C2 | 11/2016 |
| ZA | 201301067 | B | 8/2017 |

OTHER PUBLICATIONS

Archer and Keegstra, Current Views on Chloroplast Protein Import and Hypotheses on the Origin of the Transport Mechanism. J Bioenerg Biomembr. Dec. 1990;22(6):789-810.

Asano and Ugaki, Transgenic plants of Agrostis alba obtained by electroporation-mediated direct gene transfer into protoplasts. Plant Cell Rep. Feb. 1994;13(5):243-246.

Ayres and Park, Genetic Transformation of Rice. Crit Rev Plant Sci 1994;13:219-239.

Ballas et al., Efficient functioning of plant promoters and poly(A) sites in Xenopus oocytes. Nucleic Acids Res. Oct. 11, 1989;17(19):7891-7903.

Barcelo et al., Transgenic cereal (tritordeum) plants obtained at high efficiency by microprojectile bombardment of Inflorescence tissue. Plant J. Apr. 1994;5(4):583-592.

Becker et al., Fertile transgenic wheat from microprojectile bombardment of scutellar tissue. Plant J. Feb. 1994;5(2):299-307.

Beetham et al., A tool for functional plant genomics; Chimeric RNA/DNA oligonucleotides cause in vivo gene-specific mutations. Proc Natl Acad Sci U S A. Jul. 20, 1999;96(15):8774-8778.

Bokelmann and Roest, Plant Regeneration from Protoplasts of Potato (Solanum tuberosum cv. Bintje). Z Pflanzenphysiol Bd. 1983:109:259-265.

Borkowska et al., Transformation of diploid potato with an Agrobacterium tumefaciens binary vector system: I. Methodological approach. Acta Physiol Plant. 1994;16(3):225-230.

Callis et al., Introns increase gene expression in cultured maize cells. Genes Dev. Dec. 1987;1(10):1183-1200.

Campbell and Gowri, Codon Usage in Higher Plants, Green Algae, and Cyanobacteria. Plant Physiol. Jan. 1990;92(1):1-11.

Canevascini et al., Tissue-Specific Expression and Promoter Analysis of the Tobacco ltp1 Gene. Plant Physiol. Oct. 1996;112(2):513-524.

Casas et al., Transgenic sorghum plants via microprojectile bombardment. Proc Natl Acad Sci U S A. Dec. 1, 1993;90(23):11212-11216.

Chee and Slightom, Transformation of cucumber tissues by microprojectile bombardment: identification of plants containing functional and non-functional transferred genes. Gene. Sep. 10, 1992;118(2):255-260.

Christensen and Quail, Sequence analysis and transcriptional regulation by heat shock of polyubiquitin transcripts from maize. Plant Mol Biol. Jun. 1989;12(6):619-632.

Christensen et al., Maize polyubiquitin genes: structure, thermal perturbation of expression and transcript splicing, and promoter activity following transfer to protoplasts by electroporation. Plant Mol Biol. Feb. 1992;18(4):675-689.

Christou et al., The development of a variety-independent gene-transfer method for rice. Trends Biotechnol. 1992;10:239-246.

Christou, Genetic engineering of crop legumes and cereals: current status and recent advances. Agro Food Ind Hi Tech. Mar.-Apr. 1994;5:17-27.

Christou, Philosophy and Practice of Variety-Independent Gene Transfer into Recalcitrant Crops. In Vitro Cell Dev Biol—Plant 1993;29:119-124.

Clark et al., Mutations at the Transit Peptide-Mature Protein Junction Separate Two Cleavage Events During Chloroplast Import of the Chlorophyll a/b-Binding Protein. J Biol Chem. Oct. 15, 1989;264(29):17544-17550.

Cousins et al., Transformation of an Australian Cotton Cultivar: Prospects for Cotton Improvement through Genetic Engineering. Aust J Plant Physiol. 1991;18:481-494.

Datta et al., Herbicide-resistant Indica rice plants from IRRI breeding line IR72 after PEG-mediated transformation of protoplasts. Plant Mol Biol. Nov. 1992;20(4):619-629.

Davies et al., Transformation of peas. Plant Cell Rep. Jan. 1993;12(3):180-183.

De Block, Genotype-independent leaf disc transformation of potato (Solanum tuberosum) using Agrobacterium tumefaciens. Theor Appl Genet. Nov. 1988;76(5):767-774.

De Castro et al., Mitochondrial and chloroplast targeting sequences in tandem modify protein import specificity in plant organelles. Plant Mol Biol. Feb. 1996;30(4):769-780.

Della-Cioppa et al., Protein Trafficking in Plant Cells. Plant Physiol. Aug. 1987;84(4):965-968.

D'Halluin et al., Transformations of Sugarbeet (Beta vulgaris L.) and Evaluation of Herbicide Resistance in Transgenic Plants. Biotechnol. 1992;10:309-314.

Dhir et al., Regeneration of Transgenic Soybean (Glycine max) Plants from Electroporated Protoplasts. Plant Physiol. May 1992;99(1):81-88.

Dong and McHughen, Transgenic flax Plants from Agrobacterium-mediated transformation—incidence of chimeric regenerants and inheritance of transgenic plants. Plant Sci. 1993;91:139-148.

Dovzhenko et al., Thin-alginate-layer technique for pro top last culture of tobacco leaf pro top lasts: shoot formation In less than two weeks. Protoplasma 1998;204(1-2):114-118.

Duke, Overview of Herbicide Mechanisms of Action. Environ Health Perspect. Jul. 1990;87:263-271.

Eapen and George, Agrobacterium tumefaciens mediated gene transfer in peanut (Arachis hypogaea L.). Plant Cell Rep. Jul. 1994;13(10):582-586.

Frigerio et al., Free Ricin A Chain, Proricin, and Native Toxin Have Different Cellular Fates When Expressed in Tobacco Protoplasts. J Biol Chem. 1998;273: 14194-14199.

Fry et al., Transformation of Brassica napus with Agrobacterium tumefaciens based vectors. Plant Cell Rep. Oct. 1987;6(5):321-325.

Gallie et al., A comparison of eukaryotic viral 5'-leader sequences as enhancers of mRNA expression in vivo. Nucleic Acids Res. Nov. 11, 1987;15(21):8693-8711.

Gallie et al., The Regulation of Gene Expression in Transformed Maize Aleurone and Endosperm Protoplasts. Analysis of Promoter Activity, Intron Enhancement, and mRNA Untranslated Regions on Expression. Plant Physiol. Nov. 1994;106(3):929-939.

Gallois et al., Electroporation of Tobacco Leaf Protoplasts Using Plasmid DNA or Total Genomic DNA. Methods Mol Biol. 1995;55:89-107.

Gharti-Chhetri et al., Polyethylene glycol-mediated direct gene transfer in Nicotiana spp. Physiol. Plant. 1992;85:345-351.

(56)          References Cited

OTHER PUBLICATIONS

Golovkin et al., Production of transgenic maize plants by direct DNA uptake into embryogenic protoplasts . Plant Sci. 1993;90:41-52.

Guerineau et al., Effect of deletions in the cauliflower mosaic virus polyadenylation sequence on the choice of the polyadenylation sites in tobacco protoplasts. Mol Gen Genet. Apr. 1991;226(1-2):141-144.

Guevara-Garcia et al., Tissue-specific and wound-inducible pattern of expression of the mannopine synthase promoter is determined by the interaction between positive and negative cis-regulatory elements. Plant J. Sep. 1993;4(3):495-505.

Guo et al., The opium poppy genome and morphinan production. GenBank Accession No. RZC48829.1 NCBI, U.S. National Library of Medicine Bethesda MD USA Feb. 13, 2019.

Guo et al., The opium poppy genome and morphinan production. Science 2018;362(6412):343-347.

Guo, Transgenic Plants Obtained From Wheat Protoplasts Transformed by PEG-mediated Direct Gene Transfer. Chin Sci. Bull. Dec. 1993;38(24):2072-2078.

Haberlach et al., Isolation, Culture and Regeneration of Protoplasts from Potato and Several Related *Solanum* Species. Plant Sci. 1985;39:67-74.

Hansen et al., Wound-inducible and organ-specific expression of ORF13 from Agrobacterium rhizogenes 8196 T-DNA in transgenic tobacco plants. Mol Gen Genet. Apr. 16, 1997;254(3):337-343.

Hartman et al., Herbicide Resistant Turfgrass (*Agrostis palustris* Huds.) by Biolistic Transformation. Bio-Technology Sep. 1994;12:919-923.

Hinchee et al., Transformation and Regeneration of Non-Solanaceous Crop Plants. Found in Gene Manipulation in Plant Improvement II Edited by J. P. Gustafson 1990:203-212.

Joshi et al., Putative polyadenylation signals in nuclear genes of higher plants: a compilation and analysis. Nucleic Acids Res. Dec. 10, 1987;15(23):9627-9640.

Further Exam Report issued by New Zealand IPO in New Zealand Patent Application No. 607627 dated Aug. 14, 2015 (2 pages).

International Search Report issued in No. PCT/US2011/046330 dated Mar. 8, 2012 (10 pages).

International Search Report issued in No. PCT/US2011/049007 dated May 30, 2012 (12 pages).

Office Action issued by BRPTO in Brazilian Patent Application No. BR112013002543-3 dated May 16, 2019—incl Engl lang summary (8 pages).

Office Action issued by Chilean Patent Office in Chilean Patent Application No. 00341-2013 dated Feb. 20, 2015—incl Engl lang summary (16 pages total).

Office Action issued by Chilean Patent Office in Chilean Patent Application No. 00341-2013 dated Nov. 26, 2015—incl Engl lang summary (12 pages total).

Office Action issued by Chilean Patent Office in Chilean Patent Application No. 00341-2013 dated Jul. 18, 2019—incl Engl lang summary (7 pages total).

Office Action issued by CIPO in Canadian Patent Application No. 2,807,035 dated Feb. 27, 2017 (4 pages).

Office Action issued by CIPO in Canadian Patent Application No. 2,807,035 dated Feb. 1, 2018 (4 pages).

Office Action issued by SIPO in Chinese Patent Application No. 201180048304.X dated Sep. 30, 2014—incl Engl lang transl (13 pages total).

Office Action issued by SIPO in Chinese Patent Application No. 201180048304.X dated Aug. 21, 2015—incl Engl lang transl (16 pages total).

Office Action issued by SIPO in Chinese Patent Application No. 201180048304.X dated Mar. 14, 2016—incl Engl lang transl (7 pages total).

Office Action issued by SIPO in Chinese Patent Application No. 201180048304.X dated Oct. 10, 2016—incl Engl lang transl (7 pages total).

Office Action issued by the EAPO in Eurasian Patent Application No. 201390034/28 dated Nov. 27, 2014—incl Engl lang transl (4 pages total).

Office Action issued by the EAPO in Eurasian Patent Application No. 201390034/28 dated Mar. 7, 2019—incl Engl lang transl (6 pages total).

Office Action issued by the Israeli Patent Office in Israel Patent Application No. 224535 dated Jul. 7, 2015—Engl lang summary only (5 pages).

Office Action issued by the Israeli Patent Office in Israel Patent Application No. 224535 dated Aug. 21, 2016—incl Engl lang transl (7 pages total).

Office Action issued by the JPO in Japanese Patent Application No. 2013-523291 dated Aug. 18, 2015—incl Engl lang transl (10 pages total).

Office Action issued by the KIPO in Korean Patent Application No. 10-2013-7005453 dated Apr. 22, 2018—incl Engl lang transl (5 pages total).

Office Action issued by the JPO in Japanese Patent Application No. 2021-171606 dated Nov. 1, 2022—incl Engl lang transl (8 pages total).

Kawamata et al., Temporal and Spatial Pattern of Expression of the Pea Phenylalanine Ammonia-Lyase Gene1 Promoter in Transgenic Tobacco. Plant Cell Physiol. Jul. 1997;38(7):792-803.

Kipp et al., Gene Targeting in Plants via Site-Directed Mutagenesis. Methods Mol Biol. 2000;133:213-221.

Lam, Analysis of Tissue-Specific Elements in the Camv 35S Promoter. Results Probl Cell Differ. 1994;20:181-196.

Lamppa et al., The Chlorophyll a/b-binding Protein Inserts into the Thylakoids Independent of Its Cognate Transit Peptide. J Biol Chem. Oct. 15, 1988;263(29):14996-14999.

Last et al., pEmu: an improved promoter for gene expression in cereal cells. Theor Appl Genet. May 1991;81(5):581-588.

Lawrence and Kindle, Alterations in the Chlamydomonas plastocyanin transit peptide have distinct effects on in vitro import and in vivo protein accumulation. J Biol Chem. Aug. 15, 1997;272(33):20357-20363.

Lermontova et al., Cloning and Characterization of a plastidal and a mitochondrial isoform of tobacco protoporphyrinogen IX oxidase. Proc Natl Acad Sci U S A. Aug. 5, 1997;94(16):8895-8900.

Li et al., Development of Protoporphyrinogen Oxidase as an Efficient Selection Marker for Agrobacterium tumefaciens—Mediated Transformation of Maize. Plant Physiol. Oct. 2003;133(2):736-747.

Li and Nicholl, Development of PPO inhibitor-resistant cultures and crops. Pest Manag Sci. Mar. 2005;61(3):277-285.

Matsuoka et al., Tissue-specific light-regulated expression directed by the promoter of a C4 gene, maize pyruvate, orthophosphate dikinase, in a C3 plant, rice. Proc Natl Acad Sci USA. Oct. 15, 1993;90(20):9586-9590.

McBride et al., Controlled expression of plastid transgenes in plants based on a nuclear DNA-encoded and plastid-targeted T7 RNA polymerase. Proc Natl Acad Sci USA. Jul. 19, 1994;91(15):7301-7305.

McElroy et al., Isolation of an Efficient Actin Promoter for Use in Rice Transformation. Plant Cell. Feb. 1990;2(2):163-171.

Miki et al., A procedure for the microinjection of plant cells and protoplasts. Meth Cell Sci. 1989;12(4):139-144.

Mogen et al., Upstream Sequences Other than AAUAAA are Required for Efficient Messenger RNA 3'—End Formation in Plants. Plant Cell. Dec. 1990;2(12):1261-1272.

Munroe et al., Tales of poly(A): a review. Gene. Jul. 16, 1990;91(2):151-158.

Murashige and Skoog, A Revised Medium for Rapid Growth and Bio Assays with Tobacco Tissue Cultures. Physiol Plant 1962;15(3):473-497.

Murray et al., Codon usage in plant genes. Nucleic Acids Res. Jan. 25, 1989;17(2):477-498.

Odell et al., Identification of DNA sequences required for activity of the cauliflower mosaic virus 35S promoter. Nature. Feb. 28-Mar. 6, 1985;313(6005):810-812.

Orozco and Ogren, Localization of light-inducible and tissue-specific regions of the spinach ribulose bisphosphate carboxylase/

(56) References Cited

OTHER PUBLICATIONS oxygenase (rubisco) activase promoter in transgenic tobacco plants. Plant Mol Biol. Dec. 1993;23(6):1129-1138.

Patel et al., Cell Penetrating Peptides: Intracellular Pathways and Pharmaceutical Perspectives. Pharm Res. Nov. 2007;24(11):1977-1992.

Patzoldt et al., A codon deletion confers resistance to herbicides inhibiting protoporphyrinogen oxidase. Proc Natl Acad Sci USA. Aug. 15, 2006;103(33):12329-12334.

Pelletier et al., Intergeneric cytoplasmic hybridization in cruciferae by protoplast fusion. Molecular and General Genetics MGG. 1983;191:244-250.

Proudfoot, Poly(A) signals. Cell. Feb. 22, 1991;64(4):671-674.

Rinehart et al., Tissue-Specific and Developmental Regulation of Cotton Gene FbL2A. Plant Physiol. Nov. 1996;112(3):1331-1341.

Ritala et al., Fertile transgenic barley to particle bombardment of immature embryos. Plant Mol Biol. Jan. 1994;24(2):317-325.

Romer et al., Expression of the Genes Encoding the Early Carotenoid Biosynthetic Enzymes in Capsicum Annuum. Biochem Biophys Res Commun. Nov. 15, 1993;196(3):1414-1421.

Russell and Fromm, Tissue-specific expression in transgenic maize of four endosperm promoters from maize and ice. Transgenic Res. Mar. 1997;6(2):157-168.

Sanfacon et al., A dissection of the cauliflower mosaic virus polyadenylation signal. Genes Dev. Jan. 1991;5(1):141-149.

Schmidt et al., A Novel Operon Organization Involving the Genes for Chorismate Synthase (Aromatic BiosynthesisPathway) andR ibosomal GTPase Center Proteins (L11, L1, L10, L12: rpIKAJL) in Cyanobacterium Synechocystis PCC 6803. J Biol Chem. Dec. 25, 1993;268(36):27447-27457.

Schnell et al., Signal Peptide Analogs Derived from Two Chloroplast Precursors Interact with the Signal Recognition System of the Chloroplast Envelope. J Biol Chem. Feb. 15, 1991;266(5):3335-3342.

Schnorf et al., An improved approach for transformation of plant cells by microinjection: molecular and genetic analysis. Transgenic Res. Dec. 1991;1(1):23-30.

Shah et al., Engineering herbicide tolerance in transgenic plants. Science. Jul. 25, 1986;233(4762):478-481.

Skuzeski et al., Analysis of leaky viral translation termination codons in vivo by transient expression of improved beta-glucuronidase vectors. Plant Mol Biol. Jul. 1990;15(1):65-79.

Staub and Maliga, Accumulation of D1 polypeptide in tobacco plastids is regulated via the untranslated region of the psbA mRNA. EMBO J. Feb. 1993;12(2):601-606.

Svab and Maliga, High-frequency plastid transformation in tobacco by selection for a chimeric aadA gene. Proc Natl Acad Sci USA. Feb. 1, 1993;90(3):913-917.

Svab et al., Stable transformation of plastids in higher plants. Proc Natl Acad Sci USA. Nov. 1990;87(21):8526-8530.

Van Camp et al., Tissue-Specific Activity of Two Manganese Superoxide Dismutase Promoters in Transgenic Tobacco. Plant Physiol. Oct. 1996;112(2):525-535.

Veldhoen et al., Recent Developments in Peptide-Based Nucleic Acid Delivery. Int J Mol Sci. Jun. 2008;9(7):1276-1320.

Velten et al., Isolation of a dual plant promoter fragment from the Ti plasmid of Agrobacterium tumefaciens. EMBO J. Dec. 1, 1984;3(12):2723-2730.

Von Heijne et al., CHLPEP—A Database of Chloroplast Transit Peptides. Plant Mol Biol Rep. 1991;9(2):104-126.

Wan and Lemaux, Generation of Large Numbers of Independently Transformed Fertile Barley Plants. Plant Physiol. Jan. 1994;104(1):37-48.

Yamamoto et al., Light-responsive elements of the tobacco PSI-D gene are located both upstream and within the transcribed region. Plant J. Aug. 1997;12(2):255-265.

Yamamoto et al., The Promoter of a Pine Photosynthetic Gene Allows Expression of a β-Glucuronidase Reporter Gene in Transgenic Rice Plants in a Light-Independent but Tissue-Specific Manner. Plant Cell Physiol. Jul. 1994;35(5):773-778.

Zhao and Last, Immunological Characterization and Chloroplast Localization of the Tryptophan Biosynthetic Enzymes of the Flowering Plant *Arabidopsis thaliana*. J Biol Chem. Mar. 17, 1995;270(11):6081-6087.

Extended European Search Report and Written Opinion issued by EPO in European Patent Application No. 18184232 dated Nov. 26, 2018 (8 pages).

Extended European Search Report and Written Opinion issued by EPO in European Patent Application No. 11815228 dated Jan. 2, 2014 (12 pages).

First Exam Report issued by IPI in Indian Patent Application No. 188/MUMNP/2013 dated Apr. 17, 2018—incl Engl lang transl (8 pages total).

First Exam Report issued by New Zealand IPO in New Zealand Patent Application No. 607627 dated Jul. 2, 2013 (2 pages).

First Exam Report issued by the IP Australia in Australian Patent Application No. 2011285830 dated Dec. 13, 2013 (3 pages).

Further Exam Report issued by New Zealand IPO in New Zealand Patent Application No. 607627 dated Jan. 26, 2015 (3 pages).

* cited by examiner

FIG. 1

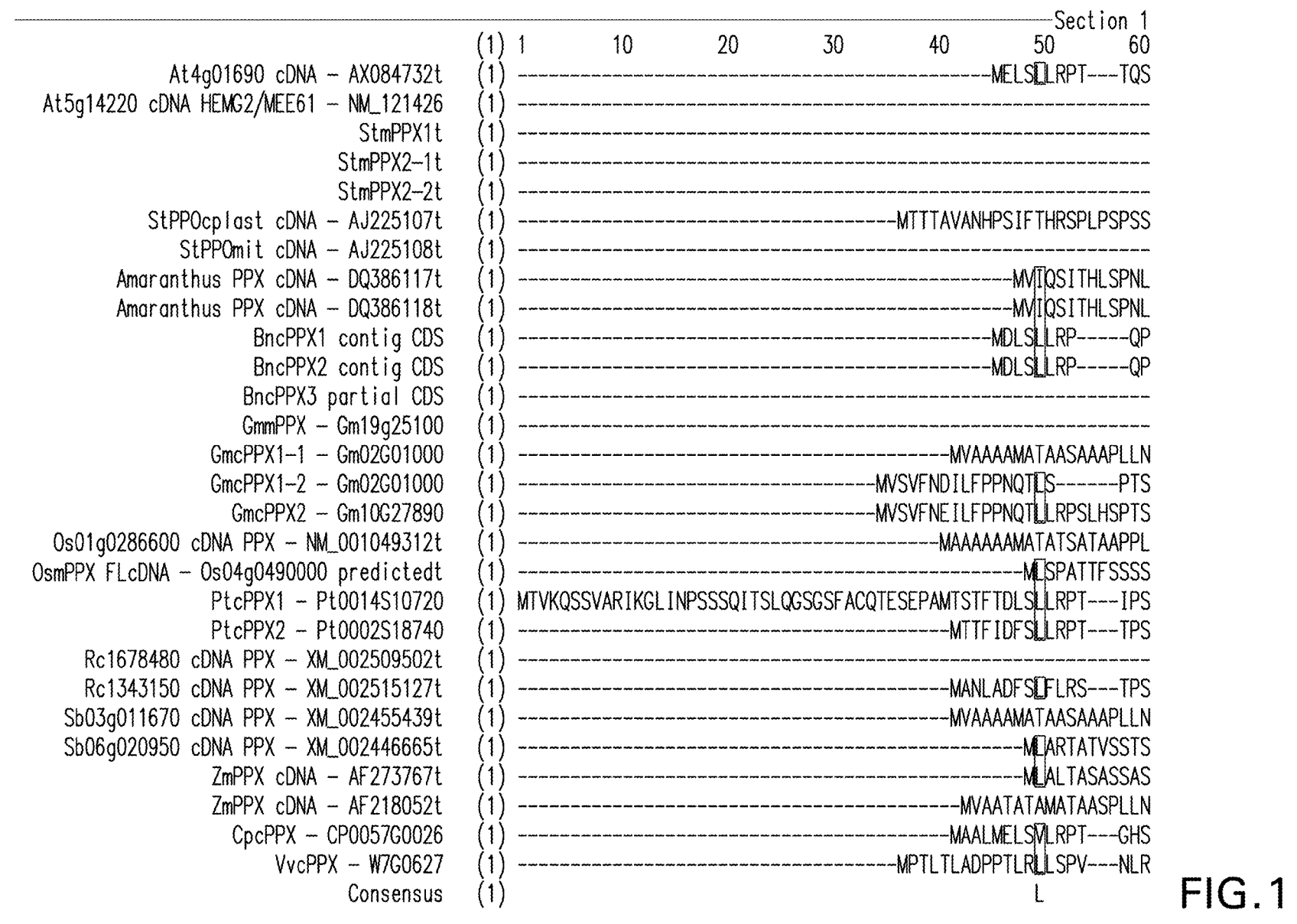

```
                                    Section 1
                 1        10        20        30        40        50        60
At4g01690 cDNA - AX084732t                                            ------MELS LRPT---TQS
At5g14220 cDNA HEMG2/MEE61 - NM_121426
StmPPX1t
StmPPX2-1t
StmPPX2-2t
StPPOcplast cDNA - AJ225107t                   ------MTTTAVANHPSIFTHRSPLPSPSS
StPPOmit cDNA - AJ225108t
Amaranthus PPX cDNA - DQ386117t                             ------MV QSITHLSPNL
Amaranthus PPX cDNA - DQ386118t                             ------MV QSITHLSPNL
BncPPX1 contig CDS                                            ----MDLS LRP-----QP
BncPPX2 contig CDS                                            ----MDLS LRP-----QP
BncPPX3 partial CDS
GmmPPX - Gm19g25100
GmcPPX1-1 - Gm02G01000                              -----MVAAAAMATAASAAAPLLN
GmcPPX1-2 - Gm02G01000                   -----MVSVFNDILFPPNQT S---PTS
GmcPPX2 - Gm10G27890                      -----MVSVFNEILFPPNQT LRPSLHSPTS
Os01g0286600 cDNA PPX - NM_0010049312t       ---MAAAAAMATATSATAAPPL
OsmPPX FLcDNA - Os04g0490000 predictedt                      ------M SPATTFSSSS
PtcPPX1 - Pt0014S10720   MTVKQSSVARIKGLINPSSSQITSLQGSGSFACQTESEPAMISTFTDLS LRPT---IPS
PtcPPX2 - Pt0002S18740                               ------MTTFIDFS LRPT---IPS
Rc1678480 cDNA PPX - XM_0025095502t                  ------MANLADFS FLRS--TPS
Rc1343150 cDNA PPX - XM_002515127t                  -----MVAAAAMATAASAAAPLLN
Sb03g011670 cDNA PPX - XM_002455439t                         ------M ARIATVSSTS
Sb06g020950 cDNA PPX - XM_0024466665t                        ------M ALTASASSAS
ZmPPX cDNA - AF2737767t                             -----MVAATATAMATAASPLLN
ZmPPX cDNA - AF2180052t                             -----MAALMELSV RPT---GHS
CpcPPX - CP0057G0026                      ------MPTLTLADPPTLR LSPV--NLR
VvcPPX - W7G0627
Consensus                                                                    L
```

```
                                                                    Section 2
                        61        70        80        90       100       110       120
At4g01690 cDNA - AX084732t                   (61)
At5g14220 cDNA HEMC2/MEE61 - NM_121426       (13) LLPSFSKPNLR-----------LNVYKPLR|RCS|VAGG-PTVGSSKIEGGGG-----T
StmPPX1t                                      (1) -----------------------------------MASGAVADHQIEAVSG----
StmPPX2-1t                                    (1) ------------------------------------MAPSAGEDKQNCP----
StmPPX2-1t                                    (1) ------------------------------------MAPSAGEDKQNCP----
StmPPX2-2t                                    (1) ------------------------------------MAPSAGEDKQNCP----
StPPOcplast cDNA - AJ225107t                 (25) SSSSPSFLFLNRTNFIPYFSTSKRNSVNCNGWRT|RCS|VAKDYTVPPSEVDGNQFP----
StPPOmit cDNA - AJ225108t                     (1) ------------------------------------MAPSAGEDKQNCP----
Amaranthus PPX cDNA - DQ386117t              (14) ALPSP-----------------LSVST|KN|YPVAVMGNIS|E|REEPTSA----
Amaranthus PPX cDNA - DQ386118t              (14) ALPSP-----------------LSVST|KN|YPVAVMGNIS|E|REEPTSA----
BncPPX1 contig CDS                           (11) FLSPFSNPFPR-----------SRPYKPLN|L|RCS|VSGG--SVVSSTIEGGGG----K
BncPPX2 contig CDS                           (11) FLSPFSNPFPR-----------SRPYKPLN|L|RCS|VSGGSVVVGSSTIEGGGG----K
BncPPX3 partial CDS                           (1)
GmmPPX - Gm19g25100                           (1) ------------------------------MASSA|T|DDNPRSV----
GmcPPX1-1 - Gm02G01000                       (20) GTRRPARLR-----------------RRGLR|V|RCAAVAGGAAEA|A|PASTGARLS----
GmcPPX1-2 - Gm02G01000                       (21) FFTSPTRKFP----------------RSRPNPIL|RCS|IAEESTESRPKTGDSPPP----
GmcPPX2 - Gm10G27890                         (27) FFTSPTRKFP----------------RSRPNPIL|RCS|IAEESTASPPKTRDSAPVD----
Os01g0286600 cDNA PPX - NM_0010049312t       (21) RIRDAARRT-----------------RRGHVRCAVASG-AAEA|A|PAAPGARVS----
OsmPPX FLcDNA -- Os04g0490000 predictedt     (13) SSSSPSRAHARAP---------TRFAVAASA|P|A|A|RFRPARAMA|A|SDDPRGG----
PtcPPX1 - Pt0014S10720                       (58) LIPSS---------F---------SKFTTHRPLK|L|RCS|LTEDSTTFIPFKLNGEAQSSAGH
PtcPPX2 - Pt0002S18740                       (17) LIPSS---------F---------SKFSTPRPFK|L|RCS|LTEESATITPSKLNGEAQSNGGH
Rc1678480 cDNA PPX - XM_0025095021           (1) ----------------------MSSVIKEDRNPSHV----
Rc1343150 cDNA PPX - XM_002515127t           (17) LVPSYP--------K--------TTINRTLKLQ|L|RCS|IIEQSTTTISPGGNSQSP----
Sb03g011670 cDNA PPX - XM_002455439t         (20) GTRRPARLR-----------------RRGLR|V|RCAAVAGGAAEA|A|PASTGARLS----
Sb06g020950 cDNA PPX - XM_0024466651         (13) SHSHP-----------------YRPTSA|R|SLRLRPVLAMAGSDDSRAAPA----
ZmPPX cDNA - AF273767t                       (13) SHPYR------------------HASAH|T|RPRLRAVLAMAGSDDPRAAPA----
ZmPPX cDNA - AF218052t                       (19) GTRIPATRR-----------------HRGLSVRCAAVAGGAAEA|A|PASTGARLS----
CpcPPX - CP0057G0026                         (17) LFPSISTSNLR-----------VKTNSSLRL|QCS|IAEG-STISPSNIDDGG----
VvcPPX - W7G0627                             (22) RSTSISSPFFCRP----------SRNNCTGPWRVRCAVAGES-TISSKVGDGNN----
Consensus                                    (61)                                       LRCS            A
```

FIG. 1 Cont.

Section 3

```
                                      (121)  121        130         140         150         160         170       180
         At4g01690 cDNA - AX084732t   (121)  TITTDCVIVGGGISGLCIAQALATKHPDAAPNLIVTEARDKPNLIVTEAKDRVGGNIITREE---NGFLWE
At5g14220 cDNA HEMG2/MEE61 - NM_121426 (54)  ----KRVAVVGAGVSGLAAAYKLKSRGLNVT------VFEADGRVGG-KLRSLSQ--NGLIWD
                            StmPPX1t   (17)  ----KRVANIGAGVSGLAAAYKLKIHGLDVT------VFEAEGRAGG-KLRSLSQ--DGLIWD
                          StmPPX2-1t   (14)  ----KRVAVIGAGVSGLAAAYKLKIHGLDVT------VFEAEGRAGG-KLRSLSQ--DGLIWD
                          StmPPX2-2t   (14)  ----KRVAVIGAGVSGLAAAYKLKIHGLDVT------VFEAEGRAGG-KLRSLSQ--DGLIWD
           StPPOcplast cDNA - AJ225107t (80)  -ELDQVVGAGISGLCIAKVLSANYPNLM-------VTEARDRAGG-NIITVER--DGYLWE
               StPPOmit cDNA - AJ225108t (14)  ----KRVANIGAGVSGLAAAYKLKIHGLNVT------VFEAEGRAGG-KLRSLSQ--DGLIWD
      Amaranthus PPX cDNA - DQ386117t   (44)  ----KRVAVVGAGVSGLAAAYKLKSHGLSVT------LFEADSPAGG-KLKTVKK--DGFIWD
      Amaranthus PPX cDNA - DQ386118t   (44)  ----KRVAVVGAGVSGLAAAYKLKSHGLSVT------LFEANSPAGG-KLKTVKK--DGFIWD
                     BncPPX1 contig CDS (52)  TVTADCVIVGGGISGLCIAQALVTKHPDAAKNVMVTEAKDRVGG-NIITREE--QCFLWE
                     BncPPX2 contig CDS (54)  TVAADCVIVGGGISGLCIAQALVTKHPDAAKSVMVTEAKDRVGG-NIITREE--QCFLWE
                 BncPPX3 partial CDS    (1)  
                          GmmPPX - Gm19g25100 (14)  ----KRVAVVGAGVSGLAAAYKLKSHGLDVT------VFEAEGRAGG-RLRSVSQ--DGLIWD
            GmcPPX1-1 - Gm02G01000      (56)  ----ADCVIVGGGISGLCIAQALATRHGVGE--VLVTEARARPCG--VLVTEVERPEEGYLNE
            GmcPPX1-2 - Gm02G01000      (60)  ----PLMEIALAVW-HRPAPRHOARQCQHC--WGDSPARDRVGGGNITIMES--GGYLWE
               GmcPPX2 - Gm10G27890     (67)  ----CVVVGGGVSG-LCIAQALATKHANAN--VVVTEARDRVGG-NIITMER--DGYLWE
   Os01g0286600 cDNA PPX - NM_0010493121t (56) ----ADCVVVGGGISGLCIAQALATKHGVGD--VLVTEARARPCG--VLVTEARAGEGYLWE
OsmPPX FLcDNA - Os04g0490000 predictedt (55)  ----RSVAVWGAGISGLCIAQALAAYRLRKPGVQVT-----VFEAADRAGG-KIRTNSE--GGFIWD
            PtcPPX1 - Pt0014S10720      (101) SATADCVIVGGGISGLCIAQALATKHMDVAPNVIVTEARDRVGG-NIITVER--DGYLWE
            PtcPPX2 - Pt0002S18740      (60)  SAAADCVIVGGGISGLCIAQALATKHRDVAPNVIVTEARDRVGG-NIITLER--DGYLWE
     Rc1678480 cDNA PPX - XM_0025095021t (15)  ----KRVAVVGAGVSGLAAAYKLKSHGLKVT------VFEAEERAGG-KLRSVNH--DGLIWD
     Rc1343150 cDNA PPX - XM_0025151271t (56)  ----ADCVIVGGGISGLCIAQALSTKHRDIATNVIVTEARDRVGG-NIITLER--DGYLWE
   Sb06g020950 cDNA PPX - XM_0024466651t (46)  ----RSVAVWGAGVSGLVAAYRLRKSGVNVT------VFEAADRAGG-KIRTNSE--QGFLWD
               ZmPPX cDNA - AF273767t   (46)  ----RSVAVWGAGVSGLAAAYRLRQSGVNVT------VFEAADRAGG-KIRTNSE--GGFVWD
               ZmPPX cDNA - AF218052t   (55)  ----ADCVVVGGGISGLCIAQALATRHGVGD--VLVTEARARPCG--VLVTEVERPEEGYLWE
          CpcPPX - CP0057G0026          (56)  IPTADCVIVGGGISGLCIAQALATKHRDVASNVIVTEARDRVGG-NIITVER--DGYLWE
              VvcPPX - VV7G0627         (66)  YSPVDCVIVGAGISGLCIAQALATKHGDVGSNVIVTEARDRVGG-NIITMEG--DGYLWE
                          Consensus     (121) VVWGAGISGLC A  L TKH  V     VTEARDR GG NI TVE   DGYLWE
```

Section 4
181          190          200          210          220          230     240

| | | Sequence |
|---|---|---|
| At4g01690 cDNA - AX084732t | (181) | EGPNSFQPSD-PMLTMVVDSGLKDDLVLGDPTIAPRFVLWNGKLRPVPSKLTDLPFFDLMS |
| At5g14220 cDNA HEMG2/MEE61 - NM_121426 | (111) | EGANTMTEAEPEVGSLLDDLGLREKQQFPISQKKRYIVRNGVPVMLPTNPIELVTSSVLS |
| StmPPX1t | (67) | EGANTMTESEGDVTFLLDSLGLREKQQFPLSQNKRYIARNGTPTLLPSNPIDLIKSNFLS |
| StmPPX2-1t | (64) | EGANTMTESEGDVTFLLDSLGLREKQQFPLSQNKRYIARNGTPTLLPSNPIDLIKSNFLS |
| StmPPX2-2t | (64) | EGANTMTESEGDVTFLLDSLGLREKQQFPLSQNKRFIARNGTPTLLPSNPIDLIKSNFLS |
| StPPOcplast cDNA - AJ225107t | (131) | EGPNSFQPSD-PMLTMAVDSGLKDDLVLGDPDAPRFVLWNGKLRPVPGKLTDLPFFDLMS |
| StPPOmit cDNA - AJ225108t | (64) | EGANTMTESEGDVTFLLDSLGLREKQQEPLSQNKRYIARNGTPTLLPSNPIDLIKSNFLS |
| Amaranthus PPX cDNA - DQ386117t | (94) | EGANTMTESEAEVSSLIDDLGLREKQQLPISQNKRYIARAGLPVLPSNPAALTSNILS |
| Amaranthus PPX cDNA - DQ386118t | (94) | EGANTMTESEAEVSSLIDDLGLREKQQLPISQNKRYIARDGLPVLPSNPAALTSNILS |
| BncPPX1 contig CDS | (109) | EGPNSFQPSD-PMLTMVVDSGLKDDLVLGDPTIAPRFVLWNGKLRPVPSKLTDLPFFDLMS |
| BncPPX2 contig CDS | (111) | EGPNSFQPSD-PMLTMVVDSGLKDDLVLGDPTIAPRFVLWNGKLRPVPSKLTDLPFFDLMS |
| BncPPX3 partial CDS | (1) | |
| GmmPPX - Gm19g25100 | (64) | EGANTMTESEIEVKGITDALGIQKQQFPISQHKRYIVANGAPLLVPTNPAALLKSKILS |
| GmcPPX1-1 - Gm02G01000 | (110) | EGPNSFQPSD-PVLSMAVDSGLKDDLVFGDPNAPRFVLWEGKLRPVPSKPADLPFFDLMS |
| GmcPPX1-2 - Gm02G01000 | (110) | EGPNSFQPSD-PMLTMVVDSGLKDDLVLGDPNAPRFVLWNGKLRPVPGKPTDLPFFDLMS |
| GmcPPX2 - Gm10G27890 | (117) | EGPNSFQPSD-PMLTMVVDSGLKDELVLGDPDAPRFVLWRKLRPVPGKLTDLPFFDLMS |
| Os01g0286600 cDNA PPX - NM_0010049312t | (110) | EGPNSEQPSD-PVLSMAVDSGLKDDLVFGDQQYPNSQHKRYIVKDGAPALPSDPLPFFDLMS |
| OsmPPX FLcDNA - Os04g0490000 predictedt | (105) | EGANTMTESELEASRIDDLGLQCKQQYPNSQHKRYIVKDGAPTLLPSDPTALMKSTVLS |
| PtcPPX1 - Pt0014S10720 | (158) | EGPNSEQPSD-PMLTMVVDSGLKEDLVLGDPNAPRFVLWEGKLRPVPGKPTDLPFFDLMS |
| PtcPPX2 - Pt0002S18740 | (117) | EGPNSEQPSD-PMLTMVVDSGLKEDLVLGDPNAPRFVLWEGKLRPVPGKPTDLPFFDLMS |
| Rc1678480 cDNA PPX - XM_0025095021 | (65) | EGANTMTESEMEVKSLIGNLGTREKQQFPISQNKRYIVRNGKPLLPTNPIALITSNILS |
| Rc1343150 cDNA PPX - XM_0025151271 | (110) | EGPNSEQPSD-PMLTMVVDSGLKDDLVFGDPNAPRFVLWEGKLRPVPSKPTDLPFFDLMS |
| Sb03g011670 cDNA PPX - XM_0024554391 | (110) | EGPNSEQPSD-PVLTMAVDSGLKDDLVFGDPNAPRFVLWEGKLRPVPSKPADLPFFDLMS |
| Sb06g020950 cDNA PPX - XM_0024466651 | (96) | EGANTMTEGELEASRIDDLGLQDKQQYPNSQHKRYIVKDGAPALPSDPTSLMKSSVLS |
| ZmPPX cDNA - AF273767t | (96) | EGANTMTEGEWEASRLIDDLGLQDKQQYPNSQHKRYIVKDGAPALIPSDPTSLMKSSVLS |
| ZmPPX cDNA - AF218052t | (109) | EGPNSFQPSD-PVLTMAVDSGLKDDLVFGDPNAPRFVLWEGKLRPVPSKPADLPFFDLMS |
| CpcPPX - CP0057G0026 | (113) | EGPNSEQPSD-PILTMVVDSGLKDDLVLGDPNAPRFVFWNGKLRPVPAKPTDLPFFDLMS |
| VvcPPX - VV7G0627 | (112) | EGPNSEQPSD-SMLTMAVDSGLKDDLVFGDPNAPRFVFWNGKLRPVPAKPTDLPFFDLMS |
| Consensus | (181) | EGPNSEQPSD-PILTMVVDSGLKDDLVLGDPNAPRFVFWNGKLRPVPAKPTDLPFFDLMS |

FIG. 1 Cont.

Section 5

```
                              241        250        260        270        280        290        300
At4g01690 cDNA - AX084732t      (241) IGGKIRAGFGALGIRPSPPG----------------------REESVEEFVRRNLGDEVFERLIEPFCSG----------
At5g14220 cDNA HEMG2/MEE61 - NM_121426 (170) TQSKFQILLEPFLMKKK----SSKVSDASAEESVSEFFQRHFGKEVMDYLIDPFVVGGTSA
StmPPX1t                        (127) TGSKLQMLFEPLLWKNKK----LTKVSDEH----ESVSGFFQRHFGKEVMDYLIDPFVVAGTCG
StmPPX2-1t                      (124) TGSKLQMLFEPLLWNKK----LTKVSDEH----ESVSGFFQRHFGKEVMDYLIDPFVVAGTCG
StmPPX2-2t                      (124) TGSKLQMLFEPLLWNKK----LTKVSDEH----ESVSGFFQRHFGKEVMDYLIDPFVVAGTCG
StPPOcplast cDNA - AJ225107t    (190) IPGKLRAGFGAIGLRPSPPG----------------------YEESVEQFVRRNLGAEVFERLIEPFCSG----------
StPPOmit cDNA - AJ225108t       (124) TGSKLQMLFEPLLWNNK----LTKVSDEH----ESVSGFFQRHFGKEVMDYLIDPFVVAGTCG
Amaranthus PPX cDNA - DQ386117t (154) AKSKLQIMLEPFLWRKHN----ATELSDEHVQESVGEFFERHFGKEFVDYVIDPFVVAGTCG
Amaranthus PPX cDNA - DQ386118t (154) AKSKLQIMLEPFLWRKHN----ATELSDEHVQESVGEFFERHFGKEFVDYVIDPFVVAGTCG
BncPPX1 contig CDS              (168) IGGKIRAGFGAIGIRPSPPG----------------------REESVEEFVRRNLGDEVFERLIEPFCSG----------
BncPPX2 contig CDS              (170) IGGKIRAGFGAIGIRPSPPG----------------------REESVEEFVRRNLGDEVFERLIEPFCSG----------
BncPPX3 partial CDS             (1)   ------------------------------------------------------------------------------------
GmmPPX - Gm19g25100             (124) AQSKTHLIFEPFMMKRSD----PSNVCDENSVESVGRFFERHFGKEVMDYLIDPFVVGGTSA
GmcPPX1-1 - Gm02G01000          (169) IPGKLRAGLGALGIRPPPPG----------------------REESVEEFVRRNLGDEVFERLIEPFCSG----------
GmcPPX1-2 - Gm02G01000          (169) IGGKIRAGFGVLGIRPPPPG----------------------VEEFVRRNLGDDVFERLIEPFCSGNT
GmcPPX2 - Gm10G27890            (176) IGGKIRAGFGALGIRPPPPG----------------------HEESVEEFVRRNLGDEVFERLIEPFCSG----------
Os01g0286600 cDNA PPX - NM_001049312t (169) IPGKLRAGLGALGVRAPPPG----------------------REESVEDFVRRNLGAEVFERLIEPFCSG----------
OsmPPX FLcDNA - Os04g0490000 predictedt (165) TKSKLKLFLEPFLYEKSSRRTSGKVSDEHLSESVASFFERHFGKEVMDYLIDPFVVAGTSG
PtcPPX1 - Pt0014S10720          (217) IGGKLRAGFGALGLRPPPPG----------------------REESVEEFVRRNLGDEVFERLIEPFCSG----------
PtcPPX2 - Pt0002S18740          (176) IGGKLRAGFGALGLRPPPPG----------------------HEESVEEFVRRNLGDEVFERLIEPFCSG----------
Rc1678480 cDNA PPX - XM_0025095021 (125) AQSKFQIILEPFLMKRE----SSETHNAYTEESVGEFFQRHFGKEVMDYLIDPFVVAGTSA
Rc1343150 cDNA PPX - XM_002515127t (169) FGGKLRAGIGALGIRPPPPG----------------------REESVEEFVRRNLGDEVFERLIEPFCSG----------
Sb03g011670 cDNA PPX - XM_002455439t (169) IPGKLRAGIGALGIRPPPPG----------------------REESVEEFVRRNLGAEVFERLIEPFCSG----------
Sb06g020950 cDNA PPX - XM_002446665t (156) TKSKIALFFEPFLYKANTRNPGKVSDEHLSESVGSFFERHFGREVMDYLIDPFVVAGTSA
ZmPPX cDNA - AF273767t          (156) TKSKIALFFEPFLYKANTRNSGKVSEEHLSESVGSFFCRHFGRELVMDYFVDPFVVAGTSA
ZmPPX cDNA - AF218052t          (168) IPGKLRAGLGALGIRPPPG----------------------REESVEEFVRRNLGAEVFERLIEPFCSG----------
CpcPPX - CP0057G0026            (172) FGGKLRAGFGALGIRPAPPG----------------------HEESVEEFVRRNLGDEVFERLIEPFCSG----------
VvcPPX - VV7G0627               (182) FPGKLRAGFGALGIRPPPPD----------------------HEESVEEFVRRNLGDEVFERLIEPFCSG----------
Consensus                       (241) GKLRAGFGALGIRP PP            EESVEEFVRRNLG EVFERLIEPFCSG
```

FIG. 1 Cont.

Section 7

```
                                                361                    370        380        390        400        410    420
At4g01690 cDNA - AX084732t              (361)  RDPRLPKPKPQGQTVGSFRKGLRMLPEAISARLG-SKVKLSWKLSGITKL------ESGGYNL
At5g14220 cDNA HEM62/MEE61 - NM_121426  (264)  KSSPGTKKGSRGSFSFLGGMQILPDTLCKSLSHDEINDSKVFSLSYN--SGSRQEWMSL
StmPPX1t                                (227)  PKTSMNKKHQRGSFSFLGGMQTLGSMQTLTDAICNDLKEDELRLNSRVLELSCSCSGDSAIDSWSI
StmPPX2-1t                              (223)  PKTSMNKKRQRGSFSFLGGMQTLTDAICNDLKEDELRLNSRVLELSCSCSGDSAIDSWSI
StmPPX2-2t                              (223)  PKTSENKKRQRGSFSFLGGMQTLTDAICNDLKEDELRLNSRVLELSCSCSGDSAIDSWSI
StPP0cplast cDNA - AJ225107t            (284)  RDPRLPTPKGQTVGSFRKGLRMLPDAICERLG-SKVKLSWKLSSITKS------EKGGYLL
StPP0mit cDNA - AJ225108t               (223)  PKTSMNKKRQRGSFSFLGGMQTLTDAICKDLKEDELRLNSRVLELSCSCSGDSAIDSWSI
Amaranthus PPX cDNA - DQ386117t         (255)  --ASIKKPRVRGSFSFQGGMQTLVDTMCKQLGEDELKLQCEMSLSYNQKGIPSLGWSV
Amaranthus PPX cDNA - DQ386118t         (254)  --ASIKKPRVRGSFSFQGGMQTLVDTMCKQLGEDELKLQCEMSLSYNQKGIPSLGWSV
BncPPX1 contig CDS                      (262)  RDPRLPKPKGQTVGSFRKGLIMLPDAISARLG-DKVKVSWKLSSISKL------PSGGYSL
BncPPX2 contig CDS                      (264)  RDPRLPKPKGQTVGSFRKGLIMLPDAISARLG-DKVKVSWKLSSISKL------PSGGYSL
BncPPX3 partial CDS                     (1)    RTALRKNKEKRGSFSPQGGMQTIDTLCKELGKDDLKINEKVLTLAYGHDGSSSSQWMSI
GmmPPX - Gm19g25100                     (225)  RDPRLPKPKGQTVASFRKGLAMLPNAITSSLG-SKVKLSWKLSSISKL------DGKGYML
GmcPPX1-1 - Gm02G01000                  (263)  RDPRLPKPKGQTVASFRKGLIMLPDAISARLG-NKVKLSWKLSSISKL------DSGEYSL
GmcPPX1-2 - Gm02G01000                  (274)  RDPRLPKPKGQTVASFRKGLIMLPDAISARLG-NKVKLSWKLSSISKL------DSGEYSL
GmcPPX2 - Gm10G27890                    (270)  RDPRLPTPKGQTVASFRKGLIMLPDAISRLG-SKVKLSWKLTSITKS------DNKGYAL
Os01g0286600 cDNA PPX - NM_0010493121   (263)  GASPGKGRNKRVSFSFHGGMQSLIDALHNEVGDGNVKLGTEMSLACCCDGVSSSGGWSI
OsmPPX FLcDNA - Os04g0490000 predicted  (269)  RDPRLPTPKGQTVGSFRKGLAMLPDAIATRLG-SNVKLSWKLSSIIKL------ENGGYSL
PtcPPX1 - Pt0014S10720                  (311)  RDPRLPTPKGQTVGSFRKGLAMLPDAIATRLG-SNVKLSWKLASVIKL------DSGGYSL
PtcPPX2 - Pt0002S18740                  (270)  KGSSVMKKQQRGSFSFFGGMQTLIDTLCKALAKDELRLESKVFSLSYNPDSKSAVEMWSL
Rc1678480 cDNA PPX - XM_0025095021      (226)  RDPRLPTPKGQTVASFRKGLIMLPDAIAKRLG-SNVKLSWKLSSITKL------ENGGYSL
Rc1343150 cDNA PPX - XM_0025151271      (263)  RDPRLPKPKGQTVASFRKGLIMLPDAISARLG-SKVKLSWKLTSITKS------DGKGYML
Sb03g011670 cDNA PPX - XM_0024554391    (263)  RDSSAKRRNRRVSFSFHGGMQSLINALHNEVGDDNVKLGTEMSLACTLDGAPAPGGWSI
Sb06g020950 cDNA PPX - XM_0024466651    (260)  HDSSGKRRNRRVSFSFHGGMQSLINALHNEVGDDNVKLGTEMSLACTFDGVPALGRWSI
ZmPPX cDNA - AF2737671                  (260)  RDARLPKPKGQTVASFRKGLAMLPNAITSSLG-SKVKLSWKLTSITKS------DDKGYML
ZmPPX cDNA - AF2180521                  (262)  RDPRLPKPKGQTVGSFRKGLIMLPEAISARLG-SKVKLSWKLSSIIKL------NNRGYCL
CpcPPX - CP0057G0026                    (266)  RDPRLPKPKGQTVGSFRKGLIMLPEAISKRLG-GKVKLSWKLSWKLSSIIRL------DDGGYSL
VvcPPX - VV7G0627                       (276)  RDPRLPKPKGQTVGSFRKGL  MLPDAI
Consensus                               (361)  RDPRLPKPKGQTVGSFRKGL   MLPDAI            LG      VKLSWKLSSISK                  GGYSL
```

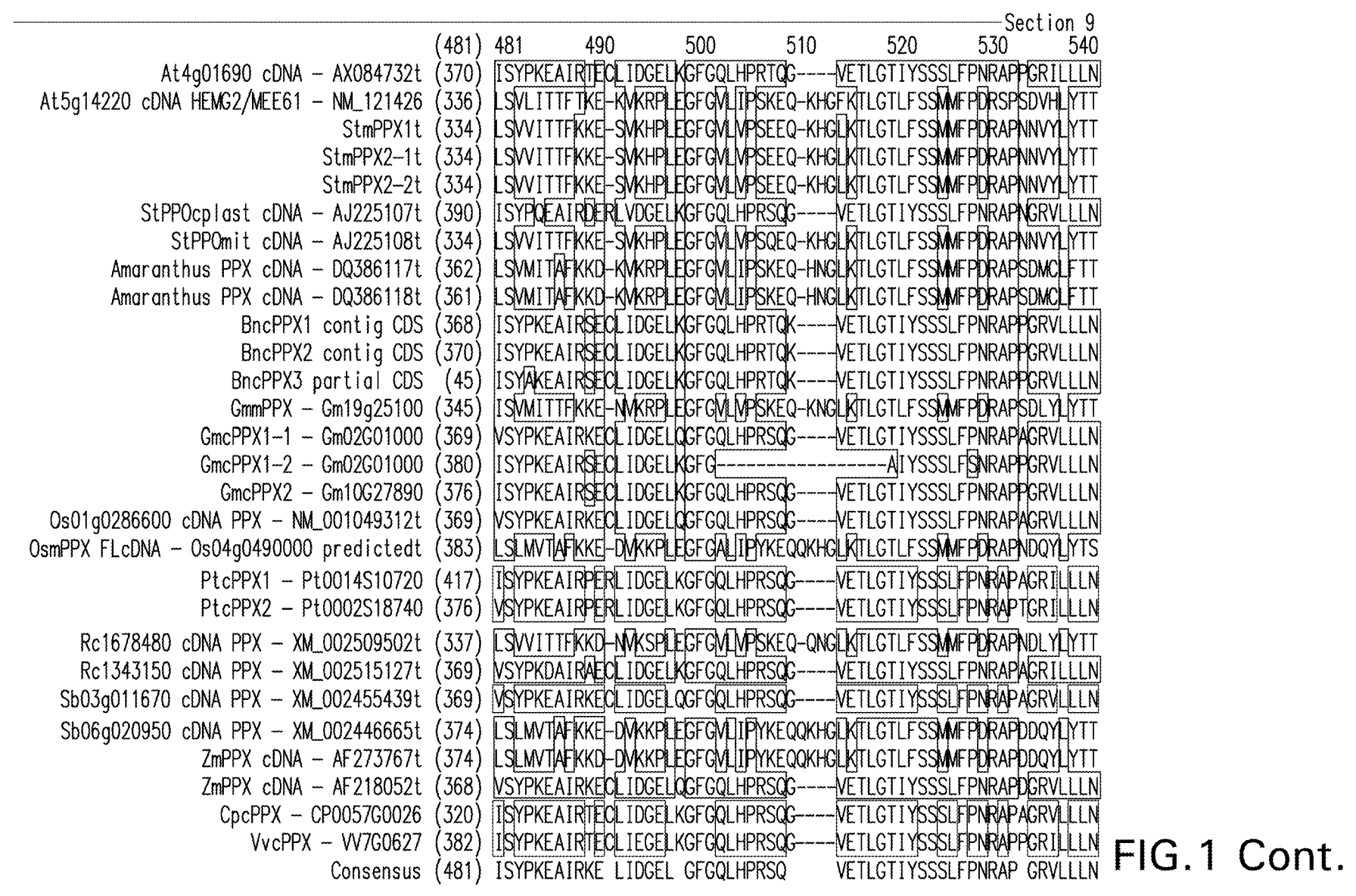

Section 9

```
                              481        490        500        510        520        530        540
At4g01690 cDNA - AX084732t    (481) ISYPKEAIRTECLIDGELKGFGQLHPRTQG-------VETLGTIYSSSLFPNRAPPGRILLLN
At5g14220 cDNA HEMG2/MEE61 - NM_121426 (370) LSWLITTFKKE-KMKRPLEGFGMLIPSKEQ-KHGFKTLGTLFSSMFPDRSPSDVHLYTT
StmPPX1t                      (336) LSWVITTFKKE-SVKHPLEGFGMLVPSEEQ-KHGLKTLGTLFSSMFPDRAPNNVMLYTT
StmPPX2-1t                    (334) LSWVITTFKKE-SVKHPLEGFGMLVPSEEQ-KHGLKTLGTLFSSMFPDRAPNNVMLYTT
StmPPX2-2t                    (334) LSWVITTFKKE-SVKHPLEGFGMLVPSEEQ-KHGLKTLGTLFSSMFPDRAPNNVMLYTT
StPPOcplast cDNA - AJ225107t  (390) ISYPQEAIRDERLVDGELKGFGQLHPRSQG-------VETLGTIYSSSLFPNRAPGRVLLLN
StPPOmit cDNA - AJ225108t     (334) LSWVITTFKKE-SVKHPLEGFGMLVPSEEQ-KHGLKTLGTLFSSMFPDRAPNNVMLYTT
Amaranthus PPX cDNA - DQ386117t (362) LSMITAFKKO-KMKRPLEGFGMLIPSKEQ-HNGLKTLGTLFSSMFPDRAPSDMCLFTT
Amaranthus PPX cDNA - DQ386118t (361) LSMITAFKKO-KMKRPLEGFGMLIPSKEQ-HNGLKTLGTLFSSMFPDRAPSDMCLFTT
BncPPX1 contig CDS            (368) ISYPKEAIRSECLIDGELKGFGQLHPRSQG-------VETLGTIYSSSLFPNRAPPGRVLLLN
BncPPX2 contig CDS            (370) ISYPKEAIRSECLIDGELKGFGQLHPRTQK-------VETLGTIYSSSLFPNRAPPGRVLLLN
BncPPX3 partial CDS           (45)  ISYAKEAIRSECLIDGELKGFGQLHPRTQK-------VETLGTIYSSSLFPNRAPPGRVLLLN
GmmPPX - Gm19g25100           (345) ISMMITTFKKE-NMKRPLEGFGMLVPSKEQ-KNGLKTLGTLFSSMFPDRAPSDLYLYTT
GmcPPX1-1 - Gm02G01000        (369) VSYPKEAIRKECLIDGELKGFGQLHPRSQG-------VETLGTIYSSSLFPNRAPAGRVLLLN
GmcPPX1-2 - Gm02G01000        (380) ISYPKEAIRSECLIDGELKGFG---------AIYSSSLFSNRAPPGRVLLLN
GmcPPX2 - Gm10G27890          (376) ISYPKEAIRKECLIDGELKGFGQLHPRSQG-------VETLGTIYSSSLFPNRAPPGRVLLLN
Os01g0286600 cDNA PPX - NM_0010493121 (369) VSYPKEAIRKECLIDGELKGFGQLHPRSQG-------VETLGTIYSSSLFPNRAPAGRVLLLN
OsmPPX FLcDNA - Os04g0490000 predictedt (383) SLMVTAFKKE-DMKKPLEGFGALIPYKEQQKHGLKTLGTLFSSMFPDRAPNDQYLYTS
PtcPPX1 - Pt0014S10720        (417) ISYPKEAIRPERLIDGELKGFGQLHPRSQG-------VETLGTIYSSSLFPNRAPAGRILLLN
PtcPPX2 - Pt0002S18740        (376) VSYPKEAIRPERLIDGELKGFGQLHPRSQG-------VETLGTIYSSSLFPNRAPTGRILLLN
Rc1678480 cDNA PPX - XM_0025095021 (337) LSWITTFKKO-NMKSPLEGFGMLVPSKEQ-QNGLKTLGTLFSSMFPDRAPNDLYLYTT
Rc1343150 cDNA PPX - XM_0025151271 (369) VSYPKOAIRAECLIDGELKGFGQLHPRSQG-------VETLGTIYSSSLFPNRAPAGRILLLN
Sb03g011670 cDNA PPX - XM_0024554391 (369) VSYPKEAIRKECLIDGELKGFGQLHPRSQG-------VETLGTIYSSSLFPNRAPAGRVLLLN
Sb06g020950 cDNA PPX - XM_0024466651 (374) SLMVTAFKKE-DMKKPLEGFGMLIPYKEQQKHGLKTLGTLFSSMFPDRAPDDQMLYTT
ZmPPX cDNA - AF273767t        (374) SLMVTAFKKO-DMKKPLEGFGMLIPYKEQQKHGLKTLGTLFSSMFPDRAPDDQMLYTT
ZmPPX cDNA - AF218052t        (368) VSYPKEAIRKECLIDGELKGFGQLHPRSQG-------VETLGTIYSSSLFPNRAPPGRVLLLN
CpcPPX - CP0057G0026          (320) ISYPKEAIRTECLIDGELIEGELKGFGQLHPRSQG-------VETLGTIYSSSLFPNRAPGRVLLLN
VvcPPX - W7G0627              (382) ISYPKEAIRKECLIDGELKGFGQLHPRSQG-------VETLGTIYSSSLFPNRAPPGRVLLLN
Consensus                     (481) ISYPKEAIRKE LIDGEL  GFGQLHPRSQ       VETLGTIYSSSLFPNRAP GRVLLLN
```

FIG. 1 Cont.

Section 10

|  | (541) | 541 | 550 | 560 | 570 | 580 | 590 | 600 |
|---|---|---|---|---|---|---|---|---|
| At4g01690 cDNA – AX084732t | (426) | FLGGSRNQ | | | | | GILSKSEGELVEAVDRDL |
| At5g14220 cDNA HEMG2/MEE61 – NM_121426 | (394) | FVGGSRNR | | | | ELAKASIDELKQVVTSDL | |
| StmPPX1t | (392) | FVGGSRNR | | | | ELAKASRTELKEIVTSDL | |
| StmPPX2-1t | (392) | FVGGSRNR | | | | ELAKASRTELKEIVTSDL | |
| StmPPX2-2t | (392) | FVGGSRNR | | | | ELAKASRTELKEIVTSDL | |
| StPPOcplast cDNA – AJ225107t | (446) | YIGGATNT | | | | EIVSKTESQLVEAVDRDL | |
| StPPOmit cDNA – AJ225108t | (392) | FVGGSRNR | | | | ELAKA | |
| Amaranthus PPX cDNA – DQ386117t | (420) | FVGGSRNR | | | | KLANASIDELKQIVSSDL | |
| Amaranthus PPX cDNA – DQ386118t | (419) | FVGGSRNR | | | | KLANASIDELKQIVSSDL | |
| BncPPX1 contig CDS | (424) | YIGGATNT | | | | GILSKSEGELVEAVDRDL | |
| BncPPX2 contig CDS | (426) | YIGGATNT | | | | GILSKSEGELVEAVDRDL | |
| BncPPX3 partial CDS | (101) | YIGGATNT | | | | GILSKSEGELVEAVDRDL | |
| GmmPPX – Gm19g25100 | (403) | FIGGTQNR | | | | ELAQASTDELRKIVTSDL | |
| GmcPPX1-1 – Gm02G01000 | (425) | YIGGATNT | | | | GIVSKTESELVEAVDRDL | |
| GmcPPX1-2 – Gm02G01000 | (423) | YIGGATNTGIYQSFSGKLQGWFKELIIFTSGLFGCFKQLRPNGLVSNTDSELVATVDRDL | | | | | |
| GmcPPX2 – Gm10G27890 | (432) | YIGGATNT | | | | GILSKTDSELVEIVDRDL | |
| Os01g0286600 cDNA PPX – NM_0010449312t | (425) | YIGGSTNT | | | | GIVSKTESELVEAVDRDL | |
| OsmPPX FLcDNA – Os04g0490000 predictedt | (442) | FIGGSHNR | | | | DLAGAPTAILKQLVTSDL | |
| PtcPPX1 – Pt0014S10720 | (473) | YIGGATNR | | | | GIVSKTESELVEAVDRDL | |
| PtcPPX2 – Pt0002S18740 | (432) | YIGGTTNP | | | | GIVSKTESELVEAVDRDL | |
| Rc1678480 cDNA PPX – XM_0025095021 | (395) | FVGGSRNK | | | | ELAKASTDDLKQIVTSDL | |
| Rc1343150 cDNA PPX – XM_0025151271 | (425) | YIGGATNP | | | | GILSKTETTELVEAVDRDL | |
| Sb03g011670 cDNA PPX – XM_0024554391 | (425) | YIGGATNT | | | | GIVSKTESELVEAVDRDL | |
| Sb06g020950 cDNA PPX – XM_0024466651 | (433) | FVGGSRNR | | | | DLAGAPTSILKQLVTSDL | |
| ZmPPX cDNA – AF273767t | (433) | FVGGSHNR | | | | DLAGAPTSILKQLVTSDL | |
| ZmPPX cDNA – AF218052t | (424) | YIGGATNT | | | | GIVSKTESELVEAVDRDL | |
| CpcPPX – CP0057G0026 | (428) | YIGGATNR | | | | GILSKTEAKLVEVVDRDL | |
| VvcPPX – VV7G0627 | (438) | YIGGATNP | | | | GILSKTESELVEAVDRDL | |
| Consensus | (541) | YIGGATN | | | | GILSKSESELVE VDRDL | |

Section 11

| | | 601 | 610 | 620 | 630 | 640 | 650 | 660 |
|---|---|---|---|---|---|---|---|---|

At4g01690 cDNA - AX084732t (452)   RKMLIKPNSTDPLKLGVRVWPQAIPQFLVGHFDILDTIAKSSITSSGYEGLFLGGNYYAGV

At5g14220 cDNA HEMG2/MEE61 - NM_121426 (420)   QRLLGVEG---EPVSVNHYYMRKAFPLYDSSYDSVMEAIDKMEND--LPGFFYAGNHRGGL

StmPPX1t (418)   KQLLGAEG---EPTYMNHVCWSKAFPLYGHNYDSVLDAIDKMEKN--LPGLFYAGNHKGGL

StmPPX2-1t (418)   KQLLGAEG---EPTYMNHVCWSKAFPLYGHNYDSVLDAIDKMEKN--LPGLFYAGNHKGGL

StmPPX2-2t (418)   KQLLGAEG---EPTYMNHVCWSKAFPLYGHNYDSVLDAIDKMEKN--LPGLFYAGNHKGGL

StPPOcplast cDNA - AJ225107t (472)   RKMLIKPVAQDPFVITGVRVWPQAIPQFLVGHLDTLGTIAKTIALSDNGLDGLFLGGNYYSGV StPPOmit cDNA - AJ225108t (405)

Amaranthus PPX cDNA - DQ386117t (446)   QQLLGTED---EPSFVMNHLFMSVAFPLYGHNYDSVLRAIDKMEKD--LPGFFYAGNHKGGL Amaranthus PPX cDNA - DQ386118t (445)   QQLLGTED---EPSFVMNHLFMSVAFPLYGHNYDSVLRAIDKMEKD--LPGFFYAGNHKGGL BncPPX1 contig CDS (450)   RKMLIKPSSITDPLVLGVKVWPQAIPQFLIGHIDLVDAAKASISSSGHEGLFLGGNYYAGV BncPPX2 contig CDS (452)   RKMLIKPSSITDPLVLGVKVWPQAIPQFLIGHIDLVDAAKASISSSGHEGLFLGGNYYAGV BncPPX3 partial CDS (127)   RKMLIKPSSITDPLVLGVKLWPQAIPQFLIGHIDLVDAAKASISSSGHEGLFLGGNYYAGV GmmPPX - Gm19g25100 (429)   RKLLGAEG---EPTFVMNHFYWSKGFPLYGRNYGSVLQAIDKIEKD--LPGFFFAGNYKGGL GmcPPX1-1 - Gm02G01000 (451)   RKMLINSTAMDPLVLGVRVWPQAIPQFLIGHIDLLEAAKSALDQGGYDGLFLGGNYYAGV GmcPPX1-2 - Gm02G01000 (483)   RKILINPNAQDPFVGVRLWPQAIPQFLIGHIDLDLDVAKASLRNITGFEGLFLGGNYYSGV GmcPPX2 - Gm10G27890 (458)   RKILINPNAQDPFVVGVRLWPQAIPQFLIGHIDLDLDVAKASIRNITGFEGLFLGGNYYSGV Os01g0286600 cDNA PPX - NM_0010049312t (451)   RKMLINPKAMDPLVLGVRVWPQAIPQFLIGHIDLLEAAKSALGKGGYDGLFLGGNYYAGV OsmPPX FLcDNA - Os04g0490000 predicted t (468)   RKLLGVEG---QPTFVMKHVHVMRNAFPLYGGNYDIVLEAIAKMENN--LPGFFYAGNNKDGL PtcPPX1 - Pt0014S10720 (499)   RKLLINPNAITDPLVLGVRVWPQAIPQFLIGHFDILDAARDALKAKGLQGLFLGGNFYSGV PtcPPX2 - Pt0002S18740 (458)   RKMLINPNAITDPLVLGVRVWPQAIPQFLIGHFDILDAARDALKAKGLQGLFLGGNYYSGV Rc1678480 cDNA PPX - XM_0025095021 (421)   RQLLGAEG---EPTFVMNHFYWSKAFPLYGRNYDAVMEAIDTMEKD--LPGFFYAGNHKGGL Rc1343150 cDNA PPX - XM_0025151271 (451)   RKMLIKPNVAKDPFVLGVRVWPQAIPQFLVGHIDILDSAKGALGDAGLEGLFLGGNYYAGV Sb03g011670 cDNA PPX - XM_0024554391 (451)   RKMLINSTAMDPLVLGVRVWPQAIPQFLIGHIDLLEVAKSALDQGGYDGLFLGGNYYAGV Sb06g020950 cDNA PPX - XM_0024466651 (459)   KKLLGVQG---QPTFVMKHIYMGHDMNSVLEAIEKMEKN--LPGFFMAGNNKDGL ZmPPX cDNA - AF273767t (459)   KKLLGVEG---QPTFVMKHYVMGNAFPLYGHDYSSVLEAIEKMEKN--LPGFFYAGNSKDGL ZmPPX cDNA - AF218052t (450)   RKMLINSTAMDPLVLGVRVWPQAIPQFLVGHIDLLEAAKVALDRGGYDGLFLGGNYYAGV CpcPPX - CP0057G0026 (454)   RKMLINPSAKDPEVLGVRVWPQAIPQFLVGHIDVLDAAKSALNSGGFEGLFLGGNYYSGV VvcPPX - VV7G0627 (464)   RKMLINPNAKDPLVLGVRVWPQAIPQFLIGHIDVLDAAKSALRDGGFQGMFLGGNYYSGV Consensus (601)   RKMLI   A DP   VLGVRVWPQAIPQFLIGH   ALK   GL GLFLGGNYYAGV

| Species | Genbank Accession # | Loc | G 52 | N 85 | R 144 | F 145 | A 180 | P 185 | A 220 | G 221 | L 226 | M 228 | S 244 | Q 272 | S 305 | S 332 | A 354 | L 357 | K 359 | L 393 | L 403 | L 424 | Y 426 | F 478 | I 525 |
|---|---|---|---|---|---|---|---|---|---|---|---|---|---|---|---|---|---|---|---|---|---|---|---|---|---|
| Arabidopsis thaliana - At4g01690 | AX084732 | P | 52 | 85 | 144 | 145 | 180 | 185 | 220 | 221 | 226 | 228 | 244 | 272 | 305 | 332 | 354 | 357 | 359 | 393 | 403 | 424 | 426 | 478 | 525 |
| Arabidopsis thaliana - At5g14220 | NM 121426 | M | NA | 41 | 101 | Y 102 | P 137 | K( 142 | 182 | A 183 | 188 | 190 | 206 | G 235 | L 269 | H 298 | G 320 | F 323 | L 325 | 358 | 371 | T 392 | F 394 | Y 444 | D 489 |
| Amaranthus tuberculatus | DQ386117 | B | NA | NA | 128 | Y 129 | P 164 | K 169 | G 210 | 211 | 216 | 218 | 234 | R 261 | L 295 | 324 | G 346 | F 349 | L 351 | 384 | 397 | T 418 | F 420 | Y 470 | E 515 |
| Solanum tuberosum | AJ225107 | P | N 76 | 105 | 164 | 165 | 200 | 205 | 240 | 241 | 246 | 248 | 264 | K 292 | 325 | 352 | 374 | 377 | S 379 | 413 | 423 | 444 | 446 | 498 | S 545 |
| Solanum tuberosum | NA see Fig 9 | M | NA | NA | 98 | Y 99 | P 134 | N 139 | G 178 | 179 | 184 | 186 | 202 | R 231 | 265 | 296 | G 318 | F 321 | L 323 | 356 | 369 | T 390 | F 392 | Y 442 | D 487 |
| Zea mays | AF218052 | P | NA | NA | 142 | 143 | 178 | 183 | 218 | 219 | 224 | 226 | 242 | K 270 | T 303 | 330 | 352 | 355 | R 357 | 391 | 401 | 422 | 424 | 476 | S 523 |
| Zea mays | AF273767 | M | NA | 70 | 130 | Y 131 | P 166 | K 171 | 215 | 216 | 221 | I 223 | 239 | N 268 | 302 | T 336 | G 358 | V 361 | L 363 | 396 | 410 | T 431 | F 433 | Y 483 | D 528 |
| Oryza sativa - Os01g0286600 | NM 001049312 | P | 51 | NA | 143 | 144 | 179 | 184 | 219 | 220 | 225 | 227 | 243 | K 271 | T 304 | T 331 | 353 | L 356 | I 358 | 392 | 402 | T 423 | 425 | 477 | S 524 |
| Oryza sativa - Os04g0490000 | NA see Fig 17 | M | D 50 | Q 79 | 139 | Y 140 | P 175 | K 180 | G 224 | 225 | 230 | I 232 | 248 | N 277 | L 311 | 345 | G 367 | F 370 | L 372 | 405 | 419 | T 440 | F 442 | Y 492 | D 537 |
| Sorghum bicolor - Sb03g011167 | XM 002455439 | P | NA | NA | 143 | 144 | 179 | 184 | 219 | 220 | 225 | 227 | 243 | K 271 | T 304 | 331 | 353 | L 356 | R 358 | 392 | 402 | 423 | 425 | 477 | A 524 |
| Sorghum bicolor - Sb06g02095 | XM 002446665 | M | N 51 | 70 | 130 | Y 131 | P 166 | K 171 | 215 | 216 | 221 | I 223 | 239 | N 268 | L 302 | T 336 | G 358 | F 361 | L 363 | 396 | 410 | T 431 | F 433 | Y 483 | D 528 |
| Ricinus communis | XM 002515127 | P | N 51 | 84 | 143 | 144 | 179 | 184 | 219 | 220 | 225 | 227 | 243 | K 271 | 304 | 331 | 353 | 356 | 358 | 392 | 402 | 423 | 425 | 477 | A 524 |
| Ricinus communis | XM 002509502 | M | NA | NA | 99 | Y 100 | P 135 | K 140 | 181 | 182 | 187 | V 189 | 205 | 234 | F 268 | 299 | R 321 | F 324 | L 326 | 359 | 372 | T 393 | F 395 | 445 | D 490 |
| Brassica napus - | NA see Fig 33 | P | 50 | 43 | 142 | 143 | 178 | 183 | 218 | 219 | 224 | 226 | 242 | K 270 | 303 | 330 | 352 | 355 | 357 | 391 | 401 | 422 | 424 | 476 | T 523 |
| Brassica napus - | NA see Fig 35 | P | 50 | S 85 | 144 | 145 | 180 | 185 | 220 | 221 | 226 | 228 | 244 | K 272 | 305 | 332 | 354 | 357 | 359 | 393 | 403 | 424 | 426 | 478 | T 525 |
| Brassica napus - | NA see Fig 37 | M | - | - | - | - | - | - | - | - | - | - | - | - | - | 7 | 29 | 32 | 34 | 68 | 78 | 99 | 101 | 153 | T 200 |
| Glycine max - GmcPPX1-1 Gm03G01000 | NA see Fig 39 | P | S 55 | E 82 | 143 | 144 | 179 | 184 | 219 | 220 | 225 | 227 | 243 | K 271 | T 304 | 331 | 353 | 356 | R 358 | 392 | 402 | 423 | 425 | 477 | A 524 |
| Glycine max - GmcPPX1-2 Gm02G01000 | NA see Fig 40 | P | P 59 | C 83 | 143 | 144 | V 179 | 184 | W 227 | 228 | I 236 | Y 238 | 254 | K 282 | 315 | T 342 | 364 | 367 | 369 | NA | NA | 421 | 423 | 509 | NA |
| Glycine max - GmcPX2 - Gm10G27890 | NA see Fig 42 | M | V 65 | 91 | 150 | 151 | 186 | 191 | 226 | 227 | 232 | 234 | 250 | K 278 | 311 | T 338 | 360 | 363 | 365 | 399 | 409 | 430 | 432 | 484 | A 531 |
| Glycine max - GmmtPX - Gm19g25100 | NA see Fig 44 | P | NA | NA | 98 | Y 99 | P 134 | R 139 | 180 | A 181 | 186 | 188 | 204 | H 233 | L 267 | K 307 | G 329 | F 332 | L 334 | 367 | 380 | 401 | F 403 | Y 453 | D 498 |

- = Unknown as a result of a partial sequence.

MUTATED PROTOPORPHYRINOGEN IX OXIDASE (PPX) GENES

CROSS REFERENCE TO RELATED PATENT APPLICATIONS

This application is a continuation of U.S. patent application Ser. No. 16/042,985, filed Jul. 23, 20181, now U.S. Pat. No. 11,111,500, which is a continuation of U.S. patent application Ser. No. 13/935,532, filed Jul. 4, 2013, which is a continuation of U.S. patent application Ser. No. 13/247, 954, filed Sep. 28, 2011, which is a continuation of PCT/US2011/046330, filed Aug. 2, 2011, which claims priority to U.S. Provisional Application No. 61/370,436, filed Aug. 3, 20101 and said Ser. No. 13/247,954 is also a continuation of PCT/US2011/049007, filed Aug. 24, 2011. The contents of these applications are incorporated herein by reference in their entirety.

BACKGROUND OF THE INVENTION

The following description is provided simply as an aid in understanding the invention and is not admitted to describe or constitute prior art.

Examples of certain mutations in the PPX genes of plants have been reported. For example, U.S. Pat. No. 5,767,373 discloses "eukaryotic DNA sequences coding for native protoporphyrinogen oxidase (protox) or modified forms of the enzyme which are herbicide tolerant;" U.S. Pat. No. 6,282,837 discloses "eukaryotic DNA sequences coding for native protoporphyrinogen oxidase (protox) or modified forms of the enzyme which are herbicide tolerant and a method for controlling weeds using plants having altered protox activity which confers tolerance to herbicides;" U.S. Pat. No. 6,308,458 discloses "methods for controlling the growth of undesired vegetation comprising applying an effective amount of a protox-inhibiting herbicide to a population of transgenic plants or plant seed transformed with a DNA sequence coding for a modified protox enzyme that is tolerant to at protox-inhibiting herbicide or to the locus where a population of the transgenic plants or plant seeds is cultivated;" U.S. Pat. No. 6,905,852 discloses "[a] protoporphyrinogen oxidase tolerant to photobleaching herbicide and derivatives thereof, comprising a polypeptide having the amino acid sequence represented by SEQ ID No. 2 [a PPX protein] or mutated peptides derived therefrom by deletion, addition, substitution, etc. of one or more amino acids in the above amino acid sequence and having an activity substantially equivalent to that of the protoporphyrinogen oxidase:" U.S. Pat. No. discloses "methods to confer resistance to protoporphyrinogen-inhibiting herbicides onto crop plants. Resistance is conferred by genetically engineering the plants to express cloned DNA encoding a protoporphyrinogen oxidase resistant to porphyric herbicides;" US Patent Application Publication No. 20020086395 discloses "[a] method for evaluating the ability of a compound to inhibit the protoporphyrinogen oxidase activity, which comprises the steps of: (1) culturing a transformant expressing a protoporphyrinogen oxidase gene present in a DNA fragment in a medium containing substantially no protoheme compounds in each comparative system of the presence and absence of a test compound to measure a growth rate of the transformant under each condition, said transformant being resulted from a host cell deficient in the growing ability based on the protoporphyrinogen oxidase activity transformed with the DNA fragment in which a promoter functionable in the host cell and a protoporphyrinogen oxidase gene are operatively linked, and (2) determining the ability of the compound to inhibit the protoporphyrinogen oxidase activity by comparing the growth rates; and the like:" Patzoldt W L, et al., PNAS USA 103:12329-34 (2006) discloses a "3-bp deletion corresponding to the G210 codon" of PPX; and Li X, et al., Plant Physiology 133:736-47 (2003) discloses "isolation of plant protoporphyrinogen oxidase (PPO) genes and the isolation of herbicide-resistant mutants." The terms PPO and PPX are used interchangeably herein.

SUMMARY OF THE INVENTION

The present disclosure relates, at least, in part to methods and compositions relating to gene and protein mutations in plants. In some aspects and embodiments, the present disclosure may also relate to compositions and methods for producing herbicide-resistant plants. The present disclosure methods and compositions relate, at least in part to mutations in a protoporphyrinogen IX oxidase (PPX) gene.

In one aspect, there is provided a plant or a plant cell including a mutated PPX gene. In certain embodiments, the mutated PPX gene encodes a mutated PPX protein. In certain embodiments, a plant having a plant cell that includes a mutated PPX gene may be herbicide-resistant; for example, resistant to a PPX-inhibiting herbicide. In certain embodiments, the plant or the plant cell is non-transgenic. In certain embodiments, the plant or the plant cell is transgenic. The disclosure also provides recombinant vectors including such mutated PPX genes, as well as transgenic plants containing such mutated PPX genes.

As used herein, the term "PPX gene" refers to a DNA sequence capable of generating a PPX polypeptide that shares homology and/or amino acid identity with amino acid sequence SEQ ID NO: 1, and/or encodes a protein that demonstrates PPX activity. In certain embodiments, the PPX gene has 70%; 75%; 80%; 85%; 90%; 95%; 96%; 97%; 98%; 99%; or 100% identity to a specific PPX gene; for example, the mitochondrial Russet Burbank PPX genes, for example, StmPPX1 or StmPPX2; or tor example, a plastidal Russet Burbank PPX gene, for example, StcPPX1. In certain embodiments, the PPX gene has 60%; 70%; 75%; 840%; 85%; 90%; 95%; 96%; 97%; 98%; 99%; or 100% identity to a sequence selected from the sequences in FIG. 2. In some embodiments, a PPX gene is a mitochondrial PPX gene; for example, StmPPX1 or StmPPX2. In some embodiments, a PPX gene is a plastidal PPX gene, for example. StcPPX1. In some embodiments, a PPX gene is a mitochondrial PPX gene allele; for example, StmPPX2.1 or StmPPX2.2. In some embodiments, a PPX gene is a plastidal PPX gene allele: for example, StcPPX1 or StcPPX1.1. In some plants, such as water hemp, the protein product of a single PPX gene is both mitochondrial and plastidal as disclosed in Patzoldt W L, et al., PNAS USA 103:12329-34 (2006).

As used herein, the term "mutation" refers to at least a single nucleotide variation in a nucleic acid sequence and/or a single amino acid variation in a polypeptide relative to the normal sequence or wild-type sequence or a reference sequence, e.g., SEQ ID NO: 1 or SEQ ID NO: 2. In some embodiments a mutation refers to at least a single nucleotide variation in a nucleic acid sequence and/or a single amino acid variation in a polypeptide relative to a nucleotide or amino acid sequence of a PPX protein that is not herbicide resistant. In certain embodiments, a mutation may include a substitution, a deletion, an inversion or an insertion. In some embodiments, a substitution, deletion, insertion, or inversion may include a variation at 1, 2, 3, 4, 5, 6, 7, 8, 9, 10, 11, 12, 13, 14, 15, 16, 17, 18, 19, 20, 21, 22, 23 or 24 nucleotides.

In some embodiments, a substitution, deletion, insertion, or inversion may include a variation at 1, 2, 3, 4, 5, 6, 7 or 18 amino acid positions. The term "nucleic acid" or "nucleic acid sequence" refers to an oligonucleotide, nucleotide or polynucleotide, and fragments or portions thereof, which may be single or double stranded, and represent the sense or antisense strand. A nucleic acid may include DNA or RNA, and may be of natural or synthetic origin. For example, a nucleic acid may include mRNA or cDNA. Nucleic acid may include nucleic acid that has been amplified (e.g., using polymerase chain reaction). The convention "NTwt###NTmut" is used to indicate a mutation that results in the wild-type nucleotide NTwt at position ### in the nucleic acid being replaced with mutant NTmut. The single letter code for nucleotides is as described in the U.S. Patent Office Manual of Patent Examining Procedure, section 2422, table 1. In this regard, the nucleotide designation "R" means purine such as guanine or adenine, "Y" means pyrimidine such as cytosine or thymine (uracil if RNA); "M" means adenine or cytosine; "K" means guanine or thymine; and "W" means adenine or thymine.

As used herein, the term "mutated PPX gene" refers to a PPX gene having one or more mutations at nucleotide positions relative to a reference PPX nucleic acid sequence. In certain embodiments a mutated PPX gene has one or more mutations relative to a corresponding wild type PPX sequence. As used herein, the term "wild-type" may be used to designate the standard allele at a locus, or the allele having the highest frequency in a particular population, in some instances, wild-type allele may be represented by a particular amino acid or nucleic acid sequence. For example, a wild-type potato plastidal PPX protein may be represented by SEQ ID NO: 7. For example, a wild-type potato mitochondrial PPX protein may be represented by SEQ ID NO: 9. In some embodiments a mutated PPX gene has one or more mutations relative to a reference PPX nucleic acid sequence, for example SEQ ID NOs: 2, 4, 6, 8, 10, 12, 14, 16, 18, 20, 22, 24, 26, 28, 30, 32, 34, 36, 38, 41 43 or 45 or at homologous positions of paralogs thereof. In some embodiments, the mutated PPX gene is modified with at least one mutation. In other embodiments, the mutated PPX gene is modified with at least two mutations. In other embodiments, the mutated PPX gene is modified with at least three mutations. In some embodiments, a mutated PPX gene encodes a mutated PPX protein. In some embodiments, a mutated PPX gene includes two or more nucleic acid sequence mutations selected from Tables 2, 3a and 3b. In some embodiments, a mutated PPX gene encodes one or more mutated mitochondrial PPX proteins. In other embodiments, a mutated PPX gene encodes one or more mutated plastidal PPX proteins. In some embodiments, a mutated PPX gene is a mutated mitochondrial PPX gene; for example, mutated StmPPX1. In some embodiments, a mutated PPX gene is a mutated mitochondrial PPX gene, for example, mutated StmPPX2. In some embodiments, a mutated PPX gene is a mutated plastidal PPX gene: for example, mutated StcPPX1. In some embodiments, a mutated PPX gene is a mutated mitochondrial PPX gene allele: for example, mutated StmPPX2.1 or mutated StmPPX2.2. In some embodiments, a mutated PPX gene is a mutated plastidal PPX gene allele; for example, mutated StcPPX1 or mutated StcPPX1.1. In some embodiments, there is at least one mutation in a plastid PPX gene and at least one mutation in a mitochondrial PPX gene. In some embodiments, one or more mutations in a PPX gene leads to herbicide resistance: for example, resistance to a PPX-inhibiting herbicide. In some embodiments, the mutated PPX gene encodes a mutated PPX protein that has increased resistance to one or more herbicides as compared to a reference PPX protein.

In some embodiments, the mutations in a mutated PPX gene encodes at protein having a combination of two or more mutations. In certain embodiments, at least one mutation is in the plastid PPX gene and at least one mutation is in a mitochondrial PPX gene. In certain embodiments, the combinations are selected from Tables 4a and 4b. In some embodiments, the mutations in a mutated PPX gene encode a protein having a combination of three or more mutations; for example, combinations selected from Tables 4a and 4b. In some embodiments, the at least one mutation in the plastidal PPX gene and the at least one mutation in the mitochondrial PPX gene are at the same corresponding position. In other embodiments, the at least one mutation in the plastid PPX gene and the at least one mutation in the mitochondrial PPX gene are at different corresponding positions.

As used herein, the term "PPX protein" refers to a protein that has homology and/or amino acid identity to a PPX protein of SEQ ID NOs: 1, 3, 5, 7, 9, 11, 13, 15, 17, 19, 21, 23, 25, 27, 29, 31, 33, 35, 37, 39, 40, 42 or 44 and/or demonstrates PPX activity. In certain embodiments, the PPX protein has 70%; 75%; 80%; 85%; 90%; 95%; 96%; 97%; 98%; 99%; or 100% identity to a specific PPX protein, such as for example, the mitochondrial Russet Burbank PPX protein or the plastidal Russet Burbank PPX proteins. In certain embodiments, the PPX protein has 70%; 75%; 80%; 85%; 90%; 95%; 96%; 97%; 98%; 99%; or 100% identity to a sequence selected from the sequences in FIGS. 1 and 3.

As used herein, the term "mutated PPX protein" refers to a PPX protein having one or more mutations at positions of amino acids relative to a reference PPX amino acid sequence, or at homologous positions of paralogs thereof. In some embodiments, a mutated PPX protein has one or more mutations relative to a reference PPX amino acid sequence, for example, a reference PPX amino acid sequence having SEQ ID NOs; 1, 3, 5, 7, 9, 11, 13, 15, 17, 19, 21, 23, 25, 27, 29, 31, 33, 35, 37, 39, 40, 42 or 44, or portions thereof, in certain embodiments a mutated PPX protein has one or more mutations relative to a corresponding wild type protein. In some embodiments a mutated PPX protein has one or more mutations relative to a corresponding protein that is not herbicide resistant. In some embodiments, the PPX protein is modified with at least one mutation. In other embodiments, the PPX protein is modified with at least two mutations. In other embodiments, the PPX protein is modified with at least three mutations. In some embodiments, one or more mitochondrial PPX proteins are mutated. In other embodiments, one or more plastidal PPX proteins are mutated. In yet another embodiment one or more mitochondrial PPX proteins and one or more plastidal PPX proteins are mutated. In some embodiments, the term mutated PPX protein refers to a PPX protein that has increased resistance to one or more herbicides as compared to a reference protein.

In some embodiments, a mutated PPX protein includes a mutation at one or more amino acid positions corresponding to a position selected from the group consisting of 52, 85, 105, 111, 130, 139, 143, 144, 145, 147, 165, 167, 170, 180, 185, 192, 193, 199, 206, 212, 219, 220, 221, 226, 228, 229, 230, 237, 244, 256, 257, 270, 271, 272, 305, 311, 316, 318, 332, 343, 354, 357, 359, 360, 366, 393, 403, 424, 426, 430, 438, 440, 444, 455, 457, 470, 478, 483, 484, 485, 487, 490, 503, 508 and 525 of SEQ ID NO: 1. In some embodiments, a mutated PPX protein includes a mutation at one or more amino acid positions corresponding to a position selected from the group consisting of 58, 64, 74, 84, 93, 97, 98, 101, 119, 121, 124, 139, 150 151, 157, 164, 170, 177, 187, 188, 195, 214, 215, 229, 230, 271, 274, 278, 283, 292 296, 307, 324, 330, 396, 404, 406, 410, 421, 423, 434, 447, 448, 449, 451, 454, 465, 470 and 500 of SEQ ID NO: 9. In some embodiments, a plant or plant cell may include a mutated protoporphyrinogen IX oxidase (PPX) gene wherein the gene encodes a protein including a mutation at one or more amino acid positions corresponding to a position selected from the group consisting of G52, N85, N105, E111, G130, D139, P143, R144, F145, L147, F165, L167, I170, A180, P185, E192, S193, R199, V206, E212, Y219, A220, G221, L226, M228, K229, A230, K237, S244, R256, R257, K270, P271, Q272, S305, E311, T316, T318, S332, S343, A354, L357, K359, L360, A366, L393, L403, L424, Y426, S430, K438, E440, V444, L455, K457, V470, F478, F483, D484, I485, D487, K490, L503, V508 and I525 of SEQ ID NO: 1. In some embodiments, a plant or plant cell may include a mutated protoporphyrinogen IX oxidase (PPX) gene wherein the gene encodes a protein including a mutation at one or more amino acid positions corresponding to a position selected from the group consisting of D58, E64, G74, G84, L93, K97, K98, A101, S119, F121, T124, N139, E150, S151, Q157, V164, D170, C177, H187, L188, N195, P214, I215, K229, K230, C271, D274, F283, A292, S296, C307, N324, D330, S396, A404, R406, K410, L421, A423, C434, D447, S448, V449, D451, D454, Y465, K470 and T500 of SEQ ID NO. 9. In some embodiments, a PPX protein is a paralog of *Arabidopsis thaliana* PPX protein (for example the PPX protein may be a potato plastidal PPX protein) and the PPX protein may have an N at the position corresponding to position 52 of SEQ ID NO:1, wherein the N is substituted with an amino acid other than an N; a K at the position corresponding to position 272 of SEQ ID NO:1, wherein the K is substituted with an amino acid other than a K; an S at the position corresponding to position 359 of SEQ ID NO:1, wherein the S is substituted with an amino acid other than an S; and/or an S at the position corresponding to position 525 of SEQ ID NO: 1, wherein the S is substituted with an amino acid other than an S. In some embodiments, a mutated PPX protein includes two or more mutations, at least one mutation of which is at the amino acid position corresponding to a position selected from the group consisting of G52, N85, N105, E111, G130, D139, P143, R144, F145, L147, F165, L167, I170, A180, P185, E192, S193, R199, V206, E212, Y219, A220, G221, I226, M228, K229, A230, K237, S244, R256, R257, K270, P271, Q272, S305, E311, T316, T318, S332, S343, A354, L357, K359, L360, A366, L393, L403, L424, Y426, S430, K438, E440, V444, L455, K457, V470, F471, F483, D484, I485, D487, K490, L503, V508, and I525 of SEQ ID NO: 1. In some embodiments, a mutated PPX protein includes two or more mutations, at least one mutation of which is at the amino acid position corresponding to a position selected from the group consisting of D58, E64, G74, G84, L93, K97, K98, A101, S119, F121, T124, N139, E150, S151, Q157, V164, D170, C117, H187, L188, N195, P214, I215, K229, K230, C271, D274, F283, A292, S296, C307, N324, D330, S396, A404, R406, K410, L421, A423, C434, D447, S448, V449, D451, D454, Y465, K470 and T500 of SEQ ID NO: 9. In some embodiments, a PPX protein is a paralog of *Arabidopsis thaliana* PPX protein (for example the PPX protein may be a potato plastidal PPX protein) and the PPX protein has two or more mutations and has one or more of (1) an N at the position corresponding to position 52 of SEQ ID NO:1 wherein the N is substituted with an amino acid other than an N; (2) a K at the position corresponding to position 272 of SEQ ID NO:1, wherein the K is substituted with an amino acid other than a K; (3) an S at the position corresponding to position 359 of SEQ ID NO:1, wherein the S is substituted with an amino acid other than an S; and/or (4) an S at the position corresponding to position 525 of SEQ ID NO: 1, wherein the S is substituted with an amino acid other than an S. In some embodiments, a mutated PPX protein includes three or more mutations, at least one mutation of which is at the amino acid position corresponding to a position selected from the group consisting of G52, N85, N105, E111, G130, D139, P143, R144, F145, L147, F165, L167, I170, A180, P185, E192, S193, R199, V206, E212, Y219, A220, G221, L226, M228, K229, A230, K237, S244, R256, R257, K270, P271, Q272, S305, E311, T316, T318, S332, S343, A354, L357, K359, L360, A366, L393, L403, L424, Y426, S430, K438, E440, V444, L455, K457, V470, F478. F483, D484, I485, D487, K490, L503, V508 and I525 of SEQ ID NO: 1. In some embodiments, a mutated PPX protein includes three or more mutations, at least one mutation of which is at the amino acid position corresponding to a position selected from the group consisting of D58, E64, G74, G84, L93, K97, K98, A101, S119, F121, T124, N139, E150, S151, Q157, V164, D170, C177, H187, L188, N195, P214, I215, K229, K230, C271, D274, F283, A292, S296, C307, N324, D330, S396, A404, R406, K410, L421, A423, C434, D447, S448, V449, D451, D454, Y465, K470 and I500 of SEQ ID NO: 9. In some embodiments, a PPX protein is a paralog of *Arabidopsis thaliana* PPX protein (for example the PPX protein may be a potato PPX protein) and the PPX protein has three or more mutations and has one or more of: (1) an N at the position corresponding to position 52 of SEQ ID NO:1, wherein the N is substituted with an amino acid other than an N; (2) a K at the position corresponding to position 272 of SEQ ID NO:1, wherein the K is substituted with an amino acid other than a K; (3) an S at the position corresponding to position 359 of SEQ ID NO:1, wherein the S is substituted with an amino acid other than an S; and/or (4) an S at the position corresponding to position 525 of SEQ ID NO: 1, wherein the S is substituted with an amino acid other than an S.

In conjunction with the various aspects, embodiments, compositions and methods disclosed herein, a mutated PPX protein includes one or more amino acid mutations selected from Tables 1, 2, 3a, 3b, 4a, 4b, 8a-f, 9a-d and 10. In some embodiments, a mutated PPX protein includes two or more amino acid mutations selected from Tables 1, 2, 3a, 3b, 4a, 4b, 8a-f, 9a-d and 10. In some embodiments, a mutated PPX protein includes three or more amino acid mutations selected from Tables 1, 2, 3a, 3b, 4a, 4b, 8a-f, 9a-d and 10. In some embodiments, a mutated PPX protein includes one or more nucleic acid sequence mutations selected from Tables 2, 3a and 3b. In some embodiments, the one or more mutations in a mutated PPX protein includes one or more mutations, two or more mutations, or three or more mutations selected from the group consisting of a glycine to lysine at a position corresponding to position 52 of SEQ ID NO: 1; an asparagine to aspartic acid at a position corresponding to position 85 of SEQ ID NO: 1; a glutamic acid to valine at a position corresponding to position 111 of SEQ ID NO: 1; a glycine to asparagine at a position corresponding to position 130 of SEQ ID NO: 1; an aspartic acid to histidine at a position corresponding to position 139 of SEQ ID NO: 1; a proline to arginine at a position corresponding to position 143 of SEQ ID NO: 1; an arginine to cysteine at a position corresponding to position 144 of SEQ ID NO: 1; an arginine to leucine at a position corresponding to position 144 of SEQ ID NO: 1; an arginine to histidine at a position corresponding to position 144 of SEQ ID NO: 1; a phenylalanine to leucine at, a positon corresponding to position 145 of SEQ ID NO: 1; a phenylalanine to tyrosine at a position corresponding to position 145 of SEQ ID NO: 1; a leucine to valine at a position corresponding to position 147 of SEQ ID NO: 1; a phenylalanine to asparagine at a position corresponding to position 165 of SEQ ID NO: 1; an alanine to threonine at a position corresponding to position 180 of SEQ ID NO: 1; a proline to arginine at a position corresponding to position 185 of SEQ ID NO: 1; a proline to histidine at a position corresponding to position 185 of SEQ ID NO: 1; a proline to tyrosine at a position corresponding to position 185 of SEQ ID NO: 1; a glutamic acid to aspartic acid at a position corresponding to position 192 of SEQ ID NO: 1; a glutamic acid to lysine at a position corresponding to position 192 of SEQ ID NO: 1; a serine to threonine at a position corresponding to position 193 of SEQ ID NO: 1; an arginine to leucine at a position corresponding to position 199 of SEQ ID NO: 1; a valine to phenylalanine at a position corresponding to position 206 of SEQ ID NO: 1; a tyrosine to serine at a position corresponding to position 219 of SEQ ID NO: 1; an alanine to cysteine at a position corresponding to position 220 of SEQ ID NO: 1; an alanine to isoleucine at a position corresponding to position 220 of SEQ ID NO: 1; an alanine to leucine at a position corresponding to position 220 of SEQ ID NO: 1; an alanine, to threonine at a position corresponding to position 220 of SEQ ID NO: 1; an alanine to valine at a position corresponding to position 220 of SEQ ID NO: 1; a leucine to methionine at a position corresponding to position 226 of SEQ ID NO: 1; a methionine to leucine at a position corresponding to position 228 of SEQ ID NO: 1; a lysine to glutamine at a position corresponding to position 229 of SEQ ID NO: 1; an alanine to phenylalanine at a position corresponding to position 230 of SEQ ID NO: 1; a serine to glycine at a position corresponding to position 244 of SEQ ID NO: 1; a serine to threonine at a position corresponding to position 244 of SEQ ID NO: 1; an arginine to histidine at a position corresponding to position 256 of SEQ ID NO: 1; an arginine to serine at a position corresponding to position 256 of SEQ ID NO: 1; a lysine to glutamic acid at a position corresponding to position 270 of SEQ ID NO: 1: a lysine to glutamine at a position corresponding to position 270 of SEQ ID NO: 1; a proline to arginine at a position corresponding to position 271 of SEQ ID NO: 1; a glutamine to phenylalanine at a position corresponding to position 272 of SEQ ID NO: 1; a serine to leucine at a position corresponding to position 305 of SEQ ID NO: 1; a glutamic acid arginine at a position corresponding to position 311 of SEQ ID NO: 1; a threonine to glycine at a position corresponding to position 316 of SEQ ID NO: 1; a threonine to glycine at a position corresponding to position 318 of SEQ ID NO: 1; a serine to cysteine at a position corresponding to position 332 of SEQ ID NO: 1; a leucine to isoleucine at a position corresponding to position 357 of SEQ ID NO: 1; a lysine to arginine at a position corresponding to position 359 of SEQ ID NO: 1; a lysine to threonine at a position corresponding to position 359 of SEQ ID NO: 1; a leucine to aspartic acid at a position corresponding to position 360 of SEQ ID NO: 1; a leucine to lysine at a position corresponding to position 360 of SEQ ID NO: 1; an alanine to glutamic acid at a position corresponding to position 366 of SEQ ID NO: 1; a leucine to methionine at a position corresponding to position 393 of SEQ ID NO: 1; a leucine to serine at a position corresponding to position 393 of SEQ ID NO: 1; a leucine to valine at a position corresponding to position 393 of SEQ ID NO: 1;

a leucine to arginine at a position corresponding to position 403 of SEQ ID NO: 1; a leucine to serine at a position corresponding to position 403 of SEQ ID NO: 1; a leucine to serine at a position corresponding to position 424 of SEQ ID NO: 1; a tyrosine to cysteine at a position corresponding to position 426 of SEQ ID NO: 1; a tyrosine to phenylalanine at a position corresponding to position 426 of SEQ ID NO: 1; a tyrosine to histidine at a position corresponding to position 426 of SEQ ID NO: 1; a tyrosine to isoleucine at a position corresponding to position 426 of SEQ ID NO: 1; a tyrosine to leucine at a position corresponding to position 426 of SEQ ID NO: 1; a tyrosine to arginine at a position corresponding to position 426 of SEQ ID NO: 1; a tyrosine to threonine at a position corresponding to position 426 of SEQ ID NO: 1; a tyrosine to valine at a position corresponding to position 426 of SEQ ID NO: 1; a serine to leucine at a position corresponding to position 430 of SEQ ID NO: 1; a lysine to serine at a position corresponding to position 438 of SEQ ID NO: 1; a glutamic acid to lysine at a position corresponding to position 440 of SEQ ID NO: 1; a valine to isoleucine at a position corresponding to position 444 of SEQ ID NO: 1; a leucine to valine at a position corresponding to position 455 of SEQ ID NO: 1; a lysine to valine at a position corresponding to position 457 of SEQ ID NO: 1; a valine to serine at a position corresponding to position 470 of SEQ ID NO: 1; a valine to tyrosine at a position corresponding to position 470 of SEQ ID NO: 1; a phenylalanine to serine at a position corresponding to position 478 of SEQ ID NO: 1; a phenylalanine to glycine at a position corresponding to position 483 of SEQ ID NO: 1; an aspartic acid to alanine at a position corresponding to position 484 of SEQ ID NO: 1; an isoleucine to glutamic acid at a position corresponding to position 485 of SEQ ID NO: 1; an aspartic acid to glycine at a position corresponding to position 487 of SEQ ID NO: 1; a lysine to asparagine at a position corresponding to position 490 of SEQ ID NO: 1; a leucine to phenylalanine at a position corresponding to position 503 of SEQ ID NO: 1; a valine to threonine at a position corresponding to position 508 of SEQ ID NO: 1; and an isoleucine to threonine, at a position corresponding to position 525 of SEQ ID NO: 1. In some embodiments, a PPX protein is a paralog of *Arabidopsis thaliana* PPX protein (for example the PPX protein may be a potato PPX protein) and the PPX protein may have an N at the position corresponding to position 52 of SEQ ID NO: 1, wherein the N is substituted with an amino acid other than an N; a K at the position corresponding to position 272 of SEQ ID NO:1, wherein the K is substituted with an amino acid other than a K; an S at the position corresponding to position 359 of SEQ ID NO:1, wherein the S is substituted with an amino acid other than an S; and/or an S at the position corresponding to position 525 of SEQ R) NO:1, wherein the S is substituted with an amino acid other than an S. In such embodiments, the one or more mutations in a mutated PPX protein includes one or more mutations, two or more mutations, or three or more mutations selected from the group consisting of an asparagine to lysine at a position corresponding to position 52 of SEQ ID NO: 1; an asparagine to aspartic acid at a position corresponding to position 85 of SEQ ID NO: 1; an arginine to cysteine at a position corresponding to position 144 of SEQ ID NO: 1; an arginine to histidine at a position corresponding to position 144 of SEQ ID NO: 1; a phenylalanine to leucine at a position corresponding to position 145 of SEQ ID NO: 1; a phenylalanine to tyrosine at a position corresponding to position 145 of SEQ ID NO: 1; an alanine to threonine at a position corresponding to position 180 of SEQ ID NO: 1; a proline to arginine at a position corresponding to position 185 of SEQ ID NO: 1; a proline to histidine at a position corresponding to position 185 of SEQ ID NO: 1; an alanine to cysteine at a position corresponding to position 220 of SEQ ID NO: 1; an alanine to isoleucine at a position corresponding to position 220 of SEQ ID NO: 1; an alanine to leucine at a position corresponding to position 220 of SEQ ID NO: 1; an alanine to threonine at a position corresponding to position 220 of SEQ ID NO: 1; an alanine to valine at a position corresponding to position 220 of SEQ ID NO: 1; a leucine to methionine at a position corresponding to position 226 of SEQ ID NO: 1; a methionine to leucine at a position corresponding to position 228 of SEQ ID NO: 1 a serine to glycine at a position corresponding to position 244 of SEQ ID NO: 1; a serine to threonine at a position corresponding to position 244 of SEQ ID NO: 1; a lysine to phenylalanine at a position corresponding to position 272 of SEQ ID NO: 1; a serine to leucine at a position corresponding to position 305 of SEQ ID NO: 1; a serine to cysteine at a position corresponding to position 332 of SEQ ID NO: 1; a leucine to isoleucine at a position corresponding to position 357 of SEQ ID NO: 1; a serine to arginine at a position corresponding to position 359 of SEQ ID NO: 1; a serine to threonine at a position corresponding to position 359 of SEQ ID NO: 1; a leucine to methionine at a position corresponding to position 393 of SEQ ID NO: 1; a leucine to serine at a position corresponding to position 393 of SEQ ID NO: 1; a leucine to valine at a position corresponding to position 393 of SEQ ID NO: 1; a leucine to arginine at a position corresponding to position 403 of SEQ ID NO: 1; a leucine to serine at a position corresponding to position 403 of SEQ ID NO: 1; a leucine to serine at a position corresponding to position 424 of SEQ ID NO: 1; a tyrosine to cysteine at a position corresponding to position 426 of SEQ ID NO: 1; a tyrosine to phenylalanine at a position corresponding to position 426 of SEQ ID NO: 1; a tryosine to histidine at a position corresponding to position 426 of SEQ ID NO: 1; a tyrosine to isoleucine at a position corresponding to position 426 of SEQ ID NO: 1; a tyrosine to leucine at a position corresponding to position 426 of SEQ ID NO: 1; a tyrosine to arginine at a position corresponding to position 426 of SEQ ID NO: 1; a tyrosine to threonine at a position corresponding to position 426 of SEQ ID NO: 1; a tyrosine to valine at a position corresponding to position 426 of SEQ ID NO: 1; a phenylalanine to serine at a position corresponding to position 478 of SEQ ID NO: 1; an isoleucine to threonine at a position corresponding to position 525 of SEQ ID NO: 1; an aspartic acid to asparagine at a position corresponding to position 58 of SEQ ID NO: 9; a glutamic acid to valine at a position corresponding to position 64 of SEQ TD NO: 9; a glycine to cysteine at a position corresponding to position 74 of SEQ ID NO: 9; a glycine to asparagine at a position corresponding to position 84 of SEQ ID NO: 9; a leucine to histidine at a position corresponding to position 93 of SEQ ID NO: 9; a lysine to arginine at a position corresponding to position 97 of SEQ ID NO: 9; an arginine to histidine at a position corresponding to position 98 of SEQ ID NO: 9; an arginine to cysteine at a position corresponding to position 98 of SEQ ID NO: 9; an arginine to leucine at a position corresponding to position 98 of SEQ ID NO:9; an alanine to valine at a position corresponding to position 101 of SEQ ID NO: 9; a serine to asparagine at a position corresponding to position 119 of SEQ ID NO: 9; a phenylalanine to leucine at a position corresponding to position 121 of SEQ ID NO: 9; a threonine to isoleucine at a position corresponding to position 124 of SEQ ID NO: 9; an asparagine to tyrosine at a position corresponding to position 139 of SEQ ID NO: 9; an asparagine to arginine at a position corresponding to position 139 of SEQ ID NO: 9; an asparagine to histidine at a position corresponding to position 139 of SEQ ID NO: 9; a glutamic acid to aspartic acid at a position corresponding to position 150 of SEQ TD NO: 9; a glutamic acid to lysine at a position corresponding to position 150 of SEQ ID NO: 9; a serine to threonine at a position corresponding to position 151 of SEQ ID NO: 9; a glutamine to leucine at a position corresponding to position 157 of SEQ ID NO: 9; a valine to phenylalanine at a position corresponding to position 164 of SEQ ID NO: 9; a valine to alanine at a position corresponding to position 164 of SEQ ID NO: 9; an aspartic acid to glutamic acid at a position corresponding to position 170 of SEQ ID NO: 9; a cysteine to serine at a position corresponding to position 177 of SEQ ID NO: 9; a histidine to glutamine at a position corresponding to position 187 of SEQ ID NO: 9; a leucine to phenylalanine at a position corresponding to position 188 of SEQ ID NO: 9; an asparagine to lysine at a position corresponding to position 195 of SEQ ID NO: 9; a proline to serine at a position corresponding to position 214 of SEQ ID NO: 9; a proline to histidine at a position corresponding to position 214 of SEQ ID NO: 9; an isoleucine to serine at a position corresponding to position 215 of SEQ TD NO: 9; an isoleucine to histidine at a position corresponding to position 215 of SEQ ID NO: 9; a lysine to glutamic acid at a position corresponding to position 229 of SEQ ID NO: 9; a lysine to glutamine at a position corresponding to position 229 of SEQ ID NO: 9; a lysine to arginine at a position corresponding to position 230 of SEQ ID NO: 9; a cysteine to arginine at a position corresponding to position 271 of SEQ ID NO: 9; an aspartic acid to glycine at a position corresponding to position 274 of SEQ ID NO: 9; a phenylalanine to glycine at a position corresponding to position 283 of SEQ ID NO: 9; an alanine to glycine at a position corresponding to position 292 of SEQ ID NO: 9; a serine to leucine at a position corresponding to position 296 of SEQ ID NO: 9; a cysteine to serine at a position corresponding to position 307 of SEQ ID NO: 9; an asparagine to aspartic acid at a position corresponding to position 324 of SEQ ID NO: 9; an asparagine to lysine at a position corresponding to position 324 of SEQ ID NO: 9; an aspartic acid to glutamic acid at a position corresponding to position 330 of SEQ ID NO: 9; a serine to leucine at a position corresponding to position 396 of SEQ ID NO: 9; an alanine to serine at a position corresponding to position 404 of SEQ ID NO: 9; an arginine to lysine at a position corresponding to position 406 of SEQ ID NO: 9; a lysine to isoleucine at a position corresponding to position 410 of SEQ ID NO: 9; a leucine to valine at a position corresponding to position 421 of SEQ ID NO: 9; an alanine to valine at a position corresponding to position 423 of SEQ ID NO: 9; a cysteine to serine at a position corresponding to position 434 of SEQ ID NO: 9; a cysteine to tyrosine at a position corresponding to position 434 of SEQ ID NO: 9; an aspartic acid to glycine at a position corresponding to position 447 of SEQ ID NO: 9; a serine to alanine at a position corresponding to position 448 of SEQ ID NO: 9; a valine to glutamic acid at a position corresponding to position 449 of SEQ ID NO: 9; an aspartic acid to glycine at a position corresponding to position 451 of SEQ ID NO: 9; an aspartic acid to asparagine at a position corresponding to position 454 of SEQ ID NO: 9; a tyrosine to phenylalanine at a position corresponding to position 465 of SEQ ID NO: 9; a lysine to threonine at a position corresponding to position 470 of SEQ ID NO: 9; and a threonine to serine at a position corresponding to position 500 of SEQ ID NO: 9.

In conjunction with any of the aspects, embodiments, methods and/or compositions disclosed herein. In certain embodiments, a mutated PPX protein may include a combination of mutations; for example a combination of mutations selected from Tables 4a and 4b. In some embodiments, the mutated PPX protein includes a combination of two or more mutations; for example, combinations selected from Tables 4a and 4b. In some embodiments, the mutated PPX protein includes a combination of three or more mutations; for example, combinations selected from Tables 4a and 4b. In some embodiments, the combination of mutations in a mutated PPX gone encode a protein having a mutation at a position corresponding to Y426 of SEQ ID NO: 1 and a mutation at one or more amino acid positions corresponding to a position selected from the group consisting of: N85, R144, F145, A180, A220, L226, and S244 of SEQ ID NO: 1. In some embodiments, the combination of mutations in a mutated PPX gene encode a protein having a mutation at a position corresponding to L393 of SEQ ID NO: 1 and a mutation at one or more amino acid positions corresponding to a position selected from the group consisting of: R144, F145, A220, S224 and S244 of SEQ ID NO: 1. In some embodiments, the combination of mutations encode a protein having a mutation at a position corresponding to L403 of SEQ ID NO: 1 and a mutation at one or more amino acid positions corresponding to a position selected from the group consisting of: F145, A220 and L226 of SEQ ID NO: 1. In some embodiments, the combination of mutations encode a protein having a mutation at a position corresponding to R144 of SEQ ID NO: 1 and a mutation at one or more amino acid positions corresponding to a position selected from the group consisting of: G52, N85, A220, S244, L226, M228, K272, S332, L393, L424, Y426 and I525 of SEQ ID NO: 1. In some embodiments, the combination of mutations encode a protein having a mutation at a position corresponding to N85 of SEQ ID NO: 1 and a mutation at one or more amino acid positions corresponding to a position selected from the group consisting of: R144, F145, A180, A220, L226, M228, and Q272 of SEQ ID NO: 1. In some embodiments, the combination of mutations encode a protein having a mutation at a position corresponding to L424 of SEQ ID NO: 1 and a mutation at the amino acid position corresponding to a position selected from the group consisting of: R144, F145, A220, L226 and L393 of SEQ ID NO: 1. In some embodiments, the combination of mutations encode a protein having a mutation at a position corresponding to I525 of SEQ ID NO: 1 and a mutation at the amino acid position corresponding to a position N85, F144, F145, A180, L226 and S244 of SEQ ID NO: 1. In some embodiments, the combination of mutations encode a protein having a mutation at a position corresponding to R144 of SEQ ID NO: 1 and a mutation at the amino acid position corresponding to a position A220 of SEQ ID NO: 1. In some embodiments, a PPX protein is a paralog of *Arabidopsis thaliana* PPX protein (for example the PPX protein may be a potato PPX protein) and the PPX protein may have an N at the position corresponding to position 52 of SEQ ID NO: 1, wherein the N is substituted with an amino acid other than an N; a K at the position corresponding to position 272 of SEQ ID NO: 1, wherein the K is substituted with an amino acid other than a K; an S at the position corresponding to position 359 of SEQ ID NO:1, wherein the S is substituted with an amino acid other than an S; and/or an S at the position corresponding to position 525 of SEQ ID NO: 1, wherein the S is substituted with an amino acid other than an S. In such embodiments, the mutated PPX protein includes a combination of two or more mutations; for example, combinations selected from Tables 4a and 4b. In such embodiments, the mutated PPX protein includes a combination of three or more mutations; for example, combinations selected from Tables 4a and 4b. In some embodiments, the combination of mutations in a mutated PPX gene encode a protein having a mutation at a position corresponding to Y426 of SEQ ID NO: 1 and a mutation at one or more amino acid positions corresponding to a position selected from the group consisting of: N5, R144, F145, A180, A220, L226, and S244 of SEQ ID NO: 1. In some embodiments, the combination of mutations in a mutated PPX gene encode a protein having a mutation at a position corresponding to L393 of SEQ ID NO: 1 and a mutation at one or more amino acid positions corresponding to a position selected from the group consisting of: R144, F145, A220, S244 and S224 of SEQ ID NO: 1. In some embodiments, the combination of mutations encode a protein having a mutation at a position corresponding to L403 of SEQ ID NO: 1 and a mutation at one or more amino acid positions corresponding to a position selected from the group consisting of: F145, A220 and L226 of SEQ ID NO: 1. In some embodiments, the combination of mutations encode a protein having a mutation at a position corresponding to R144 of SEQ ID NO: 1 and a mutation at one or more amino acid positions corresponding to a position selected from the group consisting of: N52, N85, A220, S244, L226, M228, K272, S332, L393, L424, Y426 and S525 of SEQ ID NO: 1. In some embodiments, the combination of mutations encode a protein having a mutation at a position corresponding to N85 of SEQ ID NO: 1 and a mutation at one or more amino acid positions corresponding to a position selected from the group consisting of: R144, F145, A180, A220, L226, M228, and K272 of SEQ ID NO: 1. In some embodiments, the combination of mutations encode a protein having a mutation at a position corresponding to L424 of SEQ ID NO: 1 and a mutation at the amino acid position corresponding to a position selected from the group consisting of: R144, F145, A220, L226 and L393 of SEQ ID NO: 1. In some embodiments, the combination of mutations encode a protein having a mutation at a position corresponding to S525 of SEQ ID NO: 1 and a mutation at the amino acid position corresponding to a position N85, F144, F145, A180, L226 and S244 of SEQ FD NO: 1. In some embodiments, the combination of mutations encode a protein having a mutation at a position corresponding to 98 of SEQ ID NO: 9 and a mutation at the amino acid position, corresponding to a position selected from the group consisting of 74, 93, 97, 98, 119, 121, 124, 139, 150, 151, 164, 188, 214, 229, 230, 271, 274, 292, 307, 324, 396, 410, 423, 434, 447, 448, 451, 465, 470 and 500 of SEQ ID NO: 9. In certain embodiments, the combination of mutations encode a protein having a mutation at a position corresponding to 98 of SEQ ID NO: 9 and a mutation at the amino acid position corresponding to a position selected from the group consisting of 271, 274, 292, 307, 324, 330, 396, 404, 406, 410, 423, 434, 447, 448, 454, 465, 470 and 500 of SEQ ID NO: 9. In certain embodiments, the combination of mutations encode a protein having a mutation at a position corresponding to 98 of SEQ ID NO: 9 and a mutation at the amino acid position corresponding to a position selected from the group consisting of 307 and 423 of SEQ ID NO: 9. In certain embodiments, the combination of mutations encode a protein having a mutation at a position corresponding to 98 of SEQ ID NO: 9 and a mutation at the amino acid position corresponding to a position selected from the group consisting 124, 188, 214 and 229 of SEQ ID NO: 9.

In conjunction with any of the aspects, embodiments, methods and/or compositions disclosed herein the PPX protein may be a paralog of *Arabidopsis thaliana* PPX protein (for example the PPX protein may be a potato mitochondrial PPX protein) and the PPX protein may have one or more corresponding PPX amino acids to SEQ ID NO: 9. In conjunction with any of the aspects, embodiments, methods and/or compositions disclosed herein, the one or more mutations in a mutated PPX gene may encode a mutated PPX protein having one or more mutations, two or more mutations, three or more mutations selected from the group consisting of a mutated PPX protein may include one or more mutation at the amino acid position corresponding to one or more positions selected from the group consisting of positions 58, 64, 74, 84, 93, 97, 98, 101, 119, 121, 124, 139, 150 151, 157, 164, 170, 177, 187, 188, 195, 214, 215, 229, 230, 271, 274, 278, 283, 292, 296, 307, 324, 330, 396, 404, 406, 410, 421, 423, 434, 447, 448, 449, 451, 454, 465, 470 and 500 of SEQ ID NO: 9.

In conjunction with any of the aspects, embodiments, methods and/or compositions disclosed herein, the plant cell may have a mutated PPX gene. In certain embodiments, the mutated PPX gene encodes a mutated PPX protein. In certain embodiments, the plant cell may be part of a herbicide-resistant plant. The method may include introducing into a plant cell a gene repair oligonucleobase (GRON); for example, using a GRON with a targeted mutation in a PPX gene. In certain embodiments, the plant cell produced by the method may include a PPX gene capable of expressing a mutated PPX protein. The method may further include identifying a plant cell or a plant including a plant cell that includes (1) a mutated PPX gene and/or (2) normal growth and/or catalytic activity as compared to a corresponding wild-type plant cell. The herbicide-resistant plant having a plant cell such as described herein may be identified in the presence of a PPX-inhibiting herbicide. In some embodiments, the plant cell is non-transgenic. In some embodiments, the plant cell is transgenic. A plant that includes a plant cell such as described herein may be a non-transgenic or transgenic herbicide-resistant plant; for example, the plant and/or plant cell may have a mutated PPX gene that results in resistance to at least one herbicide. In some embodiments, a plant having a plant cell as described herein may be produced asexually; for example, from one or more plant cells or from plant tissue made up of one or more plant cells; for example, from a tuber. In other embodiments, a plant having a plant cell such as described herein may be produced sexually.

In another aspect, there is provided a method for producing a herbicide-resistant plant. The method may include introducing into a plant cell a gene repair oligonucleobase (GRON); for example, using a GRON designed with a targeted mutation in a PPX gene. The mutated PPX gene may express a mutated PPX protein. The method may further include identifying a plant that has normal growth and/or catalytic activity as compared to a corresponding wild-type plant cell. The plant may be identified in the presence of a PPX-inhibiting herbicide. In some embodiments, the plant is non-transgenic. The plant may in some embodiments be a non-transgenic herbicide-resistant plant; for example, the plant may include a mutated PPX gene that results in resistance or tolerance to at least one herbicide.

In another aspect there is provided a seed including a mutated PPX gene. In some embodiments, the seed has a mutated PPX gene, it some embodiments, the mutated PPX encodes a mutated PPX protein. In some embodiments the mutated PPX protein may be resistant to a herbicide; for example, a PPX-inhibiting herbicide. In some embodiments, a plant grown from the seed is resistant to at least one herbicide; for example, a PPX-inhibiting herbicide.

In another aspect, there is provided a method for increasing the herbicide-resistance of a plant by: (a) crossing a first plant to a second plant, in which the first plant that includes a mutated PPX gene, in which the gene encodes a mutated PPX protein; (b) screening a population resulting from the cross for increased herbicide-resistance: for example, increased resistance to a PPX-inhibiting herbicide (c) selecting a member resulting from the cross having increased herbicide-resistance; and/or (d) producing seeds resulting from the cross. In some embodiments, a hybrid seed is produced by any of the methods such as described herein. In some embodiments, plants are grown from seeds produced by any of the methods such as described herein, in some embodiments, the plants and/or seeds are non-transgenic. In some embodiments, the plants and/or seeds are transgenic.

In another aspect, there is provided a method of controlling weeds in a field containing plants by applying an effective amount of at least one herbicide to a field containing weeds and plants. In some embodiments of the method, the at least one herbicide is a PPX-inhibiting herbicide. In some embodiments of the method, one or more of the plants in the field includes a mutated PPX gene; for example such as described herein. In some embodiments of the method one or more of the plants in the field includes a non-transgenic or transgenic plant having a mutated PPX gene such as described herein. In some embodiments, the mutated PPX gene encodes a mutated PPX protein. In some embodiments, one more of the plants in the field is herbicide resistant: for example, resistant to a PPX-inhibiting herbicide.

In another aspect, there is provided an isolated nucleic acid encoding a PPX protein or portion thereof. In some embodiments the isolated nucleic acid includes one or more of the PPX gene mutations such as described herein. In some embodiments, the isolated nucleic acid encodes a mutated PPX protein as disclosed herein. In certain embodiments, the isolated nucleic acid encodes a PPX protein that is herbicide resistant, for example, resistant to a PPX-inhibiting herbicide.

In another aspect, there is provided an expression vector containing an isolated nucleic acid of a mutated PPX gene. In some embodiments, the expression vector contains an isolated nucleic acid encoding a PPX protein, in some embodiments, the isolated nucleic acid encodes a protein having a mutation selected from the mutations shown in Tables 1, 2, 3a, 3b, 4a, 4b, 9a-f, 9a-d and 10. In certain embodiments, the isolated nucleic acid encodes a protein having two or more mutations. In some embodiments, the two or more mutations are selected from Tables 1, 2, 3a, 3b, 4a, 4b, 8a-f, 9a-d and 10. In certain embodiments, the isolated nucleic acid encodes a PPX protein that is herbicide resistant; for example, resistant to a PPX-inhibiting herbicide.

As used herein, the term "herbicide" refers to any chemical or substance that can kill a plant or that can halt or reduce growth and/or viability of a plant. In some embodiments, herbicide resistance is the genetically heritable ability of a plant to survive and reproduce following treatment with a concentration of herbicide that would normally kill or severely injure an unmodified wildtype plant. In some embodiments, in conjunction with any of the aspects, embodiments, methods and/or compositions disclosed herein, the herbicide is a PPX-inhibiting herbicide. In some embodiments, a PPX-inhibiting herbicide is a herbicide from a chemical family selected from the group of chemical families listed in Table 5. In some embodiments, a PPX-inhibiting herbicide is a herbicide from a chemical family selected from the group of chemical families consisting of N-phenylphthalimides, triazolinones, and pyrimidindiones. In some embodiments, a PPX-inhibiting herbicide is selected from the group of herbicides listed in Table S. In some embodiments, PPX-inhibiting herbicide is selected from the group of herbicides consisting of fluraoioxazin, sulfentrazone, and saflufenacil. In other embodiments, the PPX-inhibiting herbicide is a flumioxazin herbicide. In other embodiments, the PPX-inhibiting herbicide is a sulfentrazone herbicide. In other embodiments, the PPX-inhibiting herbicide is a saflufenacil herbicide.

In conjunction with any of the aspects, embodiments, methods and/or compositions disclosed herein, the plant or plant cell is from a plant crop selected from the group consisting of potato, sunflower, sugar beet, maize, cotton, soybean, wheat, rye, oats, rice, canola, fruits, vegetables, tobacco, barley, sorghum, tomato, mango, peach, apple, pear, strawberry, banana, melon, carrot, lettuce, onion, soya spp, sugar cane, pea, field beans, poplar, grape, citrus, alfalfa, rye, oats, turf and forage grasses, flax, oilseed rape, cucumber, morning glory, balsam, pepper, eggplant, marigold, lotus, cabbage, daisy, carnation, petunia, tulip, iris, lily, and nut-producing plants insofar as they are not already specifically mentioned. In some embodiments, the plant or plant cell is of a species selected from Table 6. In some embodiments, the plant or plant cell is of a species selected from the group consisting of *Arabidopsis thaliana, Solanum tuberosum, Solanum phureja, Oryza sativa, Amaranthus tuberculatus, Zea mays, Brassica napus*, and *Glycine max*. In some embodiments, the plant or plant cell is a Russet Burbank potato cultivar. In some embodiments, a mutated PPX gene encodes a Russet Burbank PPX protein. In some embodiments, a mutated PPX gene encodes an *Arabidopsis thaliana* PPX protein. In some embodiments, a mutated PPX gene encodes a *Solanum tuberosum* PPX protein. In some embodiments, a mutated PPX gene encodes a *Solanum phureja* PPX protein. In some embodiments, a mutated PPX gene encodes a *Zea mays* PPX protein. In some embodiments, a mutated PPX gene encodes an *Oryza sativa* PPX protein. In some embodiments, a mutated PPX gene encodes an *Amaranthus tuberculatus* PPX protein. In some embodiments, a mutated PPX gene encodes a *Sorghum bicolor* PPX protein. In some embodiments, a mutated PPX gene encodes a *Ricinus communis* PPX protein. In some embodiments, a mutated PPX gene encodes a *Brassica napus* PPX protein. In some embodiments, a mutated PPX gene encodes a *Glycine max* PPX protein. In some embodiments, a mutated PPX gene At4g01690 encodes an *Arabidopsis thaliana* PPX protein. In some embodiments a mutated PPX gene At5g14220 encodes an *Arabidopsis thaliana* PPX protein.

In any of the aspects, embodiments, methods or compositions disclosed herein may include one or more mutated PPX genes. In some embodiments, the methods and compositions involve one or more mutated PPX genes that encode one or more mitochondrial PPX proteins. In other embodiments, the methods and compositions include one or more mutated PPX genes which encode one or more plastidal PPX proteins. In some embodiments, the methods and compositions include one or more mutated PPX genes which encode one or more plastidal PPX proteins and mitochondrial PPX proteins. In some embodiments, the methods and compositions include a mitochondrial mutated PPX gene StmPPX1. In some embodiments, the methods and compositions include a mitochondrial mutated PPX gene StmPPX2. In some embodiments, the plant has the plastidal mutated PPX gene StcPPX1. In some embodiments, the methods and compositions include a mitochondrial mutated PPX gene allele StcPPX2.1. In some embodiments, the methods and compositions include a mitochondrial mutated PPX gene allele StcPPX2.2. In some embodiments, the methods and compositions include a plastidal mutated PPX gene allele StcPPX1. In some embodiments, the methods and compositions include a plastidal mutated PPX gene allele SctPPX1.1.

As used herein, the term "gene" refers to a DNA sequence that includes control and coding sequences necessary for the production of an RNA, which may have a non-coding function (e.g., a ribosomal or transfer RNA) or which may encode a polypeptide or a polypeptide precursor. The RNA or polypeptide may be encoded by a full length coding sequence or by any portion of the coding sequence so long as the desired activity or function is retained.

As used herein, the term "coding sequence" refers to a sequence of a nucleic acid or its complement, or a part thereof, that can be transcribed and/or translated to produce the mRNA for and/or the polypeptide or a fragment thereof. Coding sequences include exons in a genomic DNA or immature primary RNA transcripts, which are joined together by the cell's biochemical machinery to provide a mature mRNA. The anti-sense strand is the complement of such a nucleic acid, and the encoding sequence can be deduced therefrom.

At used herein, the term "non-coding sequence" refers to a sequence of a nucleic acid or its complement, or a part thereof, that is not transcribed into amino acid in vivo, or where tRNA does not interact to place or attempt to place an amino acid. Non-coding sequences include both intron sequences in genomic DNA or immature primary RNA transcripts, and gene-associated sequences such as promoters, enhancers, silencers, ere.

A nucleobase is a base, which in certain preferred embodiments is a purine, pyrimidine, or a derivative or analog thereof. Nucleosides are nucleobases that contain a pentosefuranosyl moiety, e.g., an optionally substituted riboside or 2'-deoxyriboside. The moiety may be any group that increases DNA binding and/or decreases nuclease degradation as compared to a nucleoside not having the moiety. Nucleosides can be linked by one of several linkage moieties, which may or may not contain phosphorus. Nucleosides that are linked by unsubstituted phosphodiester linkages are termed nucleotides. As used herein, the term "nucleobase" includes peptide nucleobases, the subunits of peptide nucleic acids, and morpholine nucleobases as well as nucleosides and nucleotides.

An oligonucleobase is a polymer comprising nucleobases; preferably at least a portion of which can hybridize by Watson-Crick base pairing to a DNA having the complementary sequence. An oligonucleobase chain may have a single 5' and 3' terminus, which are the ultimate nucleobases of the polymer. A particular oligonucleobase chain can contain nucleobases of all types. An oligonucleobase compound is a compound comprising one or more oligonucleobase chains that may be complementary and hybridized by Watson-Crick base pairing. Ribo-type nucleobases include pentosefuranosyl containing nucleobases wherein the 2' carbon is a methylene substituted with a hydroxyl, alkyloxy or halogen. Deoxyribo-type nucleobases are nucleobases other than ribo-type nucleobases and include all nucleobases that do not contain a pentosefuranosyl moiety.

In conjunction with any of the aspects, embodiments, methods and/or compositions disclosed herein, an oligonucleobase strand may include both oligonucleobase chains and segments or regions of oligonucleobase chains. An oligonucleobase strand may have a 5' end and a 3' end, and when an oligonucleobase strand is coextensive with a chain, the 5' and 3' ends of the strand are also 5' and 3' termini of the chain.

As used herein, the term "gene repair oligonucleobase" or "GRON" refers to oligonucleobases, including nixed duplex oligonucleotides, non-nucleotide containing molecules, single stranded oligodeoxynucleotides and other gene repair molecules.

As used herein, the term "transgenic" refers to an organism or cell that has DNA derived from another organism inserted into its genome. For example, in some embodiments, a transgenic organism or cell includes inserted DNA that includes a foreign promoter and/or coding region.

As used herein, the term "non-transgenic" refers to an organism or cell that does not have DNA derived from another organism inserted into its genome although a non-transgenic plant or cell may have one or more artificially introduced targeted mutations.

As used herein, the term "isolated", when referring to a nucleic acid (e.g., an oligonucleotide such as RNA, DNA, or a mixed polymer) refers to a nucleic acid that is apart from a substantial portion of the genome in which it naturally occurs and/or is substantially separated from other cellular components which naturally accompany such nucleic acid. For example, any nucleic acid that has been produced synthetically (e.g., by serial base condensation) is considered to be isolated. Likewise, nucleic acids that are recombinantly expressed, cloned, produced by a primer extension reaction (e.g., PCR), or otherwise excised Rom a genome are also considered to be isolated.

As used herein, the term "amino acid sequence" refers to a polypeptide or protein sequence. The convention "AAwt###AAmut" is used to indicate a mutation that results in the wild-type amino acid AAwt at position ### in the polypeptide being replaced with mutant AAmut.

As used herein, the term "complement" refers to the complementary sequence to a nucleic acid according to standard Watson/Crick pairing rules. A complement sequence can also be a sequence of RNA complementary to the DNA sequence or its complementary sequence, and can also be a cDNA.

As used herein, the term "substantially complementary" refers to two sequences that hybridize under near stringent hybridization conditions. The skilled artisan will understand that substantially complementary sequences need not hybridize along their entire length.

As used herein the term "codon" refers to a sequence of three adjacent nucleotides (either RNA or DNA) constituting the genetic code that determines the insertion of a specific amino acid in a polypeptide chain during protein synthesis or the signal to stop protein synthesis. The term "codon" is also used to refer to the corresponding (and complementary) sequences of three nucleotides in the messenger RNA into which the original DNA is transcribed.

As used herein, the term "homology" refers to sequence similarity among proteins and DNA. The term "homology" or "homologous" refers to a degree of identity. There may be partial homology or complete homology. A partially homologous sequence is one that has less than 100% sequence identity when compared to another sequence.

As used herein, the term "about" in quantitative terms refers to plus or minus 10%. For example, "about 3%" would encompass 2.7-3.3% and "about 10%" would encompass 9-11%. Moreover, where "about" is used herein in conjunction with a quantitative term it is understood that in addition to the value plus or minus 10%, the exact value of the quantitative term is also contemplated and described. For example, the term "about 3%" expressly contemplates, describes and includes exactly 3%.

BRIEF DESCRIPTION OF THE FIGURES

Figure 1:
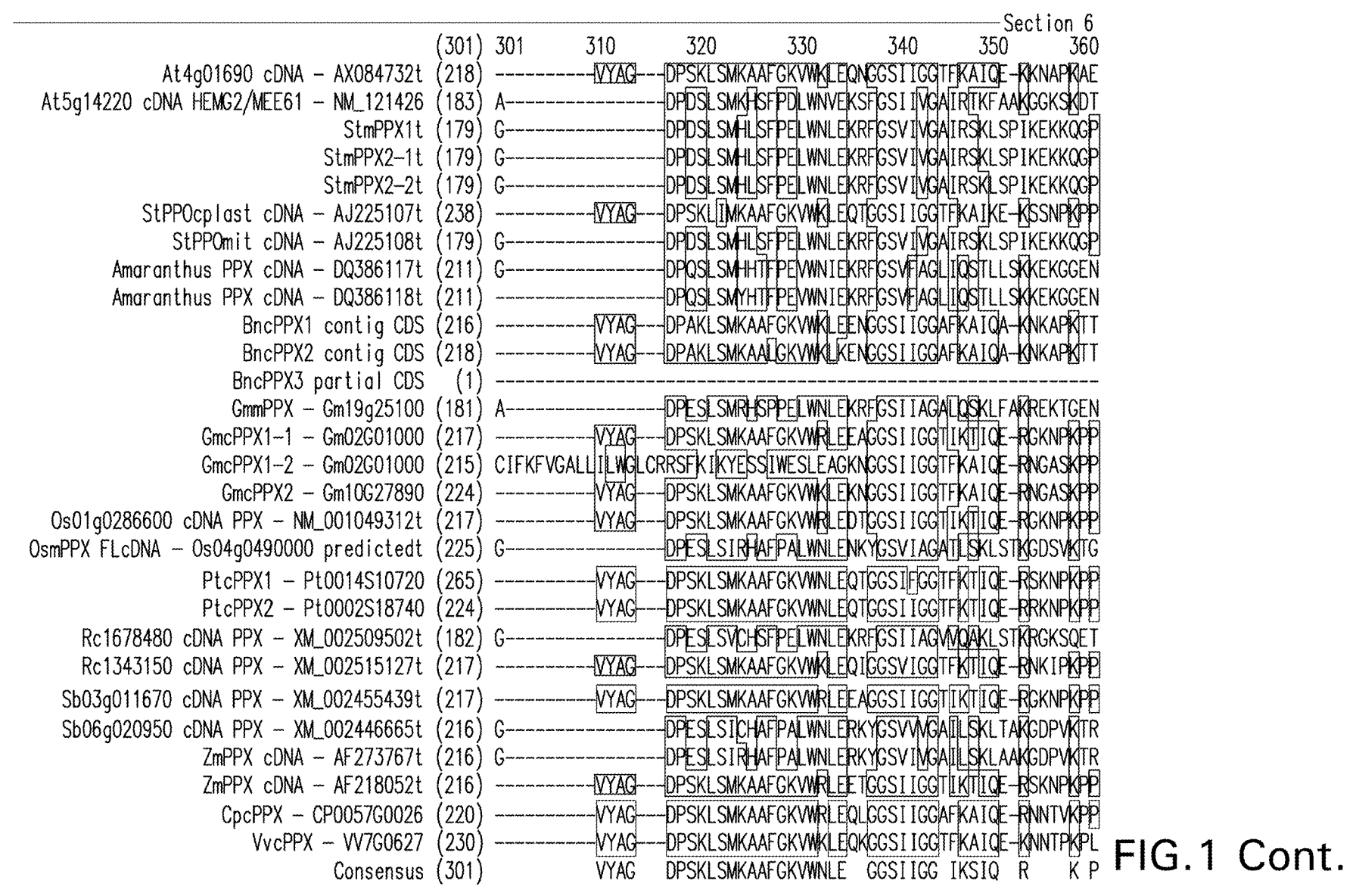
Figure 1:
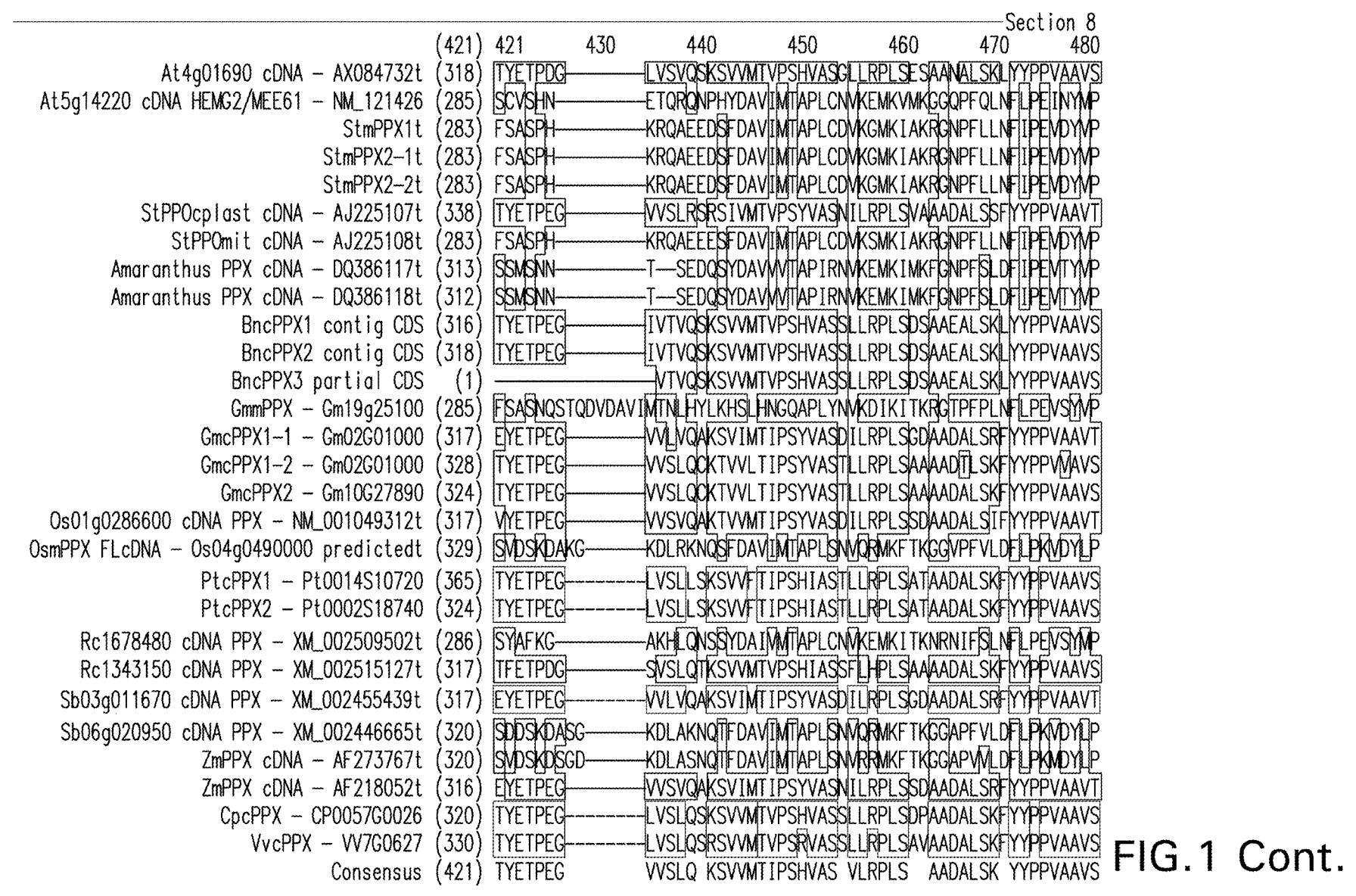
Figure 1:
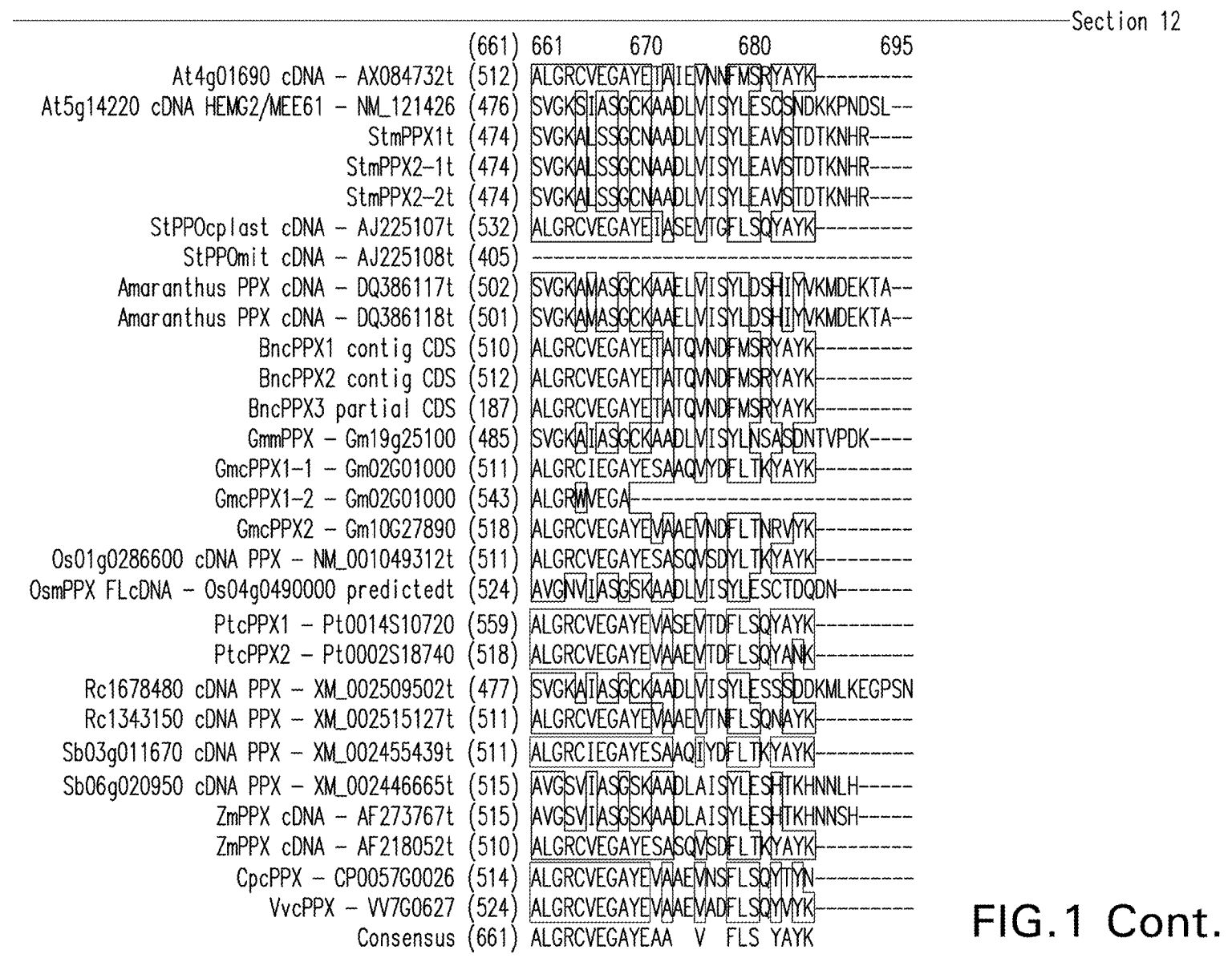

FIG. 1 is an alignment of PPX proteins of various plant species. (SEQ ID NOS: 1, 3, 9, 29, 31, 7, 51, 5, 52, 33, 35, 37, 44, 39, 40, 42, 15, 17, 53, 54, 25, 23, 55, 21, 13, 11, 56, 57 and 58, respectively).

FIG. 2 is a table of homologous amino acid positions in plant PPX amino acid sequences of various species.

FIG. 3 is a table of homologous amino acid positions in plant PPX amino acid sequences of various species.

DETAILED DESCRIPTION OF THE INVENTION

Rapid Trait Development System (RTDS™)

In any of the various aspects and embodiments of the compositions and methods disclosed herein, mutations in genes and proteins may be made using, for example, the Rapid Trait Development System (RTDS™) technology developed by Cibus. In combination or alone, plants containing any of the mutations disclosed herein can form the basis of new herbicide-resistant products. Also provided are seeds produced from the mutated plants in which the PPX genes are either homozygous or heterozygous; for the mutations. The mutations disclosed herein can be in combination with any other mutation known or with mutations discovered in the future.

As used herein, the term "heterozygous" refers to having different alleles at one or more genetic loci in homologous chromosome segments. As used herein "heterozygous" may also refer to a sample, a cell, a cell population or an organism in which different alleles at one or more genetic loci may be detected. Heterozygous samples may also be determined via methods known in the art such as, for example, nucleic acid sequencing. For example, if a sequencing electropherogram shows two peaks at a single locus and both peaks are roughly the same size, the sample may be characterized as heterozygous. Or, if one peak is smaller than another, but is at least about 25% the size of the larger peak, the sample may be characterized as heterozygous. In some embodiments, the smaller peak is at least about 15% of the larger peak. In other embodiments, the smaller peak is at least about 0.10% of the larger peak. In other embodiments, the smaller peak is at least about 5% of the larger peak. In other embodiments, a minimal amount of the smaller peak is detected.

As used herein. "homozygous" refers to having identical alleles at one or more genetic loci in homologous chromosome segments. "Homozygous" may also refer to a sample, a cell, a cell population or an organism in which the same alleles at one or more genetic loci may be detected. Homozygous samples may be determined via methods known in the art, such as, for example, nucleic acid sequencing. For example, if a sequencing electropherogram shows a single peak at a particular locus, the sample may be termed "homozygous" with respect to that locus.

The term "hemizygous" refers to a gene or gene segment being present only once in the genotype of a cell or an organism because the second allele is deleted. As used herein "hemizygous" may also refer to a sample, a cell, a cell population or an organism in which an allele at one or more genetic loci may be detected only once in the genotype.

In some embodiments, RTDS is based on altering a targeted gene by utilizing the cell's own gene repair system to specifically modify the gene sequence in situ and not insert foreign DNA and/or gene expression control sequences. This procedure may effect a precise change in the genetic sequence while the rest of the genome is left unaltered. In contrast to conventional transgenic GMOs, there is no integration of foreign genetic material, nor is any foreign genetic material left in the plant. In many embodiments, the changes in the genetic sequence introduced by RTDS are not randomly inserted. Since affected genes remain in their native location, no random, uncontrolled or adverse pattern of expression occurs.

The RTDS that effects this change is a chemically synthesized oligonucleotide (e.g., using a gene repair oligonucleobase (GRON)) which may be composed of both DNA and modified RNA bases as well as other chemical moieties, and is designed to hybridize at the targeted gene location to create a mismatched base-pair(s). This mismatched base-pair acts as a signal to attract the cell's own natural gene repair system to that site and correct (replace, insert or delete) the designated nucleotide(s) within the gene. Once the correction process is complete the RTDS molecule is degraded and the now-modified or repaired gene is expressed under that gene's normal endogenous control mechanisms.

Gene Repair Oligonucleobases ("GRON")

The methods and compositions disclosed herein can be practiced or made with "gene repair oligonucleobases" for example, having the conformations and chemistries as described in detail below. The "gene repair oligonucleobases" as contemplated herein have also been described in published scientific and patent literature using other names including "recombinogenic oligonucleobases;" "RNA/DNA chimeric oligonucleotides;" "chimeric oligonucleotides;" "mixed duplex oligonucleotides" (MDONs); "RNA DNA oligonucleotides (RDOs);" "gene targeting oligonucleotides;" "genoplasts;" "single stranded modified oligonucleotides;" "Single stranded oligodeoxynucleotide mutational vectors" (SSOMVs); "duplex mutational vectors;" and "heteroduplex mutational vectors."

Oligonucleobases having the conformations and chemistries described in U.S. Pat. No. 5,565,350 by Kmiec (Kmiec I) and U.S. Pat. No. 5,731,181 by Kmiec (Kmiec II), hereby incorporated by reference, are suitable for use as "gene repair oligonucleobases" of the present disclosure. The gene repair oligonucleobases in Kmiec I and/or Kmiec II contain two complementary strands, one of which contains at least one segment of RNA-type nucleotides (an "RNA segment") that are base paired to DNA-type nucleotides of the other strand.

Kmiec II discloses that purine and pyrimidine base-containing non-nucleotides can be substituted for nucleotides. Additional gene repair molecules that can be used for the present disclosure include, but are not limited to, those described in U.S. Pat. Nos. 5,756,325; 5,871,984; 5,760,012; 5,888,983; 5,795,972; 5,780,296; 5,945,339; 6,004,804; and 6,010,907 and in International Patent No. PCT/US00/23457; and in international Patent Publication Nos. WO 98/49350; WO 99/07865; WO 99/58723; WO 99/58702; and WO 99/40789, which are each hereby incorporated in their entirety.

In conjunction with any of the aspects, embodiments, methods and/or compositions disclosed herein, the gene repair oligonucleobase may be a mixed duplex oligonucleotides (MDON) in which the RNA-type nucleotides of the mixed duplex oligonucleotide are made RNase resistant by replacing the 2'-hydroxyl with a fluoro, chloro or bromo functionality or by placing a substituent on the 2'-O. Suitable substituents include the substituents taught by the Kmiec II.

Alternative substituents may include, but are not limited to the substituents taught by U.S. Pat. No. 5,334,711 (Sproat) and the substituents taught by patent publications EP 629 387 and EP 679 657 (collectively, the Martin Applications), which are hereby incorporated by reference. As used herein, a 2'-fluoro, chloro or bromo derivative of a ribonucleotide or a ribonucleotide having a 2'-OH substituted with a substituent described in the Martin Applications or Sproat is termed a "2'-Substituted Ribonucleotide." As used herein the term "RNA-type nucleotide" means a 2'-hydroxyl or 2'-Substituted Nucleotide that is linked to other nucleotides of a mixed duplex oligonucleotide by an unsubstituted phosphodiester linkage or any of the non-natural linkages taught by Kmiec I or Kmiec II. As used herein the term "deoxyribo-type nucleotide" means a nucleotide having a 2'-H, which can be linked to other nucleotides of a gene repair oligonucleobase by an unsubstituted phosphodiester linkage or any of the non-natural linkages taught by Kmiec I or Kmiec II.

In conjunction with any of the aspects, embodiments, methods and/or compositions disclosed herein, the gene repair oligonucleobase may be a mixed duplex oligonucleotides (MDON) that is linked solely by unsubstituted phosphodiester bonds. In alternative embodiments, the linkage is by substituted phosphodiesters, phosphodiester derivatives and non-phosphorus-based linkages as taught by Kmiec II. In yet another embodiment, each RNA-type nucleotide in the mixed duplex oligonucleotide is a 2'-Substituted Nucleotide. Particular preferred embodiments of 2'-Substituted Ribonucleotides include, but are not limited to, 2'-fluoro, 2'-methoxy, 2'-propyloxy, 2'-allyloxy, 2'-hydroxylethyloxy, 2'-methoxyethyloxy, 2'-fluoropropyloxy and 2'-trifluoropopyloxy substituted ribonucleotides. More preferred embodiments of 2'-Substituted Ribonucleotides are 2'-fluoro, 2'-methoxy, 2'-methoxyethyloxy, and 2-allyloxy substituted nucleotides. In another embodiment the mixed duplex oligonucleotide is linked by unsubstituted phosphodiester bonds.

Although mixed duplex oligonucleotides (MDONs) having only a single type of 2% substituted RNA-type nucleotide are more conveniently synthesized, the methods of the invention can also be practiced with mixed duplex oligonucleotides having two or more types of RNA-type nucleotides. The function of an RNA segment may not be affected by an interruption caused by the introduction of a deoxynucleotide between two RNA-type trinucleotides, accordingly, the term RNA segment encompasses terms such as "interrupted RNA segment." An uninterrupted RNA segment is termed a contiguous RNA segment. In an alternative embodiment an RNA segment can contain alternating RNase-resistant and unsubstituted 2'-OH nucleotides. The mixed duplex oligonucleotides preferably have fewer than 100 nucleotides and more preferably fewer than 85 nucleotides, but more than 50 nucleotides. The first and second strands are Watson-Crick base paired. In one embodiment the strands of the mixed duplex oligonucleotide are covalently bonded by a linker, such as a single stranded hexa, penta or tetranucleotide so that the first and second strands are segments of a single oligonucleotide chain having a single 3' and a single 5' end. The 3' and 5' ends can be protected by the addition of a "hairpin cap" whereby the 3' and 5' terminal nucleotides are Watson-Crick paired to adjacent nucleotides. A second hairpin cap can, additionally, be placed at the junction between the first and second strands distant from the 3' and 5' ends, so that the Watson-Crick pairing between the first and second strands is stabilized.

The first and second strands contain two regions that are homologous with two fragments of the target gene, i.e., have the same sequence as the target gene. A homologous region contains the nucleotides of an RNA segment and may contain one or more DNA-type nucleotides of connecting DNA segment and may also contain DNA-type nucleotides that are not within the intervening DNA segment. The two regions of homology are separated by, and each is adjacent to, a region having a sequence that differs from the sequence of the target gene, termed a "heterologous region." The heterologous region can contain one, two or three mismatched nucleotides. The mismatched nucleotides can be contiguous or alternatively can be separated by one or two nucleotides that are homologous with the target gene. Alternatively, the heterologous region can also contain an insertion or one, two, three or of five or fewer nucleotides. Alternatively, the sequence of the mixed duplex oligonucleotide may differ from the sequence of the target gene only by the deletion of one, two, three, or five or fewer nucleotides from the mixed duplex oligonucleotide. The length and position of the heterologous region is, in this case, deemed to be the length of the deletion, even though no nucleotides of the mixed duplex oligonucleotide are within the heterologous region. The distance between the fragments of the target gene that are complementary to the two homologous regions is identical to the length of the heterologous region where a substitution or substitutions is intended. When the heterologous region contains an insertion, the homologous regions are thereby separated in the mixed duplex oligonucleotide farther than their complementary homologous fragments are in the gene, and the converse is applicable when the heterologous region encodes a deletion.

The RNA segments of the mixed duplex oligonucleotides are each a part of a homologous region. i.e., a region that is identical in sequence to a fragment of the target gene, which segments together preferably contain at least 13 RNA-type nucleotides and preferably from 16 to 25 RNA-type nucleotides or yet more preferably 18-22 RNA-type nucleotides or most preferably 20 nucleotides. In one embodiment. RNA segments of the homology regions are separated by and adjacent to, i.e., "connected by" an intervening DNA segment. In one embodiment, each nucleotide of the heterologous region is a nucleotide of the intervening DNA segment. An intervening DNA segment that contains the heterologous region of a mixed duplex oligonucleotide is termed a "mutator segment."

In conjunction with any of the aspects, embodiments, methods and/or compositions disclosed herein, the gene repair oligonucleobase (GRON) may be a single stranded oligodeoxynucleotide mutational vector (SSOMV), for example, such as disclosed in International Patent Application PCT/US0023457. U.S. Pat. Nos. 6,271,360, 6,479,292, and 7,060,500 which are incorporated by reference in their entirety. The sequence of the SSOMV is based on the same principles as the mutational vectors described for example in U.S. Pat. Nos. 5,756,325; 5,871,984; 5,760,012; 5,888,983; 5,795,972; 5,780,296; 5,945,339; 6,004,804; and 6,010,907 and in International Publication Nos. WO 98/49350; WO 99/07865; WO 99/58723; WO 99/58702; and WO 99/40789. The sequence of the SSOMV contains two regions that are homologous with the target sequence separated by a region that contains the desired genetic alteration termed the mutator region. The mutator region can have a sequence that is the same length as the sequence that separates the homologous regions in the target sequence, but having a different sequence. Such a mutator region can cause a substitution. A Iteratively, the homologous regions in the SSOMV can be contiguous to each other, while the regions in the target gene having the same sequence are separated by one, two or more nucleotides. Such an SSOMV causes a deletion from the target gene of the nucleotides that are absent from the SSOMV. Lastly, the sequence of the target gene that is identical to the homologous regions may be adjacent in the target gene but separated by one, two, or more nucleotides in the sequence of the SSOMV. Such an SSOMV causes an insertion in the sequence of the target gene.

The nucleotides of the SSOMV are dcoxyribonucleotides that are linked by unmodified phosphodiester bonds except that the 3' terminal and/or 5' terminal internucleotide linkage or alternatively the two 3' terminal and/or 5' terminal internucleotide linkages can be a phosphorothioate or phosphoamidate. As used herein an internucleotide linkage is the linkage between nucleotides of the SSOMV and does not include the linkage between the 3' end nucleotide or 5' end nucleotide and a blocking substituent. In a specific embodiment the length of the SSOMV is between 21 and 55 deoxynucleotides and the lengths of the homology regions are, accordingly, a total length of at least 20 deoxynucleotides and at least two homology regions should each have lengths of at least 8 deoxynucleotides.

The SSOMV can be designed to be complementary to either the coding or the non-coding strand of the target gene. When the desired mutation is a substitution of a single base, it is preferred that both the mutator nucleotide and the targeted nucleotide be a pyrimidine. To the extent that is consistent with achieving the desired functional result, it is preferred that both the mutator nucleotide and the targeted nucleotide in the complementary strand be pyrimidines. Particularly preferred are SSOMVs that encode transversion mutations, i.e., a C or T mutator nucleotide is mismatched, respectively, with a C or T nucleotide in the complementary strand.

In addition to the oligodeoxynucleotide, the SSOMV can contain a 5' blocking substituent that is attached to the 5' terminal carbons through a linker. The chemistry of the linker is not critical other than its length, which should preferably be at least 6 atoms long and that the linker should be flexible. A variety of non-toxic substituents such as biotin, cholesterol or other steroids or a non-intercalating cationic fluorescent dye can be used. Particularly preferred reagents to make SSOMVs are the reagents sold as Cy3™ and Cy5™ by Glen Research. Sterling Va. (now GE Healthcare), which are blocked phosphoroamidites that upon incorporation into an oligonucleotide yield 3,3,3',3'-tetramethyl N,N'-isopropyl substituted indomonocarbocyanine and indodicarbocyanine dyes, respectively, Cy3 is particularly preferred. When the indocarbocyanine is N-oxyalkyl substituted it can be conveniently linked to the 5' terminal of the oligodeoxynucleotide as a phosphodiester with a 5' terminal phosphate. The chemistry of the dye linker between the dye and the oligodeoxynucleotide is not critical and is chosen for synthetic convenience. When the commercially available Cy3 phosphoramidite is used as directed, the resulting 5' modification consists of a blocking substituent and linker together which are a N-hydroxypropyl, N'-phosphatidylpropyl 3,3,3',3'-tetramethyl indomonocarbocyanine.

In a preferred embodiment the indocarbocyanine dye is tetra substituted at the 3 and 3' positions of the indole rings. Without limitations as to theory these substitutions prevent the dye from being an intercalating dye. The identity of the substituents at these positions is not critical. The SSOMV can in addition have a 3' blocking substituent. Again the chemistry of the 3' blocking substitute is not critical.

The mutations herein described might also be obtained by mutagenesis (random, somatic or directed) and any other DNA editing or recombination technologies including, but not limited to, gene targeting using site-specific homologous recombination by zinc finger nucleases.

Delivery of Gene Repair Oligonucleobases into Plant Cells

Any commonly known method used to transform a plant cell can be used for delivering the gene repair oligonucleobases. Illustrative methods are described below.

Microcarriers and Microfibers

The use of metallic microcarriers (microspheres) for introducing large fragments of DNA into plant cells having cellulose cell walls by projectile penetration is well known to those skilled in the relevant art (henceforth biolistic delivery), U.S. Pat. Nos. 4,945,050; 5,100,792 and 5,204,253 describe general techniques for selecting microcarriers and devices for projecting them.

Specific conditions for using microcarriers in the methods disclosed herein are described in International Publication WO 99/07865. In an illustrative technique, ice cold microcarriers (60 mg/mL), mixed duplex oligonucleotide (60 mg/mL) 2.5 M CaCl$_2$ and 0.1 M spermidine are added in that order; the mixture gently agitated, e.g., by vortexing, for 10 minutes and then left at room temperature for 10 minutes, whereupon the microcarriers are diluted in 5 volumes of ethanol, centrifuged and resuspended in 100% ethanol. Good results can be obtained with a concentration in the adhering solution of 8-10 µg/µL microcarriers, 14-17 µg/mL mixed duplex oligonucleotide, 1.1-1.4 M CaCl$_2$ and 18-22 mM spermidine. Optimal results were observed under the conditions of 8 µg/µL microcarriers, 16.5 µg/mL mixed duplex oligonucleotide, 1.3 M CaCl$_2$ and 21 mM spermidine.

Gene repair oligonucleobases can also be introduced into plant cells for the practice of the present disclosure using microfibers to penetrate the cell wall and cell membrane. U.S. Pat. No. 5,302,523 to Coffee et al. describes the use of 30.times.0.5 µm and 10.times.0.3 µm silicon carbide fibers to facilitate transformation of suspension maize cultures of Black Mexican Sweet. Any technical technique that can be used to introduce, DNA for transformation of a plant cell using microfibers can be used to deliver gene repair oligonucleobases for transmutation.

An illustrative technique for microfiber delivery of a gene repair oligonucleobase is as follows: Sterile microfibers (2 µg) are suspended in 150 µL of plant culture medium containing about 10 µg of a mixed duplex oligonucleotide. A suspension culture is allowed to settle and equal volumes of packed cells and the sterile fiber/nucleotide suspension are vortexed for 10 minutes and plated. Selective media are applied immediately or with a delay of up to about 120 h as is appropriate for the particular trait.

Protoplast Electroporation

In an alternative embodiment, the gene repair oligonucleobases can be delivered to the plant cell by electroporation of a protoplast derived from a plant part. The protoplasts are formed by enzymatic treatment of a plant part, particularly a leaf, according to techniques well known to those skilled in the art. See. e.g., Gallois et al., 1996, in Methods in Molecular Biology 55:89-107, Humana Press. Totowa, N.J.; Kipp et al., 1099, in Methods in Molecular Biology 133: 213-221, Humana Press, Totowa, N.J. The protoplasts need not be cultured in growth media prior to electroporation, illustrative conditions for electroporation are 3.times.10.sup.5 protoplasts in a total volume of 0.3 mL with a concentration of gene repair oligonucleobase of between 0.6-4 µg/mL.

Protoplast PEG-Mediated DNA Uptake

In an alternative embodiment, nucleic acids are taken up by plant protoplasts in the presence of the membrane-modifying agent polyethylene glycol, according to techniques well known to those skilled in the art (see, e.g., Gharti-Chhetri et al., 1992: Datta et al., 1992).

Microinjection

In an alternative embodiment, the gene repair oligonucleobases can be delivered by injecting it with a microcapillary into plant cells or into protoplasts (see, e.g., Miki et al., 1989; Schnorf et al., 1991).

Transgenics

Figure 2:
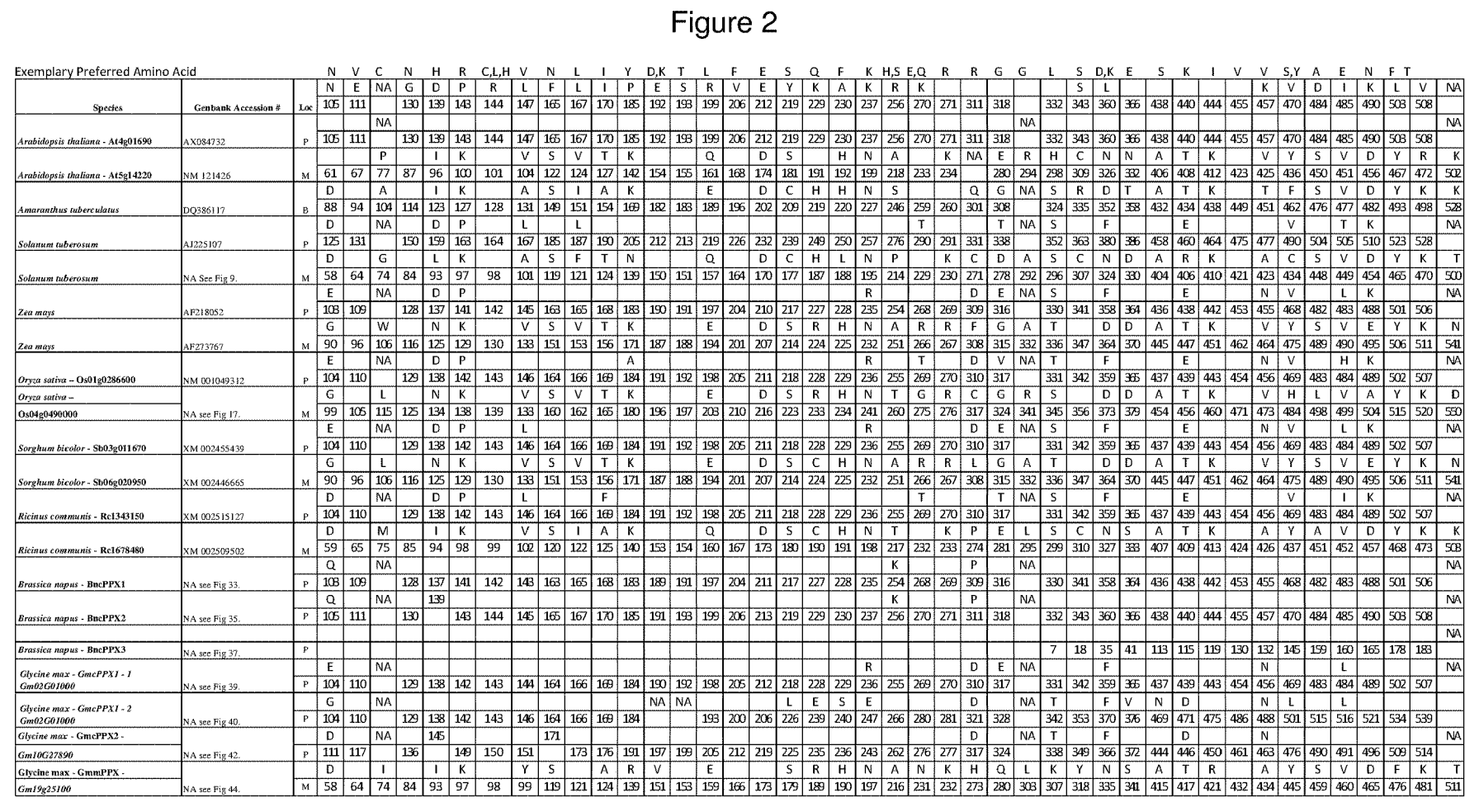

In any of the various aspects and embodiments of the compositions and methods disclosed herein, mutations in genes and proteins may be made using, for example, transgenic technology. In some embodiments, the compositions and methods include a plant or plant cell having a transformed nucleic acid construct including a promoter operably linked to a PPX nucleotide disclosed herein. The methods disclosed herein may include introducing a PPX nucleic acid construct disclosed herein into at least one plant cell and regenerating a transformed plant therefrom. The nucleic acid construct comprises at least one nucleotide that encodes a herbicide-resistant PPX protein as disclosed herein, particularly the nucleotide sequences of set forth in FIG. 2 and fragments and variants thereof. The methods further involve the use of a promoter that is capable of driving gene expression in a plant cell. In one embodiment, such a promoter is a constitutive promoter or a tissue-preferred promoter. A plant produced by these methods may have increased PPX activity, and/or particularly herbicide-tolerant PPX activity, when compared to an untransformed plant. Thus, the methods find use in enhancing or increasing the resistance of a plant to at least one herbicide that increases the activity of the PPX enzyme, particularly in the presence of a PPX-inhibiting herbicide.

In conjunction with any of the aspects, embodiments, methods and/or compositions disclosed herein, the methods for producing a herbicide-resistant plant may include transforming a plant cell with a nucleic acid construct comprising a nucleotide sequence operably linked to a promoter that drives expression in a plant cell and regenerating a transformed plant from said transformed plant cell. The nucleotide sequence is selected from those nucleotide sequences that encode the herbicide-resistant PPX disclosed herein, particularly the nucleotide sequences set forth in FIG. 2 and fragments and variants thereof. A herbicide-resistant plant produced by this method comprises enhanced resistance, compared to an untransformed plant, to at least one herbicide, particularly a herbicide that interferes with the activity of the PPX enzyme such as, for example, a PPX-inhibiting herbicide.

The disclosed nucleic acid molecules can be used in nucleic acid constructs for the transformation of plants, for example, crop plants, such as *Solanum tuberosum*. In one embodiment, such nucleic acid constructs containing the nucleic acid molecules of the present disclosure can be used to produce transgenic plants to provide for resistance to herbicides, such as herbicides that are known to inhibit PPX activity, such as PPX-inhibiting herbicides. The nucleic acid constructs can be used in expression cassettes, expression vectors, transformation vectors, plasmids and the like. The transgenic plants obtained following transformation with such constructs demonstrate increased resistance to PPX-inhibiting herbicides such as, for example, flumioxazin and sulfentrazone herbicides, Constructs The nucleic acid molecules disclosed herein (e.g., mutated PPX genes) can be used in the production of recombinant nucleic acid constructs. In one embodiment, the nucleic acid molecules of the present disclosure can be used in the preparation of nucleic acid constructs, for example, expression cassettes for expression in the plant of interest.

Expression cassettes may include regulatory sequences operably linked to the PPX nucleic acid sequences disclosed herein. The cassette may additionally contain at least one additional gene to be co-transformed into the organism. Alternatively, the additional gene(s) can be provided on multiple expression cassettes.

The nucleic acid constructs may be provided with a plurality of restriction sites for insertion of the PPX nucleic acid sequence to be under the transcriptional regulation of the regulatory regions. The nucleic acid constructs may additionally contain nucleic acid molecules encoding for selectable marker genes.

Any promoter can be used in the production of the nucleic acid constructs. The promoter may be native or analogous, or foreign or heterologous, to the plant host and/or to the PPX nucleic acid sequences disclosed herein. Additionally, the promoter may be the natural sequence or alternatively a synthetic sequence. Where the promoter is "foreign" or "heterologous" to the plant host, it is intended that the promoter is not found in the native plant into which the promoter is introduced. Where the promoter is "foreign" or "heterologous" to the PPX nucleic acid sequences disclosed herein, it is intended that the promoter is not the native or naturally occurring promoter for the operably linked PPX nucleic acid sequences disclosed herein. As used herein, a chimeric gene comprises a coding sequence operably linked to a transcription initiation region that is heterologous to the coding sequence.

In conjunction with any of the aspects, embodiments, methods and/or compositions disclosed herein, the PPX nucleic acid sequences disclosed herein may be expressed using heterologous promoters, the native promoter sequences may be used in the preparation of the constructs. Such constructs would change expression levels of the PPX protein in the plant or plant cell. Thus, the phenotype of the plant or plant cell is altered.

Any promoter can be used in the preparation of constructs to control the expression of the PPX coding sequence, such as promoters providing for constitutive, tissue-preferred, inducible, or other promoters for expression in plants. Constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) Nature 313:810-812); rice actin (McElroy et al. (1990) Plant Cell 2:163-171); ubiquitin (Christensen et al. (1989) Plant Mol. Biol. 12:619-632 and Christensen et al. (0992) Plant Mol. Biol. 18:675-689); pEMU (Last et al. (1991) Theor, Appl. Genet. 81:581-588); MAS Nelten et al. (1984) EMBO J. 3:2723-2730). ALS promoter (U.S. Pat. No. 5,659,026), and the like. Other constitutive promoters include, for example, U.S. Pat. Nos. 5,608,149; 5,608,144; 5,604,121; 5,569,597; 5,466,785; 5,399,680; 5,268,463; 5,608,142; and 6,177,611.

Tissue-preferred promoters can be utilized to direct PPX expression within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) Plant J. 12(2):255-265; Kawamata et al. (1997) Plant Cell Physiol. 38(7):792-803; Hansen et al. (1997) Mol. Gen Genet. 254

(3):337-343; Russell et al. (1997) Transgenic Res. 6(2):157-168. Rinchart et al. (1996) Plant Physiol. 1 12(3):1331-1341; Van Camp et al. (1996) Plant Physiol. 1 12(2):525-535; Canevascini et al. (1996) Plant Physiol. 112(2): 513-524; Yamamoto et al. (1994) Plant Cell Physiol. 35(5):773-778; Lam (1994) Results Probl. Cell Differ. 20:181-196; Orozco et al. (1993) Plant Mot Biol. 23(6):1129-1138: Matsuoka et al. (1993) Proc Natl. Acad. Sci. USA 90(20): 9586-9590; and Guevara-Garcia et al. (1993) Plant J. 4(3): 495-505.

The nucleic acid constructs may also include transcription termination regions. Where transcription terminations regions are used, any termination region may be used in the preparation of the nucleic acid constructs. For example, the termination region may be native to the transcriptional initiation region, may be native to the operably linked PPX sequence of interest, may be native to the plant host, or may be derived from another source (i.e., foreign or heterologous to the promoter, the PPX nucleic acid molecule of interest, the plant host, or any combination thereof). Examples of termination regions that are available for use in the constructs of the present disclosure include those from the Ti-plasmid of *A. tumefaciens*, such as the octopine synthase and nopaline synthase termination regions. See also Guerineau et al. (1991) Mol. Gen. Genet. 262:141-144; Proudfoot (1991) Cell 64:671674; Sanfacon et al., (1991) Genes Dev. 5:141-149; Mogen et al. (1990) Plant Cell 2:1261-1272; Munroe et al. (1990) Gene 91:151-158; Ballas et al. (1989) Nucleic Acids Res. 17:7891-7903; and Joshi et al. (1987) Nucleic Acid Res. 15:9627-9639.

In conjunction with any of the aspects, embodiments, methods and/or compositions disclosed herein, the nucleic acids may be optimized for increased expression in the transformed plant. That is, the nucleic acids encoding the mutant PPX proteins can be synthesized using plant-preferred codons for improved expression. Sec., for example, Campbell and Gowri (1990) Plant Physiol. 92:1-11 for a discussion of host-preferred codon usage. Methods are available in the art for synthesizing plant-preferred genes. See, for example, U.S. Pat. Nos. 5,380,831, and 5,436,391, and Murray et al. (1989) Nucleic Acids Res. 17:477-498.

In addition, other sequence modifications can be made to the nucleic acid sequences disclosed herein. For example, additional sequence modifications are known to enhance gene expression in a cellular ho-4. These include elimination of sequences encoding spurious polyadenylation signals, exon/intron splice site signals, transposon-like repeats, and other such well-characterized sequences that may be deleterious to gene expression. The G-C content of the sequence may also be adjusted to levels average for a target cellular host, as calculated by reference to known genes expressed in the host cell. In addition, the sequence can be modified to avoid predicted hairpin secondary mRNA structures.

Other nucleic acid sequences may also be used in the preparation of the constructs of the present disclosure, for example to enhance the expression of the PPX coding sequence. Such nucleic acid sequences include the introns of the maize AdhI, intron1 gene (Callis et al. (1987) Goes and Development 1:1 183-1200), and leader sequences, (W-sequence) from the Tobacco Mosaic virus (TMV). Maize Chlorotic Mottle Virus and Alfalfa Mosaic Virus (Gallie et al. (1987) Nucleic Acid Res. 15:8693-8711, and Skuzeski et al. (1990) Plant Mol. Biol. 15:65-79, 1990). The first intron from the shrunken-1 locus of maize has been shown to increase expression of genes in chimeric gene constructs. U.S. Pat. Nos. 5,424,412 and 5,593,874 disclose the use of specific introns in gene expression constructs, and Gallie et al. ((1994) Plant Physiol. 106:929-939) also have shown that introns are useful for regulating gene expression on a tissue specific basis. To further enhance or to optimize PPX gene expression, the plant expression vectors disclosed herein may also contain DNA sequences containing matrix attachment regions (MARs). Plant cell transformed with such modified expression systems, then, may exhibit overexpression or constitutive expression of a nucleotide sequence of the disclosure.

The expression constructs disclosed herein can also include nucleic acid sequences capable of directing the expression of the PPX sequence to the chloroplast. Such nucleic acid sequences include chloroplast targeting sequences that encodes a chloroplast transit peptide to direct the gene product of interest to plant cell chloroplasts. Such transit peptides are known in the art. With respect to chloroplast-targeting sequences. "operably linked" means that the nucleic acid sequence encoding a transit peptide (i.e., the chloroplast-targeting sequence) is linked to the PPX nucleic acid molecules disclosed herein such that the two sequences are contiguous and in the same reading frame. See, for example, Von Heijne et al. (1991) Plant Mol. Biol. Rep 9:104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196:1414-1421; and Shah et al. (1986) Science 233:478-481. While the PPX proteins disclosed herein may include a native chloroplast transit peptide, any chloroplast transit peptide known in the art can be fused to the amino acid sequence of a mature PPX protein by operably linking a chloroplast-targeting sequence to the 5'-end of a nucleotide sequence encoding a mature PPX protein.

Chloroplast targeting sequences are known in the art and include the chloroplast small subunit of ribulose-1,5-bisphosphate carboxylase (Rubisco) (de Castro Silva Filho et al. (1996) Plant Mol. Biol. 30:769-780; Schnell et al. (1991) J. Biol. Chem. 266(5):3335-3342); 5-(enolpyruvyl)shikimate-3-phosphate synthase (EPSPS) t Archer et al (1990) J. Bioenerg. Biomemb. 22(6):789-810); tryptophan synthase (Zhao et al. (1995) J. Biol. Chem. 270(1 i):6081-6087); plastocyanin (Lawrence et al. (1997) J. Biol. Chem. 272 (33):20357-20363); chorismate synthase (Schmidt et al. (1993) J. Biol. Chem. 268(36):27447-27457); and the light harvesting chlorophyll a/b binding protein (LHBP) (Lamppa et al, (1988) J. Biol. Chem. 263:14996-14999). See also Von Heijne et al. (1091) Plant Mol. Biol. Rep. 9:104-126; Clark et al. (1989) J. Biol. Chem. 264:17544-17550; Della-Cioppa et al. (1987) Plant Physiol. 84:965-968; Romer et al. (1993) Biochem. Biophys. Res. Commun. 196:1414-1421; and Shah et al. (1986) Science 233:478-481.

In conjunction with any of the aspects, embodiments, methods and/or compositions disclosed herein, the nucleic acid constructs may be prepared to direct the expression of the mutant PPX coding sequence from the plant cell chloroplast. Methods for transformation of chloroplasts are known in the art. See, for example, Svab et al. (1990) Proc. Natl. Acad. Sci. USA 87:8526-8530; Svab and Maliga (1993) Proc. Natl. Acad. Sci. USA 90:913-917; Svab and Maliga (1993) EMBO J. 12:601-606. The method relics on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305.

The nucleic acids of interest to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

The nucleic acid constructs can be used to transform plant cells and regenerate transgenic plants comprising the mutant PPX coding sequences. Numerous plant transformation vectors and methods for transforming plants are available. See, for example, U.S. Pat. No. 6,753,458, An, G. et al. (1986) Plant Physiol., 81:301-305; Fry, J. et al. (1987) Plant Cell Rep. 6:321-325; Block, M. (1988) Theor. Appl Genet. 76:767-774; Hinchee et al. (1990) Stadler. Genet. Symp. 203212.203-212; Cousins et alt (1991) Aust. J. Plant Physiol. 18:481-494; Chee, P. P, and Slightom, J. L. (1992) Gene. 118:255-260; Christou et al. (1992) Trends. Biotechnol. 10:239-246; D'Halluin et al. (1992) Bio/Technol. 10:309-3 14; Dhir et al., (1992) Plant Physiol. 99:81-88; Casas et al. (1993) Proc. Nat Acad Sci. USA 90:11212-11216; Christou, P. (1993) In Vitro Cell. Dev. Biol.-Plant; 29P:1 19-124; Davies, et al. (1993) Plant Cell Rep. 12:180-183; Dong, J. A, and Mc Hughen, A. (1993) Plant Sci. 91:139-148; Franklin, C. L, and Trieu. T, N. (1993) Plant. Physiol. 102:167; Golovkin et al. (1993) Plant Sci. 90:41-52; Guo Chin Sci. Bull. 38:2072-2078; Asano, et al. (1994) Plant Cell Rep. 13; Ayeres N. M. and Park, W. D. (1994) Crit. Rev. Plant. Sci. 13:219-239: Barcelo et al. (1994) Plant. J. 5:583-592; Becker, et al. (1994) Plant, J. 5:299-307; Borkowska et al. (1994) Acta. Physiol Plant. 16:225-230; Christou, P. (1994) Agro. Food. Ind. Hi Tech. 5:17-27; Eapen et al. (1994) Plant Cell Rep. 13:582-586; Hartman et al. (1994) Bio-Technology 12: 919923; Ritala et al. (1994) Plant. Mol. Biol. 24:317-325; and Wan, Y. C, and Lemaux, P. G. (1994) Plant Physiol. 104:3748. The constructs may also be transformed into plant cells using homologous recombination.

The disclosed constructs comprising the PPX nucleic acid sequences disclosed herein can be used in various methods to produce transgenic host cells, such as bacteria, yeast, and to transform plant cells and in some cases regenerate transgenic plants. For example, methods of producing a transgenic crop plant containing the PPX mutant proteins disclosed herein, where expression of the nucleic acid(s) in the plant results in herbicide tolerance as compared to wild-type plants or to known PPX mutant type plants comprising: (a) introducing into a plant cell an expression vector comprising nucleic acid encoding a mutant PPX protein, and (b) generating from the plant cell a transgenic plant which is herbicide tolerant.

PPX Mutations

The compositions and methods may relate at least in part to mutations in a PPX gene, for example mutations that render a plant resistant or tolerant to a herbicide of the PPX-inhibiting family of herbicides. The compositions and methods also in certain embodiments relate to the use of a gene repair oligonucleobase to make a desired mutation in the chromosomal or episomal sequences of a plant in the gene encoding for a PPX protein. The mutated protein, which may in some embodiments substantially maintain the catalytic activity of the wild-type protein, allowing for increased resistance or tolerance of the plant to a herbicide of the PPX-inhibiting family, and thus in some embodiments allowing for substantially normal growth or development of the plant, its organs, tissues, or cells as compared to the wild-type plant irrespective of the presence or absence of the herbicide. The compositions and methods also relate to a non-transgenic or transgenic plant cell in which a PPX gene has been mutated, a non-transgenic plant or transgenic regenerated therefrom, as well as a plant resulting from a cross using a regenerated non-transgenic or transgenic plant to a plant having a mutation in a different PPX gene, for example. These mutations may also be applied to target tolerance to these inhibitors in plants including crop plants, algae, bacteria, fingi and mammalian systems.

In conjunction with any of the aspects, embodiments, methods and/or compositions disclosed herein, at least one mutation of a mutated PPX protein may be at the amino acid position corresponding to a position selected from the group consisting of 52, 85, 105, 111, 130, 139, 143, 144, 145, 147, 165, 167, 170, 180, 185, 192, 193, 199, 206, 212, 219, 220, 221, 226, 228, 229, 230, 237, 244, 256, 257, 270, 271, 272, 305, 311, 316, 318, 332, 343, 354, 357, 359, 360, 366, 393, 403, 424, 426, 430, 438, 440, 444, 455, 457, 470, 478, 483, 484, 485, 487, 490, 503, 508, and 525 of SEQ ID NO: 1. In some embodiments, a mutated PPX protein includes a mutation at one or more amino acid positions corresponding to a position selected from the group consisting of 58, 64, 74, 84, 93, 97, 98, 101, 119, 121, 124, 139, 150 151, 157, 164, 170, 177, 187, 188, 195, 214, 215, 229, 230, 271, 274, 278, 283, 292, 296, 307, 324, 330, 396, 404, 406, 410, 421, 423, 434, 447, 448, 449, 451, 454, 465, 470 and 50 of SEQ ID NO: 9. In some embodiments, a mutated PPX protein includes a mutation at the amino acid position corresponding to position 52 of SEQ ID NO: 1. In some embodiments, a mutated PPX protein includes a mutation at the amino acid position corresponding to position 85 of SEQ ID NO: 1. In some embodiments, a mutated PPX protein includes a mutation at the amino acid position corresponding to position 111 of SEQ ID NO. 1. In some embodiments, a mutated PPX protein includes a mutation at the amino acid position corresponding to position 130 of SEQ ID NO: 1. In some embodiments, a mutated PPX protein includes a mutation at the amino acid position corresponding to position 139 of SEQ ID NO: 1. In some embodiments, a mutated PPX protein includes a mutation at the amino acid position corresponding to position 143 of SEQ ID NO: 1. In some embodiments, a mutated PPX protein includes a mutation at the amino acid position corresponding to position 144 of SEQ ID NO: 1. In some embodiments, a mutated PPX protein includes a mutation at the amino acid position corresponding to position 145 of SEQ ID NO: 1. In some embodiments, a mutated PPX protein includes a mutation at the amino acid position corresponding to position 147 of SEQ ID NO: 1. In some embodiments, a mutated PPX protein includes a mutation at the amino acid position corresponding to position 165 of SEQ ID NO: 1. In some embodiments, a mutated PPX protein includes a mutation at the amino acid position corresponding to position 180 of SEQ ID NO: 1. In some embodiments, a mutated PPX protein includes a mutation at the amino acid position corresponding to position 185 of SEQ ID NO: 1. In some embodiments, a mutated PPX protein includes a mutation at the amino acid position corresponding to position 192 of SEQ ID NO: 1. In some embodiments, a mutated PPX protein includes a mutation at the amino acid position corresponding to position 193 of SEQ ID NO: 1. In some embodiments, a mutated PPX protein includes a mutation at the amino acid position corresponding to position 199 of SEQ ID NO: 1. In some embodiments, a mutated PPX protein includes a mutation at the amino acid position corresponding to position 206 of SEQ ID NO: 1. In some embodiments, a mutated PPX protein includes a mutation at the amino acid position corresponding to position 219 of SEQ ID NO: 1. In some embodiments, a mutated PPX protein includes a mutation at the amino acid position corresponding to position 220 of SEQ ID NO: 1. In some embodiments, a mutated PPX protein includes a mutation at the amino acid position corresponding to position 226 of SEQ ID NO: 1. In some embodiments, a mutated PPX protein includes a mutation at the amino acid position corresponding to position 228 of SEQ ID NO: 1. In some embodiments, a mutated PPX protein includes a mutation at the amino acid position corresponding to position 229 of SEQ ID NO: 1. In some embodiments, a mutated PPX protein includes a mutation at the amino acid position corresponding to position 230 of SEQ ID NO: 1. In some embodiments, a mutated PPX protein includes a mutation at the amino acid position corresponding to position 244 of SEQ ID NO: 1. In some embodiments, a mutated PPX protein includes a mutation at the amino acid position corresponding to position 256 of SEQ ID NO: 1. In some embodiments, a mutated PPX protein includes a mutation at the amino acid position corresponding to position 270 of SEQ ID NO: 1. In some embodiments, a mutated PPX protein includes a mutation at the amino acid position corresponding to position 271 of SEQ ID NO: 1. In some embodiments, a mutated PPX protein includes a mutation at the amino acid position corresponding to position 272 of SEQ ID NO: 1. In some embodiments, a mutated PPX protein includes a mutation at the amino acid position corresponding to position 305 of SEQ ID NO: 1. In some embodiments, a mutated PPX protein includes a mutation at the amino acid position corresponding to position 311 of SEQ ID NO: 1. In some embodiments, a mutated PPX protein includes a mutation at the amino acid position corresponding to position 316 of SEQ ID NO: 1. In some embodiments, a mutated PPX protein includes a mutation at the amino acid position corresponding to position 318 of SEQ ID NO: 1. In some embodiments, a mutated PPX protein includes a mutation at the amino acid position corresponding to position 332 of SEQ ID NO: 1. In some embodiments, a mutated PPX protein includes a mutation at the amino acid position corresponding to position 357 of SEQ ID NO: 1. In some embodiments, a mutated PPX protein includes a mutation at the amino acid position corresponding to position 359 of SEQ ID NO: 1. In some embodiments, a mutated PPX protein includes a mutation at the amino acid position corresponding to position 360 of SEQ ID NO: 1. In some embodiments, a mutated PPX protein includes a mutation at the amino acid position corresponding to position 366 of SEQ ID NO: 1. In some embodiments, a mutated. PPX protein includes a mutation at the amino acid position corresponding to position 393 of SEQ ID NO: 1. In some embodiments, a mutated PPX protein includes a mutation at the amino acid position corresponding to position 403 of SEQ ID NO: 1. In some embodiments, a mutated PPX protein includes a mutation at the amino acid position corresponding to position 424 of SEQ ID NO: 1. In some embodiments, a mutated PPX protein includes a mutation at the amino acid position corresponding to position 426 of SEQ ID NO: 1. In some embodiments, a mutated PPX protein includes a mutation at the amino acid position corresponding to position 438 of SEQ ID NO: 1. In some embodiments, a mutated PPX protein includes a mutation at the amino acid position corresponding to position 440 of SEQ ID NO: 1. In some embodiments, a mutated PPX protein includes a mutation at the amino acid position corresponding to position 444 of SEQ ID NO: 1. In some embodiments, a mutated PPX protein includes a mutation at the amino acid position corresponding to position 455 of SEQ ID NO: 1. In some embodiments, a mutated PPX protein includes a mutation at the amino acid position corresponding to position 457 of SEQ ID NO: 1. In some embodiments, a mutated PPX protein includes a mutation at the amino acid position corresponding to position 470 of SEQ ID NO: 1. In some embodiments, a mutated PPX protein includes a mutation at the amino acid position corresponding to position 478 of SEQ ID NO: 1. In some embodiments, a mutated PPX protein includes a mutation at the amino acid position corresponding to position a phenylalanino to glycine at a position corresponding to position 483 of SEQ ID NO: 1. In some embodiments, a mutated PPX protein includes a mutation at the amino acid position corresponding to position 484 of SEQ ID NO: 1. In some embodiments, a mutated PPX protein includes a mutation at the amino acid position corresponding to position 485 of SEQ ID NO: 1. In some embodiments, a mutated PPX protein includes a mutation at the amino acid position corresponding to position 487 of SEQ ID NO: 1. In some embodiments, a mutated PPX protein includes a mutation at the amino acid position corresponding to position 490 of SEQ ID NO L. In some embodiments, a mutated PPX protein includes a mutation at the amino acid position corresponding to position 503 of SEQ ID NO: 1. In some embodiments, a mutated PPX protein includes a mutation at the amino acid position corresponding to position 508 of SEQ ID NO: 1. In some embodiments, a mutated PPX protein includes a mutation at the amino acid position corresponding to position 525 of SEQ ID NO: 1. In some embodiments, a mutated PPX protein includes a mutation at the amino acid position corresponding to position 58 of SEQ ID NO: 9. In some embodiments, a mutated PPX protein includes a mutation at the amino acid position corresponding to position 64 of SEQ ID NO: 9. In some embodiments, a mutated PPX protein includes a mutation at the amino acid position corresponding to position 74 of SEQ ID NO: 9. In some embodiments, a mutated PPX protein includes a mutation at the amino acid position corresponding to position 84 of SEQ ID NO: 9. In some embodiments, a mutated PPX protein includes a mutation at the amino acid position corresponding to position 93 of SEQ ID NO: 9. In some embodiments, a mutated PPX protein includes a mutation at the amino acid position corresponding to position 97 of SEQ ID NO: 9. In some embodiments, a mutated PPX protein includes a mutation at the amino acid position corresponding to position 98 of SEQ ID NO: 9. In some embodiments, a mutated PPX protein includes a mutation at the amino acid position corresponding to position 101 of SEQ ID NO: 9. In some embodiments, a mutated PPX protein includes a mutation at the amino acid position corresponding to position 119 of SEQ ID NO: 9. In some embodiments, a mutated PPX protein includes a mutation at the amino acid position corresponding to position 121 of SEQ ID NO: 9. In some embodiments, a mutated PPX protein includes a mutation at the amino acid position corresponding to position 124 of SEQ ID NO: 9. In some embodiments, a mutated PPX protein includes a mutation at the amino acid position corresponding to position 139 of SEQ ID NO: 9. In some embodiments, a mutated PPX protein includes a mutation at the amino acid position corresponding to position 150 of SEQ ID NO: 9. In some embodiments, a mutated PPX protein includes a mutation at the amino acid position corresponding to position 151 of SEQ ID NO: 9. In some embodiments, a mutated PPX protein includes a mutation at the amino acid position corresponding to position 157 of SEQ ID NO: 9. In some embodiments, a mutated PPX protein includes a mutation at the amino acid position corresponding to position 164 of SEQ ID NO: 9. In some embodiments, a mutated PPX protein includes a mutation at the amino acid position corresponding to position 170 of SEQ ID NO: 9. In some embodiments, a mutated PPX protein includes a mutation at the amino acid position corresponding to position 177 of SEQ ID NO: 9, in some embodiments, a mutated PPX protein includes a mutation at the amino acid position corresponding to position 187 of SEQ ID NO: 9. In some embodiments, a mutated PPX protein includes a mutation at the amino acid position corresponding to position 188 of SEQ ID NO: 9. In some embodiments, a mutated PPX protein includes a mutation at the amino acid position corresponding to position 195 of SEQ ID NO: 9. In some embodiments, a mutated PPX protein includes a mutation at the amino acid position corresponding to position 214 of SEQ ID NO: 9. In some embodiments, a mutated PPX protein includes a mutation at the amino acid position corresponding to position 215 of SEQ ID NO: 9. In some embodiments, a mutated PPX protein includes a mutation at the amino acid position corresponding to position 229 of SEQ ID NO: 9. In some embodiments, a mutated PPX protein includes a mutation at the amino acid position corresponding to position 230 of SEQ ID NO: 9. In some embodiments, a mutated PPX protein includes a mutation at the amino acid position corresponding to position 271 of SEQ ID NO: 9. In some embodiments, a mutated PPX protein includes a mutation at the amino acid position corresponding to position 274 of SEQ ID NO: 9. In some embodiments, a mutated PPX protein includes a mutation at the amino acid position corresponding to position 278 of SEQ ID NO: 9. In some embodiments, a mutated PPX protein includes a mutation at the amino acid position corresponding to position 283 of SEQ ID NO: 9. In some embodiments, a mutated PPX protein includes a mutation at the amino acid position corresponding to position 292 of SEQ ID NO: 9. In some embodiments, a mutated PPX protein includes a mutation at the amino acid position corresponding to position 296 of SEQ ID NO: 9. In some embodiments, a mutated PPX protein includes a mutation at the amino acid position corresponding to position 307 of SEQ ID NO: 0. In some embodiments, a mutated PPX protein includes a mutation at the amino acid position corresponding to position 324 of SEQ ID NO: 9. In some embodiments, a mutated PPX protein includes a mutation at the amino acid position corresponding to position 330 of SEQ ID NO: 9. In some embodiments, a mutated PPX protein includes a mutation at the amino acid position corresponding to position 396 of SEQ ID NO: 9. In some embodiments, a mutated PPX protein includes a mutation at the amino acid position corresponding to position 404 of SEQ ID NO: 9. In some embodiments, a mutated PPX protein includes a mutation at the amino acid position corresponding to position 406 of SEQ ID NO: 9. In some embodiments, a mutated PPX protein includes a mutation at the amino acid position corresponding to position 410 of SEQ ID NO: 9. In some embodiments, a mutated PPX protein includes a mutation at the amino acid position corresponding to position 421 of SEQ ID NO: 9. In some embodiments, a mutated PPX protein includes a mutation at the amino acid position corresponding to position 423 of SEQ ID NO: 9. In some embodiments, a mutated PPX protein includes a mutation at the amino acid position corresponding to position 434 of SEQ ID NO: 9. In some embodiments, a mutated PPX protein includes a mutation at the amino acid position corresponding to position 447 of SEQ ID NO: 9. In some embodiments, a mutated PPX protein includes a mutation at the amino acid position corresponding to position 448 of SEQ ID NO: 9. In some embodiments, a mutated PPX protein includes a mutation at the amino acid position corresponding to position 449 of SEQ ID NO: 9. In some embodiments, a mutated PPX protein includes a mutation at the amino acid position corresponding to position 451 of SEQ ID NO: 9. In some embodiments, a mutated PPX protein includes a mutation at the amino acid position corresponding to position 454 of SEQ ID NO: 9. In some embodiments, a mutated PPX protein includes a mutation at the amino acid position corresponding to position 465 of SEQ ID NO: 9. In some embodiments, a mutated PPX protein includes a mutation at the amino acid position corresponding to position 470 of SEQ ID. NO: 9. In some embodiments, a mutated PPX protein includes a mutation at the amino acid position corresponding to position 500 of SEQ ID NO: 9. In some embodiments, a mutated PPX protein includes two or more mutations, at least one mutation of which is at the amino acid position corresponding to a position selected from the group consisting of 52, 85, 105, 111, 130, 139, 143, 144, 145, 147, 165, 167, 170, 180, 185, 192, 193, 199, 206, 212, 219, 220, 221, 226, 228, 229, 230, 237, 244, 256, 257, 270, 271, 272, 305, 311, 316, 318, 332, 343, 354, 357, 359, 360, 360, 393, 403, 424, 426, 430, 438, 440, 444, 455, 457, 470, 478, 483, 484, 485, 497, 490, 503, 508 and 525 of SEQ ID NO: 1. In some embodiments, a mutated PPX protein includes two or more mutations, at least one mutation of which is at the amino acid position corresponding to a position selected from the group consisting of 58, 64, 74, 84, 93, 97, 98, 101, 119, 121, 124, 139, 150, 151, 157, 164, 170, 177, 187, 188, 195, 214, 215, 229, 230, 271, 274, 278, 283, 292, 296, 307, 324, 330, 396, 404, 406, 410, 421, 423, 434, 447, 448, 449, 451, 454, 465, 470 and 500 of SEQ ID NO: 9. In some embodiments, a mutated PPX protein includes three or more mutations, at least one mutation of which is at the amino acid position corresponding to a position selected from the group consisting of 52, 85, 105, 111, 130, 139, 143, 144, 145, 147, 165, 167, 170, 180, 185, 192, 193, 199, 206, 212, 219, 220, 221, 226, 228, 229, 230, 237, 244, 256, 257, 270, 271, 272, 305, 311, 316, 318, 332, 343, 354, 357, 359, 360, 366, 393, 403, 424, 426, 430, 438, 440, 444, 455, 457, 470, 478, 483, 484, 485, 487, 490, 503, 508 and 525 of SEQ ID NO: 1. In some embodiments, a mutated PPX protein includes three or more mutations, at least one mutation of which is at the amino acid position corresponding to a position selected from the group consisting of 58, 64, 74, 84, 93, 97, 98, 101, 119, 121, 124, 139, 150 151, 157, 164, 170, 177, 187, 188, 195, 214, 215, 229, 230, 271, 274, 278, 283, 292, 296, 307, 324, 330, 396, 404, 406, 410, 421, 423, 434, 447, 448, 449, 451, 454, 465, 470 and 500 of SEQ ID NO: 9.

In conjunction with any of the aspects, embodiments, methods and/or compositions disclosed herein, at least one mutation of a mutated PPX protein may be at the amino acid position corresponding to a position selected from the group consisting of G52, N85, N105, E111, G130, D139, P143, R144, F145, L147, F165, L167, I170, A180, P185, E192, S193, R199, V206, E212, Y219, A220, G221, 1.226, M228, K229, A230, K237, S244, R256, R257, K270, P271, Q272, S305, E311, T316, T318.S332, S343, A354, 1357, K359, 1360, A366, I393, L403, L424, Y426, S430, K438, E440, V444, L455, K457, V470, F478, F483, D484, I485, D487, K490, L503, V508 and I525 of SEQ ID NO: 1. In conjunction with any of the aspects, embodiments, methods and/or compositions disclosed herein, at least one mutation of a mutated PPX protein may be at the amino acid position corresponding to a position selected from the group consisting of D58, E64, G74, G84, L93, K97, K98, A101, S119, F121, T124, N139, E150, S151, Q157, V164, D170, C177, H187, L188, N195, P214, I215, K229, K230, C271, D274, F283, A292, S296, C307, N324, D330, S396, A404, R406, K410, L421, A423, C434, D447, S448, V449, D451, D454, Y465, K470 and T500 of SEQ ID NO: 9. In some embodiments, a mutated PPX protein includes a mutation at the amino acid position corresponding to position G52 of SEQ ID NO: 1. In some embodiments, a mutated PPX protein, includes a mutation at the amino acid position corresponding to position N85 of SEQ ID NO: 1. In some embodiments, a mutated PPX protein includes a mutation at the amino acid position corresponding to position E111 of SEQ ID NO: 1. In some embodiments, a mutated PPX protein includes a mutation at the amino acid position corresponding to position G130 of SEQ ID NO: 1. In some embodiments, a mutated PPX protein includes a mutation at the amino acid position corresponding to position D139 of SEQ ID NO: 1. In some embodiments, a mutated PPX protein includes a mutation at the amino acid position corresponding to position P143 of SEQ ID NO: 1. In some embodiments, a mutated PPX protein includes a mutation at the amino acid position corresponding to position R144 of SEQ ID NO: 1. In some embodiments, a mutated PPX protein includes a mutation at the amino acid position corresponding to position F145 of SEQ ID NO: 1. In some embodiments, a mutated PPX protein includes a mutation at the amino acid position corresponding to position L147 of SEQ ID NO: 1. In some embodiments, a mutated PPX protein includes a mutation at the amino acid position corresponding to position F165 of SEQ ID NO: 1. In some embodiments, a mutated PPX protein includes a mutation at the amino acid position corresponding to position L167 of SEQ ID NO: 1. In some embodiments, a mutated PPX protein includes a mutation at the amino acid position corresponding to position I170 of SEQ ID NO: 1. In some embodiments, a mutated PPX protein includes a mutation at the amino acid position corresponding to position A180 of SEQ ID NO: 1. In some embodiments, a mutated PPX protein includes a mutation at the amino acid position corresponding to position P185 of SEQ ID NO: 1. In some embodiments, a mutated PPX protein includes a mutation at the amino acid position corresponding to position E192 of SEQ ID NO: 1. In some embodiments, a mutated PPX protein includes a mutation at the amino acid position corresponding to position S193 of SEQ ID NO: 1. In some embodiments, a mutated PPX protein includes a mutation at the amino acid position corresponding to position R199 of SEQ ID NO: 1. In some embodiments, a mutated PPX protein includes a mutation at the amino acid position corresponding to position V206 of SEQ ID NO: 1. In some embodiments, a mutated PPX protein includes a mutation at the amino acid position corresponding to position E212 of SEQ ID NO: 1. In some embodiments, a mutated PPX protein includes a mutation at the amino acid position corresponding to position Y219 of SEQ ID NO: 1. In some embodiments, a mutated PPX protein includes a mutation at the amino acid position corresponding to position A220 of SEQ ID NO: 1. In some embodiments, a mutated PPX protein includes a mutation at the amino acid position corresponding to position G221 of SEQ ID NO: 1. In some embodiments, a mutated PPX protein includes a mutation at the amino acid position corresponding to position L226 of SEQ ID NO: 1. In some embodiments, a mutated PPX protein includes a mutation at the amino acid position corresponding to position M228 of SEQ ID NO: 1. In some embodiments, a mutated PPX protein includes a mutation at the amino acid position corresponding to position K229 of SEQ ID NO: 1. In some embodiments, a mutated PPX protein includes a mutation at the amino acid position corresponding to position A230 of SEQ ID NO: 1. In some embodiments, a mutated PPX protein includes a mutation at the amino acid position corresponding to position K237 of SEQ ID NO: 1. In some embodiments, a mutated PPX protein includes a mutation at the amino acid position corresponding to position S244 of SEQ ID NO: 1. In some embodiments, a mutated PPX protein includes a mutation at the amino acid position corresponding to position R256 of SEQ ID NO: 1. In some embodiments, a mutated PPX protein includes a mutation at the amino acid position corresponding to position R257 of SEQ ID NO: 1. In some embodiments, a mutated PPX protein includes a mutation at the amino acid position corresponding to position K270 of SEQ ID NO: 1. In some embodiments, a mutated PPX protein includes a mutation at the amino acid position corresponding to position P271 of SEQ ID NO: 1. In some embodiments, a mutated PPX protein includes a mutation at the amino acid position corresponding to position Q272 of SEQ ID NO: 1. In some embodiments, a mutated PPX protein includes a mutation at the amino acid position corresponding to position S305 of SEQ ID NO: 1. In some embodiments, a mutated PPX protein includes a mutation at the amino acid position corresponding to position E311 of SEQ ID NO: 1. In some embodiments, a mutated PPX protein includes a mutation at the amino acid position corresponding to position T316 of SEQ ID NO: 1. In some embodiments, a mutated PPX protein includes a mutation at the amino acid position corresponding to position T318 of SEQ ID NO: 1. In some embodiments, a mutated PPX protein includes a mutation at the amino acid position corresponding to position S332 of SEQ ID NO: 1. In some embodiments, a mutated PPX protein includes a mutation at the amino acid position corresponding to position S343 of SEQ ID NO: 1. In some embodiments, a mutated PPX protein includes a mutation at the amino acid position corresponding to position A354 of SEQ ID NO: 1. In some embodiments, a mutated PPX protein includes a mutation at the amino acid position corresponding to position L357 of SEQ ID NO: 1. In some embodiments, a mutated PPX protein includes a mutation at the amino acid position corresponding to position K359 of SEQ ID NO: 1. In some embodiments, a mutated PPX protein includes a mutation at the amino acid position corresponding to position L360 of SEQ ID NO: 1. In some embodiments, a mutated PPX protein includes a mutation at the amino acid position corresponding to position A366 of SEQ ID NO: 1. In some embodiments, a mutated PPX protein includes a mutation at the amino acid position corresponding to position L393 of SEQ ID NO: 1. In some embodiments, a mutated PPX protein includes a mutation at the amino acid position corresponding to position L403 of SEQ ID NO: 1. In some embodiments, a mutated PPX protein includes a mutation at the amino acid position corresponding to position L424 of SEQ ID NO: 1. In some embodiments, a mutated PPX protein includes a mutation at the amino acid position corresponding to position Y426 of SEQ ID NO: 1. In some embodiments, a mutated PPX protein includes a mutation at the amino acid position corresponding to position S430 of SEQ ID NO: 1. In some embodiments, a mutated PPX protein includes a mutation at the amino acid position corresponding to position K438 of SEQ ID NO: 1. In some embodiments, a mutated PPX protein includes a mutation at the amino acid position corresponding to position E440 of SEQ ID NO: 1.

In some embodiments, a mutated PPX protein includes a mutation at the amino acid position corresponding to position V444 of SEQ ID NO: 1. In some embodiments, a mutated PPX protein includes a mutation at the amino acid position corresponding to position L-455 of SEQ ID NO: 1. In some embodiments, a mutated PPX protein includes a mutation at the amino acid position corresponding to position K457 of SEQ ID NO: 1 In some embodiments, a mutated PPX protein includes a mutation at the amino acid position corresponding to position V470 of SEQ ID NO: 1. In some embodiments, a mutated PPX protein includes a mutation at the amino acid position corresponding to position F478 of SEQ ID NO: 1 In some embodiments, a mutated PPX protein includes a mutation at the amino acid position corresponding to position F483 of SEQ ID NO: 1. In some embodiments, a mutated PPX protein includes a mutation at the amino acid position corresponding to position D484 of SEQ ID NO: 1. In some embodiments, a mutated PPX protein includes a mutation at the amino acid position corresponding to position 1485 of SEQ ID NO: 1. In some embodiments, a mutated PPX protein includes a mutation at the amino acid position corresponding to position D487 of SEQ ID NO: 1. In some embodiments, a mutated PPX protein includes a mutation at the amino acid position corresponding to position K490 of SEQ ID NO: 1. In some embodiments, a mutated PPX protein includes a mutation at the amino acid position corresponding to position L503 of SEQ ID NO: 1. In some embodiments, a mutated PPX protein includes a mutation at the amino acid position corresponding to position V509 of SEQ ID NO: 1. In some embodiments, a mutated PPX protein includes a mutation at the amino acid position corresponding to position I525 of SEQ ID NO: 1. In some embodiments, a mutated PPX protein includes a mutation at the amino acid position corresponding to position D58 of SEQ ID NO: 9. In some embodiments, a mutated PPX protein includes a mutation at the amino acid position corresponding to position E64 of SEQ ID NO: 9. In some embodiments, a mutated PPX protein includes a mutation at the amino acid position corresponding to position G74 of SEQ ID NO: 9. In some embodiments, a mutated PPX protein includes a mutation at the amino acid position corresponding to position G4 of SEQ ID NO: 9. In some embodiments, a mutated PPX protein includes a mutation at the amino acid position corresponding to position L93 of SEQ ID NO: 9. In some embodiments, a mutated PPX protein includes a mutation at the amino acid position corresponding to position K97 of SEQ ID NO: 9. In some embodiments, a mutated PPX protein includes a mutation at the amino acid position corresponding to position K98 of SEQ ID NO: 9. In some embodiments, a mutated PPX protein includes a mutation at the amino acid position corresponding to position. A101 of SEQ ID NO: 9. In some embodiments, a mutated PPX protein includes a mutation at the amino acid position corresponding to position S119 of SEQ ID NO: 9. In some embodiments, a mutated PPX protein includes a mutation at the amino acid position corresponding to position F121 of SEQ ID NO: 9. In some embodiments, a mutated PPX protein includes a mutation at the amino acid position corresponding to position T124 of SEQ ID NO: 9. In some embodiments, a mutated PPX protein includes a mutation at the amino acid position corresponding to position N139 of SEQ ID NO: 9. In some embodiments, a mutated PPX protein includes a mutation at the amino acid position corresponding to position E150 of SEQ ID NO: 9. In some embodiments, a mutated PPX protein includes a mutation at the amino acid position corresponding to position S151 of SEQ ID NO: 9. In some embodiments, a mutated PPX protein includes a mutation at the amino acid position corresponding to position Q157 of SEQ ID NO: 9. In some embodiments, a mutated PPX protein includes a mutation at the amino acid position corresponding to position V164 of SEQ ID NO: 9. In some embodiments, a mutated PPX protein includes a mutation at the amino acid position corresponding to position D170 of SEQ ID NO: 9. In some embodiments, a mutated PPX protein includes a mutation at the amino acid position corresponding to position C177 of SEQ ID NO: 9, in some embodiments, a mutated PPX protein includes a mutation at the amino acid position corresponding to position H187 of SEQ ID NO: 9, in some embodiments, a mutated PPX protein includes a mutation at the amino acid position corresponding to position L188 of SEQ ID NO: 9. In some embodiments, a mutated PPX protein includes a mutation at the amino acid position corresponding to position N195 of SEQ ID NO: 9. In some embodiments, a mutated PPX protein includes a mutation at the amino acid position corresponding to position P214 of SEQ ID NO: 9. In some embodiments, a mutated PPX protein includes a mutation at the amino acid position corresponding to position I215 of SEQ ID NO: 9. In some embodiments, a mutated PPX protein includes a mutation at the amino acid position corresponding to position K:229 of SEQ ID NO: 9. In some embodiments, a mutated PPX protein includes a mutation at the amino acid position corresponding to position K230 of SEQ ID NO: 9. In some embodiments, a mutated PPX protein includes a mutation at the amino acid position corresponding to position C271 of SEQ ID NO: 9. In some embodiments, a mutated PPX protein includes a mutation at the amino acid position corresponding to position D274 of SEQ ID NO: 9. In some embodiments, a mutated PPX protein includes a mutation at the amino acid position corresponding to position F283 of SEQ ID NO: 9. In some embodiments, a mutated PPX protein includes a mutation at the amino acid position corresponding to position A292 of SEQ ID NO: 9. In some embodiments, a mutated PPX protein includes a mutation at the amino acid position corresponding to position S296 of SEQ ID NO: 9. In some embodiments, a mutated PPX protein includes a mutation at the amino acid position corresponding to position C307 of SEQ ID NO: 9. In some embodiments, a mutated PPX protein includes a mutation at the amino acid position corresponding to position N324 of SEQ ID NO: 9. In some embodiments, a mutated PPX protein includes a mutation at the amino acid position corresponding to position D330 of SEQ ID NO: 9. In some embodiments, a mutated PPX protein includes a mutation at the amino acid position corresponding to position S396 of SEQ ID NO: 9. In some embodiments, a mutated PPX protein includes a mutation at the amino acid position corresponding to position A404 of SEQ ID NO: 9. In some embodiments, a mutated PPX protein includes a mutation at the amino acid position corresponding to position R406 of SEQ ID NO: 9. In some embodiments, a mutated PPX protein includes a mutation at the amino acid position corresponding to position K410 of SEQ ID NO: 9. In some embodiments, a mutated PPX protein includes a mutation at the amino acid position corresponding to position L421 of SEQ ID NO: 9. In some embodiments, a mutated PPX protein includes a mutation at the amino acid position corresponding to position A423 of SEQ ID NO: 9. In some embodiments, a mutated PPX protein includes a mutation at the amino acid position corresponding to position C434 of SEQ ID NO: 9. In some embodiments, a mutated PPX protein includes a mutation at the amino acid position corresponding to position D447 of SEQ ID NO: 9. In some embodiments, a mutated PPX protein includes a mutation at the amino acid position corresponding to position S448 of SEQ ID NO: 9. In some embodiments, a mutated PPX protein includes a mutation at the amino acid position corresponding to position V449 of SEQ ID NO: 9. In some embodiments, a mutated PPX protein includes a mutation at the amino acid position corresponding to position D451 of SEQ ID NO: 9. In some embodiments, a mutated PPX protein includes a mutation at the amino acid position corresponding to position D454 of SEQ ID NO: 9. In some embodiments, a mutated PPX protein includes a mutation at the amino acid position corresponding to position Y465 of SEQ ID NO: 9. In some embodiments, a mutated PPX protein includes a mutation at the amino acid position corresponding to position K470 of SEQ ID NO: 9. In some embodiments, a mutated PPX protein includes a mutation at the amino acid position corresponding to position 1500 of SEQ ID NO: 9. In some embodiments, a PPX protein is a paralog of *Arabidopsis thaliana* PPX protein (for example the PPX protein may be a potato plastidal PPX protein) and the PPX protein may have an N at the position corresponding to position 52 of SEQ ID NO: 1, wherein the N is substituted with an amino acid other than an N; a K at the position corresponding to position 272 of SEQ ID NO: 1, wherein the K is substituted with an amino acid other than a K; an S at the position corresponding to position 359 of SEQ ID NO:1, wherein the S is substituted with an amino acid other than an S; and/or an S at the position corresponding to position 525 of SEQ ID NO:1, wherein the S is substituted with an amino acid other that an S. In such embodiments, a mutated PPX protein includes a mutation at the amino acid position corresponding to position N52 of SEQ ID NO: 1. In some embodiments, a mutated PPX protein includes a mutation at the amino acid position corresponding to position N95 of SEQ ID NO: 1 In some embodiments, a mutated PPX protein includes a mutation at the amino acid position corresponding to position R144 of SEQ ID NO: 1. In some embodiments, a mutated PPX protein includes a mutation at the amino acid position corresponding to position F145 of SEQ ID NO: 1. In some embodiments, a mutated PPX protein includes a mutation at the amino acid position corresponding to position A 80 of SEQ ID NO: 1. In some embodiments, a mutated PPX protein includes a mutation at the amino acid position corresponding to position P185 of SEQ ID NO 1. In some embodiments, a mutated PPX protein includes a mutation at the amino acid position corresponding to position A220 of SEQ ID NO: 1. In some embodiments, a mutated PPX protein includes a mutation at the amino acid position corresponding to position L226 of SEQ ID NO: 1. In some embodiments, a mutated PPX protein includes a mutation at the amino acid position corresponding to position M228 of SEQ ID NO: 1. In some embodiments, a mutated PPX protein includes a mutation at the amino acid position corresponding to position S244 of SEQ ID NO: 1. In some embodiments, a mutated PPX protein includes a mutation at the amino acid position corresponding to position K272 of SEQ ID NO: 1. In some embodiments, a mutated PPX protein includes a mutation at the amino acid position corresponding to S305 of SEQ ID NO: 1. In some embodiments, a mutated PPX protein includes a mutation at the amino acid position corresponding to position S332 of SEQ ID NO: 1. In some embodiments, a mutated PPX protein includes a mutation at the amino acid position corresponding to position I357 of SEQ ID NO: 1. In some embodiments, a mutated PPX protein includes a mutation at the amino acid position corresponding to position S359 of SEQ ID NO: 1. In some embodiments, a mutated PPX protein includes a mutation at the amino acid position corresponding to position I393 of SEQ ID NO: 1. In some embodiments, a mutated PPX protein includes a mutation at the amino acid position corresponding to position L403 of SEQ ID NO: 1. In some embodiments, a mutated PX protein includes a mutation at the amino acid position corresponding to position L424 of SEQ ID NO: 1. In some embodiments, a mutated PPX protein includes a mutation at the amino acid position corresponding to position Y426 of SEQ ID NO: 1. In some embodiments, a mutated PPX protein includes a mutation at the amino acid position corresponding to position F478 of SEQ ID NO: 1. In some embodiments, a mutated PPX protein includes a mutation at the amino acid position corresponding to position S525 of SEQ ID NO: 1.

In some embodiments, a mutated PPX protein includes two or more mutations, at least one mutation of which is at the amino acid position corresponding to a position selected corresponding to position 52 of SEQ ID NO:1, wherein the N is substituted with an amino acid other than an N; (2) a K at the position corresponding to position 272 of SEQ ID NO:1, wherein the K is substituted with an amino acid other than a K; (3) an S at the position corresponding to position 359 of SEQ ID NO:1, wherein the S is substituted with an amino acid other than an S; and/or (4) an S at the position corresponding to position 525 of SEQ ID NO:1 wherein the S is substituted with an amino acid other than an S. In such embodiments, a mutated PPX protein includes three or more mutations, at lea-t one mutation of which is at the amino acid position corresponding to a position selected from the group consisting of N52, N85, R144, F145, A180, P185, A220, L226, M228, S244, K272, S305, S332, L357, S359, L393, L403, L424, Y426, F478 and S525 of SEQ ID NO: 1.

In conjunction with any of the aspects, embodiments, methods and/or compositions disclosed herein, the mutated PPX protein may include one or more mutations selected from the mutations shown in Table 1.

TABLE 1

| Amino acid mutations in the *Arabidopsis thaliana* PPX protein. | | | | | | | |
|---|---|---|---|---|---|---|---|
| G52K | F145Y | A220I | M228L | S332C | L393S | Y426C | Y426R |
| N85D | A180T | A220L | S244G | L357I | L393V | Y426F | Y426T |
| R144C | P185H | A220T | S244T | K359R | L403R | Y426H | Y426V |
| R144H | P185S | A220V | Q272F | K359T | L403S | Y426I | F478S |
| F145L | A220C | L226M | S305L | L393M | L424S | Y426L | I525T |
| E111V | L147V | S193T | A230F | P271R | L360K | L455V | I485E |
| G130N | F165N | R199L | R256H | E311R | A366E | K457V | K490N |
| D139H | P185Y | V206F | R256S | T318G | K438S | V470S | L503F |
| P143R | E192D | Y219S | K270E | S332L | E440K | V470Y | V508T |
| R144L | E192K | K229Q | K270Q | L360D | V444I | D484A | | from the group consisting of G52, N85, R44, F145, A180, P185, A220, L226, M228, S244, Q272, S305, S332, L357, K359, L393, L403, L424, Y426, F478 and I525 of SEQ ID NO: 1. In some embodiments, a PPX protein is a paralog of *Arabidopsis thaliana* PPX protein (for example the PPX protein may be a potato PPX protein) and the PPX protein has two or more mutations and has one or more of: (1) an N at the position corresponding to position 52 of SEQ ID NO:1, wherein the N is substituted with an amino acid other than an N; (2) a K at the position corresponding to position 272 of SEQ ID NO:1, wherein the K is substituted with an amino acid other than a K; (3) an S at the position corresponding to position 359 of SEQ ID NO: 1, wherein the S is substituted with an amino acid other than an S; and/or (4) an S at the position corresponding to position 525 of SEQ ID NO: 1, wherein the S is substituted with an amino acid other than an S. In such embodiments, a mutated PPX protein includes two or more mutations, at least one mutation of which is at the amino acid position corresponding to a position selected from the group consisting of N52, N85, R144, F145, A180, P185, A220, I226, M228, S244, K272, S305, S332, L357, S359, L393, L403, L424, Y426, F478 and S525 of SEQ ID NO: 1. In some embodiments, a mutated PPX protein includes three or more mutations, at least one mutation of which is at the amino acid position corresponding to a position selected from the group consisting of G52, N85, R144, F145, A180, P185, A220, L226, M228, S244, Q272, S305, S332, L357, K359, L393, L403, L424, Y426, U478 and I525 of SEQ ID NO: 1. In some embodiments, a PPX protein is a paralog of *Arabidopsis thaliana* PPX protein (for example the PPX protein may be a potato PPX protein) and the PPX protein has three or more mutations and has one or more of: (1) an N at the position In conjunction with any of the aspects, embodiments, methods and/or compositions disclosed herein, the one or mom mutations in a mutated PPX gene may encode a mutated PPX protein having one or more mutations, two or more mutations, or three or more mutations selected from the group consisting of a glycine to lysine at a position corresponding to position 52 of SEQ ID NO: 1; an asparagine to aspartic acid at a position corresponding to position 85 of SEQ ID NO: 1; a glutamic acid to valine at a position corresponding to position 111 of SEQ ID NO: 1: a glycine to asparagine at a position corresponding to position 130 of SEQ ID NO: 1; an aspartic acid to histidine at a position corresponding to position 139 of SEQ ID NO: 1; a proline to arginine at a position corresponding to position 143 of SEQ ID NO: 1; an arginine to cysteine at a position corresponding to position 144 of SEQ ID NO: 1; an arginine to histidine at a position corresponding to position 144 of SEQ ID NO: 1; an arginine to leucine at a position corresponding to position 144 of SEQ ID NO: 1; a phenylalanine to leucine at a position corresponding to position 145 of SEQ ID NO: 1, a phenylalanine to tyrosine at a position corresponding to position 145 of SEQ ID NO: 1; a leucine to valine at a position corresponding to position 147 of SEQ ID NO: 1; a phenylalanine to asparagine at a position corresponding to position 165 of SEQ ID NO: 1; an alanine to threonine at a position corresponding to position 180 of SEQ ID N): 1; a proline to histidine at a position corresponding to position 185 of SEQ ID NO: 1; a proline to arginine at a position corresponding to position 185 of SEQ ID NO: 1; a proline to tyrosine at a position corresponding to position 185 of SEQ ID NO: 1; a glutamic acid to aspartic acid at a position corresponding to position 192 of SEQ ID NO: 1; a glutamic acid to lysine at a position corresponding to position 192 of SEQ ID NO: 1; a serine to threonine at a position corresponding to position 193 of SEQ ID NO: 1; an arginine to leucine at a position corresponding to position 199 of SEQ ID NO: 1; a valine to phenylalanine at a position corresponding to position 206 of SEQ ID NO: 1; a tyrosine to serine at a position corresponding to position 219 of SEQ ID NO: 1; an alanine to cysteine at a position corresponding to position 220 of SEQ ID NO: 1; an alanine to isoleucine at a position corresponding to position 220 of SEQ ID NO: 1; an alanine to leucine at a position corresponding to position 220 of SEQ ID NO: 1; an alanine to threonine at a position corresponding to position 220 of SEQ ID NO: 1; an alanine to valine at a position corresponding to position 220 of SEQ ID NO: 1; a leucine to methionine at a position corresponding to position 226 of SEQ ID NO: 1; a methionine to leucine at a position corresponding to position 228 of SEQ ID NO: 1; a lysine to glutamine, at a position corresponding to position 229 of SEQ ID NO: 1; an alanine to phenylalanine at a position corresponding to position 230 of SEQ ID NO: 1; a serine to glycine at a position corresponding to position 244 of SEQ ID NO: 1; a serine to threonine at a position corresponding to position 244 of SEQ ID NO: 1 an arginine to histidine at a position corresponding to position 256 of SEQ ID NO: 1; an arginine to serine at a position corresponding to position 256 of SEQ ID NO: 1; a lysine to glutamic acid at a position corresponding to position 270; a lysine to glutamine at a position corresponding to position 270; a proline to arginine at a position corresponding to position 271 of SEQ ID NO: 1; a glutamine to phenylalanine at a position corresponding to position 272 of SEQ ID NO: 1; a serine to leucine at a position corresponding to position 305 of SEQ ID NO: 1; a glutamic acid to arginine at a position corresponding to position 311 of SEQ ID NO: 1; a threonine to glycine at a position corresponding to position 316 of SEQ ID NO: 1; a threonine to glycine at a position corresponding to position 318 of SEQ ID NO: 1; a serine to cysteine at a position corresponding to position 332 of SEQ ID NO: 1; a serine to leucine at a position corresponding to position 332 of SEQ ID NO: 1; a leucine to isoleucine at a position corresponding to position 357 of SEQ ID NO: 1; a lysine to arginine at a position corresponding to position 359 of SEQ ID NO: 1; a lysine to threonine at a position corresponding to position 359 of SEQ ID NO: 1; a leucine to lysine at a position corresponding to position 360 of SEQ ID NO: 1; a leucine to aspartic acid at a position corresponding to position 360 of SEQ ID NO: 1; an alanine to glutamic acid at a position corresponding to position 366 of SEQ ID NO: 1; a leucine to methionine at a position corresponding to position 393 of SEQ ID NO: 1; a leucine to serine at a position corresponding to position 393 of SEQ ID NO: 1; a leucine to valine at a position corresponding to position 393 of SEQ ID NO: 1; a leucine to arginine at a position corresponding to position 403 of SEQ ID NO: 1; a leucine to serine at a position corresponding to position 403 of SEQ ID NO: 1, a leucine to serine at a position corresponding to position 424 of SEQ ID NO: 1; a tyrosine to cysteine at a position corresponding to position 426 of SEQ ID NO: 1; a tyrosine to phenylalanine at a position corresponding to position 426 of SEQ ID NO: 1; a tyrosine to histidine at a position corresponding to position 426 of SEQ ID NO: 1; a tyrosine to isoleucine at a position corresponding to position 426 of SEQ ID NO: 1; a tyrosine to leucine at a position corresponding to position 426 of SEQ ID NO: 1; a tyrosine to arginine at a position corresponding to position 426 of SEQ ID NO: 1; a tyrosine to threonine at a position corresponding to position 426 of SEQ ID NO: 1; a tyrosine to valine at a position corresponding to position 426 of SEQ ID NO: 1; a lysine to serine at a position corresponding to position 438 of SEQ ID NO: 1; a glutamic acid to lysine at a position corresponding to position 440 of SEQ ID NO: 1; a valine to isoleucine at a position corresponding to position 444 of SEQ ID NO: 1; a leucine to valine at a position corresponding to position 455 of SEQ ID NO: 1; a lysine to valine at a position corresponding to position 457 of SEQ ID NO: 1; a valine to serine at a position corresponding to position 470 of SEQ ID NO: 1; a valine to tyrosine at a position corresponding to position 470 of SEQ ID NO: 1; a phenylalanine to serine at a position corresponding to position 478 of SEQ ID NO: 1; a phenylalanine to glycine at a position corresponding to position 483 of SEQ ID NO: 1; an aspartic acid to alanine at a position corresponding to position 484 of SEQ ID NO: 1; an isoleucine to glutamic acid at a position corresponding to position 485 of SEQ ID NO: 1; a lysine to asparagine at a position corresponding to position 490 of SEQ ID NO: 1; a leucine to phenylalanine at a position corresponding to position 503 of SEQ ID NO: 1; a valine to threonine at a position corresponding to position 508 of SEQ ID NO: 1; and an isoleucine to threonine at a position corresponding to position 525 of SEQ ID NO: 1.

In conjunction with any of the aspects, embodiments, methods and/or compositions disclosed herein, a mutated PPX gene may encode a mutated PPX protein that includes an glycine to lysine at a position corresponding to position 5M of SEQ ID NO: 1. In some embodiments, a mutated PPX gone encodes a mutated PPX protein that includes an asparagine to aspartic acid at a position corresponding to position 85 of SEQ ID NO: 1. In some embodiments, a mutated PPX gene encodes a mutated PPX protein that includes a glutamic acid to valine at a position corresponding to position 111 of SEQ ID NO: 1. In some embodiments, a mutated PPX gene encodes a mutated PPX protein that includes a glycine to asparagine at a position corresponding to position 130 of SEQ ID NO: 1. In some embodiments, a mutated PPX gene encodes a mutated PPX protein that includes an aspartic acid to histidine at a position corresponding to position 139 of SEQ ID NO: 1. In some embodiments, a mutated PPX gene encodes a mutated PPX protein that includes a proline to arginine at a position corresponding to position 143 of SEQ ID NO: 1. In some embodiments, a mutated PPX gene encodes a mutated PPX protein that includes an arginine to cysteine at a position corresponding to position 144 of SEQ ID NO. 1. In some embodiments, a mutated PPX gene encodes a mutated PPX protein that includes an arginine to leucine at a position corresponding to position 144 of SEQ ID NO. 1. In some embodiments, a mutated PPX gene encodes a mutated PPX protein that includes an arginine to histidine at a position corresponding to position 144 of SEQ ID NO. 1. In some embodiments, a mutated PPX gene encodes a mutated PPX protein that includes a phenylalanine to leucine at a position corresponding to position 145 of SEQ ID NO: 1. In some embodiments, a mutated PPX gene encodes a mutated PPX protein that includes a phenylalanine to tyrosine at a position corresponding to position 145 of SEQ ID NO: 1. In some embodiments, a mutated PPX gene encodes a mutated PPX protein that includes a leucine to valine at a position corresponding to position 147 of SEQ ID NO: 1. In some embodiments, a mutated PPX gene encodes a mutated PPX protein that includes a phenylalanine to asparagine at a position corresponding to position 165 of SEQ ID NO: 1. In some embodiments, a mutated PPX gene encodes a mutated PPX protein that includes an alanine to threonine at a position corresponding to position 180 of SEQ ID NO: 1. In some embodiments, a mutated PPX gene encodes a mutated PPX protein that includes a proline to histidine at a position corresponding to position 185 of SEQ ID NO: 1. In some embodiments, a mutated PPX gene encodes a mutated PPX protein that includes a proline to arginine at a position corresponding to position 185 of SEQ ID NO: 1 In some embodiments, a mutated PPX gene encodes a mutated PPX protein that includes a proline to tyrosine at a position corresponding to position 185 of SEQ ID NO: 1. In some embodiments, a mutated PPX gene encodes a mutated PPX protein that Includes a glutamic acid to aspartic acid at a position corresponding to position 192 of SEQ ID NO: 1. In some embodiments, a mutated PPX gene encodes a mutated PPX protein that includes a glutamic acid to lysine at a position corresponding to position 192 of SEQ ID NO: 1. In some embodiments, a mutated PPX gene encodes a mutated PPX protein that includes a serine to threonine at a position corresponding to position 193 of SEQ ID NO: 1. In some embodiments, a mutated PPX gene encodes a mutated PPX protein that includes an arginine to leucine at, a position corresponding to position 199 of SEQ ID NO: 1. In some embodiments, a mutated PPX gene encodes a mutated PPX protein that includes a valine to phenylalanine at a position corresponding to position 206 of SEQ ID NO: 1 In some embodiments, a mutated PPX gene encodes a mutated PPX protein that includes a tyrosine to serine at a position corresponding to position 219 of SEQ ID NO: 1. In some embodiments, a mutated PPX gene encodes a mutated PPX protein that includes an alanine to cysteine at a position corresponding to position 220 of SEQ ID NO: 1. In some embodiments, a mutated PPX gene encodes a mutated PPX protein that includes an alanine to isoleucine at a position corresponding to position 220 of SEQ ID NO: 1. In some embodiments, a mutated PPX gene encodes a mutated PPX protein that includes an alanine to leucine at a position corresponding to position 220 of SEQ ID NO: 1. In some embodiments, a mutated PPX gene encodes a mutated PPX protein that includes an alanine to threonine at a position corresponding to position 220 of SEQ ID NO: 1. In some embodiments, a mutated PPX gene encodes a mutated PPX protein that includes an alanine to valine at a position corresponding to position 220 of SEQ ID NO: 1. In some embodiments, a mutated PPX gene encodes a mutated PPX protein that includes a leucine to methionine at a position corresponding to position 226 of SEQ ID NO: 1. In some embodiments, a mutated PPX gene encodes a mutated PPX protein that includes a methionine to leucine at a position corresponding to position 228 of SEQ ID NO: 1. In some embodiments, a mutated PPX gene encodes a mutated PPX protein that includes a lysine to glutamine at a position corresponding to position 229 of SEQ ID NO: 1. In some embodiments, a mutated PPX gene encodes a mutated PPX protein that includes an alanine to phenylalanine at a position corresponding to position 230 of SEQ ID NO: 1. In some embodiments, a mutated PPX gene encodes a mutated PPX protein that includes a serine to glycine at a position corresponding to position 244 of SEQ ID NO: 1. In some embodiments, a mutated PPX gene encodes a mutated PPX protein that includes a serine to threonine at a position corresponding to position 244 of SEQ ID NO: 1. In some embodiments, a mutated PPX gene encodes a mutated PPX protein that includes an arginine to histidine at a position corresponding to position 256 of SEQ ID NO: 1. In some embodiments, a mutated PPX gene encodes a mutated PPX protein that includes an arginine to serine at a position corresponding to position 256 of SEQ ID NO: 1. In some embodiments, a mutated PPX gene encodes a mutated PPX protein that includes a lysine to glutamic acid at a position corresponding to position 270. In some embodiments, a mutated PPX gene encodes a mutated PPX protein that includes a lysine to glutamine at a position corresponding to position 270. In some embodiments, a mutated PPX gene encodes a mutated PPX protein that includes a proline to arginine at a position corresponding to position 271 of SEQ ID NO: 1. In some embodiments, a mutated PPX gene encodes a mutated PPX protein that includes a glutamine to phenylalanine at a position corresponding to position 272 of SEQ ID NO: 1. In some embodiments, a mutated PPX gene encodes a mutated PPX protein that includes a serine to threonine at a position corresponding to position 244 of SEQ ID NO: 1. In some embodiments, a mutated PPX gene encodes a mutated PPX protein that includes a serine to leucine at a position corresponding to position 305 of SEQ ID NO: 1. In some embodiments, a mutated PPX gene encodes a mutated PPX protein that includes a glutamic acid to arginine at a position corresponding to position 311 of SEQ ID NO: 1. In some embodiments, a mutated PPX gene encodes a mutated PPX protein that includes a threonine to glycine at a position corresponding to position 316 of SEQ ID NO: 1. In some embodiments, a mutated PPX gene encodes a mutated PPX protein that includes a threonine to glycine at a position corresponding to position 318 of SEQ ID NO: 1. In some embodiments, a mutated PPX gene encodes a mutated PPX protein that includes a serine to cysteine at a position corresponding to position 332 of SEQ ID NO: 1. In some embodiments, a mutated PPX gene encodes a mutated PPX protein that includes a serine to leucine at a position corresponding to position 332 of SEQ ID NO: 1. In some embodiments, a mutated PPX gone encodes a mutated PPX protein that includes a leucine to isoleucine at a position corresponding to position 357 of SEQ ID NO: 1. In some embodiments, a mutated PPX gene encodes a mutated PPX protein that includes a lysine to arginine at a position corresponding to position 359 of SEQ ID NO: 1. In some embodiments, a mutated PPX gene encodes a mutated PPX protein that includes a lysine to threonine at a position corresponding to position 359 of SEQ ID NO: 1. In some embodiments, a mutated PPX gene encodes a mutated PPX protein that includes a leucine to lysine at a position corresponding to position 360 of SEQ ID NO 1. In some embodiments, a mutated PPX gene encodes a mutated PPX protein that includes a leucine to aspartic acid at a position corresponding to position 360 of SEQ ID NO: 1. In some embodiments, a mutated PPX gene encodes a mutated PPX protein that includes an alanine to glutamic acid at a position corresponding to position 366 of SEQ ID NO: 1. In some embodiments, a mutated PPX gene encodes a mutated PPX protein that includes a leucine to methionine at a position corresponding to position 393 of SEQ ID NO: 1. In some embodiments, a mutated PPX gene encodes a mutated PPX protein that includes leucine to serine at a position corresponding to position 393 of SEQ ID NO: 1. In some embodiments, a mutated PPX gene encodes a mutated PPX protein that includes a leucine to valine at a position corresponding to position 393 of SEQ ID NO: 1. In some embodiments, a mutated PPX gene encodes a mutated PPX protein that includes a leucine to arginine at a position corresponding to position 403 of SEQ ID NO: 1. In some embodiments, a mutated PPX gene encodes a mutated PPX protein that includes a leucine to serine at a position corresponding to position 403 of SEQ ID NO: 1. In some embodiments, a mutated PPX gene encodes a mutated PPX protein that includes a leucine to serine at a position corresponding to position 424 of SEQ ID NO: 1. In some embodiments, a mutated PPX gene encodes a mutated PPX protein that includes a tyrosine to cysteine at a position corresponding to position 426 of SEQ ID NO: 1. In some embodiments, a mutated PPX gene encodes a mutated PPX protein that includes a tyrosine to phenylalanine at a position corresponding to position 426 of SEQ ID NO: 1. In some embodiments, a mutated PPX gene encodes a mutated PPX protein that includes a tyrosine to histidine at a position corresponding to position 426 of SEQ ID NO: 1. In some embodiments, a mutated PPX gene encodes a mutated PPX protein that includes a tyrosine to isoleucine at a position corresponding to position 426 of SEQ ID NO: 1. In some embodiments, a mutated PPX gene encodes a mutated PPX protein that includes a tyrosine to leucine at a position corresponding to position 426 of SEQ ID NO: 1. In some embodiments, a mutated PPX gene encodes a mutated PPX protein that includes a tyrosine to arginine at a position corresponding to position 426 of SEQ ID NO: 1. In some embodiments, a mutated PPX gene encodes a mutated PPX protein that includes a tyrosine to threonine at a position corresponding to position 426 of SEQ ID NO: 1. In some embodiments, a mutated PPX gene encodes a mutated PPX protein that includes a tyrosine to valine at a position corresponding to position 426 of SEQ ID NO: 1, in some embodiments, a mutated PPX gene encodes a mutated PPX protein that includes a lysine to serine at a position corresponding to position 438 of SEQ ID NO: 1. In some embodiments, a mutated PPX gene encodes a mutated PPX protein that includes a glutamic acid to lysine at a position corresponding to position 440 of SEQ ID NO: 1. In some embodiments, a mutated PPX gene encodes a mutated PPX protein that includes a valine to isoleucine at a position corresponding to position 444 of SEQ ID NO: 1. In some embodiments, a mutated PPX gene encodes a mutated PPX protein that includes a leucine to valine at a position corresponding to position 455 of SEQ ID NO: 1. In some embodiments, a mutated PPX gene encodes a mutated PPX protein that includes a lysine to valine at a position corresponding to position 457 of SEQ ID NO: 1. In some embodiments, a mutated PPX gene encodes a mutated PPX protein that includes a valine to serine at a position corresponding to position 470 of SEQ ID NO: 1. In some embodiments, a mutated PPX gene encodes a mutated PPX protein that includes a valine to tyrosine at a position corresponding to position 470 of SEQ ID NO: 1. In some embodiments, a mutated PPX gene encodes a mutated PPX protein that includes a phenylalanine to serine at a position corresponding to position 478 of SEQ ID NO: 1. In some embodiments, a mutated PPX gene encodes a mutated PPX protein that includes a phenylalanine to glycine at a position corresponding to position 483 of SEQ ID NO: 1. In some embodiments, a mutated PPX gene encodes a mutated PPX protein that includes an aspartic acid to alanine at a position corresponding to position 484 of SEQ ID NO: 1. In some embodiments, a mutated PPX gene encodes a mutated PPX protein that includes an isoleucine to glutamic acid at a position corresponding to position 485 of SEQ ID NO: 1. In some embodiments, a mutated PPX gene encodes a mutated PPX protein that includes a lysine to asparagine at a position corresponding to position 490 of SEQ ID NO: 1. In some embodiments, a mutated PPX gene encodes a mutated PPX protein that includes a leucine to phenylalanine at a position corresponding to position 503 of SEQ ID NO: 1. In some embodiments, a mutated PPX gene encodes a mutated PPX protein that includes a valine to threonine at a position corresponding to position 508 of SEQ ID NO: 1. In some embodiments, a mutated PPX gene encodes a mutated PPX protein that includes an isoleucine to threonine at a position corresponding to position 525 of SEQ ID NO: 1.

TABLE 2

Summary of nucleotide/codon mutations in the *Arabidopsis* plastidal PPX gene that lead to amino acid changes that confer tolerance to PPX inhibitors. Position numbers based on numbering of *Arabidopsis* plastidal PPX gene number At4g01690 (SEQ ID NO: 1).

| AA mtn | NA mtn |
|--------|--------|
| G52K | GGG → AAA |
| N85D | AAT → GAT |
| R144C | AGG → TGC |
| | AGG → TGT |
| R144H | AGG → CAC |
| | AGG → CAT |
| F145L | TTT → CTT |
| F145Y | TTT → TAT |
| A180T | GCA → ACA |
| P185H | CCG → CAC |
| | CCG → CAT |
| P185R | CCG → CGG |
| A220C | GCT → TGT |
| A220I | GCT → ATT |
| A220L | GCT → CTT |
| A220T | GCT → ACT |
| A220V | GCT → GTT |
| L226M | GTG → ATG |
| M228L | ATG → CTG |
| S244G | AGC → GGC |
| S244T | AGC → ACC |
| Q272F | CAG → TTC |
| | CAG → TTT |
| S305L | TCA → TTA |
| S332C | TCT → TGT |
| L357I | CTC → ATC |
| K359R | AAA → AGA |
| K359T | AAA → ACT |
| L393M | TTG → ATG |
| L393S | TTG → TCG |
| L393V | TTG → GTG |
| L403R | TTA → CGA |
| L403S | TTA → TCA |
| L424S | TTG → TCG |
| Y426C | TAC → TGC |
| Y426F | TAC → TTC |
| Y426H | TAC → CAC |
| Y426I | TAC → ATC |
| Y426L | TAC → TTA |
| | TAC → CTC |
| Y426R | TAC → CGC |
| Y426T | TAC → ACC |
| Y426V | TAC → GTC |
| F478S | TTT → TCT |
| S525T | ATT → ACT |

* "AA mtn" refers to amino acid mutation;
"NA mtn" refers to nucleic acid mutation In conjunction with any of the aspects, embodiments, methods and/or compositions disclosed herein, a mutated PPX gene may include a GGG→AAA which encodes a mutated PPX protein that includes an glycine to lysine at a position corresponding to position 52 of SEQ ID NO: 1. In some embodiments, a mutated PPX gene includes a AAT→GAT nucleic acid mutation that encodes a mutated PPX protein that includes an asparagine to aspartic acid at a position corresponding to position 85 of SEQ ID NO: 1. In some embodiments, a mutated PPX gene includes a AGG→TGC or TGT nucleic acid mutation that encodes a mutated PPX protein that includes an arginine to cysteine at a position corresponding to position 144 of SEQ ID NO: 1. In some embodiments, a mutated PPX gene includes a AGG→CAC or CAT nucleic acid mutation that encodes a mutated PPX protein that includes an arginine to histidine at a position corresponding to position 144 of SEQ TD NO: 1.

In some embodiments, a mutated PPX gene includes a TTT→CTT nucleic acid mutation that encodes a mutated PPX protein that includes a phenylalanine to leucine at a position corresponding to position 145 of SEQ ID NO: 1. In some embodiments, a mutated PPX gene includes a TTT→TAT nucleic acid mutation that encodes a mutated PPX protein that includes a phenylalanine to tyrosine at a position corresponding to position 145 of SEQ ID NO: 1. In some embodiments, a mutated PPX gene includes a GCA→ACA nucleic acid mutation that encodes a mutated PPX protein that includes an alanine to threonine at, a position corresponding to position 180 of SEQ ID NO: 1. In some embodiments, a mutated PPX gene includes a CCG→CAC or CAT nucleic acid mutation that encodes a mutated PPX protein that includes a proline to arginine at a position corresponding to position 185 of SEQ ID NO: 1. In some embodiments, a mutated PPX gene includes a CCG→CGT nucleic acid mutation that encodes a mutated PPX protein that includes a proline to histidine at a position corresponding to position 185 of SEQ ID NO: 1. In some embodiments, a mutated PPX gene includes a CCG→CGG nucleic acid mutation that encodes a mutated PPX protein that includes a proline to arginine at a position corresponding to position 185 of SEQ ID NO: 1. In some embodiments, a mutated PPX gene includes a GCT→TGT nucleic acid mutation that encodes a mutated PPX protein that includes an alanine to cysteine at a position corresponding to position 220 of SEQ ID NO: 1. In some embodiments, a mutated PPX gene includes a GCT→ATT nucleic acid mutation that encodes a mutated PPX protein that includes an alanine to isoleucine at a position corresponding to position 220 of SEQ ID NO: 1. In some embodiments, a mutated PPX gene includes a GCT→CTT nucleic acid mutation that encodes a mutated PPX protein that includes an alanine to leucine at a position corresponding to position 220 of SEQ ID NO: 1. In some embodiments, a mutated PPX gene includes a GCT→ACT nucleic acid mutation that encodes a mutated PPX protein that includes an alanine to threonine at a position corresponding to position 220 of SEQ ID NO: 1. In some embodiments, a mutated PPX gene includes a GCT→GTT nucleic acid mutation that encodes a mutated PPX protein that includes an alanine to valine at a position corresponding to position 220 of SEQ ID NO: 1. In some embodiments, a mutated PPX gene includes a GTG→ATG nucleic acid mutation that encodes a mutated PPX protein that includes a leucine to methionine at a position corresponding to position 226 of SEQ ID NO: 1. In some embodiments, a mutated PPX gene includes a ATG→CTG nucleic acid mutation that encodes a mutated PPX protein that includes a methionine to leucine at a position corresponding to position 228 of SEQ ID NO: 1. In some embodiments, a mutated PPX gene includes a AGC→GGC nucleic acid mutation that encodes a mutated PPX protein that includes a serine to glycine at a position corresponding to position 244 of SEQ ID NO: 1. In some embodiments, a mutated PPX gene includes a AGC→ACC nucleic acid mutation that encodes a mutated PPX protein that includes a serine to threonine at a position corresponding to position 244 of SEQ ID NO: 1. In some embodiments, a mutated PPX gene includes a CAG→TTC or TTT nucleic acid mutation that encodes a mutated PPX protein that includes a glutamine to asparagine at a position corresponding to position 272 of SEQ ID NO: 1. In some embodiments, a mutated PPX gene includes a TCA→TTA nucleic acid mutation that encodes a mutated PPX protein that includes a serine to leucine at a position corresponding to position 305 of SEQ ID NO: 1. In some embodiments, a mutated PPX gene includes a TCT→TGT nucleic acid mutation that encodes a mutated PPX protein that includes a serine to cysteine at a position corresponding to position 332 of SEQ ID NO: 1. In some embodiments, a mutated PPX gene includes a CTC-ATC nucleic acid mutation that encodes a mutated PPX protein that includes a leucine to isoleucine at a position corresponding to position 357 of SEQ ID NO: 1. In some embodiments, a mutated PPX gene includes a AAA→AGA nucleic acid mutation that encodes a mutated PPX protein that includes a lysine to arginine at a position corresponding to position 359 of SEQ ID NO: 1. In some embodiments, a mutated PPX gene includes a AAA→ACT nucleic acid mutation that encodes a mutated PPX protein that includes a lysine to threonine at a position corresponding to position 359 of SEQ ID NO: 1. In some embodiments, a mutated PPX gene includes a TTG→ATG nucleic acid mutation that encodes a mutated PPX protein that includes a leucine to methionine at a position corresponding to position 393 of SEQ ID NO: 1. In some embodiments, a mutated PPX gene includes a TTG→TCG nucleic acid mutation that encodes a mutated PPX protein that includes leucine to serine at a position corresponding to position 393 of SEQ ID NO: 1. In some embodiments, a mutated PPX gene includes a TTG→GTG nucleic acid mutation that encodes a mutated PPX protein that includes a leucine to valine at a position corresponding to position 393 of SEQ ID NO: 1. In some embodiments, a mutated PPX gene includes a TTA→CGA nucleic acid mutation that encodes a mutated PPX protein that includes a leucine to arginine at a position corresponding to position 403 of SEQ ID NO: 1. In some embodiments, a mutated PPX gene includes a TTA→TCA nucleic acid mutation that encodes a mutated PPX protein that includes a leucine to serine at a position corresponding to position 403 of SEQ ID NO: 1. In some embodiments, a mutated PPX gene includes a TTG→TCG nucleic acid mutation that encodes a mutated PPX protein that includes a leucine to serine at a position corresponding to position 424 of SEQ ID NO: 1. In some embodiments, a mutated PPX gene includes a TAC→TGC nucleic acid mutation that encodes a mutated PPX protein that includes a tyrosine to cysteine at a position corresponding to position 426 of SEQ ID NO: 1. In some embodiments, a mutated PPX gene includes a TAC→TTC nucleic acid mutation that encodes a mutated PPX protein that includes a tyrosine to phenylalanine at a position corresponding to position 426 of SEQ ID NO: 1. In some embodiments, a mutated PPX gene includes a TAC→CAC nucleic acid mutation that encodes a mutated PPX protein that includes a tyrosine to histidine at a position corresponding to position 426 of SEQ ID NO: 1. In some embodiments, a mutated PPX gene includes a TAC→ATC nucleic acid mutation that encodes a mutated PPX protein that includes a tyrosine to isoleucine at a position corresponding to position 426 of SEQ ID NO: 1. In some embodiments, a mutated PPX gene includes a TAC→TFA or CTC nucleic acid mutation that encodes a mutated PPX protein that includes a tyrosine to leucine at a position corresponding to position 426 of SEQ ID NO: 1. In some embodiments, a mutated PPX gene includes a TAC→CGC nucleic acid mutation that encodes a mutated PPX protein that includes a tyrosine to arginine at a position corresponding to position 426 of SEQ ID NO: 1, in some embodiments, a mutated PPX gene includes a TAC→ACC nucleic acid mutation that encodes a mutated PPX protein that includes a tyrosine to threonine at a position corresponding to position 426 of SEQ ID NO: 1. In some embodiments, a mutated PPX gene includes a TAC→GTC nucleic acid mutation that encodes a mutated PPX protein that includes a tyrosine to valine at a position corresponding to position 426 of SEQ ID NO: 1. In some embodiments, a mutated PPX gene includes a TTT→TCT nucleic acid mutation that encodes a mutated PPX protein that includes a phenylalanine to serine at a position corresponding to position 478 of SEQ ID NO: 1. In some embodiments, a mutated PPX gene includes a ATT→ACT nucleic acid mutation that encodes a mutated PPX protein that includes an isoleucine to threonine at a position corresponding to position 525 of SEQ ID NO: 1.

TABLE 3A

Summary of nucleotide/codon mutations in a potato plastidal PPX gene that lead to amino acid changes that confer tolerance to PPX inhibitors. Position numbers are based on numbering of the *Arabidopsis* plastidal PPX gene number At4g01690 (SEQ ID NO: 1).

| AA mtn | NA mtn |
|--------|--------|
| N52K | AAT → AAA |
| N85D | AAT → GAT |
| R144C | CGC → TGC |
| R144H | CGC → CAC |
| F145L | TTT → CTT |
| F145Y | TTT → TAT |
| A180T | GCC → ACC |
| P185H | CCT → CAT |
| P185R | CCT → CGT |
| A220C | GCC → TGC |
| A220I | GCC → ATC |
| A220L | GCC → CTC |
| A220T | GCC → ACC |
| A220V | GCC → GTC |
| L226M | TTG → ATG |
| M228L | ATG → CTG |
| S244G | AGC → GGC |
| S244T | AGC → ACC |
| K272F | AAA → TTT |
|  | AAA → TTC |
| S305L | TCT → CTT |
| S332C | AGT → TGT |
| L357I | CTT → ATT |
| S359R | AGT → AGA |
| S359T | AGT → ACT |
| L393M | TTG → ATG |
| L393S | TTG → TCG |
| L393V | TTG → GTG |
| L403R | CTA → CGA |
| L403S | CTA → TCA |
| L424S | TTG → TCG |
| Y426C | TAC → TGC |
| Y426F | TAC → TTC |
| Y426H | TAC → CAC |
| Y426I | TAC → ATC |
| Y426L | TAC → TTA |
|  | TAC → CTC |
| Y426R | TAC → CGC |
| Y426T | TAC → ACC |
| Y426V | TAC → GTC |
| F478S | TTT → TCT |
| S525T | TCT → ACT |

\* "AA mtn" refers to amino acid mutation;
"NA mtn" refers to nucleic acid mutation In some embodiments, in conjunction with any of the aspects, embodiments, methods and/or compositions disclosed herein, the one or more mutations in a mutated PPX gene may encode a mutated PPX protein having one or more mutations, two or more mutations, or three or more mutations selected from the group consisting of a asparagine to lysine at a position corresponding to position 52 of SEQ ID NO: 1; an asparagine to aspartic acid at a position corresponding to position 85 of SEQ ID NO: 1; an arginine to cysteine at a position corresponding to position 144 of SEQ ID NO: 1; an arginine to histidine at a position corresponding to position 144 of SEQ ID NO: 1; a phenylalanine to leucine at a position corresponding to position 145 of SEQ ID NO: 1, a phenylalanine to tyrosine at a position corresponding to position 145 of SEQ ID NO: 1; an alanine to threonine at a position corresponding to position 180 of SEQ ID NO: 1; a proline to histidine at a position corresponding to position 185 of SEQ ID NO: 1; a proline to arginine at a position corresponding to position 185 of SEQ ID NO: 1; an alanine to cysteine at a position corresponding to position 2.20 of SEQ ID NO: 1; an alanine to isoleucine at a position corresponding to position 220 of SEQ ID NO. 1; an alanine to leucine at a position corresponding to position 220 of SEQ ID NO: 1; an alanine to threonine at a position corresponding to position 220 of SEQ ID NO: 1; an alanine to valine at a position corresponding to position 220 of SEQ ID NO: 1; a leucine to methionine at a position corresponding to position 226 of SEQ ID NO: 1; a methionine to leucine at a position corresponding to position 228 of SEQ ID NO: 1; a serine to glycine at a position corresponding to position 244 of SEQ ID NO: 1; a serine to threonine at a position corresponding to position 244 of SEQ ID NO: 1; a lysine to phenylalanine at a position corresponding to position 272 of SEQ ID NO: 1; a serine to leucine at a position corresponding to position 305 of SEQ ID NO: 1; a serine to cysteine at a position corresponding to position 332 of SEQ ID NO: 1; a leucine to isoleucine at a position corresponding to position 357 of SEQ ID NO: 1; a serine to arginine at a position corresponding to position 359 of SEQ ID NO: 1; a serine to threonine at a position corresponding to position 359 of SEQ ID NO: 1; a leucine to methionine at a position corresponding to position 393 of SEQ ID NO: 1; a leucine to serine at a position corresponding to position 393 of SEQ ID NO: 1; a leucine to valine at a position corresponding to position 393 of SEQ ID NO: 1; a leucine to arginine at a position corresponding to position 403 of SEQ 1) NO: 1; a leucine to serine at a position corresponding to position 403 of SEQ ID NO: 1; a leucine to serine at a position corresponding to position 424 of SEQ ID NO: 1; a tyrosine to cysteine at a position corresponding to position 426 of SEQ 1 NO: 1; a tyrosine to phenylalanine at a position corresponding to position 426 of SEQ ID NO: 1; a tyrosine to histidine at a position corresponding to position 426 of SEQ ID NO: 1; a tyrosine to isoleucine at a position corresponding to position 426 of SEQ ID NO: 1; a tyrosine to leucine at a position corresponding to position 426 of SEQ ID NO: 1; a tyrosine to arginine at a position corresponding to position 426 of SEQ ID NO: 1; a tyrosine to threonine at a position corresponding to position 426 of SEQ ID NO: 1, a tyrosine to valine at a position corresponding to position 426 of SEQ ID NO: 1; a phenylalanine to serine at a position corresponding to position 478 of SEQ ID NO: 1; and a isoleucine to threonine at a position corresponding to position 525 of SEQ ID NO: 1.

In some embodiments, in conjunction with any of the aspects, embodiments, methods and/or compositions disclosed herein, a mutated PPX gene may encode a mutated PPX protein that includes an asparagine to lysine at a position corresponding to position 52 of SEQ ID NO: 1. In some embodiments, a mutated PPX gene encodes a mutated PPX protein that includes an asparagine to aspartic acid at a position corresponding to position 85 of SEQ ID NO 1. In some embodiments, a mutated PPX gene encodes a mutated PPX protein that includes an arginine to cysteine at a position corresponding to position 144 of SEQ ID NO: 1. In some embodiments, a mutated PPX gene encodes a mutated PPX protein that includes an arginine to histidine at a position corresponding to position 144 of SEQ ID NO: 1. In some embodiments, a mutated PPX gone encodes a mutated PPX protein that includes a phenyalanine to leucine at a position corresponding to position 145 of SEQ ID NO: 1. In some embodiments, a mutated PPX gene encodes a mutated PPX protein that includes a phenylalanine to tyrosine at a position corresponding to position 145 of SEQ ID NO: 1. In some embodiments, a mutated PPX gene encodes a mutated PPX protein that includes an alanine to threonine at a position corresponding to position 180 of SEQ ID NO: 1. In some embodiments, a mutated PPX gene encodes a mutated PPX protein that includes a proline to histidine at a position corresponding to position 185 of SEQ ID NO: 1. In some embodiments, a mutated PPX gene encodes a mutated PPX protein that includes a proline to arginine at a position corresponding to position 185 of SEQ ID NO: 1. In some embodiments, a mutated PPX gene encodes a mutated PPX protein that includes an alanine to cysteine at a position corresponding to position 220 of SEQ ID NO: 1. In some embodiments, a mutated PPX gene encodes a mutated PPX protein that includes an alanine to isoleucine at a position corresponding to position 220 of SEQ ID NO: 1. In some embodiments, a mutated PPX gene encodes a mutated PPX protein that includes an alanine to leucine at a position corresponding to position 220 of SEQ ID NO: 1. In some embodiments, a mutated PPX gene encodes a mutated PPX protein that includes an alanine to threonine at a position corresponding to position 220 of SEQ ID NO: 1 In some embodiments, a mutated PPX gene encodes a mutated PPX protein that includes an alanine to valine at a position corresponding to position 220 of SEQ ID NO: 1. In some embodiments, a mutated PPX gene encodes a mutated PPX protein that includes a leucine to methionine at a position corresponding to position 226 of SEQ ID NO: 1. In some embodiments, ta mutated PPX gene encodes a mutated PPX protein that includes a methionine to leucine at a position corresponding to position 228 of SEQ ID NO: 1. In some embodiments, a mutated PPX gene encodes a mutated PPX protein that includes a serine to glycine at a position corresponding to position 244 of SEQ ID NO: 1. In some embodiments, a mutated PPX gene encodes a mutated PPX protein that includes a serine to threonine at a position corresponding to position 244 of SEQ ID NO: 1. In some embodiments, a mutated PPX gene encodes a mutated PPX protein that includes a lysine to phenylalanine at a position corresponding to position 272 of SEQ ID NO: 1. In some embodiments, a mutated PPX gene encodes a mutated PPX protein that includes a serine to threonine at a position corresponding to position 244 of SEQ ID NO: 1. In some embodiments, a mutated PPX gene encodes a mutated PPX protein that includes a serine to leucine at a position corresponding to position 305 of SEQ ID NO: 1. In some embodiments, a mutated PPX gene encodes a mutated PPX protein that includes a serine to cysteine at a position corresponding to position 332 of SEQ ID NO: 1. In some embodiments, a mutated PPX gene encodes a mutated PPX protein that includes a leucine to isoleucine at a position corresponding to position 357 of SEQ ID NO: 1. In some embodiments, a mutated PPX gene encodes a mutated PPX protein that includes a serine to arginine: at a position corresponding to position 359 of SEQ ID NO: 1. In some embodiments, a mutated PPX gene encodes a mutated PPX protein that includes a serine to threonine at a position corresponding to position 359 of SEQ ID NO: 1. In some embodiments, a mutated PPX gene encodes a mutated PPX protein that includes a leucine to methionine at a position corresponding to position 393 of SEQ ID NO: 1. In some embodiments, a mutated PPX gene encodes a mutated PPX protein that includes leucine to serine at a position corresponding to position 393 of SEQ ID NO: 1. In some embodiments, a mutated PPX gene encodes a mutated PPX protein that includes a leucine to valine at a position corresponding to position 393 of SEQ ID NO: 1. In some embodiments, a mutated PPX gene encodes a mutated PPX protein that includes a leucine to arginine at a position corresponding to position 403 of SEQ ID NO: 1. In some embodiments, a mutated PPX gene encodes a mutated PPX protein that includes a leucine to serine at a position corresponding to position 403 of SEQ ID NO: 1. In some embodiments, a mutated PPX gene encodes a mutated PPX protein that includes a leucine to serine at a position corresponding to position 424 of SEQ ID NO: 1. In some embodiments, a mutated PPX gent: encodes a mutated PPX protein that includes a tyrosine to cysteine at a position corresponding to position 426 of SEQ ID NO: 1. In some embodiments, a mutated PPX gene encodes a mutated PPX protein that includes a tyrosine to phenylalanine at a position corresponding to position 426 of SEQ ID NO: 1. In some embodiments, a mutated PPX gene encodes a mutated PPX protein that includes a tyrosine to histidine at a position corresponding to position 426 of SEQ ID NO: 1. In some embodiments, a mutated PPX gene encodes a mutated PPX protein that includes a tyrosine to isoleucine at a position corresponding to position 426 of SEQ ID NO: 1. In some embodiments, a mutated PPX gene encodes a mutated PPX protein that includes a tyrosine to leucine at a position corresponding to position 426 of SEQ ID NO: 1. In some embodiments, a mutated PPX gene encodes a mutated PPX protein that includes a tyrosine to arginine at a position corresponding to position 426 of SEQ ID NO: 1. In some embodiments, a mutated PPX gene encodes a mutated PPX protein that includes a tyrosine to threonine at a position corresponding to position 426 of SEQ ID NO: 1. In some embodiments, a mutated PPX gene encodes a mutated PPX protein that includes a tyrosine to valine at a position corresponding to position 426 of SEQ ID NO: 1. In some embodiments, a mutated PPX gene encodes a mutated PPX protein that includes a phenylalanine to serine at a position corresponding to position 478 of SEQ ID NO: 1. In some embodiments, a mutated PPX gene encodes a mutated PPX protein that includes an isoleucine to threonine at a position corresponding to position 525 of SEQ ID NO: 1.

In some embodiments, a mutated PPX gene includes a AAT→AAA nucleic acid mutation that encodes a mutated PPX protein that includes an asparagine to lysine at a position corresponding to position 52 of SEQ ID NO: 7. In some embodiments, a mutated PPX gene includes a AAT→GAT nucleic acid mutation that encodes a mutated PPX protein that includes an asparagine to aspartic acid at a position corresponding to position 85 of SEQ ID NO: 7. In some embodiments, a mutated PPX gene includes a CGC→TGC nucleic acid mutation that encodes a mutated PPX protein that includes an arginine to cysteine at a position corresponding to position 144 of SEQ ID NO: 7. In some embodiments, a mutated PPX gene includes a CGC→CAC nucleic acid mutation that encodes a mutated PPX protein that includes an arginine to histidine at a position corresponding to position 144 of SEQ ID NO: 7. In some embodiments, a mutated PPX gene includes a TTT→CTT nucleic acid mutation that encodes a mutated PPX protein that includes a phenylalanine to leucine at a position corresponding to position 145 of SEQ ID NO: 7. In some embodiments, a mutated PPX gene includes a TTT→TAT nucleic acid mutation that encodes a mutated PPX protein that includes a phenylalanine to tyrosine at a position corresponding to position 145 of SEQ ID NO: 7. In some embodiments, a mutated PPX gene includes a GCC→ACC nucleic acid mutation that encodes a mutated PPX protein that includes an alanine to threonine at, a position corresponding to position 180 of SEQ ID NO: 7. In some embodiments, a mutated PPX gene includes a CCT→CAT nucleic acid mutation that encodes a mutated PPX protein that includes a proline to arginine at a position corresponding to position 185 of SEQ ID NO: 7. In some embodiments, a mutated PPX gene includes a CCT→CGT nucleic acid mutation that encodes a mutated PPX protein that includes a proline to histidine at a position corresponding to position 185 of SEQ ID NO: 7. In some embodiments, a mutated PPX gene includes a GCC→TGC nucleic acid mutation that encodes a mutated PPX protein that includes an alanine to cysteine at a position corresponding to position 220 of SEQ ID NO: 7. In some embodiments, a mutated PPX gene includes a CC→ATC nucleic acid mutation that encodes a mutated PPX protein that includes an alanine to isoleucine at a position corresponding to position 220 of SEQ ID NO: 7. In some embodiments, a mutated PPX gene includes a GCC→CTC nucleic acid mutation that encodes a mutated PPX protein that includes an alanine to leucine at a position corresponding to position 220 of SEQ ID NO: 7. In some embodiments, a mutated PPX gene includes a GCC→ACC nucleic acid mutation that encodes a mutated PPX protein that includes an alanine to threonine at a position corresponding to position 220 of SEQ ID NO: 7. In some embodiments, a mutated PPX gene includes a GCC→GTC nucleic acid mutation that encodes a mutated PPX protein that includes an alanine to valine at a position corresponding to position 220 of SEQ ID NO: 7. In some embodiments, a mutated PPX gene includes a TTG→ATG nucleic acid mutation that encodes a mutated PPX protein that includes a leucine to methionine at a position corresponding to position 226 of SEQ ID NO: 7. In some embodiments, a mutated PPX gene includes a ATG→CTG nucleic acid mutation that encodes a mutated PPX protein that includes a methionine to leucine at a position corresponding to position 228 of SEQ ID NO: 7. In some embodiments, a mutated PPX gene includes a AGC→GGC nucleic acid mutation that encodes a mutated PPX protein that includes a serine to glycine at a position corresponding to position 244 of SEQ ID NO: 7. In some embodiments, a mutated PPX gene includes a AGC→ACC nucleic acid mutation that encodes a mutated PPX protein that includes a serine to threonine at a position corresponding to position 244 of SEQ ID NO: 7. In some embodiments, a mutated PPX gene includes a AAA→AAT nucleic acid mutation that encodes a mutated PPX protein that includes a lysine to phenylalanine at a position corresponding to position 272 of SEQ ID NO: 7. In some embodiments, a mutated PPX gene includes a TCT→CTT nucleic acid mutation that encodes a mutated PPX protein that includes a serine to leucine at a position corresponding to position 305 of SEQ ID NO: 7. In some embodiments, a mutated PPX gene includes a AGT→TGT nucleic acid mutation that encodes a mutated PPX protein that includes a serine to cysteine at a position corresponding to position 332 of SEQ ID NO: 7. In some embodiments, a mutated PPX gene includes a CTT→ATT nucleic acid mutation that encodes a mutated PPX protein that includes a leucine to isoleucine at a position corresponding to position 357 of SEQ ID NO: 7. In some embodiments, a mutated PPX gene includes a AGT→AGA nucleic acid mutation that encodes a mutated PPX protein that includes a serine to arginine at a position corresponding to position 359 of SEQ ID NO: 7. In some embodiments, a mutated PPX gene includes a AGT→ACT nucleic acid mutation that encodes a mutated PPX protein that includes a serine to threonine at a position corresponding to position 359 of SEQ ID NO: 7. In some embodiments, a mutated PPX gene includes a TTG→ATG nucleic acid mutation that encodes a mutated PPX protein that includes a leucine to methionine at a position corresponding to position 393 of SEQ ID NO: 7. In some embodiments, a mutated PPX gene includes a TTG→TCG nucleic acid mutation that encodes a mutated PPX protein that includes leucine to serine at a position corresponding to position 393 of SEQ ID NO: 7. In some embodiments, a mutated PPX gene includes a TTG→GTG nucleic acid mutation that encodes a mutated PPX protein that includes a leucine to valine at a position corresponding to position 393 of SEQ ID NO: 7. In some embodiments, a mutated PPX gene includes a CTA→CGA nucleic acid mutation that encodes a mutated PPX protein that includes a leucine to arginine at a position corresponding to position 403 of SEQ ID NO: 7. In some embodiments, a mutated PPX gene includes a CTA→TCA nucleic acid mutation that encodes a mutated PPX protein that includes a leucine to serine at a position corresponding to position 403 of SEQ ID NO: 7. In some embodiments, a mutated PPX gene includes a TTG→TCG nucleic acid mutation that encodes a mutated PPX protein that includes a leucine to serine at a position corresponding to position 424 of SEQ ID NO:7. In some embodiments, a mutated PPX gene includes a TAC→TGC nucleic acid mutation that encodes a mutated PPX protein that includes a tyrosine to cysteine at a position corresponding to position 426 of SEQ ID NO: 7. In some embodiments, a mutated PPX gene includes a TAC→AAC nucleic acid mutation that encodes a mutated PPX protein that includes a tyrosine to phenylalanine at a position corresponding to position 426 of SEQ ID NO: 7. In some embodiments, a mutated PPX gene includes a TAC→CAC nucleic acid mutation that encodes a mutated PPX protein that includes a tyrosine to histidine at a position corresponding to position 426 of SEQ ID NO: 7. In some embodiments, a mutated PPX gene includes a TAC→ATC nucleic acid mutation that encodes a mutated PPX protein that includes a tyrosine to isoleucine at a position corresponding to position 426 of SEQ ID NO: 7. In some embodiments, a mutated PPX gene includes a TAC→TTC nucleic acid mutation that encodes a mutated PPX protein that includes a tryosine to leucine at a position corresponding to position 426 of SEQ ID NO: 7. In some embodiments, a mutated PPX gene includes a TAC→CGC nucleic acid mutation that encodes a mutated PPX protein that includes a tyrosine to arginine at a position corresponding to position 426 of SEQ ID NO: 7. In some embodiments, a mutated PPX gene includes a TAC→ACC nucleic acid mutation that encodes a mutated PPX protein that includes a tyrosine to threonine at a position corresponding to position 426 of SEQ ID NO: 7. In some embodiments, a mutated PPX gene includes a TAC→GTC nucleic acid mutation that encodes a mutated PPX protein that includes a tyrosine to valine at a position corresponding to position 426 of SEQ ID NO: 7. In some embodiments, a mutated PPX gene includes a TTT→TCT nucleic acid mutation that encodes a mutated PPX protein that includes a phenylalanine to serine at a position corresponding to position 478 of SEQ TD NO: 7. In some embodiments, a mutated PPX gene includes a TCT→ACT nucleic acid mutation that encodes a mutated PPX protein that includes an isoleucine to threonine at a position corresponding to position 525 of SEQ ID NO: 7.

TABLE 3B

Summary of nucleotide/codon mutations in a potato mitochondrial
PPX gene that lead to amino acid changes that confer
tolerance to PPX inhibitors. Position numbers are based
on numbering of the Solanum tuberosum mitochondrial
PPX gene number AJ225108 (SEQ ID NO: 9).

| AA mtn | NA mtn |
|--------|--------|
| D58N | GAT –> AAT |
| E64V | GAA –> GTA |
| G74C | GGT –> TGT |
| G84N | GGA –> GAT |
| R98C | CGC –> CAC |
| R98H | CGC –> TGC |
| R98L | CGC –> CTC |
| N139Y | CCT –> TAT |
| E150D | GAA –> GAT |
| E150K | GAA –> AAA |
| T500S | ACC _> AGC |
| S151T | AGT –> ACT |
| Q157L | CAG –> CTG |
| V164F | GTT –> TTT |
| D170E | GAT –> GAA |
| I187Q | AAG –> CAG |
| L188F | CTT –> TTT |
| N195K | AAT –> AAA |
| P214H | CCT –> CAT |
| P214S | CCT –> TCT |
| K229E | AAG –> GAG |
| K229Q | AAG –> CAG |
| K230R | AAG –> AGG |
| F283G | GAC –> GGC |
| A292G | GCA –> GGA |
| S296L | TCA –> TTA |
| C307S | TGT –> AGT |
| N324D | AAT –> GAT |
| N324K | AAT –> AAA |
| D330E | GAT –> GAA |
| A404S | GCC –> TCC |
| R406K | AGG –> AAG |
| K410I | AAA –> ATA |
| A423V | GCT –> GTT |
| C434S | TGC –> AGC |
| C434Y | TGC –> TAC |
| S448A | TCA –> GCA |
| D451G | GAT –> GGT |
| D454N | GAC –> AAC |
| Y465F | TAT –> TTT |
| K470T | AAG –> ACG |

* "AA mtn" refers to amino acid mutation;
"NA mtn" refers to nucleic acid mutation In conjunction with any of the aspects, embodiments, methods and/or compositions disclosed herein, a mutated PPX gene may encode a mutated PPX protein that includes an aspartic acid to asparagine at a position corresponding to position S of SEQ ID NO: 9. In some embodiments, a mutated PPX gene encodes a mutated PPX protein that includes glutamic acid to valine at a position corresponding to position 64 of SEQ ID NO: 9. In some embodiments, a mutated PPX gene encodes a mutated PPX protein that includes glycine to cysteine at a position corresponding to position 74 of SEQ ID NO: 9. In some embodiments, a mutated PPX gene encodes a mutated PPX protein that includes glycine to asparagine at a position corresponding to position 84 of SEQ ID NO: 9. In some embodiments, a mutated PPX gene encodes a mutated PPX protein that includes leucine to histidine at a position corresponding to position 93 of SEQ ID NO: 9. In some embodiments, a mutated PPX gene encodes a mutated PPX protein that includes lysine to arginine at a position corresponding to position 97 of SEQ ID NO: 9. In some embodiments, a mutated PPX gene encodes a mutated PPX protein that includes arginine to cysteine at a position corresponding to position 98 of SEQ ID NO: 9. In some embodiments, a mutated PPX gene encodes a mutated PPX protein that includes arginine to histidine at a position corresponding to position 98 of SEQ ID NO: 9. In some embodiments, a mutated PPX gone encodes a mutated PPX protein that includes arginine to leucine at a position corresponding to position 98 of SEQ ID NO: 9. In some embodiments, a mutated PPX gene encodes a mutated PPX protein that includes alanine to valine at a position corresponding to position 101 of SEQ ID NO: 9. In some embodiments, a mutated PPX gene encodes a mutated PPX protein that includes serine to asparagine at a position corresponding to position 119 of SEQ ID NO: 9. In some embodiments, a mutated PPX gene encodes a mutated PPX protein that includes phenylalanine to leucine at a position corresponding to position 121 of SEQ ID NO: 9. In some embodiments, a mutated PPX gene encodes a mutated PPX protein that includes threonine to isoleucine at a position corresponding to position 124 of SEQ ID NO: 9. In some embodiments, a mutated PPX gene encodes a mutated PPX protein that includes asparagine to tyrosine at a position corresponding to position 139 of SEQ ID NO: 9. In some embodiments, a mutated PPX gene encodes a mutated PPX protein that includes glutamic acid to aspartic acid at a position corresponding to position ISO of SEQ ID NO: 9. In some embodiments, a mutated PPX gene encodes a mutated PPX protein that includes glutamic acid to lysine at a position corresponding to position 150 of SEQ ID NO: 9. In some embodiments, a mutated PPX gene encodes a mutated PPX protein that includes serine to threonine at a position corresponding to position 151 of SEQ ID NO: 9. In some embodiments, a mutated PPX gene encodes a mutated PPX protein that includes glutamine to leucine at a position corresponding to position 157 of SEQ ID NO: 9. In some embodiments, a mutated PPX gene encodes a mutated PPX protein that includes valine to phenylalanine at a position corresponding to position 164 of SEQ ID NO: 9. In some embodiments, a mutated PPX gene encodes a mutated PPX protein that includes valine to alanine at a position corresponding to position 164 of SEQ ID NO: 9. In some embodiments, a mutated PX gene encodes a mutated PPX protein that includes aspartic acid to glutamic acid at a position corresponding to position 170 of SEQ ID NO.: 9. In some embodiments, a mutated PPX gene encodes a mutated PPX protein that includes cysteine to serine at a position corresponding to position 177 of SEQ ID NO: 9. In some embodiments, a mutated PPX gene encodes a mutated PPX protein that includes histidine to glutamine at a position corresponding to position 187 of SEQ ID NO: 9. In some embodiments, a mutated PPX gene encodes a mutated PPX protein that includes leucine to phenylalanine at a position corresponding to position 188 of SEQ ID NO: 9. In some embodiments, a mutated PPX gene encodes a mutated PPX protein that includes asparagine to lysine at a position corresponding to position 195 of SEQ ID NO: 9. In some embodiments, a mutated PPX gene encodes a mutated PPX protein that includes a proline to histidine at a position corresponding to position 214 of SEQ ID NO: 9. In some embodiments, a mutated PPX gene encodes a mutated PPX protein that includes a proline to serine at a position corresponding to position 214 of SEQ ID NO: 9. In some embodiments, a mutated PPX gene encodes a mutated PPX protein that includes an isoleucine to histidine at a position corresponding to position 215 of SEQ ID NO: 9. In some embodiments, a mutated PPX gene encodes a mutated IPX protein that includes an isoleucine to serine at a position corresponding to position 215 of SEQ ID NO: 9. In some embodiments, a mutated PPX gene encodes a mutated PPX protein that includes lysine to glutamic acid at a position corresponding to position 229 of SEQ ID NO: 9. In some embodiments, a mutated PPX gene encodes a mutated PPX protein that includes lysine to glutamine at a position corresponding to position 229 of SEQ ID NO: 9. In some embodiments, a mutated IPX gene encodes a mutated PPX protein that includes lysine to arginine at a position corresponding to position 230 of SEQ ID NO: 9. In some embodiments, a mutated PPX gene encodes a mutated PPX protein that includes cysteine to arginine at a position corresponding to position 271 of SEQ ID NO: 9. In some embodiments, a mutated PPX gene encodes a mutated PPX protein that includes aspartic acid to glycine at a position corresponding to position 274 of SEQ ID NO: 9. In some embodiments, a mutated PPX gene encodes a mutated PPX protein that includes aspartic acid to glycine at a position corresponding to position 278 of SEQ ID NO: 9. In some embodiments, a mutated PPX gene encodes a mutated PPX protein that includes a phenylalanine to glycine at a position corresponding to position 283 of SEQ ID NO: 9. In some embodiments, a mutated PPX gene encodes a mutated PPX protein that includes alanine to glycine at a position corresponding to position 292 of SEQ ID NO: 9. In some embodiments, a mutated PPX gene encodes a mutated PPX protein that includes serine to leucine at a position corresponding to position 296 of SEQ ID NO: 9. In some embodiments, a mutated PPX gene encodes a mutated PPX protein that includes cysteine to serine at a position corresponding to position 307 of SEQ ID NO: 9. In some embodiments, a mutated PPX gene encodes a mutated PPX protein that includes asparagine to aspartic acid at a position corresponding to position 324 of SEQ ID NO: 9. In some embodiments, a mutated PPX gene encodes a mutated PPX protein that includes asparagine to lysine at a position corresponding to position 324 of SEQ ID NO: 9. In some embodiments, a mutated PPX gene encodes a mutated PPX protein that includes aspartic acid to glutamic acid at a position corresponding to position 330 of SEQ ID NO: 9. In some embodiments, a mutated PPX gene encodes a mutated PPX protein that includes serine to leucine at a position corresponding to position 396 of SEQ ID NO: 9. In some embodiments, a mutated PPX gene encodes a mutated PPX protein that includes alanine to serine at a position corresponding to position 404 of SEQ ID NO: 9. In some embodiments, a mutated PPX gene encodes a mutated PPX protein that includes arginine to lysine at a position corresponding to position 406 of SEQ ID NO: 9. In some embodiments, a mutated PPX gene encodes a mutated PPX protein that includes lysine to isoleucine at a position corresponding to position 410 of SEQ ID NO: 9. In some embodiments, a mutated PPX gene encodes a mutated PPX protein that includes leucine to valine at a position corresponding to position 421 of SEQ ID NO: 9. In some embodiments, a mutated PPX gene encodes a mutated PPX protein that includes alanine to valine at a position corresponding to position 423 of SEQ ID NO: 9. In some embodiments, a mutated PPX gene encodes a mutated PPX protein that includes cysteine to serine at a position corresponding to position 434 of SEQ ID NO: 9. In some embodiments, a mutated PPX gene encodes a mutated PPX protein that includes cysteine to tyrosine at a position corresponding to position 434 of SEQ ID NO: 9. In some embodiments, a mutated PPX gene encodes a mutated PPX protein that includes aspartic acid to glycine at a position corresponding to position 447 of SEQ ID NO: 9. In some embodiments, a mutated PPX gene encodes a mutated PPX protein that includes serine to alanine at a position corresponding to position 448 of SEQ ID NO: 9. In some embodiments, a mutated PPX gene encodes a mutated PPX protein that includes valine to glutamic acid at a position corresponding to position 449 of SEQ ID NO: 9. In some embodiments, a mutated PPX gene encodes a mutated PPX protein that includes aspartic acid to glycine at a position corresponding to position 451 of SEQ ID NO: 9. In some embodiments, a mutated PPX gene encodes a mutated PPX protein that includes aspartic acid to asparagine at a position corresponding to position 454 of SEQ ID NO: 9. In some embodiments, a mutated PPX gene encodes a mutated PPX protein that includes tyrosine to phenylalanine at a position corresponding to position 465 of SEQ ID NO: 9. In some embodiments, a mutated PPX gene encodes a mutated PPX protein that includes lysine to threonine at a position corresponding to position 470 of SEQ ID NO: 9. In some embodiments, a mutated PPX gene encodes a mutated PPX protein that includes threonine to serine at a position corresponding to position 50) of SEQ ID NO: 9.

In conjunction with any of the aspects, embodiments, methods and/or compositions disclosed herein, a mutated PPX gene includes a GAT→AAT nucleic acid mutation that encodes a mutated PPX protein that includes an aspartic acid to asparagine at a position corresponding to position 58 of SEQ ID NO: 9. In some embodiments, a mutated PPX gene includes a GAA→GTA nucleic acid mutation that encodes a mutated PPX protein that includes glutamic acid to valine at a position corresponding to position 64 of SEQ ID NO: 9. In some embodiments, a mutated PPX gene includes a GGT→TGT nucleic acid mutation that encodes a mutated PPX protein that includes glycine to cysteine at a position corresponding to position 74 of SEQ ID NO: 9. In some embodiments, a mutated PPX gene includes a GGA GAT nucleic acid mutation that encodes a mutated PPX protein that includes glycine to asparagine at a position corresponding to position 84 of SEQ ID NO: 9. In some embodiments, a mutated PPX gene includes a CGC→TGC nucleic acid mutation that encodes a mutated PPX protein that includes arginine to cysteine at a position corresponding to position 9% of SEQ ID NO: 9. In some embodiments, a mutated PPX gene includes a CGC→CAC nucleic acid mutation that encodes a mutated PPX protein that includes arginine to histidine at a position corresponding to position 98 of SEQ ID NO: 9. In some embodiments, a mutated PPX gene includes a CGC→CTC nucleic acid mutation that encodes a mutated PPX protein that includes arginine to leucine at a position corresponding to position 98 of SEQ ID NO: 9. In some embodiments, a mutated PPX gene includes a AAT-→TAT nucleic acid mutation that encodes a mutated PPX protein that includes asparagine to tyrosine at a position corresponding to position 139 of SEQ ID NO: 9. In some embodiments, a mutated PPX gene includes a GAA→GAT nucleic acid mutation that encodes a mutated PPX protein that includes glutamic acid to aspartic acid at a position corresponding to position 150 of SEQ ID NO: 9. In some embodiments, a mutated PPX gene includes a GAA→AAA nucleic acid mutation that encodes a mutated PPX protein that includes glutamic acid to lysine at a position corresponding to position 150 of SEQ ID NO: 9. In some embodiments, a mutated PPX gene includes a AGT→ACT nucleic acid mutation that encodes a mutated PPX protein that includes serine to threonine at a position corresponding to position 151 of SEQ ID NO: 9. In some embodiments, a mutated PPX gene includes a CAG→CG nucleic acid mutation that encodes a mutated PPX protein that includes glutamine to leucine at a position corresponding to position 157 of SEQ ID NO: 9. In some embodiments, a mutated PPX gene includes a GTT→TTT nucleic acid mutation that encodes a mutated PPX protein that includes valine to phenylalanine at a position corresponding to position 164 of SEQ ID NO: 9. In some embodiments, a mutated PPX gene includes a GAT→GAA nucleic acid mutation that encodes a mutated PPX protein that includes aspartic acid to glutamic acid at a position corresponding to position 170 of SEQ ID NO: 9. In some embodiments, a mutated PPX genie includes a CAC→CAG nucleic acid mutation that encodes a mutated PPX protein that includes histidine to glutamine at a position corresponding to position 187 of SEQ ID NO: 9. In some embodiments, a mutated PPX gene includes a CTT→TTT nucleic acid mutation that encodes a mutated PPX protein that includes leucine to phenylalanine at a position corresponding to position 188 of SEQ ID NO: 9. In some embodiments, a mutated PPX gene includes a AAT→AAA nucleic acid mutation that encodes a mutated PPX protein that includes asparagine to lysine at a position corresponding to position 195 of SEQ ID NO: 9. In some embodiments, a mutated PPX gene includes a CCT→CAT nucleic acid mutation that encodes a mutated PPX protein that includes proline to histidine at a position corresponding to position 214 of SEQ ID NO: 9. In some embodiments, a mutated PPX gene includes a CCT→TCT nucleic acid mutation that encodes a mutated PPX protein that includes proline to serine at a position corresponding to position 214 of SEQ ID NO: 9. In some embodiments, a mutated PPX gene includes a AAG→GAG nucleic acid mutation that encodes a mutated PPX protein that includes lysine to glutamic acid at a position corresponding to position 229 of SEQ ID NO: 9. In some embodiments, a mutated PPX gene includes a AAG→CAG nucleic acid mutation that encodes a mutated PPX protein that includes lysine to glutamine at a position corresponding to position 229 of SEQ ID NO: 9. In some embodiments, a mutated PPX gene includes a AAG→AGG nucleic acid mutation that encodes a mutated PPX protein that includes lysine to arginine at a position corresponding to position 230 of SEQ ID NO: 9. In some embodiments, a mutated PPX gene includes a GAC→GGC nucleic acid mutation that encodes a mutated PPX protein that includes aspartic acid to glycine at a position corresponding to position 283 of SEQ ID NO: 9. In some embodiments, a mutated PPX gene includes a TCA→TA nucleic acid mutation that encodes a mutated PPX protein that includes serine to leucine at a position corresponding to position 296 of SEQ ID NO. 9. In some embodiments, a mutated PPX gene includes a TGT→AGT nucleic acid mutation that encodes a mutated PPX protein that includes cysteine to serine at a position corresponding to position 307 of SEQ ID NO: 9. In some embodiments, a mutated PPX gene includes a AAT→GAT nucleic acid mutation that encodes a mutated PPX protein that includes asparagine to aspartic acid at a position corresponding to position 324 of SEQ ID NO: 9. In some embodiments, a mutated PPX gene includes a AAT→AAA nucleic acid mutation that encodes a mutated PPX protein that includes asparagine to lysine at a position corresponding to position 324 of SEQ ID NO: 9, in some embodiments, a mutated PPX gene includes a GAT→GAA nucleic acid mutation that encodes a mutated PPX protein that includes aspartic acid to glutamic acid at a position corresponding to position 330 of SEQ ID NO: 9. In some embodiments, a mutated PPX gene includes a GCC→TCC nucleic acid mutation that encodes a mutated PPX protein that includes alanine to serine at a position corresponding to position 404 of SEQ ID NO: 9. In some embodiments, a mutated PPX gene includes a AGG→AAG nucleic acid mutation that encodes a mutated PPX protein that includes arginine to lysine at a position corresponding to position 406 of SEQ ID NO: 9. In some embodiments, a mutated PPX gene includes a AAA→ATA nucleic acid mutation that encodes a mutated PPX protein that includes lysine to isoleucine at a position corresponding to position 410 of SEQ ID NO: 9. In some embodiments, a mutated PPX gene includes a XXX GCT→GTT nucleic acid mutation that encodes a mutated PPX protein that includes alanine to valine at a position corresponding to position 423 of SEQ ID NO: 9. In some embodiments, a mutated PPX gene includes a TGC→AGC nucleic acid mutation that encodes a mutated PPX protein that includes cysteine to serine at a position corresponding to position 434 of SEQ ID NO: 9. In some embodiments, a mutated PPX gene includes a TGC→TAC nucleic acid mutation that encodes a mutated PPX protein that includes cysteine to tyrosine at a position corresponding to position 434 of SEQ ID NO: 9. In some embodiments, a mutated PPX gene includes a TCA→GCA nucleic acid mutation that encodes a mutated PPX protein that includes serine to alanine at a position corresponding to position 448 of SEQ ID NO: 9. In some embodiments, a mutated PPX gene includes a GAT→GGT nucleic acid mutation that encodes a mutated PPX protein that includes aspartic acid to glycine at a position corresponding to position 451 of SEQ ID NO: 9. In some embodiments, a mutated PPX gene includes a GAC→AAC nucleic acid mutation that encodes a mutated PPX protein that includes aspartic acid to asparagine at a position corresponding to position 454 of SEQ ID NO: 9. In some embodiments, a mutated PPX gene includes a TAT→TTT nucleic acid mutation that encodes a mutated PPX protein that includes tyrosine to phenylalanine at a position corresponding to position 465 of SEQ ID NO: 9. In some embodiments, a mutated PPX gene includes a AAG→ACG nucleic acid mutation that encodes a mutated PPX protein that includes lysine to threonine at a position corresponding to position 470 of SEQ ID NO: 9. In some embodiments, a mutated IPX gene includes a ACC→AGC nucleic acid mutation that encodes a mutated PPX protein that includes threonine to serine at a position corresponding to position 500 of SEQ ID NO: 9.

In conjunction with any of the aspects, embodiments, methods and/or compositions disclosed herein, a mutated PPX gene may include a CGG→AAA which encodes a mutated PPX protein that includes an glycine to lysine at a position corresponding to position 52 of SEQ ID NO: 1. In some embodiments, a mutated PPX gene includes a AAT→GAT nucleic acid mutation that encodes a mutated PPX protein that includes an asparagine to aspartic acid at a position corresponding to position 85 of SEQ ID NO: 1.

In some embodiments, in conjunction with any of the aspects, embodiments, methods and/or compositions disclosed herein, a mutated PPX gene may include a combination of mutations, for example, two or more, three or more, four or more, five or more or six or more mutations in a PPX gene. In certain embodiments, the combination of mutations is selected from the combinations of mutations shown in Tables 4a and 4b.

TABLE 4 A

Combinations of Amino Acid Mutations (each row of each of the three grouped columns represents a combination of mutations). Position numbers are based on numbering of the Arabidopsis plastidal PPX gene number 401690 (SEQ ID NO: 1)

| | | | | | |
|------|------|------|------|------|------|
| R144C | A220T | L226M | L424S | F145L | L424S |
| R144H | S332C | L226M | Y426F | A220T | Y426H |
| R144C | Q272F | A220T | Y426F | F145Y | L393V |
| R144C | K272F | A220T | Y426H | S244T | Y426F |

TABLE 4 A-continued

Combinations of Amino Acid Mutations (each row of each of the
three grouped columns represents a combination of mutations).
Position numbers are based on numbering of the Arabidopsis
plastidal PPX gene number 401690 (SEQ ID NO: 1)

| | | | | | | |
|------|------|------|------|------|------|------|
| G52K | R144H | S244T | R144C | Y426F | F145Y | L424S |
| N52K | R144H | S244T | N85D | Y426H | A220T | L403R |
| N85D | A220T | | R144C | Y426H | L226M | Y426F |
| RI 44H | S244T | | S244T | Y426H | N85D | Y426H |
| R144C | L226M | | S244G | Y426H | L226M | L424S |
| N85D | L226M | | A180T | Y426H | F145Y | L403R |
| N85D | F145Y | | L226M | Y426H | S244G | L393V |
| R144C | M228L | | F145L | Y426H | A180T | Y426H |
| N85D | A180T | | A220T | Y426H | R144C | Y426H |
| N85D | R144C | | N85D | Y426H | N85D | S525T |
| N85D | Q272F | | F145L | L393V | L226M | S525T |
| N85D | K272F | | L226M | L424S | FT45Y | S525T |
| N85D | M228L | | L226M | Y426F | F145L | S525T |
| A180T | Y426F | | A220T | L393V | S244G | S525T |
| F145L | Y426H | | A220T | Y426F | A180T | S525T |
| S244G | Y426F | | R144C | Y426F | R144C | S525T |
| F145L | L403R | | NS5D | I525T | | |
| F145Y | L424S | | L226M | I525T | | |
| R144C | L424S | | F145Y | I525T | | |
| L226M | Y426H | | F145L | I525T | | |
| A220T | L424S | | R144C | I525T | | |
| F145Y | Y426F | | R144C | Y426H | | |
| R144C | L393V | | A180T | Y426H | | |
| S244G | I525T | | A220T | Y426H | | |
| A180T | I525T | | L226M | Y426H | | |
| S244G | L393V | | S244T | L393V | | |
| L226M | L403R | | F145Y | Y426H | | |

In conjunction with any of the aspects, embodiments, methods and/or compositions disclosed herein, a mutated PPX protein includes an arginine to cysteine at a position corresponding to position 144 of SEQ ID NO: 1 and an alanine to threonine at a position corresponding to position 120 of SEQ ID NO: 1. In some embodiments, a mutated PPX protein includes an arginine to histidine at a position corresponding to position 144 of SEQ ID NO: 1 and a serine to cysteine at a position corresponding to position 332 of SEQ ID NO: 1. While in other embodiments, a mutated PPX protein includes an arginine to cysteine at a position corresponding to position 144 of SEQ ID NO: 1 and a glutamine to phenylalanine at a position corresponding to position 272 of SEQ ID NO: 1. In some embodiments, a mutated PPX protein includes an glycine to lysine at a position corresponding to position 52 of SEQ ID NO: 1, an arginine to histidine at a position corresponding to position 144 of SEQ ID NO: 1 and a serine to threonine at a position corresponding to position 244 of SEQ ID NO: 1. In some embodiments, a mutated PPX protein includes an asparagine to aspartic acid at a position corresponding to position 85 of SEQ ID NO: 1 and an alanine to threonine at a position corresponding to position 220 of SEQ ID NO: 1. In some embodiments, a mutated PPX protein includes an arginine to histidine at a position corresponding to position 144 of SEQ ID NO: 1 and a serine to threonine at a position corresponding to position 244 of SEQ ID NO: 1. In some embodiments, a mutated PPX protein includes an arginine to cysteine at a position corresponding to position 144 of SEQ ID NO: 1 and a leucine to methionine at a position corresponding to position 226 of SEQ ID NO: 1. In some embodiments, a mutated PPX protein includes an asparagine to aspartic acid at a position corresponding to position 85 of SEQ ID NO: 1 and a leucine to methionine at a position corresponding to position 226 of SEQ ID NO: 1. In some embodiments, a mutated PPX protein includes an asparagine to aspartic acid at a position corresponding to position 85 of SEQ ID NO: 1 and a phenylalanine to tyrosine at a position corresponding to position 145 of SEQ ID NO: 1. In some embodiments, a mutated PPX protein includes an arginine to cysteine at a position corresponding to position 144 of SEQ ID NO: 1 and a methionine to leucine at a position corresponding to position 228 of SEQ ID NO: 1. In some embodiments, a mutated PPX protein includes an asparagine to aspartic acid at a position corresponding to position 85 of SEQ ID NO: 1 and an alanine to threonine at a position corresponding to position 180 of SEQ ID NO: 1. In some embodiments, a mutated PPX protein includes an asparagine to aspartic acid at a position corresponding to position 85 of SEQ ID NO: 1 and an arginine to cysteine at a position corresponding to position 144 of SEQ ID NO: 1. In some embodiments, a mutated PPX protein includes an asparagine to aspartic acid at a position corresponding to position 85 of SEQ ID NO: 1 and a glutamine to phenylalanine at a position corresponding to position 272 of SEQ ID NO: 1. In some embodiments, a mutated PPX protein includes an asparagine to aspartic acid at a position corresponding to position 85 of SEQ ID NO: 1 and a methionine to leucine at a position corresponding to position 228 of SEQ ID NO: 1. In some embodiments, a mutated PPX protein includes an alanine to threonine at a position corresponding to position 180 of SEQ ID NO: 1 and a tyrosine to phenylalanine at a position corresponding to position 426 of SEQ ID NO: 1. In some embodiments, a mutated PPX protein includes a phenylalanine to leucine at a position corresponding to position 145 of SEQ ID NO: 1 and a tyrosine to histidine at a position corresponding to position 426 of SEQ ID NO: 1. In some embodiments, a mutated PPX protein includes a serine to glycine at a position corresponding to position 244 of SEQ ID NO: 1 and a tyrosine to phenylalanine at a position corresponding to position 426 of SEQ ID NO: 1. In some embodiments, a mutated PPX protein includes a phenylalanine to leucine at a position corresponding to position 145 of SEQ ID NO: 1 and a leucine to arginine at a position corresponding to position 403 of SEQ ID NO: 1. In some embodiments, a mutated PPX protein includes a phenylalanine to tyrosine at a position corresponding to position 145 of SEQ ID NO: 1 and a leucine to serine at a position corresponding to position 424 of SEQ ID NO: 1. In some embodiments, a mutated PPX protein includes an arginine to cysteine at a position corresponding to position 144 of SEQ ID NO: 1 and a leucine to serine at a position corresponding to position 424 of SEQ ID NO: 1. In some embodiments, a mutated PPX protein includes a leucine to methionine at a position corresponding to position 226 of SEQ ID NO: 1 and a tyrosine to histidine at a position corresponding to position 426 of SEQ ID NO: 1. In some embodiments, a mutated PPX protein includes an alanine to threonine at a position corresponding to position 220 of SEQ ID NO: 1 and a leucine to serine at a position corresponding to position 424 of SEQ ID NO: 1. In some embodiments, a mutated PPX protein includes a phenylalanine to tyrosine at a position corresponding to position 145 of SEQ ID NO: 1 and a tyrosine to phenylalanine at a position corresponding to position 426 of SEQ ID NO: 1. In some embodiments, a mutated PPX protein includes an arginine to cysteine at a position corresponding to position 144 of SEQ ID NO: 1 and a leucine to valine at a position corresponding to position 393 of SEQ ID NO: 1. In some embodiments, a mutated PPX protein includes a serine to glycine at a position corresponding to position 244 of SEQ ID NO: 1 and a leucine to valine at a position corresponding to position 393 of SEQ ID NO: 1, in some embodiments, a mutated PPX protein includes a leucine to methionine at a position corresponding to position 226 of SEQ ID NO: 1 and a leucine to arginine at a position corresponding to position 403 of SEQ ID NO: 1. In some embodiments, a mutated PPX protein includes a leucine to methionine at a position corresponding to position 226 of SEQ ID NO: 1 and a leucine to serine at a position corresponding to position 424 of SEQ ID NO: 1. In some embodiments, a mutated PPX protein includes a leucine to methionine at a position corresponding to position 226 of SEQ ID NO: 1 and a tyrosine to phenylalanine at a position corresponding to position 426 of SEQ ID NO: 1. In some embodiments, a mutated PPX protein includes an alanine to threonine at a position corresponding to position 220 of SEQ ID NO: 1 and a tyrosine to phenylalanine at a position corresponding to position 426 of SEQ ID NO: 1. In some embodiments, a mutated PPX protein includes an alanine to threonine at a position corresponding to position 220 of SEQ ID NO: 1 and a tyrosine to histidine at a position corresponding to position 426 of SEQ ID NO: 1. In some embodiments, a mutated PPX protein includes an arginine to cysteine at a position corresponding to position 144 of SEQ ID NO: 1 and a tyrosine to phenylalanine at, a position corresponding to position 426 of SEQ ID NO: 1. In some embodiments, a mutated PPX protein includes an asparagine to aspartic acid at a position corresponding to position 85 of SEQ ID NO: 1 and a tyrosine to histidine at a position corresponding to position 426 of SEQ ID NO: 1 In some embodiments, a mutated PPX protein includes an arginine to cysteine at a position corresponding to position 144 of SEQ ID NO: 1 and a tyrosine to histidine at a position corresponding to position 426 of SEQ ID NO: 1. In some embodiments, a mutated PPX protein includes a serine to threonine at a position corresponding to position 244 of SEQ ID NO: 1 and a tyrosine to histidine at a position corresponding to position 426 of SEQ ID NO: 1. In some embodiments, a mutated PPX protein includes a serine to glycine at a position corresponding to position 244 of SEQ ID NO: 1 and a tyrosine to histidine at a position corresponding to position 426 of SEQ ID NO: 1. In some embodiments, a mutated PPX protein includes an alanine to threonine at a position corresponding to position 180 of SEQ ID NO: 1 and a tyrosine to histidine at a position corresponding to position 426 of SEQ ID NO: 1. In some embodiments, a mutated PPX protein includes a leucine to methionine at a position corresponding to position 226 of SEQ ID NO: 1 and a tyrosine to histidine at a position corresponding to position 426 of SEQ ID NO: 1. In some embodiments, a mutated PPX protein includes a phenylalanine to leucine at a position corresponding to position 145 of SEQ ID NO: 1 and a tyrosine to histidine at a position corresponding to position 426 of SEQ ID NO: 1. In some embodiments, a mutated PPX protein includes an alanine to threonine at a position corresponding to position 220 of SEQ ID NO: 1 and a tyrosine to histidine at a position corresponding to position 426 of SEQ ID NO: 1. In some embodiments, a mutated PPX protein includes an asparagine to aspartic acid at a position corresponding to position E85 of SEQ ID NO: 1 and a tyrosine to histidine at a position corresponding to position 426 of SEQ ID NO: 1. In some embodiments, a mutated PPX protein includes a phenylalanine to leucine at a position corresponding to position 145 of SEQ ID NO: 1 and a leucine to valine at a position corresponding to position 393 of SEQ ID NO: 1. In some embodiments, a mutated PPX protein includes a leucine to methionine at a position corresponding to position 226 of SEQ ID NO: 1 and a leucine to serine at, a position corresponding to position 424 of SEQ ID NO: 1. In some embodiments, a mutated PPX protein includes a leucine to methionine at a position corresponding to position 226 of SEQ ID NO: 1 and a tyrosine to phenylalanine at a position corresponding to position 426 of SEQ ID NO: 1 In some embodiments, a mutated PPX protein includes an alanine to threonine at a position corresponding to position 220 of SEQ ID NO: 1 and a leucine to valine at a position corresponding to position 393 of SEQ ID NO: 1. In some embodiments, a mutated PPX protein includes an alanine to threonine at a position corresponding to position 220 of SEQ ID NO: 1 and a tyrosine to phenylalanine at a position corresponding to position 426 of SEQ ID NO: 1. In some embodiments, a mutated PPX protein includes an arginine to cysteine at a position corresponding to position 144 of SEQ ID NO: 1 and a tyrosine to phenylalanine at a position corresponding to position 426 of SEQ ID NO: 1. In some embodiments, a mutated PPX protein includes an arginine to cysteine at a position corresponding to position 144 of SEQ ID NO: 1 and a tyrosine to histidine at a position corresponding to position 426 of SEQ ID NO: 1. In some embodiments, a mutated PPX protein includes an alanine to threonine at a position corresponding to position 180 of SEQ ID NO: 1 and a tyrosine to histidine at a position corresponding to position 426 of SEQ ID NO: 1. In some embodiments, a mutated PPX protein includes an alanine to threonine at a position corresponding to position 220 of SEQ ID NO: 1 and a tyrosine to histidine at a position corresponding to position 426 of SEQ ID NO: 1. In some embodiments, a mutated PPX protein includes a leucine to methionine at a position corresponding to position 226 of SEQ ID NO: 1 and a tyrosine to histidine at a position corresponding to position 426 of SEQ ID NO: 1. In some embodiments, a mutated PPX protein includes a serine to threonine at a position corresponding to position 244 of SEQ ID NO: 1 and a leucine to valine at a position corresponding to position 393 of SEQ ID NO: 1. In some embodiments, a mutated PPX protein includes a phenylalanine to tyrosine at a position corresponding to position 145 of SEQ ID NO: 1 and a tyrosine to histidine at a position corresponding to position 426 of SEQ ID NO: 1. In some embodiments, a mutated PPX protein includes an arginine to cysteine at a position corresponding to position 144 of SEQ ID NO: 1 and an isoleucine to threonine at a position corresponding to position 525 of SEQ ID NO: 1. In some embodiments, a mutated PPX protein includes a phenylalanine to leucine at a position corresponding to position 145 of SEQ ID NO: 1 and a leucine to serine at a position corresponding to position 424 of SEQ ID NO: 1 in some embodiments, a mutated PPX protein includes an alanine to threonine at a position corresponding to position 220 of SEQ ID NO: 1 and a tyrosine to histidine at a position corresponding to position 426 of SEQ ID NO: 1. In some embodiments, a mutated PPX protein includes a phenylalanine to tyrosine at a position corresponding to position 145 of SEQ ID NO: 1 and a leucine to valine at a position corresponding to position 393 of SEQ ID NO: 1 In some embodiments, a mutated PPX protein includes a serine to threonine at a position corresponding to position 244 of SEQ ID NO: 1 and a tyrosine to phenylalanine at a position corresponding to position 426 of SEQ ID NO: 1. In some embodiments, a mutated PPX protein includes a phenylalanine to tyrosine at a position corresponding to position 145 of SEQ ID NO: 1 and a leucine to serine at a position corresponding to position 424 of SEQ ID NO: 1. In some embodiments, a mutated PPX protein includes an alanine to threonine at a position corresponding to position 220 of SEQ ID NO: 1 and a leucine to arginine at a position corresponding to position 403 of SEQ ID NO: 1. In some embodiments, a mutated PPX protein includes a leucine to methionine at a position corresponding to position 226 of SEQ ID NO: 1 and a tyrosine to phenylalanine at a position corresponding to position 426 of SEQ ID NO: 1. In some embodiments, a mutated PPX protein includes an asparagine to aspartic acid at a position corresponding to position 85 of SEQ ID NO: 1 and a tyrosine to histidine at a position corresponding to position 426 of SEQ ID NO: 1. In some embodiments, a mutated PPX protein includes a leucine to methionine at a position corresponding to position 226 of SEQ ID NO: 1 and a leucine to serine at a position corresponding to position 424 of SEQ ID NO: 1. In some embodiments, a mutated PPX protein includes a phenylalanine to tyrosine at a position corresponding to position 145 of SEQ ID NO: 1 and a leucine to arginine at a position corresponding to position 403 of SEQ ID NO: 1. In some embodiments, a mutated PPX protein includes a serine to glycine at a position corresponding to position 244 of SEQ ID NO: 1 and a leucine to valine at a position corresponding to position 393 of SEQ ID NO: 1. In some embodiments, a mutated PPX protein includes an alanine to threonine at a position corresponding to position 180 of SEQ ID NO: 1 and a tyrosine to histidine at a position corresponding to position 426 of SEQ ID NO: 1. In some embodiments, a mutated PPX protein includes an arginine to cysteine at a position corresponding to position 144 of SEQ ID NO: 1 and a tyrosine to histidine at a position corresponding to position 426 of SEQ ID NO: 1. In some embodiments, a mutated PPX protein includes a serine to glycine at a position corresponding to position 244 of SEQ ID NO: I and an isoleucine to threonine at a position corresponding to position 525 of SEQ ID NO: 1. In some embodiments, a mutated PPX protein includes an alanine to threonine at a position corresponding to position 180 of SEQ ID NO: 1 and an isoleucine to threonine at a position corresponding to position 525 of SEQ ID NO: 1. In some embodiments, a mutated PPX protein includes a phenylalanine to leucine at a position corresponding to position 145 of SEQ ID NO: 1 and an isoleucine to threonine at a position corresponding to position 525 of SEQ ID NO: 1. In some embodiments, a mutated PPX protein includes a phenylalanine to tyrosine at a position corresponding to position 145 of SEQ ID NO: 1 and an isoleucine to threonine at a position corresponding to position 525 of SEQ ID NO. 1. In some embodiments, a mutated PPX protein includes an asparagine to aspartic acid at a position corresponding to position 85 of SEQ ID NO: 1 and an isoleucine to threonine at a position corresponding to position 525 of SEQ ID NO: 1. In some embodiments, a mutated PPX protein includes a leucine to methionine at a position corresponding to position 226 of SEQ ID NO: 1 and an isoleucine to threonine at a position corresponding to position 525 of SEQ ID NO: 1.

In conjunction with any of the aspects, embodiments, methods and/or compositions disclosed herein, a mutated PPX protein includes an arginine to cysteine at a position corresponding to position 144 of SEQ ID NO: 1 and an alanine to threonine at a position corresponding to position 220 of SEQ ID NO: 1. In some embodiments, a mutated PPX protein includes an arginine to histidine at a position corresponding to position 144 of SEQ 10 NO: 1 and a serine to cysteine at a position corresponding to position 332 of SEQ ID NO: 1. In some embodiments, a mutated PPX protein includes an arginine to cysteine at a position corresponding to position 144 of SEQ ID NO: 7 and a lysine to phenylalanine at a position corresponding to position 272 of SEQ ID NO: 7. In some embodiments, a mutated PPX protein includes an asparagine to lysine at a position corresponding to position 52 of SEQ ID NO: 7, an arginine to histidine at a position corresponding to position 144 of SEQ ID NO. 7 and a serine to threonine at a position corresponding to position 244 of SEQ ID NO: 7. In some embodiments, a mutated PPX protein includes an asparagine to aspartic acid at a position corresponding to position 85 of SEQ ID NO: 1 and an alanine to threonine at a position corresponding to position 220 of SEQ ID NO: 1. In some embodiments, a mutated PPX protein includes an arginine to histidine at a position corresponding to position 144 of SEQ ID NO: 1 and a serine to threonine at a position corresponding to position 244 of SEQ ID NO: 1. In some embodiments, a mutated PPX protein includes an arginine to cysteine at a position corresponding to position 144 of SEQ ID NO: 1 and a leucine to methionine at a position corresponding to position 226 of SEQ ID NO: 1. In some embodiments, a mutated PPX protein includes an asparagine to aspartic acid at a position corresponding to position 85 of SEQ ID NO: 1 and a leucine to methionine at a position corresponding to position 226 of SEQ ID NO: 1. In some embodiments, a mutated PPX protein includes an asparagine to aspartic acid at a position corresponding to position 85 of SEQ ID NO: 1 and a phenylalanine to tyrosine at a position corresponding to position 145 of SEQ ID NO: 1. In some embodiments, a mutated PPX protein includes an arginine to cysteine at a position corresponding to position 144 of SEQ ID NO: 1 and a methionine to leucine at a position corresponding to position 228 of SEQ ID NO: 1. In some embodiments, a mutated PPX protein includes an asparagine to aspartic acid at a position corresponding to position 85 of SEQ ID NO: 1 and an alanine to threonine at a position corresponding to position 180 of SEQ ID NO: 1. In some embodiments, a mutated PPX protein includes an asparagine to aspartic acid at a position corresponding to position 85 of SEQ ID NO: 1 and an arginine to cysteine at a position corresponding to position 144 of SEQ ID NO: 1. In some embodiments, a mutated PPX protein includes an asparagine to aspartic acid at a position corresponding to position 85 of SEQ ID NO: 1 and an lysine to phenylalanine at a position corresponding to position 272 of SEQ ID NO: 1. In some embodiments, a mutated PPX protein includes an asparagine to aspartic acid at a position corresponding to position 85 of SEQ ID NO: 1 and a methionine to leucine at a position corresponding to position 228 of SEQ ID NO: 1. In some embodiments, a mutated PPX protein includes an alanine to threonine at a position corresponding to position 180 of SEQ ID NO: 1 and a tyrosine to phenylalanine at a position corresponding to position 426 of SEQ ID NO: 1. In some embodiments, a mutated PPX protein includes a phenylalanine to leucine at a position corresponding to position 145 of SEQ ID NO: 1 and a tyrosine to histidine at a position corresponding to position 426 of SEQ ID NO: 1. In some embodiments, a mutated PPX protein includes a serine to glycine at a position corresponding to position 244 of SEQ ID NO: 1 and a tyrosine to phenylalanine at a position corresponding to position 426 of SEQ ID NO: 1. In some embodiments, a mutated PPX protein includes a phenylalanine to leucine at a position corresponding to position 145 of SEQ ID NO: 1 and a leucine to arginine at a position corresponding to position 403 of SEQ ID NO: 1. In some embodiments, a mutated PPX protein includes a phenylalanine to tyrosine at a position corresponding to position 145 of SEQ ID NO: 1 and a leucine to serine at a position corresponding to position 424 of SEQ HD NO: 1. In some embodiments, a mutated PPX protein includes an arginine to cysteine at a position corresponding to position 144 of SEQ ID NO: 1 and a leucine to serine at a position corresponding to position 424 of SEQ ID NO: 1. In some embodiments, a mutated PPX protein includes a leucine to methionine at a position corresponding to position 226 of SEQ ID NO: 1 and a tyrosine to histidine at a position corresponding to position 426 of SEQ TD NO: 1. In some embodiments, a mutated PPX protein includes an alanine to threonine at a position corresponding to position 220 of SEQ ID NO: 1 and a leucine to serine at a position corresponding to position 424 of SEQ ID NO: 1. In some embodiments, a mutated PPX protein includes a phenylalanine to tyrosine at a position corresponding to position 145 of SEQ ID NO: 1 and a tyrosine to phenylalanine at a position corresponding to position 426 of SEQ ID NO: 1. In some embodiments, a mutated PPX protein includes an arginine to cysteine at a position corresponding to position 144 of SEQ ID NO: 1 and a leucine to valine at a position corresponding to position 393 of SEQ ID NO: 1. In some embodiments, a mutated PPX protein includes a serine to glycine at a position corresponding to position 244 of SEQ ID NO: 1 and a leucine to valine at a position corresponding to position 393 of SEQ ID NO: 1. In some embodiments, a mutated PPX protein includes a leucine to methionine at a position corresponding to position 226 of SEQ ID NO: 1 and a leucine to arginine at a position corresponding to position 403 of SEQ ID NO: 1. In some embodiments, a mutated PPX protein includes a leucine to methionine at a position corresponding to position 226 of SEQ ID NO: 1 and a leucine to serine at a position corresponding to position 424 of SEQ ID NO: 1. In some embodiments, a mutated PPX protein includes a leucine to methionine at a position corresponding to position 226 of SEQ ID NO: 1 and a tyrosine to phenylalanine at a position corresponding to position 426 of SEQ ID NO: 1. In some embodiments, a mutated PPX protein includes an alanine to threonine at a position corresponding to position 220 of SEQ ID NO: 1 and a tyrosine to phenylalanine at a position corresponding to position 426 of SEQ ID NO: 1. In some embodiments, a mutated PPX protein includes an alanine to threonine at a position corresponding to position 220 of SEQ ID NO: 1 and a tyrosine to histidine at a position corresponding to position 426 of SEQ ID NO: 1. In some embodiments, a mutated PPX protein includes an arginine to cysteine at a position corresponding to position 144 of SEQ ID NO: 1 and a tyrosine to phenylalanine at a position corresponding to position 426 of SEQ ID NO: 1. In some embodiments, a mutated PPX protein includes an asparagine to aspartic acid at a position corresponding to position 85 of SEQ ID NO: 1 and a tyrosine to histidine at a position corresponding to position 426 of SEQ ID NO: 1. In some embodiments, a mutated PPX protein includes an arginine to cysteine at a position corresponding to position 144 of SEQ ID NO: 1 and a tyrosine to histidine at a position corresponding to position 426 of SEQ ID NO: 1. In some embodiments, a mutated PPX protein includes a serine to threonine at a position corresponding to position 244 of SEQ ID NO: i and a tyrosine to histidine at a position corresponding to position 426 of SEQ ID NO: 1. In some embodiments, a mutated PPX protein includes a serine to glycine at a position corresponding to position 244 of SEQ ID NO: 1 and a tyrosine to histidine at, a position corresponding to position 426 of SEQ ID NO: 1. In some embodiments, a mutated PPX protein includes an alanine to threonine at a position corresponding to position 180 of SEQ ID NO: 1 and a tyrosine to histidine at a position corresponding to position 426 of SEQ ID NO: 1 In some embodiments, a mutated PPX protein includes a leucine to methionine at a position corresponding to position 226 of SEQ ID NO: 1 and a tyrosine to histidine at a position corresponding to position 426 of SEQ ID NO: 1. In some embodiments, a mutated PPX protein includes a phenylalanine to leucine at a position corresponding to position 145 of SEQ ID NO: 1 and a tyrosine to histidine at a position corresponding to position 426 of SEQ ID NO: 1. In some embodiments, a mutated PPX protein includes an alanine to threonine at a position corresponding to position 220 of SEQ ID NO: 1 and a tyrosine to histidine at a position corresponding to position 426 of SEQ ID NO: 1. In some embodiments, a mutated PPX protein includes an asparagine to aspartic acid at a position corresponding to position 85 of SEQ ID NO: 1 and a tyrosine to histidine at, a position corresponding to position 426 of SEQ ID NO: 1. In some embodiments, a mutated PPX protein includes a phenylalanine to leucine at a position corresponding to position 145 of SEQ ID NO: 1 and a leucine to valine at a position corresponding to position 393 of SEQ ID NO: 1. In some embodiments, a mutated PPX protein includes a leucine to methionine at a position corresponding to position 226 of SEQ ID NO: 1 and a leucine to serine at a position corresponding to position 424 of SEQ ID NO: 1. In some embodiments, a mutated PPX protein includes a leucine to methionine at a position corresponding to position 226 of SEQ ID NO: 1 and a tyrosine to phenylalanine at a position corresponding to position 426 of SEQ ID NO: 1. In some embodiments, a mutated PPX protein includes an alanine to threonine at a position corresponding to position 220 of SEQ ID NO: 1 and a leucine to valine at a position corresponding to position 393 of SEQ ID NO: 1. In some embodiments, a mutated PPX protein includes an alanine to threonine at a position corresponding to position 220 of SEQ ID NO: 1 and a tyrosine to phenylalanine at a position corresponding to position 426 of SEQ ID NO: 1. In some embodiments, a mutated PPX protein includes an arginine to cysteine at a position corresponding to position 144 of SEQ ID NO: 1 and a tyrosine to phenylalanine at a position corresponding to position 426 of SEQ ID NO: 1. In some embodiments, a mutated PPX protein includes an arginine to cysteine at a position corresponding to position 144 of SEQ ID NO: 1 and a tyrosine to histidine at a position corresponding to position 426 of SEQ ID NO: 1. In some embodiments, a mutated PPX protein includes an alanine to threonine at a position corresponding to position 180 of SEQ ID NO: 1 and a tyrosine to histidine at a position corresponding to position 426 of SEQ ID NO: 1. In some embodiments, a mutated PPX protein includes an alanine to threonine at a position corresponding to position 220 of SEQ ID NO: 1 and a tyrosine to histidine at a position corresponding to position 426 of SEQ ID NO: 1. In some embodiments, a mutated PPX protein includes a leucine to methionine at a position corresponding to position 226 of SEQ ID NO: 1 and a tyrosine to histidine at a position corresponding to position 426 of SEQ ID NO: 1. In some embodiments, a mutated PPX protein includes a serine to threonine at a position corresponding to position 244 of SEQ ID NO: 1 and a leucine to valine at a position corresponding to position 393 of SEQ ID NO: 1. In some embodiments, a mutated PPX protein includes a phenylalanine to tyrosine at a position corresponding to position 145 of SEQ ID NO: 1 and a tyrosine to histidine at a position corresponding to position 426 of SEQ ID NO: 1. In some embodiments, a mutated PPX protein includes an arginine to cysteine at a position corresponding to position 144 of SEQ ID NO: 7 and an isoleucine to threonine at a position corresponding to position 525 of SEQ ID NO: 7. In some embodiments, a mutated PPX protein includes a phenylalanine to leucine at a position corresponding to position 145 of SEQ ID NO: 1 and a leucine to serine at a position corresponding to position 424 of SEQ ID NO: 1. In some embodiments, a mutated PPX protein includes an alanine to threonine at a position corresponding to position 220 of SEQ ID NO: 1 and a tyrosine to histidine at a position corresponding to position 426 of SEQ ID NO: 1. In some embodiments, a mutated PPX protein includes a phenylalanine to tyrosine at a position corresponding to position 145 of SEQ ID NO: 1 and a leucine to valine at a position corresponding to position 393 of SEQ ID NO: 1. In some embodiments, a mutated PPX protein includes a serine to threonine at a position corresponding to position 244 of SEQ ID NO: 1 and a tyrosine to phenylalanine at a position corresponding to position 426 of SEQ ID NO: 1. In some embodiments, a mutated PPX protein includes a phenylalanine to tyrosine at a position corresponding to position 145 of SEQ ID NO: 1 and a leucine to serine at a position corresponding to position 424 of SEQ ID NO: 1. In some embodiments, a mutated PPX protein includes an alanine to threonine at a position corresponding to position 220 of SEQ ID NO: 1 and a leucine to arginine at a position corresponding to position 403 of SEQ ID NO: 1. In some embodiments, a mutated PPX protein includes a leucine to methionine at a position corresponding to position 226 of SEQ ID NO: 1 and a tyrosine to phenylalanine at a position corresponding to position 426 of SEQ ID NO: 1. In some embodiments, a mutated PPX protein includes an asparagine to aspartic acid at a position corresponding to position 85 of SEQ ID NO: 1 and a tyrosine to histidine at a position corresponding to position 426 of SEQ ID NO: 1. In some embodiments, a mutated PPX protein includes a leucine to methionine at a position corresponding to position 226 of SEQ ID NO: i and a leucine to serine at a position corresponding to position 424 of SEQ ID NO: 1. In some embodiments, a mutated PPX protein includes a phenylalanine to tyrosine at a position corresponding to position 145 of SEQ ID NO: 1 and a leucine to arginine at a position corresponding to position 403 of SEQ ID NO: 1. In some embodiments, a mutated PPX protein includes a serine to glycine at a position corresponding to position 244 of SEQ ID NO: 1 and a leucine to valine at a position corresponding to position 393 of SEQ ID NO: 1 in some embodiments, a mutated PPX protein includes an alanine to threonine at a position corresponding to position 180 of SEQ ID NO: 1 and a tyrosine to histidine at a position corresponding to position 426 of SEQ ID NO: 1. In some embodiments, a mutated PPX protein includes an arginine to cysteine at a position corresponding to position 144 of SEQ ID NO: 1 and a tyrosine to histidine at a position corresponding to position 426 of SEQ ID NO: 1. In some embodiments, a mutated PPX protein includes a serine to glycine at a position corresponding to position 244 of SEQ ID NO: 1 and an isoleucine to threonine at a position corresponding to position 525 of SEQ ID NO: 1. In some embodiments, a mutated PPX protein includes a serine to glycine at a position corresponding to position 244 of SEQ ID NO: 7 and an isoleucine to threonine at a position corresponding to position 525 of SEQ ID NO: 7. In some embodiments, a mutated PPX protein includes an alanine to threonine at a position corresponding to position 180 of SEQ ID NO: 7 and an isoleucine to threonine at a position corresponding to position 525 of SEQ ID NO: 7. In some embodiments, a mutated PPX protein includes a phenylalanine to leucine at a position corresponding to position 145 of SEQ ID NO: 7 and an isoleucine to threonine at a position corresponding to position 525 of SEQ ID: NO: 7. In some embodiments, a mutated PPX protein includes a phenylalanine to tyrosine at a position corresponding to position 145 of SEQ ID NO: 7 and an isoleucine to threonine at a position corresponding to position 525 of SEQ ID NO: 7. In some embodiments, a mutated PPX protein includes an asparagine to aspartic acid at a position corresponding to position 85 of SEQ ID NO: 7 and an isoleucine to threonine at a position corresponding to position 525 of SEQ ID NO: 7. In some embodiments, a mutated PPX protein includes a leucine to methionine at a position corresponding to position 226 of SEQ ID NO: 7 and an isoleucine to threonine at a position corresponding to position 525 of SEQ ID NO: 7.

TABLE 4B

Combinations of Amino Acid Mutations (each row of each of the two grouped columns represents a combination of mutations). Position numbers are based on numbering of the Solanum tuberosum mitochondrial PPX gene number AJ225108 (SEQ ID NO: 9).

| | | | | |
|---|---|---|---|---|
| G74C | R98C | | | |
| L93H | V164A | | | |
| R98L | P214H | | | |
| R98L | T124I | L188F | K229Q | |
| R98L | T124I | P214H | K229Q | |
| R98L | T124I | K229Q | | |
| S119N | N139Y | | | |
| F121L | E150D | | | |
| S151T | K229E | K230R | | |
| Q157L | H187Q | | | |
| C271R | D274G | | | |
| C307S | A423V | | | |
| S396L | K410I | | | |
| C434S | T500S | | | |
| D447G | A292G | | | |
| S448A | N324D | | | |
| Y465F | K470T | | | |
| R98L | P214H | A243V | | |
| R98L | T124I | L188F | K229Q | A243V |
| R98L | T124I | P214H | K229Q | A243V |
| R98L | T124I | K229Q | A423V | |
| R98L | P214H | C307S | | |
| R98L | T124I | L188F | K229Q | C307S |
| R98L | T124I | P214H | K229Q | C307S |
| R98L | T124I | K229Q | C307S | |
| R98C | P214H | | | |
| R98C | T124I | L188F | K229Q | |
| R98C | T124I | P214H | K229Q | |
| R98C | T124I | K229Q | | |
| R98C | P214H | A423V | | |
| R98C | T124I | L188F | K229Q | A423V |
| R98C | T124I | P214H | K229Q | A423V |
| R98C | T124I | K229Q | A423V | |
| R98C | P214H | C307S | | |
| R98C | T124I | L188F | K229Q | C307S |
| R98C | T124I | P214H | K229Q | C307S |
| R98C | T124I | K229Q | C307S | |
| R98H | P214H | | | |
| R98H | T124I | L188F | K229Q | |
| R98H | T124I | P214H | K229Q | |
| R98H | T124I | K229Q | | |
| R98H | P214H | A423V | | |
| R98H | T124I | L188F | K229Q | A423V |
| R98H | T124I | P214H | K229Q | A423V |
| R98H | T124I | K229Q | A423V | |
| R98H | P214H | C307S | | |
| R98H | T124I | L188F | K229Q | C307S |
| R98H | T124I | P214H | K229Q | C307S |
| R98H | T124I | K229Q | C307S | |

In conjunction with any of the aspects, embodiments, methods and/or compositions disclosed herein, a mutated PPX protein includes a glycine to cysteine at a position corresponding to position 74 of SEQ ID NO: 9 and an arginine to cysteine at a position corresponding to position 98 of SEQ ID NO: 9. In some embodiments, a mutated PPX protein includes an leucine to histidine at a position corresponding to position 93 of SEQ ID NO: 9 and a valine to alanine at a position corresponding to position 164 of SEQ ID NO: 9. In some embodiments, a mutated PPX protein includes an arginine to leucine at a position corresponding to position 98 of SEQ ID NO: 9 and a proline to histidine at a position corresponding to position 214 of SEQ ID NO. 9. In some embodiments, a mutated PPX protein includes an arginine to leucine at a position corresponding to position 98 of SEQ ID NO: 9, a threonine to isoleucine at a position corresponding to position 124 of SEQ ID NO: 9, a leucine to phenylalanine at a position corresponding to position 181 of SEQ ID NO: 9, and a lysine to glutamine at a position corresponding to position 229 of SEQ ID NO: 9, in some embodiments, a mutated PPX protein includes an arginine to leucine at a position corresponding to position 98 of SEQ ID NO: 9, a thromine to isoleucine at a position corresponding to position 124 of SEQ ID NO: 9, a proline to histidine at a position corresponding to position 214, and a lysine to glutamine at a position corresponding to position 229 of SEQ ID NO: 9. In some embodiments, a mutated PPX protein includes an arginine to leucine at, a position corresponding to position 98 of SEQ ID NO: 9, a threonine to isoleucine at a position corresponding to position 124 of SEQ ID NO: 9, and a lysine to glutamine at a position corresponding to position 229 of SEQ ID NO: 9. In some embodiments, a mutated PPX protein includes a serine to asparagine at a position corresponding to position 119 of SEQ ID NO: 9 and an asparagine to tyrosine at a position corresponding to position 139 of SEQ ID NO: 9. In some embodiments, a mutated PPX protein includes a phenylalanine to leucine at a position corresponding to position 121 of SEQ ID NO: 9 and a glutamic acid to aspartic acid at a position corresponding to position 150 of SEQ ID NO: 9. In some embodiments, a mutated PPX protein includes a serine to threonine at a position corresponding to position 151 of SEQ ID NO: 9, a lysine to glutamic acid at a position corresponding to position 229 of SEQ ID NO: 9, and a lysine to arginine at a position corresponding to position 230 of SEQ ID NO: 9. In some embodiments, a mutated PPX protein includes a glutamine to leucine at a position corresponding to position 157 of SEQ ID NO: 9 and a histidine to glutamic at a position corresponding to position 187 of SEQ ID NO: 9. In some embodiments, a mutated PPX protein includes a cysteine to arginine at a position corresponding to position 271 of SEQ ID NO: 9 and a aspartic acid to glycine at a position corresponding to position 274 of SEQ ID NO: 9. In some embodiments, a mutated PPX protein includes a cysteine to serine at a position corresponding to position 307 of SEQ ID NO: 9 and an alanine to valine at a position corresponding to position 423 of SEQ ID NO: 9. In some embodiments, a mutated PPX protein includes a serine to leucine at a position corresponding to position 396 of SEQ ID NO: 9 and a lysine to isoleucine at a position corresponding to position 410 of SEQ ID NO: 9. In some embodiments, a mutated PPX protein includes a cysteine to serine at a position corresponding to position 434 of SEQ ID NO: 9 and a threonine to serine at a position corresponding to position 500 of SEQ ID NO: 9. In some embodiments, a mutated PPX protein includes an aspartic acid to glycine at a position corresponding to position 447 of SEQ ID NO: 9 and an alanine to glycine at a position corresponding to position 292 of SEQ ID NO: 9. In some embodiments, a mutated PPX protein includes a serine to alanine at a position corresponding to position 448 of SEQ ID NO: 9 and an asparagine to aspartic acid at a position corresponding to position 324 of SEQ ID NO: 9. In some embodiments, a mutated PPX protein includes a tyrosine to phenylalanine at a position corresponding to position 465 of SEQ ID NO: 9 and a lysine to threonine at a position corresponding to position 470 of SEQ ID NO: 9. In some embodiments, a mutated PPX protein includes an arginine to leucine at a position corresponding to position 98 of SEQ ID NO: 9, a proline to histidine at a position corresponding to position 214 of SEQ ID NO: 9, and an alanine to valine at a position corresponding to position 243 of SEQ ID NO: 9. In some embodiments, a mutated PPX protein includes an arginine to leucine at a position corresponding to position 98 of SEQ ID NO: 9, a threonine to isoleucine at a position corresponding to position 124 of SEQ ID NO: 9, a leucine to phenylalanine at a position corresponding to position 188 of SEQ ID NO: 9, a lysine to glutamine at a position corresponding to position 229 of SEQ ID NO: 9, and an alanine to valine at a position corresponding to position 243 of SEQ ID NO: 9. In some embodiments, a mutated PPX protein includes an arginine to leucine at a position corresponding to position 98 of SEQ ID NO: 9, a threonine to isoleucine at a position corresponding to position 124 of SEQ ID NO: 9, a proline to histidine at a position corresponding to position 214 of SEQ ID NO: 9, a lysine to glutamine at a position corresponding to position 229 of SEQ ID NO: 9, and an alanine to valine at a position corresponding to position 243 of SEQ ID NO: 9. In some embodiments, a mutated PPX protein includes an arginine to leucine at a position corresponding to position 98 of SEQ ID NO: 9, a threonine to isoleucine at a position corresponding to position 124 of SEQ ID NO: 9, a lysine to glutamine at a position corresponding to position 229 of SEQ ID NO: 9, and an alanine to valine at a position corresponding to position 243 of SEQ ID NO: 9. In some embodiments, a mutated PPX protein includes an arginine to leucine at a position corresponding to position 98 of SEQ ID NO: 9, a proline to histidine at a position corresponding to position 214 of SEQ ID NO: 9, and a cysteine to serine at a position corresponding to position 307 of SEQ ID NO: 9. In some embodiments, a mutated PPX protein includes an arginine to leucine at a position corresponding to position 98 of SEQ ID NO: 9, a threonine to isoleucine at a position corresponding to position 124 of SEQ IL NO: 9, a leucine to phenylalanine at a position corresponding to position 18$ of SEQ ID NO: 9, a lysine to glutamine at a position corresponding to position 229 of SEQ ID NO: 9, and a cysteine to serine at a position corresponding to position 307 of SEQ ID NO: 9. In some embodiments, a mutated PPX protein includes an arginine to leucine at a position corresponding to position 98 of SEQ ID NO: 9, a threonine to isoleucine at a position corresponding to position 124 of SEQ ID NO: 9, a proline to histidine at a position corresponding to position 214 of SEQ ID NO: 9, a lysine to glutamine at a position corresponding to position 229 of SEQ ID NO: 9, and a cysteine to serine at a position corresponding to position 307 of SEQ ID NO: 9. In some embodiments, a mutated IPX protein includes an arginine to leucine at a position corresponding to position 98 of SEQ ID NO: 9, a threonine to isoleucine at a position corresponding to position 124 of SEQ ID NO: 9, a lysine to glutamine at a position corresponding to position 229 of SEQ ID NO: 9, and a cysteine to serine at a position corresponding to position 307 of SEQ ID NO: 9. In some embodiments, a mutated PPX protein includes an arginine to cysteine at a position corresponding to position 98 of SEQ ID NO: 9 and at proline to histidine at a position corresponding to position 214 of SEQ ID NO: 9. In some embodiments, a mutated PPX protein includes an arginine to cysteine at a position corresponding to position 98 of SEQ ID NO: 9; a threonine to isoleucine at a position corresponding to position 124 of SEQ ID NO: 9; a leucine to phenylalanine at a position corresponding to position 188 of SEQ ID NO: 9 and a lysine to glutamine at a position corresponding to position 229 SEQ ID NO: 9 In some embodiments, a mutated PPX protein includes an arginine to cysteine at a position corresponding to position 98 of SEQ ID NO: 9; a threonine to isoleucine at a position corresponding to position 124 of SEQ ID NO: 9; a proline to histidine at a position corresponding to position 214 of SEQ ID NO: 9 and a lysine to glutamine at a position corresponding to position 229 SEQ ID NO: 9. In some embodiments, a mutated PPX protein includes an arginine to cysteine at a position corresponding to position 98 of SEQ ID NO: 9; a threonine to isoleucine at a position corresponding to position 124 of SEQ ID NO: 9; and a lysine to glutamine at a position corresponding to position 229 SEQ ID NO: 9. In some embodiments, a mutated PPX protein includes an arginine to cysteine at a position corresponding to position 98 of SEQ ID NO: 9; a proline to histidine at a position corresponding to position 214 of SEQ ID NO: 9; and an alanine to valine at a position corresponding to position 423 of SEQ If NO: 9. In some embodiments, a mutated PPX protein includes an arginine to cysteine at a position corresponding to position 98 of SEQ ID NO: 9; a threonine to isoleucine at a position corresponding to position 124 of SEQ ID NO: 9: a leucine to phenylalanine at a position corresponding to position 188 of SEQ ID NO: 9; a lysine to glutamine at a position corresponding to position 229 SEQ ID NO: 9; and an alanine to valine at a position corresponding to position 423 of SEQ ID NO: 9. In some embodiments, a mutated PPX protein includes an arginine to cysteine at a position corresponding to position 98 of SEQ ID NO: 9; a threonine to isoleucine at a position corresponding to position 124 of SEQ ID NO: 9; a proline to histidine at a position corresponding to position 214 of SEQ ID NO: 9; a lysine to glutamine at a position corresponding to position 229 SEQ ID NO: 9; and an alanine to valine at a position corresponding to position 423 of SEQ ID NO: 9. In some embodiments, a mutated PPX protein includes an arginine to cysteine at a position corresponding to position 98 of SEQ ID NO: 9; a threonine to isoleucine at a position corresponding to position 124 of SEQ ID NO: 9; a lysine to glutamine at a position corresponding to position 229 SEQ ID NO: 9; and an alanine to valine at a position corresponding to position 423 of SEQ ID NO: 9. In some embodiments, a mutated PPX protein includes an arginine to cysteine at a position corresponding to position 98 of SEQ f) NO: 9; a proline to histidine at a position corresponding to position 214 of SEQ ID NO: 9; and a cysteine to serine at a position corresponding to position 307 of SEQ ID NO: 9. In some embodiments, a mutated PPX protein includes an arginine to cysteine at a position corresponding to position 99 of SEQ ID NO: 9; a threonine to isoleucine at a position corresponding to position 124 of SEQ ID NO: 9; a leucine to phenylalanine at a position corresponding to position 188 of SEQ ID NO: 9; a lysine to glutamine at a position corresponding to position 229 SEQ ID NO: 9; and a cysteine to serine at a position corresponding to position 307 of SEQ ID NO: 9. In some embodiments, a mutated PPX protein includes an arginine to cysteine at a position corresponding to position 98 of SEQ ID NO: 9; a threonine to isoleucine at a position corresponding to position 124 of SEQ ID NO: 9; a proline to histidine at a position corresponding to position 214 of SEQ ID NO: 9; a lysine to glutamine at a position corresponding to position 229 SEQ ID NO: 9; and a cysteine to serine at a position corresponding to position 307 of SEQ ID NO: 9. In some embodiments, a mutated PPX protein includes an arginine to cysteine at a position corresponding to position 98 of SEQ ID NO: 9; a threonine to isoleucine at a position corresponding to position 124 of SEQ ID NO: 9; a lysine to glutamine at a position corresponding to position 229 SEQ ID NO: 9; and a cysteine to serine at a position corresponding to position 307 of SEQ ID NO: 9. In some embodiments, a mutated PPX protein includes an arginine to histidine at a position corresponding to position 98 of SEQ ID NO: 9 and a proline to histidine at a position corresponding to position 214 of SEQ ID NO: 9. In some embodiments, a mutated PPX protein includes an arginine to histidine at a position corresponding to position 98 of SEQ ID NO: 9; a threonine to isoleucine at a position corresponding to position 124 of SEQ ID NO: 9; a leucine to phenylalanine at a position corresponding to position 188 of SEQ ID NO: 9 and a lysine to glutamine at a position corresponding to position 229 SEQ ID NO: 9. In some embodiments, a mutated PPX protein includes an arginine to histidine at a position corresponding to position 98 of SEQ ID NO: 9; a threonine to isoleucine at a position corresponding to position 124 of SEQ ID NO: 9; a proline to histidine at a position corresponding to position 214 of SEQ ID NO: 9 and a lysine to glutamine at a position corresponding to position 229 SEQ ID NO: 9. In some embodiments, a mutated PPX protein includes an arginine to histidine at a position corresponding to position 98 of SEQ ID NO: 9: a threonine to isoleucine at a position corresponding to position 124 of SEQ ID NO: 9; and a lysine to glutamine at a position corresponding to position 229 SEQ ID NO: 9. In some embodiments, a mutated PPX protein includes an arginine to histidine at a position corresponding to position 98 of SEQ ID NO: 9; a proline to histidine at a position corresponding to position 214 of SEQ ID NO: 9; and an alanine to valine at a position corresponding to position 423 of SEQ ID NO: 9. In some embodiments, a mutated PPX protein includes an arginine to histidine at a position corresponding to position 98 of SEQ ID NO: 9; a threonine to isoleucine at a position corresponding to position 124 of SEQ ID NO: 9; a leucine to phenylalanine at a position corresponding to position 188 of SEQ ID NO: 9; a lysine to glutamine at a position corresponding to position 229 SEQ ID NO: 9; and an alanine to valine at a position corresponding to position 423 of SEQ ID NO: 9 in some embodiments, a mutated PPX protein includes an arginine to histidine at a position corresponding to position 99 of SEQ ID NO: 9; a threonine to isoleucine at a position corresponding to position 124 of SEQ ID NO: 9; a proline to histidine at a position corresponding to position 214 of SEQ ID NO: 9; a lysine to glutamine at a position corresponding to position 229 SEQ ID NO: 9; and an alanine to valine at a position corresponding to position 423 of SEQ ID NO: 9. In some embodiments, a mutated PPX protein includes an arginine to histidine at a position corresponding to position 98 of SEQ ID NO: 9; a threonine to isoleucine at a position corresponding to position 124 of SEQ ID NO: 9; a lysine to glutamine at a position corresponding to position 229 SEQ ID NO: 9; and an alanine to valine at a position corresponding to position 423 of SEQ ID NO: 9. In some embodiments, a mutated PPX protein includes an arginine to histidine at a position corresponding to position 98 of SEQ ID NO: 9; a proline to histidine at a position corresponding to position 2.14 of SEQ ID NO: 9; and a cysteine to serine at a position corresponding to position 307 of SEQ ID NO: 9. In some embodiments, a mutated PPX protein includes an arginine to histidine at a position corresponding to position 98 of SEQ ID NO: 9; a threonine to isoleucine at a position corresponding to position 124 of SEQ ID NO: 9; a leucine to phenylalanine at a position corresponding to position 188 of SEQ ID NO: 9; a lysine to glutamine at a position corresponding to position 229 SEQ ID NO: 9; and a cysteine to serine at a position corresponding to position 307 of SEQ ID NO: 9. In some embodiments, a mutated PPX protein includes an arginine to histidine at a position corresponding to position 98 of SEQ ID NO: 9; a threonine to isoleucine at a position corresponding to position 124 of SEQ ID NO: 9; a proline to histidine at a position corresponding to position 214 of SEQ ID NO: 9; a lysine to glutamine at a position corresponding to position 229 SEQ ID NO: 9; and a cysteine to serine at a position corresponding to position 307 of SEQ ID NO: 9. In some embodiments, a mutated PPX protein includes an arginine to histidine at a position corresponding to position 98 of SEQ ID NO: 9; a threonine to isoleucine at a position corresponding to position 124 of SEQ ID NO: 9; a lysine to glutamine at a position corresponding to position 229 SEQ ID No: 9; and a cysteine to serine at a position corresponding to position 307 of SEQ ID NO: 9.

Paralogs

The subject mutations in the PPX gene are generally described herein using the *Solanum tuberosum* plastidal PPX genes and proteins (see e.g., amino acid positions referenced to positions in *Arabidopsis thaliana* (SEQ ID NO: 11. The compositions and methods also encompass mutant PPX genes and proteins of other species (paralogs). However, due to variations in the PPX genes of different species, the number of the amino acid residue to be changed in one species may be different in another species. Nevertheless, the analogous position is readily identified by one of skill in the art by sequence homology. For example, Table 6 summarizes the homologous amino acid positions in various plant PPX coding sequence paralogs. Thus, analogous positions in these and other paralogs can be identified and mutated.

Herbicides

The compositions and methods provided herein include PPX genes and PPX proteins that confer resistance to PPX-inhibiting herbicides. In some embodiments, PPX-inhibiting herbicides include the chemical families of diphenylether, phenylpyrazoles N-phenylphthalimides, thiadiazoles, oxadiazoles, triazolinones, oxazolidinediones, pyrimidindiones. Exemplary PPX-inhibiting herbicide active ingredients and their respective chemical family are summarized in Table 5.

TABLE 5

Exemplary PPX-inhibiting Herbicides.

| Chemical Family | Herbicide Active Ingredient |
|---|---|
| Diphenylethers | acifluorfen-Na |
| | Bifenox |
| | Chlomethoxyfen |
| | fluoroglycofen-ethyl |
| | Fomesafen |
| | Halosafen |
| | Lactofen |
| | Oxyfluorfen |
| Phenylpyrazoles | Fluazolate |
| | pyraflufen-ethyl |
| N-phenylphthalimides | cinidon-ethyl |
| | Flumioxazin |
| | flumiclorac-pentyl |
| Thiadiazolos | fluthiacct-methyl |
| | Thidiazimin |
| Oxadiazoles | Oxadiazon |
| | Oxadiargyl |
| Triazolinones | Azafenidin |
| | carfentrazone-ethyl |
| | Sulfentrazone |
| Oxazolidinediones | Pentoxazone |
| Pyrimidindiones | Benzfendizone |
| | Butafenacil |
| | Saflufenacil |
| Others | Pyrazogyl |
| | Profluazol |

In some embodiments, PPX-inhibiting herbicide is acifluorfen-Na. In some embodiments. PPX-inhibiting herbicide is bifenox, in some embodiments, PPX-inhibiting herbicide is chlomethoxyfen. In some embodiments, PPX-inhibiting herbicide is fluoroglycofen-ethyl. In some embodiments, PPX-inhibiting herbicide is fomesafen. In some embodiments, PPX-inhibiting herbicide is halosafen, in some embodiments. PPX-inhibiting herbicide is lactofen. In some embodiments, PPX-inhibiting herbicide is oxyfluorfen. In some embodiments. PPX-inhibiting herbicide is fluazolate. In some embodiments, PPX-inhibiting herbicide is pyraflufen-ethyl. In some embodiments, PPX-inhibiting herbicide is cinidon-ethyl. In some embodiments, PPX-inhibiting herbicide is flumioxazin. In some embodiments. PPX-inhibiting herbicide is flumiclorac-pentyl. In some embodiments, PPX-inhibiting herbicide is fluthiacet-methyl. In some embodiments PPX-inhibiting herbicide is thidiazimin. In some embodiments, PPX-inhibiting herbicide is oxadiazon. In some embodiments, PPX-inhibiting herbicide is oxadiargyl. In some embodiments, PPX-inhibiting herbicide is azafenidin. In some embodiments, PPX-inhibiting herbicide is carfentrazone-ethyl. In some embodiments, PPX-inhibiting herbicide is sulfentrazone. In some embodiments, PPX-inhibiting herbicide is pentoxazone. In some embodiments, PPX-inhibiting herbicide is benzfendizone. In some embodiments, PPX-inhibiting herbicide is butafenacil. In some embodiments, PPX-inhibiting herbicide is saflufenacil. In some embodiments, PPX-inhibiting herbicide is pyrazogyl in some embodiments, PPX-inhibiting herbicide is profluazol.

Also provided is a transgenic or non-transgenic plant or plant cell having one or more mutations in the PPX gene, for example, such as disclosed herein. In certain embodiments, the plant or plant cell having one or more mutations in a PPX gene has increased resistance or tolerance to a member of PPX-inhibiting herbicides. In certain embodiments, the plant or plant cell having one or more mutations in a PPX gene may exhibit substantially normal growth or development of the plant, its organs, tissues or cells, as compared to the corresponding wild-type plant or cell. In particular aspects and embodiments provided are transgenic or non-transgenic plants having a mutation in a PPX gene, for example, such as disclosed herein, which in certain embodiments has increased resistance or tolerance to one or more members of the PPX-inhibiting herbicide chemical families and may exhibit substantially normal growth or development of the plant, its organs, tissues or cells, as compared to the corresponding wild-type plant or cell, i.e., in the presence of one or more herbicide such as for example, flumioxazin, sulfentrazone or saflufenacil, the mutated PPX protein has substantially the same catalytic activity as compared to the wild-type PPX protein.

Further provided are methods for producing a plant having a mutated PPX gene, for example, having one or more mutations as described herein: preferably the plant substantially maintains the catalytic activity of the wild-type protein irrespective of the presence or absence of a relevant herbicide. In certain embodiments, the methods include introducing into a plant cell a gene repair oligonucleobase with one or more targeted mutations in the PPX gene (for example, such as disclosed herein) and identifying a cell, seed, or plant having a mutated PPX gene.

Plant Species

In conjunction with any of the aspects, embodiments, methods and/or compositions disclosed herein, plants as disclosed herein can be of any species of dicotyledonous, monocotyledonous or gymnospermous plant, including any woody plant species that grows as a tree or shrub, any herbaceous species, or any species that produces edible fruits, seeds or vegetables, or any species that produces colorful or aromatic flowers. For example, the plant or plant cell may be selected from a species of plant from the group consisting of potato, sunflower, sugar beet, maize, cotton, soybean, wheat, rye, oats, rice, canola, fruits, vegetables, tobacco, barley, sorghum, tomato, mango, peach, apple, pear, strawberry, banana, melon, carrot, lettuce, onion, soya spp, sugar cane, pea, field beans, poplar, grape, citrus, alfalfa, rye, oats, turf and forage grasses, flax, oilseed rape, cucumber, morning glory, balsam, pepper, eggplant, marigold, lotus, cabbage, daisy, carnation, petunia, tulip, iris, lily, and nut-producing plants insofar as they are not already specifically mentioned. The plant or plant cell may also be of a species selected from Table 6. The plant or plant cell may also be of a species selected from the group consisting of *Arabidopsis thaliana, Solanum tuberosum, Solanum phureja, Oryza sativa, Amaranthus tuberculatus, Sorghum bicolor, Ricinus communis* and *Zea mays*.

TABLE 6

Summary of homologous amino acid positions in plant PPX amino acid sequences of various species.

| Species | Genbank Accession # | Loc | G 52 | N 85 | R 144 | F 145 | A 180 | P 185 | A 220 | L 226 | M 228 | S 244 | Q 272 | S 305 | S 332 | L 357 | K 359 | L 393 | L 403 | L 424 | Y 426 | F 478 | I 525 |
|---|---|---|---|---|---|---|---|---|---|---|---|---|---|---|---|---|---|---|---|---|---|---|---|
| *Arabidopsis thaliana* - At4g01690 | AX084732 | P | 52 | 85 | 144 | 145 | 180 | 185 | 220 | 226 | 228 | 244 | 272 | 305 | 332 | 357 | 359 | 393 | 403 | 424 | 426 | 478 | 525 |
| *Arabidopsis thaliana* - At5g14220 | NM_121426 | M | NA | 41 | 101 | Y 102 | P 137 | K 147 | 182 | 188 | 190 | 206 | G 235 | L 269 | H 298 | F 323 | L 325 | 358 | 371 | T 392 | F 394 | Y 444 | D 489 |
| *Amaranthus tuberculatus* | DQ386117 | B | NA | NA | 128 | Y 129 | P 164 | K 169 | G 210 | 216 | 218 | 234 | R 261 | L 295 | 324 | F 349 | L 351 | 384 | 397 | T 418 | F 420 | Y 470 | E 515 |
| *Solanum tuberosum* | AJ225107 | P | N 76 | 105 | 164 | 165 | 200 | 205 | 240 | 246 | 248 | 264 | K 292 | 325 | 352 | 377 | S 379 | 413 | 423 | 444 | 446 | 498 | S 545 |
| *Solanum tuberosum* | NA see FIG. 27. | M | NA | NA | 98 | Y 99 | P 134 | N 139 | G 178 | 184 | 186 | 202 | R 231 | L 265 | 296 | F 321 | L 323 | 356 | 369 | T 390 | F 392 | Y 442 | D 487 |
| *Zea mays* | AF218052 | P | NA | NA | 142 | 143 | 178 | P183 | 218 | 224 | 226 | 242 | K 265 | T 303 | 330 | 355 | R 357 | 391 | 401 | 422 | 424 | 476 | S 523 |
| *Zea mays* | AF273767 | M | NA | 70 | 130 | Y 131 | P 166 | K 171 | 215 | 221 | I 223 | 239 | N 268 | 302 | T 336 | V 361 | L 363 | 396 | 410 | T 431 | F 433 | Y 483 | D 528 |
| *Oryza sativa* - Os01g0286600 | NM_001049312 | P | G 51 | NA | 143 | Y 144 | P 179 | K 184 | 219 | 225 | I 227 | 243 | K 271 | T 304 | T 331 | L 356 | I 358 | 392 | 402 | 423 | 425 | 477 | S 524 |
| *Oryza sativa* - Os04g0490000 | NA see FIG. 17. | M | D 50 | Q 79 | 139 | Y 140 | P 175 | K 180 | G 224 | 230 | I 232 | 248 | N 277 | L 311 | L 345 | F 370 | L 372 | 405 | 419 | T 440 | F 442 | Y 492 | D 537 |
| *Sorghum bicolor* - Sb03g011670 | XM_002455439 | P | NA | NA | 143 | Y 144 | P 179 | K 184 | 219 | 225 | I 227 | 243 | K 271 | T 304 | 331 | L 356 | R 358 | 392 | 402 | 473 | 425 | 477 | A 534 |
| *Sorghum bicolor* - Sb06g020950 | XM_002446665 | M | NA | 70 | 130 | Y 131 | P 166 | K 171 | 215 | 221 | I 223 | 239 | N 268 | L 302 | T 336 | F 361 | L 363 | 396 | 410 | T 431 | F 433 | Y 483 | D 528 |
| *Ricinus communis* - Rc1343150 | XM_002515127 | P | N 51 | 84 | 143 | Y 144 | P 179 | 184 | 219 | 225 | 227 | 243 | K 271 | 304 | 331 | F 356 | L 358 | 392 | 402 | 423 | 425 | 477 | A 524 |
| *Ricinus communis* - Rc1678480 | XM_002509502 | M | NA | NA | 99 | Y 100 | P 135 | K 140 | 181 | 187 | V 189 | 205 | 234 | F 268 | F 299 | F 324 | L 326 | 359 | 372 | T 393 | F 395 | Y 445 | D 490 |

† G210 deleted in DQ386118 leading to tolerance to PPX inhibitor

P is plastidal; M is mitochondrial; B is both

The gene repair oligonucleobase can be introduced into a plant cell using any method commonly used in the art, including but not limited to, microcarriers (biolistic delivery), microfibers, polyethylene glycol (PEG-mediated uptake, electroporation, and microinjection.

Also provided are methods and compositions related to the culture of cells mutated according to methods as disclosed herein in order to obtain a plant that produces seeds, henceforth a "fertile plant", and the production of seeds and additional plants from such a fertile plant.

Also provided are methods of selectively controlling weeds in a field, the field comprising plants with the disclosed PPX gene alterations and weeds, the method comprising application to the field of a herbicide to which the plants have been tendered resistant.

Also provided are mutations in the PPX gene that confer resistance or tolerance to a member of the relevant herbicide to a plant or wherein the mutated PPX gene has substantially the same enzymatic activity as compared to wild-type PPX. Selection of Herbicide Resistant Plants and Application of Herbicide Plants and plant cells can be tested for resistance or tolerance to a herbicide using commonly known methods in the art, e.g., by growing the plant or plant cell in the presence of a herbicide and measuring the rate of growth as compared to the growth rate in the absence of the herbicide.

As used herein, substantially normal growth of a plant, plant organ, plant tissue or plant cell is defined as a growth rate or rate of cell division of the plant, plant organ, plant tissue, or plant cell that is at least 35%, at least 50%, at least 60%, or at least 75% of the growth rate or rate of cell division in a corresponding plant, plant organ, plant tissue or plant cell expressing the wild-type PPX protein.

As used herein, substantially normal development of a plant, plant organ, plant tissue or plant cell is defined as the occurrence of one or more development events in the plant, plant organ, plant tissue or plant cell that are substantially the same as those occurring in a corresponding plant, plant organ, plant tissue or plant cell expressing the wild-type PPX protein.

In conjunction with any of the aspects, embodiments, methods and/or compositions disclosed herein, plant organs provided herein may include, but are not limited to, leaves, stems, roots, vegetative buds, floral buds, meristems, embryos, cotyledons, endosperm, sepals, petals, pistils, carpels, stamens, anthers, microspores, pollen, pollen tubes, ovules, ovaries and fruits, or sections, slices or discs taken therefrom. Plant tissues include, but are not limited to, callus tissues, ground tissues, vascular tissues, storage tissues, meristematic tissues, leaf tissues, shoot tissues, root tissues, gall tissues, plant tumor tissues, and reproductive tissues. Plant cells include, but are not limited to, isolated cells with cell walls, variously sized aggregates thereof, and protoplasts.

Plants are substantially "tolerant" to a relevant herbicide when they are subjected to it and provide a dose/response curve which is shifted to the right when compared with that provided by similarly subjected non-tolerant like plant. Such dose/response curves have "dose" plotted on the X-axis and "percentage kill", "herbicidal effect", etc., plotted on the y-axis. Tolerant plants will require more herbicide than non-tolerant like plants in order to produce a given herbicidal effect. Plants that are substantially "resistant" to the herbicide exhibit few, if any, necrotic, lytic, chlorotic or other lesions, when subjected to herbicide at concentrations and rates which are typically employed by the agrochemical community to kill weeds in the field. Plants which are resistant to a herbicide are also tolerant of the herbicide.

In some embodiments an "increased resistance to a herbicide" or "increased tolerance to a herbicide" refers to a level of resistance or tolerance that a plant, seed, or plant part having a mutated PPX gene or protein as disclosed herein has to plant herbicides above a defined reference level. The defined reference level of resistance to a herbicide is the level of resistance displayed by a plant of the same species without the corresponding mutation(s). In some embodiments, resistance is substantially increased above the defined reference level, e.g., greater than or equal to 20% above, 50% above, 75% above; or 100% above the defined reference level.

EXAMPLES

The following are examples, which illustrate procedures for practicing the invention. These examples should not be construed as limiting. All percentages are by weight and all solvent mixture proportions are by volume unless otherwise noted.

Example 1: Plastidal and Mitochondrial PPX Gene Cloning and Characterization Plastidal and mitochondrial PPX genes were amplified from both cDNA and genomic DNA front a Russet Burbank cultivar. The plastidal PPX clones fall into two classes, given the names StcPPX1 and StcPPX1.1 likely representing alleles of a single PPX gene in potato. Within the amino acid coding sequence, these clones differ by 10 polymorphisms, 3 of which lead to amino acid differences with only two being found in the mature protein. One amino acid difference is in the chloroplast transit peptide. In one of the StcPPX1.1 clones, intron 3 was unspliced.

A full length error-free genomic clone of the plastidal PPX was obtained. The analysis of about 5 Kb of genomic sequence from 5 independent clones and StcPPX cDNA sequencing results indicates that the Russet Burbank variety subject to characterization is heterozygous, with very few polymorphisms existing between the two alleles.

First, five full-length StmPPX genomic DNA clones were cloned and sequenced. These five represented both alleles, having the same SNPs as found in the cDNA. Genomic DNA fragments of a shorter amplicon were cloned and sequenced to test for additional alleles. Cloning this internal amplicon of the mitochondrial PPX indicated that there were three alleles; 6 out of 22 clones had a deletion within one of the introns and the other 16 clones had an even distribution of the two alleles observed in the cDNA clones. Next, another 12 full length StmPPX genomic DNA clones were sequenced.

The completed sequencing of the mitochondrial PPX genes in Russet Burbank potato indicated that there are two genes, which we have termed StmPPX1 and StmPPX2. There are two StmPPX2 alleles with 8 SNPs identified between them. Between StmPPX1 and StmPPX2.1 there is 1 insertion, 4 deletions and 30 SNPs, whereas between StmPPX1 and StmPPX2.2 there is 1 insertion, 4 deletions and 29 SNPs. Additional detail is presented in Table 7.

Gene sequences of the plastidal and mitochondrial potato PPX genes from Russet Burbank (*Solanum tuberosum*) were compared, using the Basic Local Alignment Search Tool (BLAST), with our locally installed database based on scaffolds for the recent release of the first full potato (*Solanum phureja*) genome. Only a single plastidal and a single mitochondrial PPX gene were found.

TABLE 7

Allelic differences between the mitochondrial forms of PPX in Russet Burbank potato.

| StmPPX nt Position | nt Gene 1 | aa Gene 1 | nt Gene 2, Allele 1 | aa Gene 2, Allele 1 | nt Gene 2, Allele 2 | aa Gene 2, Allele 2 | StmPPX aa position | AtcPPX aa position |
|---|---|---|---|---|---|---|---|---|
| 296 | A (TAC) | Y | A (TAC) | Y | T (TTC) | F | 99 | 145 |
| 360 | C (AAC) | N | T (AAT) | N | T (AAT) | N | 120 | 166 |
| 402 | T (CCT) | P | A (CCA) | P | A (CCA) | P | 134 | 180 |
| 528 | G (ACG) | T | A (ACA) | T | A (ACA) | T | 176 | 218 |
| 680 | T (GTA) | V | T (GTA) | V | A (GAA) | E | 227 | 269\|270 |
| 692 | A (CAC) | H | G (CGC) | R | G (CGC) | R | 231 | 272 |

Example 2: PPX Complementation

StcPPX1, less its chloroplast transit peptide was cloned from CDNA into Cibus' proprietary functional screening vector. This vector may be used both for functional screening, and for GRON QC. The potato PPX genes were used to complement the HemG mutant strain of *E. coli*, which lacks a functional HemG gene, a bacterial homolog of PPX. Without a complementing gene, the media must be supplemented with hematin for *E. coli* growth. Clones for the plastidal PPX gene (pACYStcPPX Col6) and the mitochondrial PPX gene (pACYStmPPX Col 6, 12 and 21) were transformed and all genes/alleles were shown to complement the HemG mutant *E. coli* strain, allowing it to grow in the absence of hematin.

In order to assess mutations that confer tolerance to PPX inhibitors such as Chateau (flumioxazin—Valent/Sumitomo), Naja (diphenylether—MAI) or Kixsor (saflufenacil—BASF). PPX inhibiting herbicides are shown in Table 5. Pure active ingredients for the PPX inhibiting herbicides Chateau (flumioxazin—Valent/Sumitomo), Spurtan (sulfentrazone—FMC) and Kixor/Sharpen (saflufenacil—BASF) were obtained. The wild-type potato plastidal PPX clone (pACYStcPPX Col6) was transformed to complement the hemG mutant *E. coli* strain and selected with a series of concentrations of the active ingredient for the PPX inhibiting herbicide Spartan (sulfentrazone—FMC) to determine the concentration at which the complemented HemG minus strain does not grow. The wildtype construct did not grow on 2.5 mM sulfentrazone, therefore, selection for tolerant mutants was performed at this concentration. This was further refined, and 0.75 mM sulfentrazone was also used to select for tolerance. The wildtype construct had limited growth at 10 mM flumioxazin in liquid selection and no growth at 0.3 mM saflufenacil in plate based selection, concentrations used to test for tolerant mutants. All potato mitochondrial PPX genes and alleles were tested for natural tolerance to sulfentrazone and flumioxazin, but none were tolerant.

Example 3: PPX PCR-Mutagenesis and Selection of Mutagenized Clones

Mutagenesis experiments were initially performed on two overlapping fragments (5' and 3') of the potato plastidal PPX gene, to identify mutations in the potato plastidal PPX coding sequence that confer herbicide tolerance
Liquid Selection Standardization Liquid culture selection conditions were developed for both sulfentrazone and flumioxazin. Cultures of 1 mL volume were tested with sulfentrazone and flumioxazin concentrations ranging from 0 to 10 mM. The 0 mM samples had 25 µL DMSO (2.5%) to mimic the concentration of DMSO in the samples containing 10 mM herbicide. Each tube was inoculated with 10 µL of an overnight culture of HemG cells complemented with the wildtype PPX plasmid to ensure uniformity. Spectrophotometric readings (OD600) were taken for each sample (1:4 dilution) and a sample of each plated on LB-Chlor-IPTG plates to determine whether the OD600 correlated with the number of viable colonies. A 10% dilution of the overnight culture was plated for the sulfentrazone-treated cells and a 1% dilution for the cells treated with flumioxazin was plated (see results in Tables 8a-f and 9a-d).

Both sulfentrazone and flumioxazin precipitate out in the liquid media, causing it to appear opaque even before inoculating bacteria. As the ODs for sulfentrazone show, this herbicide eventually goes into solution while flumioxazin does not. Flumioxazin's deficient solubility skews the GD readings, however, flumioxazin demonstrated steadily decreasing colony numbers against the WT gene, indicating the cells ability to absorb the flumioxazin from the media.
5' End Mutagenesis The 5' end of the PPX gene was mutagenized using Stratagene Gene Morph II Random Mutagenesis Kit and cloned into XL-1 Blue to check the mutation rate. Results showed 14 out of 16 colonics sequenced were mutants. The 90% XL-1 Blue plates (approximately 4000 colonies) were scraped, plasmid prepped, and transformed into HemG and plated on 2.5 mM sulfentrazone. The sulfentrazone plates grew approximately 200 colonies and the 10% LB-Chlor-IPTG plates grew a lawn of colonies. Tables 9a-d describe the nucleotide and amino acid substitutions found in the tolerant clones.
Selection of Mutagenized Clones Randomly mutagenized plasmids (5' and 3' ends) were transformed into XL1-Blue *E. coli* cells. The resulting colonies were pooled, plasmid DNA isolated and transformed into HemG (PPX mutant *E. coli*) cells. For selection with flumioxazin, cells were recovered for 1 h in liquid minimal media followed by the addition of herbicide and overnight recovery of the cells. The next day, the cells were plated at an appropriate dilution on LB plates containing antibiotic to select for the complementing plasmid. Colonies from each plate were sequenced. After liquid selection in 10 mM flumioxazin, approximately 30 colonies appeared on plates with the wild type (WT) PPX compared to approximately 200-1200 colonies with mutagenized plasmids. For sulfentrazone selection, cultures were grown in minimal media overnight, diluted and plated plates with 0 and 0.75 mM concentration of sulfentrazone. Colony counts were compared between the two and mutation tolerance determined based on the percentage of colonies on the 0.75 mM sulfentrazone plates as compared with those on the 0 mM plates. The number of colonies appearing on the plates served as a method to rank the mutations.

3' End Mutagenesis

Mutagenesis was performed on the 3' end of the PPX gene. Clones were transformed into HemG and grown overnight in 2.5, 5, and 10 mM flumioxazin for selection. Selection at 5 mM flumioxazin had many more colonies than on the 10 mM selection plates. Selection for mutagenized clones using 10 mM flumioxazin yielded four clones. Selection for mutagenized clones ursine 5 mM flumioxazin yielded 200 colonies. The top third of the 200 colonies obtained for 3' end mutagenesis were screened in 10 mM flumioxazin. All tolerant colonies (approximately 130) were sequenced and the best flumioxazin tolerant mutants, assessed by colony count on flumioxazin, the 3' end assessed for tolerance to sulfentrazone.

Example 4: Analysis of Amino Acid Substitutions Conferring Tolerance

Tolerance of all possible amino acid substitutions at each position displaying tolerance to sulfentrazone or flumioxazin were tested. Next, single amino acid substitutions were combined in all permutations and combinations to assess complementation and herbicide tolerance. Results of single and multiple mutant combinations to flumioxazin are shown in Tables 8a, 8b, and 8c, where the last column shows the number of colonies reported for each mutation on 10 mM flumioxazin. Results of single and multiple mutant combinations to sulfentrazone are shown in Tables 9a and 9b, where the last column shows the number of colonies reported for each mutation on 0.75 mM sulfentrazone. Results of single and multiple mutant combinations to saflufenacil are shown in Table 10, where the fourth column shows the number of colonies reported for each mutation on 0.3 mM saflufenacil.

TABLE 8a

Tolerance of single and multiple mutant combinations in the potato plastidal PPX coding sequence to flumioxazin.

| Mutation | | Plasmid | Avg # of Flumioxazin Resistant Clones |
|---|---|---|---|
| — | L393V | F1125 | 0 |
| — | L403R | F1155 | 2 |
| A180T | Y426F | SD5083 | 2 |
| — | L424S | F1154 | 2 |
| F145L | Y426I | SD5055 | 3 |
| S244G | Y426F | SD5087 | 10 |
| F145L | L403R | SD5115 | 10 |
| — | Y426F | F1165 | 11 |
| F145Y | L424S | SD5106 | 13 |
| R144C | L424S | SD5102 | 41 |
| L226M | Y426H | SD5059 | 55 |
| A220T | L403R | SD5114 | 69 |
| — | Y426H | F1180 | 71 |
| A220T | L424S | SD5104 | 72 |
| F145Y | Y426F | SD5086 | 75 |
| R144C | L393V | SD5092 | 81 |
| A220T | L393V | SD5094 | 107 |
| S244G | L393V | SD5097 | 114 |
| L226M | L403R | SD5119 | 123 |
| A180T | Y426H | SD5053 | 129 |
| L226M | L424S | SD5109 | 137 |
| L226M | Y426F | SD5089 | 143 |
| A220T | Y426F | SD5084 | 147 |
| A220T | Y426H | SD5054 | 151 |
| R144C | Y426F | SD5082 | 155 |
| — | — | wt | 0 |

TABLE 8b

Tolerance of single and multiple mutant combinations in the potato plastidal PPX coding sequence to flumioxazin.

| Mutation | | | Plasmid | Avg # of Flumioxazin Resistant Clones |
|---|---|---|---|---|
| R144C | A220T | | SD5011 Col 1 | 701 |
| A220T | | | F113 | 667 |
| R144H | S332C | | F76 | 517 |
| R144C | K272F | | SD5014 Col 1 | 300 |
| N52K | R144H | S244T | F72 | 202 |
| N85D | A220T | | SD5007 Col 1 | 196 |
| R144H | S244T | | F96 | 174 |
| R144C | | | S7 | 139 |
| R144C | L226M | | SD5012 Col 1 | 117 |
| M228L | | | S37 | 107 |
| L226M | | | F114 | 102 |
| N85D | L226M | | SD5008 Col 2 | 50 |
| F145Y | | | S32 | 38 |
| N85D | F145Y | | SD5004 Col 3 | 37 |
| S244G | | | S120 | 31 |
| R144C | M228L | | SD5013 Col 2 | 31 |
| P185R | | | SD5016 Col 1 | 27 |
| N52K | | | SD5001 Col 3 | 23 |
| N85D | A180T | | SD5005 Col 1 | 23 |
| A180T | | | F17 | 22 |
| N85D | R144C | | SD5002 Col 1 | 21 |
| S332C | | | SD5019 Col 1 | 20 |
| F145L | | | S118 | 19 |
| N85D | | | F80 | 16 |
| K272F | | | F7 | 15 |
| S244T | | | SD5018 Col 3 | 10 |
| N85D | K272F | | SD5010 Col 4 | 7 |
| N85D | M228L | | SD5009 Col 3 | 6 |
| | | | WT | 43 |

TABLE 8c

Tolerance of single and multiple mutant combinations in the potato plastidal PPX coding sequence to flumioxazin.

| Mutation | | Plasmid | Avg # of Flumioxazin Resistant Clones |
|---|---|---|---|
| N85D | Y426H | SD5051 | 30 |
| R144C | Y426H | SD5052 | 48 |
| F145Y | Y426H | SD5056 | 52 |
| S244T | Y426H | SD5058 | 73 |
| S244G | Y426H | SD5057 | 80 |
| A180T | Y426H | SD5053 | 128 |
| L226M | Y426H | SD5059 | 228 |
| F145L | Y426H | SD5055 | 305 |
| A220T | Y426H | SD5054 | 391 |
| — | Y426H | F1180 | 210 |
| — | — | wt | 32 |

TABLE 8d

Tolerance of single and multiple mutant combinations in the potato mitochondrial PPX coding sequence to 5 mM flumioxazin.

| A404S | |
|---|---|
| C271R | D274G |
| C307S | A423V |
| C434S | T500S |
| C434Y | |
| D330E | |
| D447G | A292G |
| D454N | |
| N324K | |
| R406K | |
| S396L | K410I |
| S448A | N324D |
| Y465F | K470T |

TABLE 8e

Tolerance of single and multiple mutant combinations in the potato mitochondrial PPX coding sequence to 5 mM flumioxazin.

| | | | |
|---|---|---|---|
| A101V | | | |
| C177S | | | |
| D170E | | | |
| D58N | | | |
| E150K | | | |
| E64V | | | |
| F121L | E150D | | |
| G74C | R98C | | |
| G84N | | | |
| K97R | | | |
| L93H | V164A | | |
| N195K | | | |
| P214S | | | |
| Q157L | H187Q | | |
| R98C | | | |
| R98H | | | |
| R98L | | | |
| R98L | P214H | | |
| R98L | T124I | L188F | K229Q |
| S119N | N139Y | | |
| S151T | K229E | K230R | |
| V164F | | | |

TABLE 8f

Tolerance of single and multiple mutant combinations in the potato mitochondrial PPX coding sequence to 10 mM flumioxazin.

| Mutant | # Colonies with 10 mM Flumioxazin |
|---|---|
| wt | 42 |
| R98L | 83 |
| P214H | 51 |
| R98L/P214H | 88 |
| R98L/P214H/T124I | 110 |
| R98L/P214H/T124I/K229Q | 109 |

TABLE 9a

Tolerance of single and multiple mutant combinations in the potato plastidal PPX coding sequence to sulfentrazone.

| Mutation | | Plasmid | Avg 0.75 mM Sulf | Avg 0 mM | 0.75 mM/0 mM |
|---|---|---|---|---|---|
| — | Y426F | F1165 | 8 | 91 | 0.8% |
| — | L393V | F1125 | 6 | 57 | 1.0% |
| L226M | Y426H | SD5059 | 14 | 79 | 1.8% |
| S244T | L393V | SD5098 | 11 | 53 | 2.1% |
| F145Y | Y426H | SD5056 | 16 | 72 | 2.2% |
| — | L403R | F1155 | 16 | 72 | 2.2% |
| R144C | S525T | SD5072 | 19 | 76 | 2.6% |
| A220T | L393V | SD5094 | 20 | 55 | 3.6% |
| — | L424S | F1154 | 21 | 56 | 3.7% |
| F145L | L424S | SD5105 | 18 | 48 | 3.8% |
| — | Y426H | F1180 | 29 | 68 | 4.2% |
| A220T | Y426H | SD5054 | 19 | 39 | 5.0% |
| F145Y | L393V | SD5096 | 55 | 86 | 6.3% |
| S244T | Y426F | SD5088 | 58 | 88 | 6.5% |
| F145Y | L424S | SD5106 | 49 | 69 | 7.1% |
| A220T | L403R | SD5114 | 50 | 63 | 7.9% |
| L226M | Y426F | SD5089 | 117 | 67 | 17.4% |
| N85D | Y426H | SD5051 | 200 | 92 | 21.8% |
| L226M | L424S | SD5109 | 91 | 40 | 22.6% |
| F145Y | L403R | SD5116 | 315 | 110 | 28.5% |
| F145L | L393V | SD5095 | 381 | 121 | 31.6% |
| L226M | L403R | SD5119 | 252 | 75 | 33.8% |
| R144C | Y426F | SD5082 | 400 | 117 | 34.3% |
| S244G | L393V | SD5097 | 433 | 125 | 34.7% |
| — | S525T | F1061 | 278 | 79 | 35.3% |
| A180T | Y426H | SD5053 | 331 | 80 | 41.4% |

TABLE 9a-continued

Tolerance of single and multiple mutant combinations in the potato plastidal PPX coding sequence to sulfentrazone.

| Mutation | | Plasmid | Avg 0.75 mM Sulf | Avg 0 mM | 0.75 mM/0 mM |
|---|---|---|---|---|---|
| R144C | Y426H | SD5052 | 709 | 125 | 56.6% |
| — | — | wt | 0 | 85 | 0.0% |

TABLE 9b

Tolerance of single and multiple mutant combinations in the potato plastidal PPX coding sequence to sulfentrazone.

| Mutation(s) | | | Plasmid | Avg # of Sulfentrazone Resistant Clones |
|---|---|---|---|---|
| R144C | M228L | | SD5013 Col 2 | 267 |
| R144C | A220T | | SD5011 Col 1 | 260 |
| F145Y | | | S32 | 233 |
| R144C | L226M | | SD5012 Col 1 | 186 |
| A220T | | | F113 | 149 |
| P185R | | | SD5016 Col 1 | 133 |
| R144C | K272F | | SD5014 Col 1 | 118 |
| N52K | | | SD5001 Col 3 | 90 |
| M228L | | | S37 | 78 |
| N85D | A180T | | SD5005 Col 1 | 75 |
| S244G | | | S120 | 68 |
| R144H | S332C | | F76 | 64 |
| N85D | F145Y | | SD5004 Col 3 | 62 |
| K272F | | | F7 | 61 |
| L226M | | | F114 | 57 |
| R144C | | | S7 | 55 |
| S244T | | | SD5018 Col 3 | 32 |
| R144H | S244T | | F96 | 31 |
| F145L | | | S118 | 29 |
| S332C | | | SD5019 Col 1 | 28 |
| N85D | R144C | | SD5002 Col 1 | 25 |
| N85D | A220T | | SD5007 Col 1 | 19 |
| N85D | L226M | | SD5008 Col 2 | 18 |
| A180T | | | F17 | 18 |
| N52K | R144H | S244T | F72 | 18 |
| N85D | M228L | | SD5009 Col 3 | 12 |
| N85D | | | F80 | 6 |
| N85D | K272F | | SD5010 Col 4 | 6 |
| | | | WT | 23 |

TABLE 9c

Tolerance of single and multiple mutant combinations in the potato mitochondrial PPX coding sequence to sulfentrazone.

| Sulf Conc | Mutant(s) | Colonies | % age |
|---|---|---|---|
| 0 mM | R98L/P214H | 1341 | |
| 0.5 mM | R98L/P214H | 349 | 26.0% |
| 0.9 mM | R98L/P214H | 127 | 9.5% |
| 1.0 mM | R98L/P214H | 77 | 5.7% |
| 1.1 mM | R98L/P214H | 67 | 5.0% |
| 1.2 mM | R98L/P214H | 48 | 3.6% |
| 0 mM | R98L | 1541 | |
| 0.5 mM | R98L | 339 | 22.0% |
| 0.9 mM | R98L | 145 | 9.4% |
| 1.0 mM | R98L | 110 | 7.1% |
| 1.1 mM | R98L | 76 | 4.9% |
| 1.2 mM | R98L | 54 | 3.5% |
| 0 mM | R98L/T124I/K229Q | 1220 | |
| 0.5 mM | R98L/T124I/K229Q | 312 | 25.6% |
| 0.9 mM | R98L/T124I/K229Q | 88 | 7.2% |
| 1.0 mM | R98L/T124I/K229Q | 66 | 5.4% |
| 1.1 mM | R98L/T124I/K229Q | 40 | 3.3% |

TABLE 9d

Tolerance of single and multiple mutant combinations in the potato mitochondrial PPX coding sequence to sulfentrazone.

| Sulf Conc | Mutant(s) | Colonies | % age |
|---|---|---|---|
| 0 mM | R98L/P214H | 1088 | |
| 0.4 mM | R98L/P214H | 251 | 23.1% |
| 0.5 mM | R98L/P214H | 150 | 13.8% |
| 0.6 mM | R98L/P214H | 105 | 9.7% |
| 0.7 mM | R98L/P214H | 108 | 9.9% |
| 0.8 mM | R98L/P214H | 51 | 4.7% |
| 0 mM | R98L | 1171 | |
| 0.4 mM | R98L | 174 | 14.9% |
| 0.5 mM | R98L | 104 | 8.9% |
| 0.6 mM | R98L | 98 | 8.4% |
| 0.7 mM | R98L | 92 | 7.9% |
| 0.8 mM | R98L | 51 | 4.4% |
| 0 mM | R98L/T124I/P214H/K229Q | 1134 | |
| 0.4 mM | R98L/T124I/P214H/K229Q | 724 | 63.8% |
| 0.5 mM | R98L/T124I/P214H/K229Q | 654 | 57.7% |
| 0.6 mM | R98L/T124I/P214H/K229Q | 402 | 35.4% |
| 0.7 mM | R98L/T124I/P214H/K229Q | 302 | 26.6% |
| 0.8 mM | R98L/T124I/P214H/K229Q | 280 | 24.7% |
| 0 mM | P214H | 1184 | |
| 0.4 mM | P214H | 0 | 0.0% |

TABLE 9d-continued

Tolerance of single and multiple mutant combinations in the potato mitochondrial PPX coding sequence to sulfentrazone.

| Sulf Conc | Mutant(s) | Colonies | % age |
|---|---|---|---|
| 0.5 mM | P214H | 0 | 0.0% |
| 0.6 mM | P214H | 0 | 0.0% |

TABLE 9d-continued

Tolerance of single and multiple mutant combinations in the potato mitochondrial PPX coding sequence to sulfentrazone.

| Sulf Conc | Mutant(s) | Colonies | % age |
|---|---|---|---|
| 0.7 mM | P214H | 0 | 0.0% |
| 0.8 mM | P214H | 0 | 0.0% |

TABLE 10

Tolerance of single and multiple mutant combinations in the potato plastidal PPX coding sequence to saflufenacil measured by number of colonies reported.

| Mutation | | Plasmid | Avg # of saflufenacil resistant clones | Avg 0 mM | 0.3 mM/0 mM |
|---|---|---|---|---|---|
| — | S525T | F1061 | 0 | 69 | 0.0% |
| N85D | Y426H | SD5051 | 0 | 64 | 0.0% |
| F145L | L393V | SD5095 | 0 | 114 | 0.0% |
| S244G | L393V | SD5097 | 0 | 111 | 0.0% |
| F145Y | L403R | SD5116 | 0 | 104 | 0.0% |
| L226M | L424S | SD5109 | 6 | 50 | 1.3% |
| L226M | Y426F | SD5089 | 15 | 96 | 1.5% |
| A220T | L393V | SD5094 | 116 | 99 | 11.7% |
| A220T | Y426F | SD5084 | 190 | 87 | 22.0% |
| L226M | L403R | SD5119 | 225 | 69 | 32.5% |
| R144C | Y426F | SD5082 | 319 | 61 | 52.6% |
| R144C | Y426H | SD5052 | 415 | 75 | 55.4% |
| A180T | Y426H | SD5053 | 394 | 60 | 65.7% |
| A220T | Y426H | SD5054 | 356 | 46 | 77.5% |
| — | — | wt | 0 | 96 | 0.0% |

Example 5: Plant Cell Culture—Herbicide Kill Curves

Flumioxazin Kill Curves

Herbicide selection experiments were performed to determine the concentration of herbicide necessary to kill protoplast derived microcalli in a defined treatment period, in light of an initial kill curve result where a concentration of 125 µM was sufficient to kill all cells within a week, a new kill curve was designed using lower concentrations of flumioxazin aimed at determining the concentration at which 99% of the cells are killed (see Table 11). The herbicide was suspended in DMSO, with the final concentration of DMSO in the herbicide treatments being 1%. Development of cells was evaluated under the microscope once a week. Excepting the control treatments, division in all treatments with flumioxazin was prevented after one week and after one month no microcalli developed at any concentration tested. A flumioxazin concentration of 0.032 mM is sufficient to prevent microcallus development from potato protoplasts.

TABLE 11

Summary of results of flumioxazin kill curve experiments with cell suspension and shoot tip-derived protoplasts. Protoplasts were exposed to flumioxazin for a period of one month.

| Non treated protoplast + PEG | # Of calli in 3 beads | | Stop-GFP + Correcting GRON | # of calli in 3 beads | |
|---|---|---|---|---|---|
| Flumioxazin Conc. µM | # | % | Flumioxazin Conc. µM | # | % |
| Control #1* | 185 | | Control | 230 | |
| Control #2** | 150 | | Control | 190 | |
| Av. Cont 1 + Cont 2 | 157.5 | 100 | Av. Cont 1 + Cont 2 | 210 | 100 |
| 0.0156 | 40 | 25 | 0.0156 | 83 | 39 |
| 0.0312 | 8 | 5 | 0.0312 | 11 | 4 |
| 0.0468 | 0.0 | 0.0 | 0.0468 | 0.0 | 0.0 |
| 0.0624 | 0 | 0 | 0.0624 | 0 | 0 |

*Culture medium, no herbicide
**Culture medium with 1% DMSO, no herbicide

Sulfentrazone Kill Curves

Kill curves with sulfentrazone on shoot tip-derived protoplasts and cell suspension showed concentrations of 7.8 µM sulfentrazone are sufficient to kill all protoplast-derived cells (see Table 12). Therefore new kill curves were initiated with lower concentrations of 0, 0.5, 0.6, 0.7 and 0.8 µM of sulfentrazone, shown in Table 13. The results suggest that GRON treated protoplasts may be selected at concentrations between 0.6 µM and 0.7 µM of the herbicide.

TABLE 12

Summary of results of sulfentrazone kill curve experiments with cell suspension and shoot tip-derived protoplasts. Protoplasts were exposed to sulfentrazone for a period of one month.

| Sulfentrazone treatment [µM] | Microcallus formation |
|---|---|
| Control: 1* | Yes; abundant |
| Control: 2** | Yes; abundant |
| 62.5 | No |
| 31.25 | No |
| 15.6 | No |
| 7.8 | No |

*Culture medium, no herbicide
**Culture medium with 1% DMSO, no herbicide

20

TABLE 13

Summary of results of sulfentrazone kill curve experiments with cell suspension and shoot tip-derived protoplasts. Protoplasts were exposed to the herbicide for a period of one month.

| Non treated protoplast + PEG | # Of calli in 3 beads | | Stop-GFP + Correcting GRON | # of calli in beads | |
|---|---|---|---|---|---|
| Sulfentrazon Conc. µM | # | % | Sulfentrazonel Conc. µM | # | % |
| 0.0 | 115 | 100 | 0.0 | 125 | 100% |
| 0.5 | 45 | 30 | 0.5 | 38 | 30.2 |
| 0.6 | 8 | 6.9 | 0.6 | 12 | 9.6 |
| 0.7 | 2 | 1.7 | 0.7 | 7 | 5.6 |
| 0.8 | 0.0 | 0.0 | 0.8 | 0.0 | 0.0 |

* Culture medium, no herbicide
** Culture medium with 1% DMSO, no herbicide

Example 6: Leaf Disk Kill Curves

Aimed at establish the concentration of sulfentrazone that will inhibit callus formation in leaf disc explants, leaf discs were punched with a sterile hole punch from 5 weeks old in vitro grown potato plants. The leaf discs were cultured in petri dishes containing solid Haberlach culture medium containing various concentrations of Sulfentrazone in a final concentration of 1% DMSO. Six leaf discs cultured at each herbicide concentration. Plates were scaled with micropore tape and incubated at room temperature (approximately 23° C.). In an initial experiment, 7.8 µM sulfentrazone, the lowest concentration tested in that experiment, was sufficient to stop callas formations and bleach all leaf discs within 20 days. Results of kill curve with lower concentrations of sulfentrazone showed that a concentration of 3.0 µM of Sulfentrazone was sufficient to inhibit callus formation in almost all leaf discs after 20 days, whereas callus initiated after 13 days on the leaf veins of some leaf discs grown on 2.0 µM of Sulfentrazone. Similar leaf disc kill curve experiments were performed using saflufenacil where 0.5 µM of this herbicide was sufficient to inhibit callus formation in almost all leaf discs after 20 days.

Example 7: Materials and Methods for Cell Culture
and GRON Introduction

TABLE 14

| GRON Sequences | |
| --- | --- |
| GRON | Sequence |
| StcPPX1144/C/47/5'Cy3/3'idC | VGTTGGGAGATCCTGATGCGCCTTGCTTTGTCTTG TGGAAGGATAAACH (SEQ ID NO: 33) |
| StcPPX1144/NC/47/5'Cy3/3'idC | VGTTTATCCTTCCACAAGACAAAGCAAGGCGCATC AGGATCTCCCAACH (SEQ ID NO: 34) |
| StcPPX1220/C/47/5'Cy3/3'idC | VCATCATTTTACAGGTGTTTACACCGGTGACCCCT CAAAATTGH (SEQ ID NO: 35) |
| StcPPX1220/NC/47/5'Cy3/3'idC | VCAATTTTGAGGGGTCACCGGTGTAAACACCTGTA AAATGATGH (SEQ ID NO: 36) |

The converting base is shown in bold.
V = CY3; H = 3'DMT dC CPG

Cell Culture Work Description. Shoots, for example, derived from seeds, tubers, axillary buds, leaves, steams, mots, callus, or from microspore-derived embryos, are propagated under sterile conditions in vitro. Explants are subcultured, for example, every 3-4 weeks and cultured in Magenta GA7 culture vessels (Phytotechnology Laboratories. Shawnee Mission, KS, USA) with vented lids in a volume of about 100 mL culture medium, for example MS medium, according to Murashige and Skoog (A revised medium for rapid growth and bioassays with tobacco cultures. Physiol. Plant 15 (1962) 473-49), or modifications thereof. The vessels may be sealed with Micropore tape (3M Company). Young leaves, shoot tips, roots, microtuber or long stem segments possessing a leaf and axillary bud, as well as callus derived from these tissues, may be used for protoplast isolation. Protoplasts may also be isolated from suspension culture cells derived from young leaves, shoot tips, roots, microtubers or long stem segments possessing a leaf and axillary bud, as well as callus derived from these tissues, Protoplast Isolation from Shoot Tips About 200 shoot tips of 2-8 week-old in vitro shoots that have been cultured under a regular day/night regime, or, preferably were kept for two days before protoplast isolation in the dark, shoots may be cut into small pieces with a scalpel in a petri dish with sterile water. After all tips have been cut, the water is replaced with protoplast culture medium, preferably BN (B5 Salts and Vitamins (Phytotechnology Laboratories), glucose 20 g/L, mannitol 70 g/L, alpha naphthalene acetic acid 5 mg/L, additional $CaCl_2 \times 2H_2O$ 600 mg/L, casein hydrolysate 250 mg/l, cysteine-HCL 10 mg/L, polyvinylpyrrolidone (MW 10,000) 5 g/L. After approximately 1-2 h, the protoplast culture medium is replaced with enzyme solution, for example consisting of medium BN, in which 0.5% (w/v) Cellulase YC and 0.75% (w/v) Macerozyme R10 (both from Karlan Research Products, Cottonwood, Arizona), 1 g/i bovine serum albumin, and 1 g/L 2-morpholinoethanesulfonic acid are dissolved. The ratio of the number of shoot tips over the volume of enzyme solution can be between 10 and 16, preferably 13 The dish with shoot tip pieces in enzyme solution is incubated for at 25° C.-30° C. preferably 28° C., in darkness on a shaker set to about 50 rpm. After overnight incubation the protoplast suspension is purified using an iodixanol density gradient (adapted from Optiprep Application Sheet C18;

Purification of Intact Plant Protoplasts; Axis-Shield USA. 10 Commerce Way, Norton, MA 02776). After the density gradient centrifugation, the band with purified protoplasts is removed together with about 5 mL W5 medium (Frigerio et al., 1998). The protoplast density and yield are determined with a hemocytometer. The protoplasts density is adjusted to $1 \times 10^6$/mL in BN medium containing 2 mg/L 2,6-dichlorobenzonitrile (cellulose synthase inhibitor), and the protoplasts are cultured in darkness at 30° C., for about 16 h.

Protoplast Isolation from Cell Suspensions

The isolation of protoplasts from cell suspensions follows the same protocol as described for the isolation of protoplasts from shoot tips, with the following exceptions:

1. Fast growing cell suspensions are used, preferably three days after their last subculture. 1.5 mL settled cell volume is transferred to about 15 ml BN medium, which after 2 h is replaced with enzyme solution. 2. The protoplast purification is followed immediately by the GRON/PEG treatment.

Gene Repair Oligonucleotide (GRON) Introduction

The protoplast suspension is mixed with an equal volume of W5 medium, transferred to a 50 mL centrifuge tube, and centrifuged for 10 min at the lowest setting of a clinical centrifuge (about 50×g). The supernatant is removed and replaced with TM medium (Klaus, S. Markerfreie transplastome Tabakpilanzen (Marker-free transplastomic tobacco plants). PhD Dissertation, 2002, Ludwig-Maximilians-Universitxt München, 109 pp), adjusting the protoplast density to $5 \times 10^6$/mL. Aliquots of 100 µL containing $5 \times 10^5$ protoplasts each are distributed into 12 mL round bottom centrifuge tubes. GRONs (such as those shown in Table 14) targeted at one or more mutations in one or both of the mitochondrial and plastidal PPX genes are then introduced into the protoplasts using a PEG treatment. To introduce the GRONs into the protoplasts, 12.5 µg GRON dissolved in 25 µL purified water and 125 µL of a polyethylene glycol solution (5 g PEG MW 1500, 638 mg mannitol, 207 mg $CaNO_3 \times 4H_2O$ and 8.75 mL purified water; pH adjusted to about 9.0) is added. After a 10-30 min incubation on ice, the protoplast-PEG suspension is washed with W5 medium and resuspended in medium BN. The suspension is kept overnight in darkness at room temperature.

GRONs may be introduced into protoplasts by electroporation, cationic lipids, nanoparticles, polycations such as hexadimethrine bromide (polybrene) or spermidine, or by using GRONs complexed to a variety of cell penetrating peptides (CPPs) including but not limited to TAT, pVEC, transportan, nona-arginine, BAX inhibiting peptide (VPMLK), or such as those listed in Patel et al. Cell Penetrating Peptides; Intracellular Pathways and Pharmaceutical Perspectives. Pharmaceutical Research, 24 (2007) 1477-1992, or Veldhoen et al. Recent developments in peptide-based nucleic acid delivery. International Journal of Molecular Science (2008) 1276-1320. In another embodiment, GRONs are introduced into protoplasts through negatively charged polymers including, but not limited to dendrimers such as Polyamidoamine (PAMAM).

GRONs may also be delivered into whole tissues or cells using methods that may include microinjection, biolistics with the GRONs coated on carriers such as gold or directly in the form of droplets of a GRON suspension, GRON coated whiskers or using GRONs complexed to a variety of cell penetrating peptides (CPPs) negatively charged polymers as mentioned in the preceding paragraph. Other embodiments envision the use of ultrasound, imbibition m GRON containing solutions, or permeabilization of cell walls, for example through agents such as toluene or saponin.

Embedding of Protoplasts in Calcium Alginate

One day after the GRON introduction, protoplasts are embedded in calcium alginate. The embedding of protoplasts in gel substrates (e.g., agarose, alginate) has been shown to enhance protoplast survival and to increase division frequencies of protoplast-derived cells. The method applied is based on that described in Dovzhenko et al. (Thin-alginate-layer technique for protoplast culture of tobacco leaf protoplasts: shoot formation in less than two weeks. Protoplasma 204 (1991) 114-118).

Protoplast Culture and Selection of Herbicide-Resistant Calli

The selection of herbicide-resistant calli is carried out using sequential subcultures of the alginates in liquid media according to Pelletier et al. (1983). Selection may be started one week after the PEG/GRON treatment at an appropriate concentration of PPX-inhibiting herbicide; for example, 32 µM flumioxazin, or 0.25 µM, 0.5 µM, 1 µM, 2 µM, 3 µM, 4 µM, 5 µM, 6 µM, 7 µM, 7.8 µM, 15.6 µM, 31.2 µM or 625 µM sulfentrazone.

Before the end of the selection phase in liquid medium, cells and colonies are released from the alginate by treating them for 30-45 min with culture medium containing 50 mM sodium citrate. At the moment of transferring released colonies from liquid to solid medium CuI (taberlach et al. Isolation, culture and regeneration of protoplasts from potato and several related *Solanum* species. Plant Science, 39 (1985) 67-74), the majority of colonies may be either dead, or consist of a greenish center, covered with outer layers of dead cells. On the solidified selection medium (CuI+herbicide) the majority of microcalli that still contain living cells may stop growing and turn brownish. Limited growth of individual calli continues occasionally, but all non-resistant calli eventually turn brown and die. Two to three weeks after the transfer to solidified selection medium (occasionally earlier), actively growing calli may appear among a background of brownish cells and microcalli.

Regeneration of plants from protoplast-derived, herbicide-tolerant calli with a confirmed mutation in a PPX gene is performed. PPX-inhibiting herbicide-tolerant calli that develop on solidified selection medium and whose DNA upon analysis shows the presence of a mutation are transferred to herbicide-free medium CuI to accelerate development. Individual callus lines vary in their growth rate and morphologies. In general, the development towards shoot regeneration follows these steps:

Undifferentiated, Green Callus→Callus with Dark Green Areas→Development of Shout Initials→Development of a Plant.

The development of individual callus lines is variable, but through continuous subculture and multiplication on CuI medium or by changing the media formulation to differentiation medium including but not limited to Haberlach differentiation medium, for an acceptable period of time (1-6 months) followed by transfer of the callus lines to regeneration media including but not limited to Bokelmann regeneration medium (Bokelmann G. S. and Roest S., Z. Pflanzenphysiol, vol. 109, p. 259-265 (1983), eventually many produce shoots.

Once shoots with three to four leaves are formed on regeneration medium, they are transferred to propagation medium including but not limited to MS medium. On this medium, over time, shoots and leaves develop that are morphologically 'normal'. After in vitro plantlets produce roots, standard protocols are used for the adaptation to greenhouse conditions.

Molecular Screening

Using standard molecular techniques and more sensitive PCR based technologies can be used to monitor the frequency of PPX mutations following an RTDS treatment. These molecular techniques include and are not limited to, allele specific PCR. DNA sequencing and other SNP identification technologies using non-PCR techniques. These techniques allow for monitoring the frequency of PPX targeted mutations early in the procedure. In certain embodiments, the mutations can be measured in populations of single cells. These techniques can then be applicable throughout the culture process to confirm and monitor mutations are present in selected calli and regenerated plants.

Example 8: Herbicide Spray

*Solanum tuberosum* or Russet Burbank potato cultivar plants when they are 2-6" tall (generally the 5-4 leaf stage) are sprayed with various PPX-inhibiting herbicides. Herbicides are sprayed in the presence of 0.25% AU391 surfactant. The herbicides are sprayed, for example, at the following rates:

Flumioxazin 2 oz active ingredient/Acre (ai/A)

Sulfentrazone 4.5 oz ai/A

Saflufenacil I-13 oz ai/A

Herbicides are applied by foliar spray with control plants being left unsprayed. PPX-inhibiting herbicide trials are evaluated 14 days post spraying using a damage scale of 1-10 with I being dead, and 10 being the undamaged unsprayed controls. Individual plant lines are scored at each spray rate compared to the performance of the controls at that particular rate. PPX inhibiting herbicides have a potentially wide window of application and can be used as a "pre" or "post" application for crops including potato. Herbicide evaluations include both greenhouse and field applications to monitor plant (crop) damage and/or weed control. Products from RTDS work can allow farmers to plant crops like potato and apply PPX inhibiting herbicides to eliminate or control weeds in the fields while not damaging crops.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof. It is recognized that various modifications are possible within the scope of the invention claimed.

Thus, it should be understood that although the present invention has been specifically disclosed by preferred embodiments and optional features, modification, improvement, and variation of the inventions disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other embodiments are set forth within the following claims.

---

What is claimed is:

1. A non-transgenic, gene-edited plant comprising a protoporphyrinogen IX oxidase (PPX) gene edited to encode a protein comprising a phenylalanine to tyrosine substitution at position corresponding to position 145 of SEQ ID NO: 1, and optionally one or more substitutions selected from the group consisting of a tyrosine to phenylalanine substitution at position 426 of SEQ ID NO: 1, a leucine to arginine substitution at position corresponding to position 426 of SEQ ID NO: 1, and a leucine to valine substitution at position corresponding to position 393 of SEQ ID NO: 1.

2. The plant of claim 1, wherein said plant is selected from the group consisting of potato, sunflower, sugar beet, maize, cotton, soybean, wheat, rye, oats, rice, canola, fruits, vegetables, tobacco, barley, sorghum, tomato, mango, peach, apple, pear, strawberry, banana, melon, carrot, lettuce, onion, soya spp, sugar cane, pea, field beans, poplar, grape, citrus, alfalfa, rye, oats, turf and forage grasses, flax, oilseed rape, cucumber, morning glory, balsam, pepper, eggplant, marigold, lotus, cabbage, daisy, carnation, petunia, tulip, iris, lily, and nut-producing plants.

3. The plant of claim 1, wherein said plant is asexually reproduced, or produced from a tuber.

4. The plant of claim 1, wherein said plant is resistant to one or more PPX-inhibiting herbicides selected from the group consisting of acifluorfen-Na, Bifenox, Chlomethoxyfen, fluoroglycofen-ethyl, Fomesafen, Halosafen, Lactofen, Oxyfluorfen, Fluazolate, pyraflufen-ethyl, cinidon-ethyl, Flumioxazin, flumiclorac-pentyl, fluthiacetmethyl, Thidiazimin, Oxadiazon, Oxadiargyl, Azafenidin, carfentrazone-ethyl, Sulfentrazone, Pentoxazone, Benzfendizone, Butafenacil, Saflufenacil, Pyrazogyl, and Profluazol.

5. A non-transgenic, gene-edited plant cell comprising a protoporphyrinogen IX oxidase (PPX) gene edited to encode a protein comprising a phenylalanine to tyrosine substitution at position corresponding to position 145 of SEQ ID NO: 1, and optionally one or more substitutions selected from the group consisting of a tyrosine to phenylalanine substitution at position 426 of SEQ ID NO: 1, a leucine to arginine substitution at position corresponding to position 426 of SEQ ID NO: 1, and a leucine to valine substitution at position corresponding to position 393 of SEQ ID NO: 1.

6. The plant cell of claim 5, wherein said plant is selected from the group consisting of potato, sunflower, sugar beet, maize, cotton, soybean, wheat, rye, oats, rice, canola, fruits, vegetables, tobacco, barley, sorghum, tomato, mango, peach, apple, pear, strawberry, banana, melon, carrot, lettuce, onion, soya spp, sugar cane, pea, field beans, poplar, grape, citrus, alfalfa, rye, oats, turf and forage grasses, flax, oilseed rape, cucumber, morning glory, balsam, pepper, eggplant, marigold, lotus, cabbage, daisy, carnation, petunia, tulip, iris, lily, and nut-producing plants.

7. The plant cell of claim 5, wherein said plant is resistant to one or more PPX-inhibiting herbicides selected from the group consisting of acifluorfen-Na, Bifenox, Chlomethoxyfen, fluoroglycofen-ethyl, Fomesafen, Halosafen, Lactofen, Oxyfluorfen, Fluazolate, pyraflufen-ethyl, cinidon-ethyl, Flumioxazin, flumiclorac-pentyl, fluthiacetmethyl, Thidiazimin, Oxadiazon, Oxadiargyl, Azafenidin, carfentrazone-ethyl, Sulfentrazone, Pentoxazone, Benzfendizone, Butafenacil, Saflufenacil, Pyrazogyl, and Profluazol.

8. A method for producing a non-transgenic, gene-edited plant cell with a mutated PPX gene, comprising introducing into a plant cell a gene repair oligonucleobase (GRON) configured and arranged to introduce a targeted phenylalanine to tyrosine substitution in an endogenous PPX gene of the plant cell at position corresponding to position 145 of SEQ ID NO: 1, and optionally to introduce one or more additional targeted substitutions selected from the group consisting of a tyrosine to phenylalanine substitution at position 426 of SEQ ID NO: 1, a leucine to arginine substitution at position corresponding to position 426 of SEQ ID NO: 1, and a leucine to valine substitution at position corresponding to position 393 of SEQ ID NO: 1, under conditions where the targeted substitution(s) are introduced into the endogenous PPX gene.

9. The method of claim 8, further comprising:

identifying a plant cell having the targeted substitution(s), and having substantially normal growth and catalytic activity as compared to a corresponding wild-type plant cell in the presence of an herbicide; and regenerating from said plant cell a non-transgenic herbicide-resistant plant expressing the mutated PPX gene.

10. The method of claim 8, wherein said plant cell is of a plant selected from the group consisting of potato, sunflower, sugar beet, maize, cotton, soybean, wheat, rye, oats, rice, canola, fruits, vegetables, tobacco, barley, sorghum, tomato, mango, peach, apple, pear, strawberry, banana, melon, carrot, lettuce, onion, soya spp, sugar cane, pea, field beans, poplar, grape, citrus, alfalfa, rye, oats, turf and forage grasses, flax, oilseed rape, cucumber, morning glory, balsam, pepper, eggplant, marigold, lotus, cabbage, daisy, carnation, petunia, tulip, iris, lily, and nut-producing plants.

11. The method of claim 8, wherein said plant cell is of a species selected from the group consisting of *Solanum tuberosum, Oryza sativa, Sorghum bicolor, Ricinus communis, Brassica napus, Glycine max*, and *Zea mays*.

12. The method of claim 8, wherein said plant cell is resistant to one or more PPX-inhibiting herbicides selected from the group consisting of acifluorfen-Na, Bifenox, Chlomethoxyfen, fluoroglycofen-ethyl, Fomesafen, Halosafen, Lactofen, Oxyfluorfen, Fluazolate, pyraflufenethyl, cinidon-ethyl, Flumioxazin, flumiclorac-pentyl, fluthiacet-methyl, Thidiazimin, Oxadiazon, Oxadiargyl, Azafenidin, carfentrazone-ethyl, Sulfentrazone, Pentoxazone, Benzfendizone, Butafenacil, Saflufenacil, Pyrazogyl, and Profluazol.

13. The method of claim 9, further comprising propagating the non-transgenic herbicide-resistant plant asexually.

14. The plant of claim 1, wherein the plant is a *Solanum tuberosum* plant.

15. The plant of claim 1, wherein the plant is an *Oryza sativa* plant.

16. The plant of claim 1, wherein the plant is a *Zea mays* plant.

17. The plant of claim 5, wherein the plant is a *Solanum tuberosum* plant.

18. The plant of claim 5, wherein the plant is an *Oryza sativa* plant.

19. The plant of claim 5, wherein the plant is a *Zea mays* plant.

20. The method of claim 11 wherein the plant cell of species *Solanum tuberosum* is of cultivar Russet Burbank.

\* \* \* \* \*

SEQUENCE LISTING

```
<160> NUMBER OF SEQ ID NOS: 58

<210> SEQ ID NO 1
<211> LENGTH: 537
<212> TYPE: PRT
<213> ORGANISM: Arabidopsis thaliana

<400> SEQUENCE: 1

Met Glu Leu Ser Leu Leu Arg Pro Thr Thr Gln Ser Leu Leu Pro Ser
1               5                   10                  15

Phe Ser Lys Pro Asn Leu Arg Leu Asn Val Tyr Lys Pro Leu Arg Leu
            20                  25                  30

Arg Cys Ser Val Ala Gly Gly Pro Thr Val Gly Ser Ser Lys Ile Glu
        35                  40                  45

Gly Gly Gly Gly Thr Thr Ile Thr Thr Asp Cys Val Ile Val Gly Gly
    50                  55                  60

Gly Ile Ser Gly Leu Cys Ile Ala Gln Ala Leu Ala Thr Lys His Pro
65                  70                  75                  80

Asp Ala Ala Pro Asn Leu Ile Val Thr Glu Ala Lys Asp Arg Val Gly
                85                  90                  95

Gly Asn Ile Ile Thr Arg Glu Glu Asn Gly Phe Leu Trp Glu Glu Gly
            100                 105                 110

Pro Asn Ser Phe Gln Pro Ser Asp Pro Met Leu Thr Met Val Val Asp
        115                 120                 125

Ser Gly Leu Lys Asp Asp Leu Val Leu Gly Asp Pro Thr Ala Pro Arg
    130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                165                 170                 175

Gly Phe Gly Ala Leu Gly Ile Arg Pro Ser Pro Pro Gly Arg Glu Glu
            180                 185                 190

Ser Val Glu Glu Phe Val Arg Arg Asn Leu Gly Asp Glu Val Phe Glu
        195                 200                 205

Arg Leu Ile Glu Pro Phe Cys Ser Gly Val Tyr Ala Gly Asp Pro Ser
    210                 215                 220
```

```
Lys Leu Ser Met Lys Ala Ala Phe Gly Lys Val Trp Lys Leu Glu Gln
225                 230                 235                 240

Asn Gly Gly Ser Ile Ile Gly Gly Thr Phe Lys Ala Ile Gln Glu Arg
                245                 250                 255

Lys Asn Ala Pro Lys Ala Glu Arg Asp Pro Arg Leu Pro Lys Pro Gln
                260                 265                 270

Gly Gln Thr Val Gly Ser Phe Arg Lys Gly Leu Arg Met Leu Pro Glu
            275                 280                 285

Ala Ile Ser Ala Arg Leu Gly Ser Lys Val Lys Leu Ser Trp Lys Leu
        290                 295                 300

Ser Gly Ile Thr Lys Leu Glu Ser Gly Gly Tyr Asn Leu Thr Tyr Glu
305                 310                 315                 320

Thr Pro Asp Gly Leu Val Ser Val Gln Ser Lys Ser Val Val Met Thr
                325                 330                 335

Val Pro Ser His Val Ala Ser Gly Leu Leu Arg Pro Leu Ser Glu Ser
                340                 345                 350

Ala Ala Asn Ala Leu Ser Lys Leu Tyr Tyr Pro Pro Val Ala Ala Val
            355                 360                 365

Ser Ile Ser Tyr Pro Lys Glu Ala Ile Arg Thr Glu Cys Leu Ile Asp
        370                 375                 380

Gly Glu Leu Lys Gly Phe Gly Gln Leu His Pro Arg Thr Gln Gly Val
385                 390                 395                 400

Glu Thr Leu Gly Thr Ile Tyr Ser Ser Ser Leu Phe Pro Asn Arg Ala
                405                 410                 415

Pro Pro Gly Arg Ile Leu Leu Leu Asn Tyr Ile Gly Gly Ser Thr Asn
            420                 425                 430

Thr Gly Ile Leu Ser Lys Ser Glu Gly Glu Leu Val Glu Ala Val Asp
            435                 440                 445

Arg Asp Leu Arg Lys Met Leu Ile Lys Pro Asn Ser Thr Asp Pro Leu
        450                 455                 460

Lys Leu Gly Val Arg Val Trp Pro Gln Ala Ile Pro Gln Phe Leu Val
465                 470                 475                 480

Gly His Phe Asp Ile Leu Asp Thr Ala Lys Ser Ser Leu Thr Ser Ser
                485                 490                 495

Gly Tyr Glu Gly Leu Phe Leu Gly Gly Asn Tyr Val Ala Gly Val Ala
            500                 505                 510

Leu Gly Arg Cys Val Glu Gly Ala Tyr Glu Thr Ala Ile Glu Val Asn
        515                 520                 525

Asn Phe Met Ser Arg Tyr Ala Tyr Lys
530                 535
```

```
<210> SEQ ID NO 2
<211> LENGTH: 1719
<212> TYPE: DNA
<213> ORGANISM: Arabidopsis thaliana

<400> SEQUENCE: 2
tgacaaaatt ccgaattctc tgcgatttcc atggagttat ctcttctccg tccgacgact      60
caatcgcttc ttccgtcgtt ttcgaagccc aatctccgat taaatgttta taagcctctt     120
agactccgtt gttcagtggc cggtggacca accgtcggat cttcaaaaat cgaaggcgga     180
ggaggcacca ccatcacgac ggattgtgtg attgtcggcg gaggtattag tggtctttgc     240
atcgctcagg cgcttgctac taagcatcct gatgctgctc cgaatttaat tgtgaccgag     300
gctaaggatc gtgttggagg caacattatc actcgtgaag agaatggttt tctctgggaa     360
```

-continued

```
gaaggtcccca atagttttca accgtctgat cctatgctca ctatggtggt agatagtggt    420
ttgaaggatg atttggtgtt gggagatcct actgcgccaa ggtttgtgtt gtggaatggg    480
aaattgaggc cggttccatc gaagctaaca gacttaccgt tctttgattt gatgagtatt    540
ggtgggaaga ttagagctgg ttttggtgca cttggcattc gaccgtcacc tccaggtcgt    600
gaagaatctg tggaggagtt tgtacggcgt aacctcggtg atgaggtttt tgagcgcctg    660
attgaaccgt tttgttcagg tgtttatgct ggtgatcctt caaaactgag catgaaagca    720
gcgtttggga aggtttggaa actagagcaa aatggtggaa gcataatagg tggtactttt    780
aaggcaattc aggagaggaa aaacgctccc aaggcagaac gagacccgcg cctgccaaaa    840
ccacagggcc aaacagttgg ttctttcagg aagggacttc gaatgttgcc agaagcaata    900
tctgcaagat taggtagcaa agttaagttg tcttggaagc tctcaggtat cactaagctg    960
gagagcggag gatacaactt aacatatgag actccagatg gtttagtttc cgtgcagagc   1020
aaaagtgttg taatgacggt gccatctcat gttgcaagtg gtctcttgcg ccctctttct   1080
gaatctgctg caaatgcact ctcaaaacta tattacccac cagttgcagc agtatctatc   1140
tcgtacccga aagaagcaat ccgaacagaa tgtttgatag atggtgaact aaagggtttt   1200
gggcaattgc atccacgcac gcaaggagtt gaaacattag gaactatcta cagctcctca   1260
ctctttccaa atcgcgcacc gcccggaaga attttgctgt tgaactacat tggcgggtct   1320
acaaacaccg gaattctgtc caagtctgaa ggtgagttag tggaagcagt tgacagagat   1380
ttgaggaaaa tgctaattaa gcctaattcg accgatccac ttaaattagg agttagggta   1440
tggcctcaag ccattcctca gtttctagtt ggtcactttg atatccttga cacggctaaa   1500
tcatctctaa cgtcttcggg ctacgaaggg ctatttttgg gtggcaatta cgtcgctggt   1560
gtagccttag gccggtgtgt agaaggcgca tatgaaaccg cgattgaggt caacaacttc   1620
atgtcacggt acgcttacaa gtaaatgtaa aacattaaat ctcccagctt gcgtgagttt   1680
tattaaatat tttgagatat ccaaaaaaaa aaaaaaaaa                           1719
```

```
<210> SEQ ID NO 3
<211> LENGTH: 508
<212> TYPE: PRT
<213> ORGANISM: Arabidopsis thaliana

<400> SEQUENCE: 3

Met Ala Ser Gly Ala Val Ala Asp His Gln Ile Glu Ala Val Ser Gly
1               5                   10                  15

Lys Arg Val Ala Val Val Gly Ala Gly Val Ser Gly Leu Ala Ala Ala
            20                  25                  30

Tyr Lys Leu Lys Ser Arg Gly Leu Asn Val Thr Val Phe Glu Ala Asp
        35                  40                  45

Gly Arg Val Gly Gly Lys Leu Arg Ser Val Met Gln Asn Gly Leu Ile
    50                  55                  60

Trp Asp Glu Gly Ala Asn Thr Met Thr Glu Ala Glu Pro Glu Val Gly
65                  70                  75                  80

Ser Leu Leu Asp Asp Leu Gly Leu Arg Glu Lys Gln Gln Phe Pro Ile
                85                  90                  95

Ser Gln Lys Lys Arg Tyr Ile Val Arg Asn Gly Val Pro Val Met Leu
            100                 105                 110

Pro Thr Asn Pro Ile Glu Leu Val Thr Ser Ser Val Leu Ser Thr Gln
        115                 120                 125
```

-continued

```
Ser Lys Phe Gln Ile Leu Leu Glu Pro Phe Leu Trp Lys Lys Lys Ser
    130                 135                 140

Ser Lys Val Ser Asp Ala Ser Ala Glu Glu Ser Val Ser Glu Phe Phe
145                 150                 155                 160

Gln Arg His Phe Gly Gln Glu Val Val Asp Tyr Leu Ile Asp Pro Phe
                165                 170                 175

Val Gly Gly Thr Ser Ala Ala Asp Pro Asp Ser Leu Ser Met Lys His
            180                 185                 190

Ser Phe Pro Asp Leu Trp Asn Val Glu Lys Ser Phe Gly Ser Ile Ile
            195                 200                 205

Val Gly Ala Ile Arg Thr Lys Phe Ala Ala Lys Gly Gly Lys Ser Arg
    210                 215                 220

Asp Thr Lys Ser Ser Pro Gly Thr Lys Lys Gly Ser Arg Gly Ser Phe
225                 230                 235                 240

Ser Phe Lys Gly Gly Met Gln Ile Leu Pro Asp Thr Leu Cys Lys Ser
                245                 250                 255

Leu Ser His Asp Glu Ile Asn Leu Asp Ser Lys Val Leu Ser Leu Ser
            260                 265                 270

Tyr Asn Ser Gly Ser Arg Gln Glu Asn Trp Ser Leu Ser Cys Val Ser
            275                 280                 285

His Asn Glu Thr Gln Arg Gln Asn Pro His Tyr Asp Ala Val Ile Met
    290                 295                 300

Thr Ala Pro Leu Cys Asn Val Lys Glu Met Lys Val Met Lys Gly Gly
305                 310                 315                 320

Gln Pro Phe Gln Leu Asn Phe Leu Pro Glu Ile Asn Tyr Met Pro Leu
                325                 330                 335

Ser Val Leu Ile Thr Thr Phe Thr Lys Glu Lys Val Lys Arg Pro Leu
            340                 345                 350

Glu Gly Phe Gly Val Leu Ile Pro Ser Lys Glu Gln Lys His Gly Phe
            355                 360                 365

Lys Thr Leu Gly Thr Leu Phe Ser Ser Met Met Phe Pro Asp Arg Ser
    370                 375                 380

Pro Ser Asp Val His Leu Tyr Thr Thr Phe Ile Gly Gly Ser Arg Asn
385                 390                 395                 400

Gln Glu Leu Ala Lys Ala Ser Thr Asp Glu Leu Lys Gln Val Val Thr
                405                 410                 415

Ser Asp Leu Gln Arg Leu Leu Gly Val Glu Gly Glu Pro Val Ser Val
            420                 425                 430

Asn His Tyr Tyr Trp Arg Lys Ala Phe Pro Leu Tyr Asp Ser Ser Tyr
            435                 440                 445

Asp Ser Val Met Glu Ala Ile Asp Lys Met Glu Asn Asp Leu Pro Gly
    450                 455                 460

Phe Phe Tyr Ala Gly Asn His Arg Gly Gly Leu Ser Val Gly Lys Ser
465                 470                 475                 480

Ile Ala Ser Gly Cys Lys Ala Ala Asp Leu Val Ile Ser Tyr Leu Glu
                485                 490                 495

Ser Cys Ser Asn Asp Lys Lys Pro Asn Asp Ser Leu
            500                 505
```

<210> SEQ ID NO 4
<211> LENGTH: 1822
<212> TYPE: DNA
<213> ORGANISM: Arabidopsis thaliana

<400> SEQUENCE: 4

```
tttccgtcac tgctttcgac tggtcagaga ttttgactct gaattgttgc agatagcaat      60
ggcgtctgga gcagtagcag atcatcaaat tgaagcggtt tcaggaaaaa gagtcgcagt     120
cgtaggtgca ggtgtaagtg gacttgcggc ggcttacaag ttgaaatcga ggggtttgaa     180
tgtgactgtg tttgaagctg atggaagagt aggtgggaag ttgagaagtg ttatgcaaaa     240
tggtttgatt tgggatgaag gagcaaacac catgactgag gctgagccag aagttgggag     300
tttacttgat gatcttgggc ttcgtgagaa acaacaattt ccaatttcac agaaaaagcg     360
gtatattgtg cggaatggtg tacctgtgat gctacctacc aatcccatag agctggtcac     420
aagtagtgtg ctctctaccc aatctaagtt tcaaatcttg ttggaaccat ttttatggaa     480
gaaaaagtcc tcaaaagtct cagatgcatc tgctgaagaa agtgtaagcg agttctttca     540
acgccatttt ggacaagagg ttgttgacta tctcatcgac cctttgttg gtggaacaag      600 tgctgcggac cctgattccc tttcaatgaa gcattctttc ccagatctct ggaatgtaga     660
gaaaagtttt ggctctatta tagtcggtgc aatcagaaca aagtttgctg ctaaaggtgg     720
taaaagtaga gacacaaaga gttctcctgg cacaaaaaag ggttcgcgtg ggtcattctc     780
ttttaagggg ggaatgcaga ttcttcctga tacgttgtgc aaaagtctct cacatgatga     840
gatcaattta gactccaagg tactctcttt gtcttacaat tctggatcaa gacaggagaa     900
ctggtcatta tcttgtgttt cgcataatga aacgcagaga caaaccccc attatgatgc      960 tgtaattatg acggctcctc tgtgcaatgt gaaggagatg aaggttatga aaggaggaca    1020
accctttcag ctaaactttc tccccgagat taattacatg cccctctcgg ttttaatcac    1080
cacattcaca aaggagaaag taaagagacc tcttgaaggc tttggggtac tcattccatc    1140
taaggagcaa aagcatggtt tcaaaactct aggtacactt ttttcatcaa tgatgtttcc    1200
agatcgttcc cctagtgacg ttcatctata tacaactttt attggtggga gtaggaacca    1260
ggaactagcc aaagcttcca ctgacgaatt aaaacaagtt gtgacttctg accttcagcg    1320
actgttgggg gttgaaggtg aacccgtgtc tgtcaaccat tactattgga ggaaagcatt    1380
cccgttgtat gacagcagct atgactcagt catggaagca attgacaaga tggagaatga    1440
tctacctggg ttcttctatg caggtaatca tcgagggggg ctctctgttg ggaaatcaat    1500
agcatcaggt tgcaaagcag ctgaccttgt gatctcatac ctggagtctt gctcaaatga    1560
caagaaacca aatgacagct ataacattg tcaaggttcg tccctttta tcacttactt      1620 tgtaaacttg taaaatgcaa caagccgccg tgcgattagc caacaactca gcaaaaccca    1680
gattctcata aggctcacta attccagaat aaactattta tgtattgttt ggtctgtttt    1740
cttgttgcat cactggtatg gtctgtctag gtagaagaat atgatagggt gagggatttt    1800
aggattgaag aatctttaaa ac                                             1822
```

<210> SEQ ID NO 5
<211> LENGTH: 534
<212> TYPE: PRT
<213> ORGANISM: Amaranthus tuberculatus

<400> SEQUENCE: 5

```
Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
            20                  25                  30

Asn Ile Ser Glu Arg Glu Glu Pro Thr Ser Ala Lys Arg Val Ala Val
        35                  40                  45
```

```
Val Gly Ala Gly Val Ser Gly Leu Ala Ala Ala Tyr Lys Leu Lys Ser
    50              55              60

His Gly Leu Ser Val Thr Leu Phe Glu Ala Asp Ser Arg Ala Gly Gly
65              70              75              80

Lys Leu Lys Thr Val Lys Lys Asp Gly Phe Ile Trp Asp Glu Gly Ala
            85              90              95

Asn Thr Met Thr Glu Ser Glu Ala Glu Val Ser Ser Leu Ile Asp Asp
            100             105             110

Leu Gly Leu Arg Glu Lys Gln Gln Leu Pro Ile Ser Gln Asn Lys Arg
            115             120             125

Tyr Ile Ala Arg Ala Gly Leu Pro Val Leu Leu Pro Ser Asn Pro Ala
    130             135             140

Ala Leu Leu Thr Ser Asn Ile Leu Ser Ala Lys Ser Lys Leu Gln Ile
145             150             155             160

Met Leu Glu Pro Phe Leu Trp Arg Lys His Asn Ala Thr Glu Leu Ser
            165             170             175

Asp Glu His Val Gln Glu Ser Val Gly Glu Phe Phe Glu Arg His Phe
            180             185             190

Gly Lys Glu Phe Val Asp Tyr Val Ile Asp Pro Phe Val Ala Gly Thr
            195             200             205

Cys Gly Gly Asp Pro Gln Ser Leu Ser Met His His Thr Phe Pro Glu
    210             215             220

Val Trp Asn Ile Glu Lys Arg Phe Gly Ser Val Phe Ala Gly Leu Ile
225             230             235             240

Gln Ser Thr Leu Leu Ser Lys Lys Glu Lys Gly Gly Glu Asn Ala Ser
            245             250             255

Ile Lys Lys Pro Arg Val Arg Gly Ser Phe Ser Phe Gln Gly Gly Met
            260             265             270

Gln Thr Leu Val Asp Thr Met Cys Lys Gln Leu Gly Glu Asp Glu Leu
            275             280             285

Lys Leu Gln Cys Glu Val Leu Ser Leu Ser Tyr Asn Gln Lys Gly Ile
    290             295             300

Pro Ser Leu Gly Asn Trp Ser Val Ser Ser Met Ser Asn Asn Thr Ser
305             310             315             320

Glu Asp Gln Ser Tyr Asp Ala Val Val Val Thr Ala Pro Ile Arg Asn
            325             330             335

Val Lys Glu Met Lys Ile Met Lys Phe Gly Asn Pro Phe Ser Leu Asp
            340             345             350

Phe Ile Pro Glu Val Thr Tyr Val Pro Leu Ser Val Met Ile Thr Ala
            355             360             365

Phe Lys Lys Asp Lys Val Lys Arg Pro Leu Glu Gly Phe Gly Val Leu
    370             375             380

Ile Pro Ser Lys Glu Gln His Asn Gly Leu Lys Thr Leu Gly Thr Leu
385             390             395             400

Phe Ser Ser Met Met Phe Pro Asp Arg Ala Pro Ser Asp Met Cys Leu
            405             410             415

Phe Thr Thr Phe Val Gly Gly Ser Arg Asn Arg Lys Leu Ala Asn Ala
            420             425             430

Ser Thr Asp Glu Leu Lys Gln Ile Val Ser Ser Asp Leu Gln Gln Leu
            435             440             445

Leu Gly Thr Glu Asp Glu Pro Ser Phe Val Asn His Leu Phe Trp Ser
    450             455             460
```

-continued

```
Asn Ala Phe Pro Leu Tyr Gly His Asn Tyr Asp Ser Val Leu Arg Ala
465             470             475             480

Ile Asp Lys Met Glu Lys Asp Leu Pro Gly Phe Phe Tyr Ala Gly Asn
            485             490             495

His Lys Gly Gly Leu Ser Val Gly Lys Ala Met Ala Ser Gly Cys Lys
        500             505             510

Ala Ala Glu Leu Val Ile Ser Tyr Leu Asp Ser His Ile Tyr Val Lys
    515             520             525

Met Asp Glu Lys Thr Ala
    530
```

```
<210> SEQ ID NO 6
<211> LENGTH: 1605
<212> TYPE: DNA
<213> ORGANISM: Amaranthus tuberculatus

<400> SEQUENCE: 6
atggtaattc aatccattac ccacctttca ccaaaccttg cattgccatc gccattgtca      60
gtttcaacca agaactaccc agtagctgta atgggcaaca tttctgagcg ggaagaaccc     120
acttctgcta aaagggttgc tgttgttggt gctggagtta gtggacttgc tgctgcatat     180
aagctaaaat cccatggttt gagtgtgaca ttgtttgaag ctgattctag agctggaggc     240
aaacttaaaa ctgttaaaaa agatggtttt atttgggatg aggggcaaa tactatgaca     300 gaaagtgagg cagaggtctc gagtttgatc gatgatcttg ggcttcgtga gaagcaacag     360
ttgccaattt cacaaaataa aagatacata gctagagccg tcttcctgt gctactacct      420 tcaaatcccg ctgcactact cacgagcaat atcctttcag caaaatcaaa gctgcaaatt      480
atgttggaac catttctctg gagaaaacac aatgctactg aacttctga tgagcatgtt      540 caggaaagcg ttggtgaatt ttttgagcga cattttggga aagagtttgt tgattatgtt     600 attgacccctt ttgttgcggg tacatgtggt ggagatcctc aatcgctttc catgcaccat      660
acatttccag aagtatggaa tattgaaaaa aggtttggct ctgtgtttgc cggactaatt      720
caatcaacat tgttatctaa gaaggaaaag ggtggagaaa atgcttctat taagaagcct      780
cgtgtacgtg gttcattttc atttcaaggt ggaatgcaga cacttgttga cacaatgtgc      840
aaacagcttg gtgaagatga actcaaactc cagtgtgagg tgctgtcctt gtcatataac      900 cagaaggga tcccctcact agggaattgg tcagtctctt ctatgtcaaa taataccagt      960
gaagatcaat cttatgatgc tgtggttgtc actgctccaa ttcgcaatgt caaagaaatg    1020
aagattatga aatttggaaa tccattttca cttgactta ttccagaggt gacgtacgta     1080
cccctttccg ttatgattac tgcattcaaa aaggataaag tgaagagacc tcttgagggc    1140
ttcggagttc ttatccctc taaagagcaa cataatggac tgaagactct tggtacttta    1200
ttttcctcca tgatgtttcc tgatcgtgct ccatctgaca tgtgtctctt tactacattt    1260
gtcggaggaa gcagaaatag aaaacttgca aacgcttcaa cggatgaatt gaagcaaata    1320
gtttcttctg accttcagca gctgttgggc actgaggacg aaccttcatt tgtcaatcat    1380
ctcttttgga gcaacgcatt cccattgtat ggacacaatt acgattctgt tttgagagcc    1440
atagacaaga tggaaaagga tcttcctgga ttttttatg caggtaacca taagggtgga    1500
ctttcagtgg gaaaagcgat ggcctccgga tgcaaggctg cggaacttgt aatatcctat    1560
ctggactctc atatatacgt gaagatggat gagaagaccg cgtaa               1605
```

<210> SEQ ID NO 7

```
<211> LENGTH: 557
<212> TYPE: PRT
<213> ORGANISM: Solanum tuberosum

<400> SEQUENCE: 7

Met Thr Thr Thr Ala Val Ala Asn His Pro Ser Ile Phe Thr His Arg
1               5                   10                  15

Ser Pro Leu Pro Ser Pro Ser Ser Ser Ser Ser Pro Ser Phe Leu
            20                  25                  30

Phe Leu Asn Arg Thr Asn Phe Ile Pro Tyr Phe Ser Thr Ser Lys Arg
        35                  40                  45

Asn Ser Val Asn Cys Asn Gly Trp Arg Thr Arg Cys Ser Val Ala Lys
    50                  55                  60

Asp Tyr Thr Val Pro Pro Ser Glu Val Asp Gly Asn Gln Phe Pro Glu
65                  70                  75                  80

Leu Asp Cys Val Val Val Gly Ala Gly Ile Ser Gly Leu Cys Ile Ala
                85                  90                  95

Lys Val Ile Ser Ala Asn Tyr Pro Asn Leu Met Val Thr Glu Ala Arg
            100                 105                 110

Asp Arg Ala Gly Gly Asn Ile Thr Thr Val Glu Arg Asp Gly Tyr Leu
            115                 120                 125

Trp Glu Glu Gly Pro Asn Ser Phe Gln Pro Ser Asp Pro Met Leu Thr
    130                 135                 140

Met Ala Val Asp Cys Gly Leu Lys Asp Asp Leu Val Leu Gly Asp Pro
145                 150                 155                 160

Asp Ala Pro Arg Phe Val Leu Trp Lys Asp Lys Leu Arg Pro Val Pro
                165                 170                 175

Gly Lys Leu Thr Asp Leu Pro Phe Phe Asp Leu Met Ser Ile Pro Gly
            180                 185                 190

Lys Leu Arg Ala Gly Phe Gly Ala Ile Gly Leu Arg Pro Ser Pro Pro
            195                 200                 205

Gly Tyr Glu Glu Ser Val Glu Gln Phe Val Arg Arg Asn Leu Gly Ala
    210                 215                 220

Glu Val Phe Glu Arg Leu Ile Glu Pro Phe Cys Ser Gly Val Tyr Ala
225                 230                 235                 240

Gly Asp Pro Ser Lys Leu Ile Met Lys Ala Ala Phe Gly Lys Val Trp
            245                 250                 255

Lys Leu Glu Gln Thr Gly Gly Ser Ile Ile Gly Gly Thr Phe Lys Ala
            260                 265                 270

Ile Lys Glu Arg Ser Ser Asn Pro Lys Pro Pro Arg Asp Pro Arg Leu
            275                 280                 285

Pro Thr Pro Lys Gly Gln Thr Val Gly Ser Phe Arg Lys Gly Leu Arg
    290                 295                 300

Met Leu Pro Asp Ala Ile Cys Glu Arg Leu Gly Ser Lys Val Lys Leu
305                 310                 315                 320

Ser Trp Lys Leu Ser Ser Ile Thr Lys Ser Glu Lys Gly Gly Tyr Leu
            325                 330                 335

Leu Thr Tyr Glu Thr Pro Glu Gly Val Val Ser Leu Arg Ser Arg Ser
            340                 345                 350

Ile Val Met Thr Val Pro Ser Tyr Val Ala Ser Asn Ile Leu Arg Pro
            355                 360                 365

Leu Ser Val Ala Ala Ala Asp Ala Leu Ser Ser Phe Tyr Tyr Pro Pro
    370                 375                 380

Val Ala Ala Val Thr Ile Ser Tyr Pro Gln Glu Ala Ile Arg Asp Glu
```

```
385              390              395              400

Arg Leu Val Asp Gly Glu Leu Lys Gly Phe Gly Gln Leu His Pro Arg
                405              410              415

Ser Gln Gly Val Glu Thr Leu Gly Thr Ile Tyr Ser Ser Ser Leu Phe
                420              425              430

Pro Asn Arg Ala Pro Asn Gly Arg Val Leu Leu Leu Asn Tyr Ile Gly
            435              440              445

Gly Ala Thr Asn Thr Glu Ile Val Ser Lys Thr Glu Ser Gln Leu Val
    450              455              460

Glu Ala Val Asp Arg Asp Leu Arg Lys Met Leu Ile Lys Pro Lys Ala
465              470              475              480

Gln Asp Pro Phe Val Thr Gly Val Arg Val Trp Pro Gln Ala Ile Pro
            485              490              495

Gln Phe Leu Val Gly His Leu Asp Thr Leu Gly Thr Ala Lys Thr Ala
            500              505              510

Leu Ser Asp Asn Gly Leu Asp Gly Leu Phe Leu Gly Gly Asn Tyr Val
        515              520              525

Ser Gly Val Ala Leu Gly Arg Cys Val Glu Gly Ala Tyr Glu Ile Ala
    530              535              540

Ser Glu Val Thr Gly Phe Leu Ser Gln Tyr Ala Tyr Lys
545              550              555

<210> SEQ ID NO 8
<211> LENGTH: 1674
<212> TYPE: DNA
<213> ORGANISM: Solanum tuberosum

<400> SEQUENCE: 8
atgacaacaa cggccgtcgc caaccatcct agcattttca ctcaccggtc gccgctgccg      60
tcgccgtcgt cctcctcctc atcgccgtca tttttatttt taaaccgtac gaatttcatt     120
ccttactttt ccacctccaa gcgcaatagt gtcaattgca atggctggag aacacgatgt     180
tccgttgcca aggattatac agttcctccc tcggaagtcg acggtaatca gttcccggag     240
ctggattgtg tggtagttgg agcaggaatt agtggactct gcattgctaa ggtgatttcg     300
gctaattatc ccaatttgat ggtgacggag gcgagggatc gtgccggtgg aaacataacg     360
acggtggaaa gagatggata cttatgggaa gaaggtccta cagtttcca gccttcggat      420 cctatgttga caatggctgt agattgtgga ttgaaggatg atttggtgtt gggagatcct     480
gatgcgcctc gctttgtctt gtggaaggat aaactaaggc ctgttcccgg caagctcact     540
gatcttccct tctttgattt gatgagtatc cctggcaagc tcagagctgg ttttggtgcc     600
attggccttc gcccttcacc tccaggttat gaggaatcag ttgagcagtt cgtgcgtcgt     660
aatcttggtg cagaagtctt tgaacgtttg attgaaccat tttgttctgg tgtttacgcc     720
ggtgacccct caaaattgat tatgaaagca gcatttggga aagtgtggaa gctagaacaa     780
actggtggta gcattattgg gggaaccttt aaagcaatta aggagagatc cagtaaccct     840
aaaccgcctc gtgatccgcg tttaccaaca ccaaaaggac aaactgttgg atcatttagg     900
aagggtctga aatgctgcc ggatgcaatt tgtgaaagac tgggaagcaa agtaaaacta      960
tcatggaagc tttctagcat tacaaagtca gaaaaaggag gatatctctt gacatacgag    1020
acaccagaag gagtagtttc tctgcgaagt cgaagcattg tcatgactgt tccatcctat    1080
gtagcaagca acatattacg ccctctttcg gtcgctgcag cagatgcact ttcaagtttc    1140
tactatcccc cagtagcagc agtgacaatt tcatatcctc aagaggctat tcgtgatgag    1200
```

-continued

```
cgtctggttg atggtgaact aaagggattt gggcagttgc atccacgttc acagggagtg        1260
gaaacactag gaacaatata tagttcatca ctctttccta accgtgctcc aaatggccgg        1320
gtgctactct tgaactacat tggaggagca acaaatactg aaattgtgtc taagacggag        1380
agccaacttg tggaagcagt tgaccgtgac ctcagaaaaa tgcttataaa acccaaagca        1440
caagatccct ttgttacggg tgtgcgagta tggccacaag ctatcccaca gtttttggtc        1500
ggacatctgg atacactagg tactgcaaaa actgctctaa gtgataatgg gcttgacggg        1560
ctattccttg ggggtaatta tgtgtctggt gtagcattgg gaaggtgtgt tgaaggtgct        1620
tatgaaatag catctgaggt aactggattt ctgtctcagt atgcatacaa atga            1674
```

<210> SEQ ID NO 9
<211> LENGTH: 504
<212> TYPE: PRT
<213> ORGANISM: Solanum tuberosum

<400> SEQUENCE: 9

```
Met Ala Pro Ser Ala Gly Glu Asp Lys Gln Asn Cys Pro Lys Arg Val
1               5                   10                  15

Ala Val Ile Gly Ala Gly Val Ser Gly Leu Ala Ala Ala Tyr Lys Leu
            20                  25                  30

Lys Ile His Gly Leu Asp Val Thr Val Phe Glu Ala Glu Gly Arg Ala
        35                  40                  45

Gly Gly Lys Leu Arg Ser Leu Ser Gln Asp Gly Leu Ile Trp Asp Glu
    50                  55                  60

Gly Ala Asn Thr Met Thr Glu Ser Glu Gly Asp Val Thr Phe Leu Leu
65                  70                  75                  80

Asp Ser Leu Gly Leu Arg Glu Lys Gln Gln Phe Pro Leu Ser Gln Asn
            85                  90                  95

Lys Arg Tyr Ile Ala Arg Asn Gly Thr Pro Thr Leu Ile Pro Ser Asn
            100                 105                 110

Pro Ile Asp Leu Ile Lys Ser Asn Phe Leu Ser Thr Gly Ser Lys Leu
        115                 120                 125

Gln Met Leu Phe Glu Pro Leu Leu Trp Lys Asn Lys Lys Leu Thr Lys
        130                 135                 140

Val Ser Asp Glu His Glu Ser Val Ser Gly Phe Phe Gln Arg His Phe
145                 150                 155                 160

Gly Lys Glu Val Val Asp Tyr Leu Ile Asp Pro Phe Val Ala Gly Thr
                165                 170                 175

Cys Gly Gly Asp Pro Asp Ser Leu Ser Met His Leu Ser Phe Pro Glu
                180                 185                 190

Leu Trp Asn Leu Glu Lys Arg Phe Gly Ser Val Ile Val Gly Ala Ile
            195                 200                 205

Arg Ser Lys Leu Ser Pro Ile Lys Glu Lys Lys Gln Gly Pro Pro Lys
        210                 215                 220

Thr Ser Val Asn Lys Lys His Gln Arg Gly Ser Phe Ser Phe Leu Gly
225                 230                 235                 240

Gly Met Gln Thr Leu Thr Asp Ala Ile Cys Asn Asp Leu Lys Glu Asp
                245                 250                 255

Glu Leu Arg Leu Asn Ser Arg Val Leu Glu Leu Ser Cys Ser Cys Ser
            260                 265                 270

Gly Asp Ser Ala Thr Asp Ser Trp Ser Ile Phe Ser Ala Ser Pro His
            275                 280                 285
```

-continued

```
Lys Arg Gln Ala Glu Glu Asp Ser Phe Asp Ala Val Ile Met Thr Ala
    290                 295                 300

Pro Leu Cys Asp Val Lys Gly Met Lys Ile Ala Lys Arg Gly Asn Pro
305                 310                 315                 320

Phe Leu Leu Asn Phe Ile Pro Glu Val Asp Tyr Val Pro Leu Ser Val
                325                 330                 335

Val Ile Thr Thr Phe Lys Lys Glu Ser Val Lys His Pro Leu Glu Gly
            340                 345                 350

Phe Gly Val Leu Val Pro Ser Glu Glu Gln Lys His Gly Leu Lys Thr
            355                 360                 365

Leu Gly Thr Leu Phe Ser Ser Met Met Phe Pro Asp Arg Ala Pro Asn
    370                 375                 380

Asn Val Tyr Leu Tyr Thr Thr Phe Val Gly Gly Ser Arg Asn Arg Glu
385                 390                 395                 400

Leu Ala Lys Ala Ser Arg Thr Glu Leu Lys Glu Ile Val Thr Ser Asp
                405                 410                 415

Leu Lys Gln Leu Leu Gly Ala Glu Gly Glu Pro Thr Tyr Val Asn His
            420                 425                 430

Val Cys Trp Ser Lys Ala Phe Pro Leu Tyr Gly His Asn Tyr Asp Ser
            435                 440                 445

Val Leu Asp Ala Ile Asp Lys Met Glu Lys Asn Leu Pro Gly Leu Phe
    450                 455                 460

Tyr Ala Gly Asn His Lys Gly Gly Leu Ser Val Gly Lys Ala Leu Ser
465                 470                 475                 480

Ser Gly Cys Asn Ala Ala Asp Leu Val Ile Ser Tyr Leu Glu Ala Val
                485                 490                 495

Ser Thr Asp Thr Lys Asn His Arg
                500
```

```
<210> SEQ ID NO 10
<211> LENGTH: 1608
<212> TYPE: DNA
<213> ORGANISM: Solanum tuberosum

<400> SEQUENCE: 10
atggctccat ctgccggaga agataaacaa aattgtccca agagagttgc agtcattggt        60
gctggcgtca gtggacttgc tgcagcatac aagttgaaaa ttcatggctt ggatgtcaca       120
gtattcgaag cagaagggag agctggaggg aagttacgaa gcctgagtca agatggccta       180
atatgggatg aaggcgcaaa tactatgact gaaagtgaag gtgatgtcac atttttgctt       240
gattcgcttg gactccgaga aaaacaacaa tttccacttt cacagaacaa gcgctacatt       300
gccagaaatg gtactcctac tctgatacct tcaaatccaa ttgacctgat caaaagcaac       360
tttctttcca ctggatcaaa gcttcagatg cttttcgagc ctcttttgtg gaagaataaa       420
aagcttacaa aggtgtctga cgaacacgaa agtgtcagtg gattcttcca gcgtcatttt       480
ggaaaggagg ttgttgacta tctaattgat ccttttgttg ctggaacgtg tggtggtgat       540
cctgactcgc tttcaatgca cctttcgttt ccagagttgt ggaatttaga gaaaaggttt       600
ggctcagtca tagttggggc aattcgatcc aagttatcac ctataaagga aaagaaacaa       660
ggaccaccca aaacttcagt aaataagaag caccagcggg ggtccttttc atttttgggc       720
ggaatgcaaa cacttactga cgcaatatgc aatgatctca agaagatga  acttaggcta       780 aactctagag ttctggaatt atcttgtagc tgtagtgggg actctgcgac agatagctgg       840
tcaatttttt ctgcctcacc acacaagcgg caagcagaag aagattcatt tgatgctgta       900
```

-continued

```
attatgacgg cccctctctg tgacgttaag ggtatgaaga ttgctaagag aggaaatcca      960
tttctgctca actttattcc tgaggttgat tatgtaccac tatctgttgt tataaccaca     1020
tttaagaagg agagtgtaaa gcatcctctt gagggttttg gagtgcttgt accttccgag     1080
gagcaaaaac atggtctgaa gacattaggc accctcttct cttctatgat gtttccagat     1140
cgtgcaccca acaatgtcta tctctatact acatttgttg gtggaagccg aaatagagaa     1200
ctcgcgaaag cctcgaggac tgagctgaaa gagatagtaa cttctgacct taagcagttg     1260
ttgggtgctg agggagagcc aacatatgtg aatcatgtat gctggagtaa agcatttccg     1320
ttgtacgggc ataactatga ttcagtcctc gatgcaattg acaaaatgga gaaaaatctt     1380
cctggattat tctatgcagg taaccacaag ggaggattgt cagttggcaa agcactatct     1440
tctgatgtta atgcagcaga tcttgttata tcatatcttg aagccgtttc aacggacacc     1500
aaaaaccata ggtgaaatct attctctcat gcagcttgcc gttctttgtt ccacaaaatc     1560
gtttaacttc atgacgagga gcaactttaa cgtgcagcca gtgacgca                  1608
```

<210> SEQ ID NO 11
<211> LENGTH: 535
<212> TYPE: PRT
<213> ORGANISM: Zea mays

<400> SEQUENCE: 11

```
Met Val Ala Ala Thr Ala Thr Ala Met Ala Thr Ala Ala Ser Pro Leu
1               5                   10                  15

Leu Asn Gly Thr Arg Ile Pro Ala Arg Leu Arg His Arg Gly Leu Ser
            20                  25                  30

Val Arg Cys Ala Ala Val Ala Gly Gly Ala Ala Glu Ala Pro Ala Ser
        35                  40                  45

Thr Gly Ala Arg Leu Ser Ala Asp Cys Val Val Gly Gly Gly Ile
    50                  55                  60

Ser Gly Leu Cys Thr Ala Gln Ala Leu Ala Thr Arg His Gly Val Gly
65                  70                  75                  80

Asp Val Leu Val Thr Glu Ala Arg Ala Arg Pro Gly Gly Asn Ile Thr
                85                  90                  95

Thr Val Glu Arg Pro Glu Glu Gly Tyr Leu Trp Glu Glu Gly Pro Asn
            100                 105                 110

Ser Phe Gln Pro Ser Asp Pro Val Leu Thr Met Ala Val Asp Ser Gly
        115                 120                 125

Leu Lys Asp Asp Leu Val Phe Gly Asp Pro Asn Ala Pro Arg Phe Val
    130                 135                 140

Leu Trp Glu Gly Lys Leu Arg Pro Val Pro Ser Lys Pro Ala Asp Leu
145                 150                 155                 160

Pro Phe Phe Asp Leu Met Ser Ile Pro Gly Lys Leu Arg Ala Gly Leu
                165                 170                 175

Gly Ala Leu Gly Ile Arg Pro Pro Pro Gly Arg Glu Glu Ser Val
            180                 185                 190

Glu Glu Phe Val Arg Arg Asn Leu Gly Ala Glu Val Phe Glu Arg Leu
        195                 200                 205

Ile Glu Pro Phe Cys Ser Gly Val Tyr Ala Gly Asp Pro Ser Lys Leu
    210                 215                 220

Ser Met Lys Ala Ala Phe Gly Lys Val Trp Arg Leu Glu Glu Thr Gly
225                 230                 235                 240

Gly Ser Ile Ile Gly Gly Thr Ile Lys Thr Ile Gln Glu Arg Ser Lys
```

```
                      245                 250                 255
Asn Pro Lys Pro Pro Arg Asp Ala Arg Leu Pro Lys Pro Lys Gly Gln
            260                 265                 270
Thr Val Ala Ser Phe Arg Lys Gly Leu Ala Met Leu Pro Asn Ala Ile
            275                 280                 285
Thr Ser Ser Leu Gly Ser Lys Val Lys Leu Ser Trp Lys Leu Thr Ser
        290                 295                 300
Ile Thr Lys Ser Asp Asp Lys Gly Tyr Val Leu Glu Tyr Glu Thr Pro
305                 310                 315                 320
Glu Gly Val Val Ser Val Gln Ala Lys Ser Val Ile Met Thr Ile Pro
                325                 330                 335
Ser Tyr Val Ala Ser Asn Ile Leu Arg Pro Leu Ser Ser Asp Ala Ala
            340                 345                 350
Asp Ala Leu Ser Arg Phe Tyr Tyr Pro Pro Val Ala Ala Val Thr Val
            355                 360                 365
Ser Tyr Pro Lys Glu Ala Ile Arg Lys Glu Cys Leu Ile Asp Gly Glu
        370                 375                 380
Leu Gln Gly Phe Gly Gln Leu His Pro Arg Ser Gln Gly Val Glu Thr
385                 390                 395                 400
Leu Gly Thr Ile Tyr Ser Ser Ser Leu Phe Pro Asn Arg Ala Pro Asp
                405                 410                 415
Gly Arg Val Leu Leu Leu Asn Tyr Ile Gly Gly Ala Thr Asn Thr Gly
            420                 425                 430
Ile Val Ser Lys Thr Glu Ser Glu Leu Val Glu Ala Val Asp Arg Asp
            435                 440                 445
Leu Arg Lys Met Leu Ile Asn Ser Thr Ala Val Asp Pro Leu Val Leu
        450                 455                 460
Gly Val Arg Val Trp Pro Gln Ala Ile Pro Gln Phe Leu Val Gly His
465                 470                 475                 480
Leu Asp Leu Leu Glu Ala Ala Lys Ala Ala Leu Asp Arg Gly Gly Tyr
                485                 490                 495
Asp Gly Leu Phe Leu Gly Gly Asn Tyr Val Ala Gly Val Ala Leu Gly
            500                 505                 510
Arg Cys Val Glu Gly Ala Tyr Glu Ser Ala Ser Gln Ile Ser Asp Phe
            515                 520                 525
Leu Thr Lys Tyr Ala Tyr Lys
        530                 535

<210> SEQ ID NO 12
<211> LENGTH: 1608
<212> TYPE: DNA
<213> ORGANISM: Zea mays

<400> SEQUENCE: 12
atggtcgccg ccacagccac cgccatggcc accgctgcat cgccgctact caacgggacc      60
cgaatacctg cgcggctccg ccatcgagga ctcagcgtgc gctgcgctgc tgtggcgggc     120
ggcgcggccg aggcaccggc atccaccggc gcgcggctgt ccgcggactg cgtcgtggtg     180
ggcggaggca tcagtggcct ctgcaccgcg caggcgctgg ccacgcggca cggcgtcggg     240
gacgtgcttg tcacggaggc ccgcgcccgc cccggcggca acattaccac cgtcgagcgc     300
cccgaggaag ggtacctctg gaggaggggt cccaacagct tccagccctc cgaccccgtt     360
ctcaccatgg ccgtggacag cggactgaag gatgacttgg tttttgggga cccaaacgcg     420
ccgcgtttcg tgctgtggga ggggaagctg aggcccgtgc catccaagcc cgccgacctc     480
```

```
ccgttcttcg atctcatgag catcccaggg aagctcaggg ccggtctagg cgcgcttggc    540
atccgcccgc ctcctccagg ccgcgaagag tcagtggagg agttcgtgcg ccgcaacctc    600
ggtgctgagg tctttgagcg cctcattgag cctttctgct caggtgtcta tgctggtgat    660
ccttctaagc tcagcatgaa ggctgcattt gggaaggttt ggcggttgga agaaactgga    720
ggtagtatta ttggtggaac catcaagaca attcaggaga ggagcaagaa tccaaaacca    780
ccgagggatg cccgccttcc gaagccaaaa gggcagacag ttgcatcttt caggaagggt    840
cttgccatgc ttccaaatgc cattacatcc agcttgggta gtaaagtcaa actatcatgg    900
aaactcacga gcattacaaa atcagatgac aagggatatg ttttggagta tgaaacgcca    960
gaaggggttg tttcggtgca ggctaaaagt gttatcatga ctattccatc atatgttgct   1020
agcaacattt tgcgtccact ttcaagcgat gctgcagatg ctctatcaag attctattat   1080
ccaccggttg ctgctgtaac tgtttcgtat ccaaaggaag caattagaaa agaatgctta   1140
attgatgggg aactccaggg ctttggccag ttgcatccac gtagtcaagg agttgagaca   1200
ttaggaacaa tatacagttc ctcactcttt ccaaatcgtg ctcctgacgg tagggtgtta   1260
cttctaaact acataggagg tgctacaaac acaggaattg tttccaagac tgaaagtgag   1320
ctggtcgaag cagttgaccg tgacctccga aaaatgctta taaattctac agcagtggac   1380
cctttagtcc ttggtgttcg agtttggcca caagccatac ctcagttcct ggtaggacat   1440
cttgatcttc tggaagccgc aaaagctgcc ctggaccgag gtggctacga tgggctgttc   1500
ctaggaggga actatgttgc aggagttgcc ctgggcagat gcgttgaggg cgcgtatgaa   1560
agtgcctcgc aaatatctga cttcttgacc aagtatgcct acaagtga                1608
```

```
<210> SEQ ID NO 13
<211> LENGTH: 544
<212> TYPE: PRT
<213> ORGANISM: Zea mays

<400> SEQUENCE: 13

Met Leu Ala Leu Thr Ala Ser Ala Ser Ser Ala Ser Ser His Pro Tyr
1               5                   10                  15

Arg His Ala Ser Ala His Thr Arg Arg Pro Arg Leu Arg Ala Val Leu
            20                  25                  30

Ala Met Ala Gly Ser Asp Asp Pro Arg Ala Ala Pro Ala Arg Ser Val
        35                  40                  45

Ala Val Val Gly Ala Gly Val Ser Gly Leu Ala Ala Ala Tyr Arg Leu
    50                  55                  60

Arg Gln Ser Gly Val Asn Val Thr Val Phe Glu Ala Ala Asp Arg Ala
65                  70                  75                  80

Gly Gly Lys Ile Arg Thr Asn Ser Glu Gly Gly Phe Val Trp Asp Glu
                85                  90                  95

Gly Ala Asn Thr Met Thr Glu Gly Glu Trp Glu Ala Ser Arg Leu Ile
            100                 105                 110

Asp Asp Leu Gly Leu Gln Asp Lys Gln Gln Tyr Pro Asn Ser Gln His
        115                 120                 125

Lys Arg Tyr Ile Val Lys Asp Gly Ala Pro Ala Leu Ile Pro Ser Asp
        130                 135                 140

Pro Ile Ser Leu Met Lys Ser Ser Val Leu Ser Thr Lys Ser Lys Ile
145                 150                 155                 160

Ala Leu Phe Phe Glu Pro Phe Leu Tyr Lys Lys Ala Asn Thr Arg Asn
                165                 170                 175
```

```
Ser Gly Lys Val Ser Glu Glu His Leu Ser Glu Ser Val Gly Ser Phe
        180                 185                 190

Cys Glu Arg His Phe Gly Arg Glu Val Val Asp Tyr Phe Val Asp Pro
        195                 200                 205

Phe Val Ala Gly Thr Ser Ala Gly Asp Pro Glu Ser Leu Ser Ile Arg
        210                 215                 220

His Ala Phe Pro Ala Leu Trp Asn Leu Glu Arg Lys Tyr Gly Ser Val
225                 230                 235                 240

Ile Val Gly Ala Ile Leu Ser Lys Leu Ala Ala Lys Gly Asp Pro Val
                245                 250                 255

Lys Thr Arg His Asp Ser Ser Gly Lys Arg Arg Asn Arg Arg Val Ser
        260                 265                 270

Phe Ser Phe His Gly Gly Met Gln Ser Leu Ile Asn Ala Leu His Asn
        275                 280                 285

Glu Val Gly Asp Asp Asn Val Lys Leu Gly Thr Glu Val Leu Ser Leu
        290                 295                 300

Ala Cys Thr Phe Asp Gly Val Pro Ala Leu Gly Arg Trp Ser Ile Ser
305                 310                 315                 320

Val Asp Ser Lys Asp Ser Gly Asp Lys Asp Leu Ala Ser Asn Gln Thr
                325                 330                 335

Phe Asp Ala Val Ile Met Thr Ala Pro Leu Ser Asn Val Arg Arg Met
                340                 345                 350

Lys Phe Thr Lys Gly Gly Ala Pro Val Val Leu Asp Phe Leu Pro Lys
        355                 360                 365

Met Asp Tyr Leu Pro Leu Ser Leu Met Val Thr Ala Phe Lys Lys Asp
370                 375                 380

Asp Val Lys Lys Pro Leu Glu Gly Phe Gly Val Leu Ile Pro Tyr Lys
385                 390                 395                 400

Glu Gln Gln Lys His Gly Leu Lys Thr Leu Gly Thr Leu Phe Ser Ser
                405                 410                 415

Met Met Phe Pro Asp Arg Ala Pro Asp Asp Gln Tyr Leu Tyr Thr Thr
                420                 425                 430

Phe Val Gly Gly Ser His Asn Arg Asp Leu Ala Gly Ala Pro Thr Ser
        435                 440                 445

Ile Leu Lys Gln Leu Val Thr Ser Asp Leu Lys Lys Leu Leu Gly Val
        450                 455                 460

Glu Gly Gln Pro Thr Phe Val Lys His Val Tyr Trp Gly Asn Ala Phe
465                 470                 475                 480

Pro Leu Tyr Gly His Asp Tyr Ser Ser Val Leu Glu Ala Ile Glu Lys
                485                 490                 495

Met Glu Lys Asn Leu Pro Gly Phe Phe Tyr Ala Gly Asn Ser Lys Asp
                500                 505                 510

Gly Leu Ala Val Gly Ser Val Ile Ala Ser Gly Ser Lys Ala Ala Asp
        515                 520                 525

Leu Ala Ile Ser Tyr Leu Glu Ser His Thr Lys His Asn Asn Ser His
        530                 535                 540
```

```
<210> SEQ ID NO 14
<211> LENGTH: 2042
<212> TYPE: DNA
<213> ORGANISM: Zea mays

<400> SEQUENCE: 14
ctctcctacc tccacctcca cgacaacaag caaatcccca tccagttcca aaccctaact      60
```

-continued

```
caaatgctcg ctttgactgc ctcagcctca tccgcttcgt cccatcctta tcgccacgcc    120
tccgcgcaca ctcgtcgccc ccgcctacgt gcggtcctcg cgatggcggg ctccgacgac    180
ccccgtgcag cgcccgccag atcggtcgcc gtcgtcggcg ccgggggtcag cgggctcgcg    240 gcggcgtaca ggctcagaca gagcggccgtg aacgtaacgg tgttcgaagc ggccgacagg    300
gcgggaggaa agatacggac caattccgag ggcgggtttg tctgggatga aggagctaac    360
accatgacag aaggtgaatg ggaggccagt agactgattg atgatcttgg tctacaagac    420
aaacagcagt atcctaactc ccaacacaag cgttacattg tcaaagatgg agcaccagca    480
ctgattcctt cggatcccat ttcgctaatg aaaagcagtg ttctttcgac aaaatcaaag    540
attgcgttat tttttgaacc atttctctac aagaaagcta acacaagaaa ctctggaaaa    600
gtgtctgagg agcacttgag tgagagtgtt gggagcttct gtgaacgcca ctttggaaga    660
gaagttgttg actattttgt tgatccattt gtagctggaa caagtgcagg agatccagag    720
tcactatcta ttcgtcatgc attcccagca ttgtggaatt tggaaagaaa gtatggttca    780
gttattgttg gtgccatctt gtctaagcta gcagctaaag gtgatccagt aaagacaaga    840
catgattcat cagggaaaag aaggaataga cgagtgtcgt tttcatttca tggtggaatg    900
cagtcactaa taaatgcact tcacaatgaa gttggagatg ataatgtgaa gcttggtaca    960
gaagtgttgt cattggcatg tacatttgat ggagttcctg cactaggcag gtggtcaatt   1020
tctgttgatt cgaaggatag cggtgacaag gaccttgcta gtaaccaaac ctttgatgct   1080
gttataatga cagctccatt gtcaaatgtc cggaggatga agttcaccaa aggtggagct   1140
ccggttgttc ttgactttct tcctaagatg gattatctac cactatctct catggtgact   1200
gcttttaaga aggatgatgt caagaaacct ctggaaggat ttggggtctt aataccttac   1260
aaggaacagc aaaaacatgg tctgaaaacc cttgggactc tcttttcctc aatgatgttc   1320
ccagatcgag ctcctgatga ccaatattta tatacaacat ttgttggggg tagccacaat   1380
agagatcttg ctggagctcc aacgtctatt ctgaaacaac ttgtgacctc tgaccttaaa   1440
aaactcttgg gcgtagaggg gcaaccaact tttgtcaagc atgtatactg gggaaatgct   1500
tttcctttgt atggccatga ttatagttct gtattggaag ctatagaaaa gatggagaaa   1560
aaccttccag ggttcttcta cgcaggaaat agcaaggatg ggcttgctgt tggaagtgtt   1620
atagcttcag gaagcaaggc tgctgacctt gcaatctcat atcttgaatc tcacaccaag   1680
cataataatt cacattgaaa gtgtctgacc tatcctctag cagttgtcga caaatttctc   1740
cagttcatgt acagtagaaa ccgatgcgtt gcagtttcag aacatcttca cttcttcaga   1800
tattaaccct tcgttgaaca tccaccagaa aggtagtcac atgtgtaagt gggaaaatga   1860
ggttaaaaac tattatggcg gccgaaatgt tccttttgt tttcctcaca agtggcctac   1920
gacacttgat gttggaaata catttaaatt tgttgaattg tttgagaaca catgcgtgac   1980
gtgtaatatt tgcctattgt gattttagca gtagtcttgg ccagattatg ctttacgcct   2040
tt                                                                    2042
```

<210> SEQ ID NO 15
<211> LENGTH: 536
<212> TYPE: PRT
<213> ORGANISM: Oryza sativa

<400> SEQUENCE: 15

```
Met Ala Ala Ala Ala Ala Ala Met Ala Thr Ala Thr Ser Ala Thr Ala
1               5                   10                  15
```

-continued

Ala Pro Pro Leu Arg Ile Arg Asp Ala Ala Arg Arg Thr Arg Arg Arg
            20                  25                  30

Gly His Val Arg Cys Ala Val Ala Ser Gly Ala Ala Glu Ala Pro Ala
            35                  40                  45

Ala Pro Gly Ala Arg Val Ser Ala Asp Cys Val Val Val Gly Gly Gly
    50                  55                  60

Ile Ser Gly Leu Cys Thr Ala Gln Ala Leu Ala Thr Lys His Gly Val
65                  70                  75                  80

Gly Asp Val Leu Val Thr Glu Ala Arg Ala Arg Pro Gly Gly Asn Ile
                85                  90                  95

Thr Thr Ala Glu Arg Ala Gly Glu Gly Tyr Leu Trp Glu Glu Gly Pro
            100                 105                 110

Asn Ser Phe Gln Pro Ser Asp Pro Val Leu Thr Met Ala Val Asp Ser
            115                 120                 125

Gly Leu Lys Asp Asp Leu Val Phe Gly Asp Pro Asn Ala Pro Arg Phe
    130                 135                 140

Val Leu Trp Glu Gly Lys Leu Arg Pro Val Pro Ser Lys Pro Gly Asp
145                 150                 155                 160

Leu Pro Phe Phe Asp Leu Met Ser Ile Pro Gly Lys Leu Arg Ala Gly
            165                 170                 175

Leu Gly Ala Leu Gly Val Arg Ala Pro Pro Pro Gly Arg Glu Glu Ser
            180                 185                 190

Val Glu Asp Phe Val Arg Arg Asn Leu Gly Ala Glu Val Phe Glu Arg
            195                 200                 205

Leu Ile Glu Pro Phe Cys Ser Gly Val Tyr Ala Gly Asp Pro Ser Lys
            210                 215                 220

Leu Ser Met Lys Ala Ala Phe Gly Lys Val Trp Arg Leu Glu Asp Thr
225                 230                 235                 240

Gly Gly Ser Ile Ile Gly Gly Thr Ile Lys Thr Ile Gln Glu Arg Gly
            245                 250                 255

Lys Asn Pro Lys Pro Pro Arg Asp Pro Arg Leu Pro Thr Pro Lys Gly
            260                 265                 270

Gln Thr Val Ala Ser Phe Arg Lys Gly Leu Thr Met Leu Pro Asp Ala
            275                 280                 285

Ile Thr Ser Arg Leu Gly Ser Lys Val Lys Leu Ser Trp Lys Leu Thr
    290                 295                 300

Ser Ile Thr Lys Ser Asp Asn Lys Gly Tyr Ala Leu Val Tyr Glu Thr
305                 310                 315                 320

Pro Glu Gly Val Val Ser Val Gln Ala Lys Thr Val Val Met Thr Ile
            325                 330                 335

Pro Ser Tyr Val Ala Ser Asp Ile Leu Arg Pro Leu Ser Ser Asp Ala
            340                 345                 350

Ala Asp Ala Leu Ser Ile Phe Tyr Tyr Pro Pro Val Ala Ala Val Thr
            355                 360                 365

Val Ser Tyr Pro Lys Glu Ala Ile Arg Lys Glu Cys Leu Ile Asp Gly
    370                 375                 380

Glu Leu Gln Gly Phe Gly Gln Leu His Pro Arg Ser Gln Gly Val Glu
385                 390                 395                 400

Thr Leu Gly Thr Ile Tyr Ser Ser Leu Phe Pro Asn Arg Ala Pro
            405                 410                 415

Ala Gly Arg Val Leu Leu Leu Asn Tyr Ile Gly Gly Ser Thr Asn Thr
            420                 425                 430

-continued

```
Gly Ile Val Ser Lys Thr Glu Ser Glu Leu Val Glu Ala Val Asp Arg
        435             440             445

Asp Leu Arg Lys Met Leu Ile Asn Pro Lys Ala Val Asp Pro Leu Val
        450             455             460

Leu Gly Val Arg Val Trp Pro Gln Ala Ile Pro Gln Phe Leu Ile Gly
465             470             475             480

His Leu Asp His Leu Glu Ala Ala Lys Ser Ala Leu Gly Lys Gly Gly
            485             490             495

Tyr Asp Gly Leu Phe Leu Gly Gly Asn Tyr Val Ala Gly Val Ala Leu
            500             505             510

Gly Arg Cys Val Glu Gly Ala Tyr Glu Ser Ala Ser Gln Ile Ser Asp
        515             520             525

Tyr Leu Thr Lys Tyr Ala Tyr Lys
        530             535

<210> SEQ ID NO 16
<211> LENGTH: 1907
<212> TYPE: DNA
<213> ORGANISM: Oryza sativa

<400> SEQUENCE: 16
atccactcct ctccagtctc cccgccgctc cgcatcccgc agccgctcgt cagcgacgga        60
catggccgcc gccgccgcag ccatggccac cgccacctcc gccacggcag cgccgccgct       120
ccgcattcgc gacgccgcga ggaggacccg ccgacgcggc cacgttcgct gcgccgtcgc       180
cagcggcgcg gccgaggcgc ccgcggcgcc cggggcgcgg gtgtcggcgg actgcgtcgt       240
ggtgggcggc ggcatcagcg ggctctgcac cgcgcaggcg ctggccacaa agcacggcgt       300
cggcgacgtg ctcgtcacgg aggcccgcgc ccgcccaggc ggcaacatca ccaccgccga       360
gcgcgccggc gagggctacc tctgggagga ggggcccaac agcttccagc cttccgaccc       420
cgtcctcacc atggccgtgg acagcgggct caaggacgat ctcgtgttcg ggaccccaa       480 cgcgccgcgg ttcgtgctgt gggaggggaa gctaaggccg gtgccgtcca gcccggcga       540 cctgccgttc ttcgacctca tgagcatccc cggcaagctc agggccggcc ttggcgcgct       600
cggcgttcga gcgccacctc cagggcgtga ggagtcggtg gaggacttcg tgcggcgcaa       660
cctcggcgcg gaggtctttg agcgcctcat tgagcctttc tgctcaggtg tgtatgctgg       720
tgatccttca aagctcagta tgaaggctgc atttgggaag gtgtgggaggc tggaggatac      780 tggaggtagc attattggtg gaaccatcaa aacaatccag gagaggggga aaaaccccaa       840
accgccgagg gatccccgcc ttccaacgcc aaaggggcag acagttgcat ctttcaggaa       900
gggtctgact atgctcccgg atgctattac atctaggttg ggtagcaaag tcaaactttc      960
atggaagttg acaagcatta caaagtcaga caacaaagga tatgcattag tgtatgaaac     1020
accagaaggg gtggtctcgg tgcaagctaa aactgttgtc atgaccatcc catcatatgt     1080
tgctagtgat atcttgcggc cactttcaag tgatgcagca gatgctctgt caatattcta     1140
ttatccacca gttgctgctg taactgtttc atatccaaaa gaagcaatta gaaaagaatg     1200
cttaattgac ggagagctcc agggtttcgg ccagctgcat ccgcgtagtc agggagttga     1260
gactttagga acaatatata gctcatcact cttccaaat cgtgctccag ctggaagggt      1320
gttacttctg aactacatag gaggttctac aaatacaggg attgtttcca agactgaaag     1380
tgagctggta gaagcagttg accgtgacct caggaagatg ctgataaatc ctaaagcagt     1440
ggaccctttg gtccttggcg tccgggtatg gccacaagcc ataccacagt tcctcattgg     1500
```

-continued

```
ccatcttgat catcttgagg ctgcaaaatc tgccctgggc aaaggtggtt atgatggatt   1560
gttcctcgga gggaactatg ttgcaggagt tgccctgggc cgatgcgttg aaggtgcata   1620
tgagagtgcc tcacaaatat ctgactactt gaccaagtac gcctacaagt gatcaaagtt   1680
ggcctgctcc ttttggcaca tagatgtgag gcttctagca gcaaaaattt catgggcatc   1740 ttttttatcct gattctaatt agttagaatt tagaattgta gaggaatgtt ccatttgcag   1800
ttcataatag ttgttcagat ttcagccatt caatttgtgc agccatttac tatatgtagt   1860
atgatcttgt aagtactact aagaacaaat caattatatt ttcctgc            1907
```

```
<210> SEQ ID NO 17
<211> LENGTH: 551
<212> TYPE: PRT
<213> ORGANISM: Oryza sativa

<400> SEQUENCE: 17

Met Leu Ser Pro Ala Thr Thr Phe Ser Ser Ser Ser Ser Ser Ser
1               5                   10                  15

Pro Ser Arg Ala His Ala Arg Ala Pro Thr Arg Phe Ala Val Ala Ala
            20                  25                  30

Ser Ala Arg Ala Ala Arg Phe Arg Pro Ala Arg Ala Met Ala Ala Ser
        35                  40                  45

Asp Asp Pro Arg Gly Gly Arg Ser Val Ala Val Val Gly Ala Gly Val
    50                  55                  60

Ser Gly Leu Ala Ala Ala Tyr Arg Leu Arg Lys Arg Gly Val Gln Val
65                  70                  75                  80

Thr Val Phe Glu Ala Ala Asp Arg Ala Gly Gly Lys Ile Arg Thr Asn
                85                  90                  95

Ser Glu Gly Gly Phe Ile Trp Asp Glu Gly Ala Asn Thr Met Thr Glu
                100                 105                 110

Ser Glu Leu Glu Ala Ser Arg Leu Ile Asp Asp Leu Gly Leu Gln Gly
            115                 120                 125

Lys Gln Gln Tyr Pro Asn Ser Gln His Lys Arg Tyr Ile Val Lys Asp
        130                 135                 140

Gly Ala Pro Thr Leu Ile Pro Ser Asp Pro Ile Ala Leu Met Lys Ser
145                 150                 155                 160

Thr Val Leu Ser Thr Lys Ser Lys Leu Lys Leu Phe Leu Glu Pro Phe
                165                 170                 175

Leu Tyr Glu Lys Ser Ser Arg Arg Thr Ser Gly Lys Val Ser Asp Glu
            180                 185                 190

His Leu Ser Glu Ser Val Ala Ser Phe Phe Glu Arg His Phe Gly Lys
        195                 200                 205

Glu Val Val Asp Tyr Leu Ile Asp Pro Phe Val Ala Gly Thr Ser Gly
    210                 215                 220

Gly Asp Pro Glu Ser Leu Ser Ile Arg His Ala Phe Pro Ala Leu Trp
225                 230                 235                 240

Asn Leu Glu Asn Lys Tyr Gly Ser Val Ile Ala Gly Ala Ile Leu Ser
                245                 250                 255

Lys Leu Ser Thr Lys Gly Asp Ser Val Lys Thr Gly Gly Ala Ser Pro
            260                 265                 270

Gly Lys Gly Arg Asn Lys Arg Val Ser Phe Ser Phe His Gly Gly Met
        275                 280                 285

Gln Ser Leu Ile Asp Ala Leu His Asn Glu Val Gly Asp Gly Asn Val
    290                 295                 300
```

```
Lys Leu Gly Thr Glu Val Leu Ser Leu Ala Cys Cys Cys Asp Gly Val
305                 310                 315                 320

Ser Ser Ser Gly Gly Trp Ser Ile Ser Val Asp Ser Lys Asp Ala Lys
                325                 330                 335

Gly Lys Asp Leu Arg Lys Asn Gln Ser Phe Asp Ala Val Ile Met Thr
                340                 345                 350

Ala Pro Leu Ser Asn Val Gln Arg Met Lys Phe Thr Lys Gly Gly Val
                355                 360                 365

Pro Phe Val Leu Asp Phe Leu Pro Lys Val Asp Tyr Leu Pro Leu Ser
        370                 375                 380

Leu Met Val Thr Ala Phe Lys Lys Glu Asp Val Lys Lys Pro Leu Glu
385                 390                 395                 400

Gly Phe Gly Ala Leu Ile Pro Tyr Lys Glu Gln Gln Lys His Gly Leu
                405                 410                 415

Lys Thr Leu Gly Thr Leu Phe Ser Ser Met Met Phe Pro Asp Arg Ala
                420                 425                 430

Pro Asn Asp Gln Tyr Leu Tyr Thr Ser Phe Ile Gly Gly Ser His Asn
        435                 440                 445

Arg Asp Leu Ala Gly Ala Pro Thr Ala Ile Leu Lys Gln Leu Val Thr
    450                 455                 460

Ser Asp Leu Arg Lys Leu Leu Gly Val Glu Gly Gln Pro Thr Phe Val
465                 470                 475                 480

Lys His Val His Trp Arg Asn Ala Phe Pro Leu Tyr Gly Gln Asn Tyr
                485                 490                 495

Asp Leu Val Leu Glu Ala Ile Ala Lys Met Glu Asn Asn Leu Pro Gly
                500                 505                 510

Phe Phe Tyr Ala Gly Asn Asn Lys Asp Gly Leu Ala Val Gly Asn Val
                515                 520                 525

Ile Ala Ser Gly Ser Lys Ala Ala Asp Leu Val Ile Ser Tyr Leu Glu
        530                 535                 540

Ser Cys Thr Asp Gln Asp Asn
545                 550
```

```
<210> SEQ ID NO 18
<211> LENGTH: 1972
<212> TYPE: DNA
<213> ORGANISM: Oryza sativa

<400> SEQUENCE: 18
cgatccgaag gacgaacccc gcacaagaca acaagtaaat ccccatccat agctatccaa       60
gagccccaaa tcagatgctc tctcctgcca ccaccttctc ctcctcctcc tcctcctcgt      120
cgccgtcgcg cgcccacgct cgcgctccca cccgcttcgc ggtcgcagca tccgcgcgcg      180
ccgcacggtt ccgccccgcg cgcgccatgg ccgcctccga cgaccccgc ggcgggaggt       240 ccgtcgccgt cgtcggcgcc ggcgtcagtg ggctcgcggc ggcgtacagg ctgaggaagc      300
gcggcgtgca ggtgacggtg ttcgaggcgg ccgacagggc gggtgggaag atacggacca      360
actccgaggg cgggttcatc tgggacgaag gggccaacac catgacagag agtgaattgg      420
aggcaagcag gcttattgac gatcttggcc tacaaggcaa acagcagtat cctaactcac      480
aacacaagcg ttacattgtc aaagatggag caccaacact gattccctca gatcccattg      540
cgctcatgaa aagcactgtt ctttctacaa aatcaaagct caagctattt ctggaaccat      600
ttctctatga gaaatctagc agaaggacct cgggaaaagt gtctgatgaa catttaagtg      660
agagtgttgc aagtttcttt gaacgccact ttggaaaaga ggttgttgat tatcttattg      720
```

```
atccatttgt ggctggaaca agcggaggag atcctgagtc attatcaatt cgtcatgcat      780
ttccagcatt atggaatttg gagaataagt atggctctgt cattgctggt gccatcttgt      840
ccaaactatc cactaagggt gattcagtga agacaggagg tgcttcgcca gggaaaggaa      900
ggaataaacg tgtgtcattt tcatttcatg gtggaatgca gtcactaata gatgcacttc      960
acaatgaagt tggagatggt aacgtgaagc ttggtacaga agtgttgtca ttggcatgtt     1020
gctgtgatgg agtctcttct tctggtggtt ggtcaatttc tgttgattca aaagatgcta     1080
aagggaaaga tctcagaaag aaccaatctt tcgatgctgt tataatgact gctccattgt     1140
ctaatgtcca gaggatgaag tttacaaaag gtggagttcc ctttgtgcta gactttcttc     1200
ctaaggtcga ttatctacca ctatctctca tggtaacagc ttttaagaag gaagatgtca     1260
aaaaaccatt ggaaggattt ggtgccttga taccctataa ggaacagcaa aagcatggtc     1320
tcaaaaccct tgggacccte ttctcctcga tgatgtttcc agatcgagct cctaatgatc     1380
aatatctata tacatctttc attgggggga gccataatag agacctcgct ggggctccaa     1440
cggctattct gaaacaactt gtgacctctg acctaagaaa gctcttgggt gttgagggac     1500
aacctacttt tgtgaagcat gtacattgga gaaatgcttt tcctttatat ggccagaatt     1560
atgatctggt actggaagct atagcaaaaa tggagaacaa tcttccaggg ttcttttacg     1620
caggaaataa caaggatggg ttggctgttg gaaatgttat agcttcagga agcaaggctg     1680
ctgaccttgt gatctcttat cttgaatctt gcacagatca ggacaattag catttaaggt     1740
atctgacctt aagcaatttc agacaaattt gctcacttta tgtaaattga aaaggttcac     1800
atgatttcca gtttcatatt tttctcttgc tatagtatat ccactcatgt aaagatggga     1860
acatagtcct aaaagacatt atggtcgctt gagatgctca tgttttttttg aacagtgatt     1920 cttgacttgt actattttt gacaaccaaa taaatttctc aatgtttccg ag            1972
```

```
<210> SEQ ID NO 19
<211> LENGTH: 551
<212> TYPE: PRT
<213> ORGANISM: Sorghum bicolor

<400> SEQUENCE: 19

Met Leu Ser Pro Ala Thr Thr Phe Ser Ser Ser Ser Ser Ser Ser
1               5                   10                  15

Pro Ser Arg Ala His Ala Arg Ala Pro Thr Arg Phe Ala Val Ala Ala
            20                  25                  30

Ser Ala Arg Ala Ala Arg Phe Arg Pro Ala Arg Ala Met Ala Ala Ser
        35                  40                  45

Asp Asp Pro Arg Gly Gly Arg Ser Val Ala Val Val Gly Ala Gly Val
    50                  55                  60

Ser Gly Leu Ala Ala Ala Tyr Arg Leu Arg Lys Arg Gly Val Gln Val
65                  70                  75                  80

Thr Val Phe Glu Ala Ala Asp Arg Ala Gly Gly Lys Ile Arg Thr Asn
                85                  90                  95

Ser Glu Gly Gly Phe Ile Trp Asp Glu Gly Ala Asn Thr Met Thr Glu
            100                 105                 110

Ser Glu Leu Glu Ala Ser Arg Leu Ile Asp Asp Leu Gly Leu Gln Gly
        115                 120                 125

Lys Gln Gln Tyr Pro Asn Ser Gln His Lys Arg Tyr Ile Val Lys Asp
    130                 135                 140

Gly Ala Pro Thr Leu Ile Pro Ser Asp Pro Ile Ala Leu Met Lys Ser
```

```
145                150                155                160

Thr Val Leu Ser Thr Lys Ser Lys Leu Lys Leu Phe Leu Glu Pro Phe
                 165                170                175

Leu Tyr Glu Lys Ser Ser Arg Arg Thr Ser Gly Lys Val Ser Asp Glu
                 180                185                190

His Leu Ser Glu Ser Val Ala Ser Phe Phe Glu Arg His Phe Gly Lys
             195                200                205

Glu Val Val Asp Tyr Leu Ile Asp Pro Phe Val Ala Gly Thr Ser Gly
         210                215                220

Gly Asp Pro Glu Ser Leu Ser Ile Arg His Ala Phe Pro Ala Leu Trp
225                230                235                240

Asn Leu Glu Asn Lys Tyr Gly Ser Val Ile Ala Gly Ala Ile Leu Ser
                 245                250                255

Lys Leu Ser Thr Lys Gly Asp Ser Val Lys Thr Gly Gly Ala Ser Pro
                 260                265                270

Gly Lys Gly Arg Asn Lys Arg Val Ser Phe Ser Phe His Gly Gly Met
                 275                280                285

Gln Ser Leu Ile Asp Ala Leu His Asn Glu Val Gly Asp Gly Asn Val
         290                295                300

Lys Leu Gly Thr Glu Val Leu Ser Leu Ala Cys Cys Cys Asp Gly Val
305                310                315                320

Ser Ser Ser Gly Gly Trp Ser Ile Ser Val Asp Ser Lys Asp Ala Lys
                 325                330                335

Gly Lys Asp Leu Arg Lys Asn Gln Ser Phe Asp Ala Val Ile Met Thr
                 340                345                350

Ala Pro Leu Ser Asn Val Gln Arg Met Lys Phe Thr Lys Gly Gly Val
                 355                360                365

Pro Phe Val Leu Asp Phe Leu Pro Lys Val Asp Tyr Leu Pro Leu Ser
         370                375                380

Leu Met Val Thr Ala Phe Lys Lys Glu Asp Val Lys Lys Pro Leu Glu
385                390                395                400

Gly Phe Gly Ala Leu Ile Pro Tyr Lys Glu Gln Gln Lys His Gly Leu
                 405                410                415

Lys Thr Leu Gly Thr Leu Phe Ser Ser Met Met Phe Pro Asp Arg Ala
                 420                425                430

Pro Asn Asp Gln Tyr Leu Tyr Thr Ser Phe Ile Gly Gly Ser His Asn
                 435                440                445

Arg Asp Leu Ala Gly Ala Pro Thr Ala Ile Leu Lys Gln Leu Val Thr
         450                455                460

Ser Asp Leu Arg Lys Leu Leu Gly Val Glu Gly Gln Pro Thr Phe Val
465                470                475                480

Lys His Val His Trp Arg Asn Ala Phe Pro Leu Tyr Gly Gln Asn Tyr
                 485                490                495

Asp Leu Val Leu Glu Ala Ile Ala Lys Met Glu Asn Asn Leu Pro Gly
                 500                505                510

Phe Phe Tyr Ala Gly Asn Asn Lys Asp Gly Leu Ala Val Gly Asn Val
             515                520                525

Ile Ala Ser Gly Ser Lys Ala Ala Asp Leu Val Ile Ser Tyr Leu Glu
         530                535                540

Ser Cys Thr Asp Gln Asp Asn
545                550
```

<210> SEQ ID NO 20

-continued

<211> LENGTH: 1922
<212> TYPE: DNA
<213> ORGANISM: Sorghum bicolor

<400> SEQUENCE: 20
atggtcgccg ccgccgccat ggccaccgct gcatcggcgg ccgcgccgct actcaacggg      60
acccgaaggc ctgcgaggct ccgccgtcgc ggactccgcg tgcgctgcgc cgctgtggcg     120
ggcggcgcgg ccgaggcacc ggcctccacc ggcgcgcggc tgtccgcgga ctgcgtcgtg     180
gtgggcggcg ggatcagtgg cctctgcacc gcgcaggcgc tggccacgcg cacggcgtc     240 ggggaggtgc ttgtcacgga ggcccgcgcc cgacccggcg gcaacatcac caccgtcgag     300
cgccccgagg aagggtacct ctgggaggag ggtcccaaca gcttccagcc atccgacccc     360
gttctctcca tggccgtgga cagcgggctg aaggatgacc tggttttttgg ggatcccaac     420 gcgccgcggt tcgtgctgtg ggagggggaag ctgaggcccg tgccatccaa gcccgccgac     480
ctcccgttct tcgatctcat gagcatccct ggcaagctca gggccggtct cggcgcgctt     540
ggcatccgcc cgcctcctcc aggccgcgag gagtcagtgg aggagtttgt gcgccgcaac     600
ctcggtgctg aggtctttga gcgcctaatt gagcctttct gctcaggtgt ctatgctggt     660
gatccttcca agctcagtat gaaggctgca tttgggaagg tgtggcggtt agaagaagct     720
ggaggtagta ttattggtgg aaccatcaag acgattcagg agagaggcaa gaatccaaaa     780
ccaccgaggg atccccgcct tccgaagcca aaagggcaga cagttgcatc tttcaggaag     840
ggtcttgcca tgcttccaaa tgccatcaca tccagcttgg gtagtaaagt caaactatca     900
tggaaactca cgagcattac aaaatcagat ggcaaggggg atgttttgga gtatgaaaca     960
ccagaagggg ttgttttggt gcaggctaaa agtgttatca tgaccattcc atcatatgtt    1020
gctagcgaca ttttgcgtcc actttcaggt gatgctgcag atgctctatc aagattctat    1080
tatccaccag ttgctgctgt aacggtttcg tatccaaagg aagcaattag aaaagaatgc    1140
ttaattgatg gggaactcca gggtttttggc cagttgcatc cacgtagtca aggagttgag    1200
acattaggaa caatatacag ctcatcactc tttccaaatc gtgctcctgc tggtagggtg    1260
ttacttctaa actacatagg aggtgctaca aacacaggaa ttgtttccaa gactgaaagt    1320
gagctggtag aagcagttga ccgtgacctc cgaaaaatgc ttataaattc tacagcagtg    1380 gacccttttag tccttggtgt ccgagtttgg ccacaagcca tacctcagtt cctggtagga    1440
catcttgatc ttctggaggt cgcaaaatct gccctggacc aaggtggcta tgatgggctg    1500
ttcctaggag ggaactatgt tgcaggagtt gccctgggca gatgcattga gggcgcatat    1560
gagagtgccg cacaaatata tgacttcttg accaagtatg cctacaagtg atggaagaag    1620
tggagcgctg cttgttaatt gttatgttgc atagatgagg tgagaccagg agtagtaaaa    1680
ggcattacga gtattttca ttcttatttt gtaaattgca cttctgtttt tttttcctgt    1740
cagtaattag ttagatttta gttctgtagg agattgttgt gttcactgcc ctgcaaaaga    1800 attttattt tgcattcgtt tatgagagct gtgcagactt atgtaacgtt ttactgtaag    1860
tatcaacaaa atcagatact attctgcaag agctaacaga atgtgcaact gagattgcct    1920
tg                                                                   1922

<210> SEQ ID NO 21
<211> LENGTH: 544
<212> TYPE: PRT
<213> ORGANISM: Sorghum bicolor

<400> SEQUENCE: 21

```
Met Leu Ala Arg Thr Ala Thr Val Ser Ser Thr Ser Ser His Ser His
1               5                   10                  15

Pro Tyr Arg Pro Thr Ser Ala Arg Ser Leu Arg Leu Arg Pro Val Leu
                20                  25                  30

Ala Met Ala Gly Ser Asp Asp Ser Arg Ala Ala Pro Ala Arg Ser Val
            35                  40                  45

Ala Val Val Gly Ala Gly Val Ser Gly Leu Val Ala Ala Tyr Arg Leu
        50                  55                  60

Arg Lys Ser Gly Val Asn Val Thr Val Phe Glu Ala Ala Asp Arg Ala
65                  70                  75                  80

Gly Gly Lys Ile Arg Thr Asn Ser Glu Gly Gly Phe Leu Trp Asp Glu
                85                  90                  95

Gly Ala Asn Thr Met Thr Glu Gly Glu Leu Glu Ala Ser Arg Leu Ile
            100                 105                 110

Asp Asp Leu Gly Leu Gln Asp Lys Gln Gln Tyr Pro Asn Ser Gln His
            115                 120                 125

Lys Arg Tyr Ile Val Lys Asp Gly Ala Pro Ala Leu Ile Pro Ser Asp
            130                 135                 140

Pro Ile Ser Leu Met Lys Ser Ser Val Leu Ser Thr Lys Ser Lys Ile
145                 150                 155                 160

Ala Leu Phe Phe Glu Pro Phe Leu Tyr Lys Lys Ala Asn Thr Arg Asn
                165                 170                 175

Pro Gly Lys Val Ser Asp Glu His Leu Ser Glu Ser Val Gly Ser Phe
                180                 185                 190

Phe Glu Arg His Phe Gly Arg Glu Val Val Asp Tyr Leu Ile Asp Pro
                195                 200                 205

Phe Val Ala Gly Thr Ser Ala Gly Asp Pro Glu Ser Leu Ser Ile Cys
            210                 215                 220

His Ala Phe Pro Ala Leu Trp Asn Leu Glu Arg Lys Tyr Gly Ser Val
225                 230                 235                 240

Val Val Gly Ala Ile Leu Ser Lys Leu Thr Ala Lys Gly Asp Pro Val
                245                 250                 255

Lys Thr Arg Arg Asp Ser Ser Ala Lys Arg Arg Asn Arg Arg Val Ser
                260                 265                 270

Phe Ser Phe His Gly Gly Met Gln Ser Leu Ile Asn Ala Leu His Asn
            275                 280                 285

Glu Val Gly Asp Asp Asn Val Lys Leu Gly Thr Glu Val Leu Ser Leu
            290                 295                 300

Ala Cys Thr Leu Asp Gly Ala Pro Ala Pro Gly Gly Trp Ser Ile Ser
305                 310                 315                 320

Asp Asp Ser Lys Asp Ala Ser Gly Lys Asp Leu Ala Lys Asn Gln Thr
            325                 330                 335

Phe Asp Ala Val Ile Met Thr Ala Pro Leu Ser Asn Val Gln Arg Met
            340                 345                 350

Lys Phe Thr Lys Gly Gly Ala Pro Phe Val Leu Asp Phe Leu Pro Lys
            355                 360                 365

Val Asp Tyr Leu Pro Leu Ser Leu Met Val Thr Ala Phe Lys Lys Glu
        370                 375                 380

Asp Val Lys Lys Pro Leu Glu Gly Phe Gly Val Leu Ile Pro Tyr Lys
385                 390                 395                 400

Glu Gln Gln Lys His Gly Leu Lys Thr Leu Gly Thr Leu Phe Ser Ser
                405                 410                 415
```

-continued

```
Met Met Phe Pro Asp Arg Ala Pro Asp Asp Gln Tyr Leu Tyr Thr Thr
            420             425             430

Phe Val Gly Gly Ser His Asn Arg Asp Leu Ala Gly Ala Pro Thr Ser
        435             440             445

Ile Leu Lys Gln Leu Val Thr Ser Asp Leu Lys Lys Leu Leu Gly Val
        450             455             460

Gln Gly Gln Pro Thr Phe Val Lys His Ile Tyr Trp Gly Asn Ala Phe
465             470             475             480

Pro Leu Tyr Gly His Asp Tyr Asn Ser Val Leu Glu Ala Ile Glu Lys
            485             490             495

Met Glu Lys Asn Leu Pro Gly Phe Phe Tyr Ala Gly Asn Asn Lys Asp
            500             505             510

Gly Leu Ala Val Gly Ser Val Ile Ala Ser Gly Ser Lys Ala Ala Asp
        515             520             525

Leu Ala Ile Ser Tyr Leu Glu Ser His Thr Lys His Asn Asn Leu His
        530             535             540
```

<210> SEQ ID NO 22
<211> LENGTH: 1635
<212> TYPE: DNA
<213> ORGANISM: Sorghum bicolor

<400> SEQUENCE: 22

```
atgctcgctc ggactgccac ggtctcctcc acttcgtccc actcccatcc ttatcgcccc      60
acctccgctc gcagtctccg cctacgtccg gtcctcgcga tggcgggctc cgacgactcc     120
cgcgcagctc ccgccaggtc ggtcgccgtc gtcggcgccg gggtcagcgg gctcgtggcg     180
gcgtacaggc tcaggaagag cggcgtgaat gtgacggtgt tcgaggcggc cgacagggcg     240
ggaggaaaga tacggaccaa ttccgagggc gggtttctct gggatgaagg agcgaacacc     300
atgacagaag gtgaattgga ggccagtaga ctgatagatg atctcggtct acaagacaaa     360
cagcagtatc ctaactccca acacaagcgt tacattgtca agatggagc accagcactg      420 attccttcgg atcccatttc gctgatgaaa agcagtgttc tttctacaaa atcaaagatt     480
gcgttatttt ttgaaccatt tctctacaag aaagctaaca caagaaaccc tggaaaagta     540
tctgatgagc atttgagtga gagtgttggg agcttctttg aacgccactt cggaagagaa     600
gttgttgact atcttattga tccatttgta gctggaacaa gtgcaggaga tccagagtca     660
ctatctattt gtcatgcatt cccagcactg tggaatttgg aaagaaaata tggttcagtt     720
gttgttggtg ccatcttgtc taagctaaca gctaaaggtg atccagtaaa gacaagacgt     780
gattcatcag cgaaaagaag gaatagacgc gtgtcgtttt catttcatgg tggaatgcag     840
tcactaataa atgcacttca caatgaagtt ggagatgata atgtgaagct tggtacagaa     900
gtgttgtcat tggcgtgtac attagatgga gcccctgcac caggcgggtg gtcaatttct     960
gatgattcga aggatgctag tggcaaggac cttgctaaaa accaaacctt tgatgctgtt    1020
ataatgacag ctccattgtc aaatgtccag aggatgaagt tcacaaaagg tggagctcct    1080
tttgttctag actttcttcc taaggtggat tatctaccac tatctctcat ggtgactgct    1140
tttaagaagg aagatgtcaa gaaacctctg gaaggatttg gcgtcttaat accctacaag    1200
gaacagcaaa aacatggtct aaaaaccctt gggactctct tctcctcaat gatgttccca    1260
gatcgagctc ctgacgacca atatttatat acaacatttg ttgggggtag ccacaataga    1320
gatcttgctg gagctccaac gtctattctg aaacaacttg tgacctctga ccttaaaaaa    1380
ctcttaggcg tacaggggca accaactttt gtcaagcata tatactgggg aaatgctttt    1440
```

-continued

```
cctttgtatg gtcatgatta caattctgta ttggaagcta tagaaaagat ggagaaaaat   1500
cttccagggt tcttctacgc aggaaataac aaggatgggc ttgctgttgg gagtgttata   1560
gcttcaggaa gcaaggctgc tgaccttgca atctcgtatc ttgaatctca caccaagcat   1620
aataatttac attga                                                    1635
```

```
<210> SEQ ID NO 23
<211> LENGTH: 536
<212> TYPE: PRT
<213> ORGANISM: Ricinus communis

<400> SEQUENCE: 23
```

```
Met Ala Asn Leu Ala Asp Phe Ser Leu Phe Leu Arg Ser Thr Pro Ser
1               5                   10                  15

Leu Val Pro Ser Tyr Pro Lys Thr Thr Ile Asn Arg Thr Leu Lys Leu
            20                  25                  30

Gln Leu Arg Cys Ser Ile Thr Glu Gln Ser Thr Thr Thr Ile Ser Pro
        35                  40                  45

Gly Gly Asn Ser Gln Ser Pro Ala Asp Cys Val Ile Val Gly Gly Gly
    50                  55                  60

Ile Ser Gly Leu Cys Ile Ala Gln Ala Leu Ser Thr Lys His Arg Asp
65                  70                  75                  80

Ile Ala Thr Asn Val Ile Val Thr Glu Ala Arg Asp Arg Val Gly Gly
                85                  90                  95

Asn Ile Thr Thr Ile Glu Arg Asp Gly Tyr Leu Trp Glu Glu Gly Pro
            100                 105                 110

Asn Ser Phe Gln Pro Ser Asp Pro Met Leu Thr Met Val Val Asp Ser
            115                 120                 125

Gly Leu Lys Asp Asp Leu Val Leu Gly Asp Pro Asn Ala Pro Arg Phe
        130                 135                 140

Val Leu Trp Asn Gly Lys Leu Arg Pro Val Pro Ser Lys Pro Thr Asp
145                 150                 155                 160

Leu Pro Phe Phe Asp Leu Met Ser Phe Gly Gly Lys Ile Arg Ala Gly
                165                 170                 175

Phe Gly Ala Leu Gly Leu Arg Pro Pro Pro Gly His Glu Glu Ser
            180                 185                 190

Val Glu Glu Phe Val Arg Arg Asn Leu Gly Asp Glu Val Phe Glu Arg
            195                 200                 205

Leu Ile Glu Pro Phe Cys Ser Gly Val Tyr Ala Gly Asp Pro Ser Lys
        210                 215                 220

Leu Ser Met Lys Ala Ala Phe Gly Lys Val Trp Lys Leu Glu Gln Ile
225                 230                 235                 240

Gly Gly Ser Val Ile Gly Gly Thr Phe Lys Thr Ile Gln Glu Arg Asn
                245                 250                 255

Lys Ile Pro Lys Pro Pro Arg Asp Pro Arg Leu Pro Thr Pro Lys Gly
            260                 265                 270

Gln Thr Val Gly Ser Phe Arg Lys Gly Leu Ile Met Leu Pro Asp Ala
            275                 280                 285

Ile Ala Lys Arg Leu Gly Ser Asn Val Lys Leu Ser Trp Lys Leu Ser
        290                 295                 300

Ser Ile Thr Lys Leu Glu Asn Gly Gly Tyr Ser Leu Thr Phe Glu Thr
305                 310                 315                 320

Pro Asp Gly Ser Val Ser Leu Gln Thr Lys Ser Val Val Met Thr Val
                325                 330                 335
```

Pro Ser His Ile Ala Ser Ser Phe Leu His Pro Leu Ser Ala Ala Ala
        340                 345                 350

Ala Asp Ala Leu Ser Lys Phe Tyr Tyr Pro Pro Val Ala Ala Val Ser
        355                 360                 365

Val Ser Tyr Pro Lys Asp Ala Ile Arg Ala Glu Cys Leu Ile Asp Gly
        370                 375                 380

Glu Leu Lys Gly Phe Gly Gln Leu His Pro Arg Ser Gln Gly Val Glu
385                 390                 395                 400

Thr Leu Gly Thr Ile Tyr Ser Ser Ser Leu Phe Pro Asn Arg Ala Pro
                405                 410                 415

Ala Gly Arg Ile Leu Leu Leu Asn Tyr Ile Gly Gly Ala Thr Asn Pro
        420                 425                 430

Gly Ile Leu Ser Lys Thr Glu Thr Glu Leu Val Glu Ala Val Asp Arg
        435                 440                 445

Asp Leu Arg Lys Met Leu Ile Lys Pro Asn Ala Lys Asp Pro Phe Val
        450                 455                 460

Leu Gly Val Arg Val Trp Pro Gln Ala Ile Pro Gln Phe Leu Val Gly
465                 470                 475                 480

His Leu Asp Ile Leu Asp Ser Ala Lys Gly Ala Leu Gly Asp Ala Gly
                485                 490                 495

Leu Glu Gly Leu Phe Leu Gly Gly Asn Tyr Val Ser Gly Val Ala Leu
                500                 505                 510

Gly Arg Cys Val Glu Gly Ala Tyr Glu Val Ala Ala Glu Val Thr Asn
        515                 520                 525

Phe Leu Ser Gln Asn Ala Tyr Lys
        530                 535

<210> SEQ ID NO 24
<211> LENGTH: 1671
<212> TYPE: DNA
<213> ORGANISM: Ricinus communis

<400> SEQUENCE: 24
caccacctga gttacagaag agtcatccgg tgtgattgcc tctcgaattc gaattctgcc      60
atggccaatc tcgcagactt ctctcttttt ctccggtcaa caccctccct tgtcccctcc     120
tatccgaaaa ccacaatcaa cagaacgtta aaactccaac tccggtgctc aatcacagag     180
caatcgacta ctacaatttc ccctggcgga aattcccaat caccagcgga ttgcgtgatt     240
gtaggaggcg gaattagcgg cctatgcatc gcccaagctc tctctaccaa gcaccgtgat     300
atagctacca atgtgattgt cactgaggcc agagaccgcg ttggtggcaa catcacaacc     360
atcgaaagag acggttatct ttgggaagag ggccccaata gtttccagcc ctccgatcct     420
atgctaacca tggtggtgga tagtgggtta aaagatgatt tagtttttggg agatcctaat     480 gcgcctcgtt ttgtgctctg aatgggaaa ttgagaccag ttccgtcaaa gcctactgac     540
ttgccctttt ttgacttgat gagctttggt gggaaaatta gagctggatt tggtgctctt     600
ggacttcgac ctccaccacc aggacatgag gagtcagttg aagagtttgt ccggcgtaat     660
cttggtgatg aagtttttga gcgtctaatc gagcccttt gttcaggtgt ttatgcaggt     720
gatccttcaa aactaagcat gaaagcagca tttggaaaag tttggaagct ggagcaaatt     780
ggtggcagtg tcattggcgg cactttcaaa acaattcagg agagaaataa gatacccaag     840
cctcctcgag acccgcgctt accaacaccg aagggtcaaa cagtaggatc ttttagaaag     900
ggacttatca tgttgcctga tgcgattgcc aaaaggttgg gtagcaatgt taaattgtct     960

```
tggaagcttt caagtattac taaattggaa aatggagggt atagtctaac atttgaaaca    1020
cctgatgggt cagtttcgct gcaaacgaaa agtgttgtaa tgacagttcc atcccacatt    1080
gcaagcagct tcttacatcc tctttctgct gctgctgctg acgccctatc aaaattttat    1140
tacccgccag ttgcagcagt gtcagtttca tacccaaaag atgcaattcg ggcagaatgc    1200
ttaatagatg gtgagcttaa ggggttcggc cagttgcatc cacggagcca aggggtagaa    1260
acattaggaa ctatatacag ctcctcactt tttcccaatc gtgcaccagc aggaaggatt    1320
ttgctcttga actacattgg aggggcgacc aatcctggga ttttgtccaa gacggaaact    1380
gaacttgtag aggcagttga ccgtgatttg aggaagatgc tcataaaacc caatgcgaag    1440
gatccatttg ttctaggtgt gcgagtgtgg ccccaagcca ttccacaatt cttggttggt    1500
catttagata tcctagatag tgcaaaaggt gctctgggag atgcaggctt ggaagggctg    1560
tttcttgggg gcaactatgt atcaggcgtt gctttgggcc gatgtgtgga aggagcatat    1620
gaagttgcag cagaggtgac caatttcctc tcgcagaatg cttataaatg a    1671
```

```
<210> SEQ ID NO 25
<211> LENGTH: 511
<212> TYPE: PRT
<213> ORGANISM: Ricinus communis

<400> SEQUENCE: 25

Met Ser Ser Val Ile Lys Glu Asp Arg Asn Pro Ser His Val Lys Arg
1               5                   10                  15

Val Ala Val Val Gly Ala Gly Val Ser Gly Leu Ala Ala Ala Tyr Lys
            20                  25                  30

Leu Lys Ser His Gly Leu Lys Val Thr Val Phe Glu Ala Glu Glu Arg
        35                  40                  45

Ala Gly Gly Lys Leu Arg Ser Val Asn His Asp Gly Leu Ile Trp Asp
    50                  55                  60

Glu Gly Ala Asn Thr Met Thr Glu Ser Glu Met Glu Val Lys Ser Leu
65                  70                  75                  80

Ile Gly Asn Leu Gly Ile Arg Glu Lys Gln Gln Phe Pro Ile Ser Gln
                85                  90                  95

Asn Lys Arg Tyr Ile Val Arg Asn Gly Lys Pro Ile Leu Ile Pro Thr
            100                 105                 110

Asn Pro Ile Ala Leu Ile Thr Ser Asn Ile Leu Ser Ala Gln Ser Lys
        115                 120                 125

Phe Gln Ile Ile Leu Glu Pro Phe Leu Trp Lys Lys Arg Glu Ser Ser
    130                 135                 140

Glu Thr His Asn Ala Tyr Thr Glu Glu Ser Val Gly Glu Phe Phe Gln
145                 150                 155                 160

Arg His Phe Gly Lys Glu Val Val Asp Tyr Leu Ile Asp Pro Phe Val
            165                 170                 175

Ala Gly Thr Ser Ala Gly Asp Pro Glu Ser Leu Ser Val Cys His Ser
            180                 185                 190

Phe Pro Glu Leu Trp Asn Leu Glu Lys Arg Phe Gly Ser Ile Ile Ala
        195                 200                 205

Gly Val Val Gln Ala Lys Leu Ser Thr Lys Arg Gly Lys Ser Gln Glu
    210                 215                 220

Thr Lys Gly Ser Ser Val Lys Lys Lys Gln Gln Arg Gly Ser Phe Ser
225                 230                 235                 240

Phe Phe Gly Gly Met Gln Thr Leu Thr Asp Thr Leu Cys Lys Ala Leu
```

-continued

```
                       245             250             255
Ala Lys Asp Glu Leu Arg Leu Glu Ser Lys Val Phe Ser Leu Ser Tyr
        260             265             270

Asn Pro Asp Ser Lys Ser Ala Val Glu Asn Trp Ser Leu Ser Tyr Ala
        275             280             285

Phe Lys Gly Ala Lys His Leu Gln Asn Ser Ser Tyr Asp Ala Ile Val
        290             295             300

Met Thr Ala Pro Leu Cys Asn Val Lys Glu Met Lys Ile Thr Lys Asn
305             310             315             320

Arg Asn Ile Phe Ser Leu Asn Phe Leu Pro Glu Val Ser Tyr Met Pro
                325             330             335

Leu Ser Val Val Ile Thr Thr Phe Lys Lys Asp Asn Val Lys Ser Pro
        340             345             350

Leu Glu Gly Phe Gly Val Leu Val Pro Ser Lys Glu Gln Gln Asn Gly
        355             360             365

Leu Lys Thr Leu Gly Thr Leu Phe Ser Ser Met Met Phe Pro Asp Arg
        370             375             380

Ala Pro Asn Asp Leu Tyr Leu Tyr Thr Thr Phe Val Gly Gly Ser Arg
385             390             395             400

Asn Lys Glu Leu Ala Lys Ala Ser Thr Asp Asp Leu Lys Gln Ile Val
                405             410             415

Thr Ser Asp Leu Arg Gln Leu Leu Gly Ala Glu Gly Glu Pro Thr Phe
                420             425             430

Val Asn His Phe Tyr Trp Ser Lys Ala Phe Pro Leu Tyr Gly Arg Asn
        435             440             445

Tyr Asp Ala Val Leu Glu Ala Ile Asp Thr Met Glu Lys Asp Leu Pro
        450             455             460

Gly Phe Phe Tyr Ala Gly Asn His Lys Gly Gly Leu Ser Val Gly Lys
465             470             475             480

Ala Ile Ala Ser Gly Cys Lys Ala Ala Asp Leu Val Ile Ser Tyr Leu
                485             490             495

Glu Ser Ser Ser Asp Asp Lys Met Leu Lys Glu Gly Pro Ser Asn
        500             505             510
```

```
<210> SEQ ID NO 26
<211> LENGTH: 1536
<212> TYPE: DNA
<213> ORGANISM: Ricinus communis

<400> SEQUENCE: 26
atgtcttcag ttatcaaaga agacagaaac ccaagtcatg ttaaaagagt agctgttgta      60
ggtgctgggg ttagtgggct tgctgcagct tacaaactga aatcacatgg cttgaaagtt     120
acagtatttg aagctgaaga agagctgga  gggaagctga gaagcgttaa ccatgatggt     180
ttaatttggg atgaaggtgc aaataccatg actgagagtg aaatggaggt caaaagttta     240
attggcaatc ttgggattcg tgaaaagcaa caatttccga tttcacagaa caaaaggtat     300
attgtaagaa atgggaagcc aatattaata cccacaaatc ccatcgcact gatcaccagc     360
aacattctct ctgcacagtc aaagtttcaa atcattctgg agccattttt gtggaagaaa     420
cgtgaatctt cagaaacgca caatgcttat actgaggaaa gtgttggtga gttttttccaa    480 cgtcattttg gtaaagaggt tgttgattat cttattgacc cttttgttgc gggcactagt     540
gctggagatc tgaatctct  ttctgtatgc cattcttttc cagagctatg gaatctggag     600
aaacgatttg gatctattat agctggggta gttcaggcaa aattatctac caaaagaggg     660
```

```
aagagccaag aaaccaaagg atcatcggta agaagaagc agcagcgtgg ttcattctct    720 tttttttggtg gaatgcagac gctaactgat acattgtgca aagcacttgc gaaggatgag    780
cttagattag aatcaaaggt cttctctttg tcttacaatc ctgattctaa gtcagcagta    840
gagaattggt cactttctta tgcttttaag ggcgccaagc atttgcaaaa ctcatcttat    900
gatgctattg tcatgacggc accattgtgc aatgttaaag aaatgaagat cacaaaaaac    960
agaaatatct tttcactgaa ttttcttcct gaggtgagtt atatgccgct atcagttgtt    1020
attaccactt ttaagaagga taatgtcaag agcccccttg aaggctttgg agttcttgtt    1080
ccttctaagg agcaacagaa tggtctaaaa acccttggta cactcttttc ctctatgatg    1140
tttccagatc gtgcacccaa tgatctgtat ctctatacaa cctttgttgg agggagtcga    1200
aacaaggaac tggcaaaagc ttcaacggat gatctgaagc agattgttac ctccgacctt    1260
aggcaattgc taggagcaga aggcgagccc acatttgtta atcatttcta ctggagtaaa    1320
gcatttccat tatatgggag gaactatgat gcagtacttg aagccattga tacgatggaa    1380
aaagatcttc ctggattctt ctatgcaggt aaccacaaag gtggactatc ggttggcaaa    1440
gcaatagcct ctggatgcaa agcagctgat cttgtaatat cctatttgga atcttcttca    1500
gatgacaaga tgctgaagga agggccatca aattag                               1536
```

```
<210> SEQ ID NO 27
<211> LENGTH: 504
<212> TYPE: PRT
<213> ORGANISM: Solanum tuberosum
<220> FEATURE:
<221> NAME/KEY: VARIANT
<222> LOCATION: (38)..(38)
<223> OTHER INFORMATION: Any amino acid
<220> FEATURE:
<221> NAME/KEY: VARIANT
<222> LOCATION: (60)..(60)
<223> OTHER INFORMATION: Any amino acid
<220> FEATURE:
<221> NAME/KEY: VARIANT
<222> LOCATION: (140)..(140)
<223> OTHER INFORMATION: Any amino acid
<220> FEATURE:
<221> NAME/KEY: VARIANT
<222> LOCATION: (360)..(360)
<223> OTHER INFORMATION: Any amino acid
<220> FEATURE:
<221> NAME/KEY: VARIANT
<222> LOCATION: (500)..(500)
<223> OTHER INFORMATION: Any amino acid

<400> SEQUENCE: 27

Met Ala Pro Ser Ala Gly Glu Asp Lys Gln Asn Cys Pro Lys Arg Val
1               5                   10                  15

Ala Val Ile Gly Ala Gly Val Ser Gly Leu Ala Ala Ala Tyr Lys Leu
            20                  25                  30

Lys Ile His Gly Leu Xaa Val Thr Val Phe Glu Ala Glu Gly Arg Ala
        35                  40                  45

Gly Gly Lys Leu Arg Ser Leu Ser Gln Asp Gly Xaa Ile Trp Asp Glu
    50                  55                  60

Gly Ala Asn Thr Met Thr Glu Ser Glu Gly Asp Val Thr Phe Leu Leu
65                  70                  75                  80

Asp Ser Leu Gly Leu Arg Glu Lys Gln Gln Phe Pro Leu Ser Gln Asn
                85                  90                  95

Lys Arg Tyr Ile Ala Arg Asn Gly Thr Pro Thr Leu Ile Pro Ser Asn
            100                 105                 110
```

```
Pro Ile Asp Leu Ile Lys Ser Asn Phe Leu Ser Thr Gly Ser Lys Leu
        115                 120                 125

Gln Met Leu Phe Glu Pro Leu Leu Trp Lys Asn Xaa Lys Leu Thr Lys
        130                 135                 140

Val Ser Asp Glu His Glu Ser Val Ser Gly Phe Phe Gln Arg His Phe
145                 150                 155                 160

Gly Lys Glu Val Val Asp Tyr Leu Ile Asp Pro Phe Val Ala Gly Thr
                165                 170                 175

Cys Gly Gly Asp Pro Asp Ser Leu Ser Met His Leu Ser Phe Pro Glu
                180                 185                 190

Leu Trp Asn Leu Glu Lys Arg Phe Gly Ser Val Ile Val Gly Ala Ile
        195                 200                 205

Arg Ser Lys Leu Ser Pro Ile Lys Glu Lys Lys Gln Gly Pro Pro Lys
        210                 215                 220

Thr Ser Val Asn Lys Lys Arg Gln Arg Gly Ser Phe Ser Phe Leu Gly
225                 230                 235                 240

Gly Met Gln Thr Leu Thr Asp Ala Ile Cys Lys Asp Leu Lys Glu Asp
                245                 250                 255

Glu Leu Arg Leu Asn Ser Arg Val Leu Glu Leu Ser Cys Ser Cys Ser
                260                 265                 270

Gly Asp Ser Ala Ile Asp Ser Trp Ser Ile Phe Ser Ala Ser Pro His
                275                 280                 285

Lys Arg Gln Ala Glu Glu Glu Ser Phe Asp Ala Val Ile Met Thr Ala
        290                 295                 300

Pro Leu Cys Asp Val Lys Ser Met Lys Ile Ala Lys Arg Gly Asn Pro
305                 310                 315                 320

Phe Leu Leu Asn Phe Ile Pro Glu Val Asp Tyr Val Pro Leu Ser Val
                325                 330                 335

Val Ile Thr Thr Phe Lys Lys Glu Ser Val Lys His Pro Leu Glu Gly
                340                 345                 350

Phe Gly Val Leu Val Pro Ser Xaa Glu Gln Lys His Gly Leu Lys Thr
                355                 360                 365

Leu Gly Thr Leu Phe Ser Ser Met Met Phe Pro Asp Arg Ala Pro Asn
        370                 375                 380

Asn Val Tyr Leu Tyr Thr Thr Phe Val Gly Gly Ser Arg Asn Arg Glu
385                 390                 395                 400

Leu Ala Lys Ala Ser Arg Thr Glu Leu Lys Glu Ile Val Thr Ser Asp
                405                 410                 415

Leu Lys Gln Leu Leu Gly Ala Glu Gly Glu Pro Thr Tyr Val Asn His
                420                 425                 430

Val Cys Trp Ser Lys Ala Phe Pro Leu Tyr Gly His Asn Tyr Asp Ser
        435                 440                 445

Val Leu Asp Ala Ile Asp Lys Met Glu Lys Asn Leu Pro Gly Leu Phe
        450                 455                 460

Tyr Ala Gly Asn His Lys Gly Gly Leu Ser Val Gly Lys Ala Leu Ser
465                 470                 475                 480

Ser Gly Cys Asn Ala Ala Asp Leu Val Ile Ser Tyr Leu Glu Ala Val
                485                 490                 495

Ser Thr Asp Xaa Lys Asn His Ser
                500
```

<210> SEQ ID NO 28
<211> LENGTH: 1515

```
<212> TYPE: DNA
<213> ORGANISM: Solanum tuberosum

<400> SEQUENCE: 28
atggctccat ctgccggaga agataaacaa aattgtccma agagagttgc agtcattggt      60
gctggcgtca gtggacttgc tgcagcatac aagttgaaaa tycatggstt gratgtcaca     120
gtattygaag cagaagggag agctggaggg aagttacgaa gcctgagtca agatggsmta     180
atatgggatg aaggcgcaaa tactatgact gaaagtgaag gtgatgtcac attttttgctt    240 gattcgcttg gactccgaga aaarcaacaa tttccacttt cacagaacaa rcgctacatt     300
gccagaaatg gyactcctac tctgatacct tcaaatccaa ttgacctgat caaaagcaat     360
tttctttcca ctggatcaaa gcttcagatg cttttcgagc cacttttgtg gaagaataaw     420
aagcttacaa aggtgtctga cgaacacgaa agtgtcagtg gattcttcca gcgtcatttt     480
ggraaggagg ttgttgacta tctaattgay ccttttgttg ctggaacatg tggtggtgat     540
cctgactcgc tttcaatgca cctttcgttt ccagagttgt ggaatttaga gaaaaggttt     600
ggctcagtca tagttggggc aattcgatcc aagttatcac ctataaagga aaagaaacaa     660
gggccaccca aaacttcagt aaataagaag cgccagcggg ggtccttttc atttttgggc     720
ggaatgcaaa cacttactga cgcaatatgc aaagatctca aagaagatga acttaggcta     780
aactctagag ttctggaatt atcttgtagc tgtagtgggg actctgcgat agatagctgg     840
tcaatttttt ctgcctcacc acacaagcgg caagcagaag aagaatcatt tgatgctgta     900
attatgacgg cccctctctg tgacgttaag agtatgaaga ttgctaagag aggaaatcca     960
tttctgctca actttattcc tgaggtygat tatgtaccac tatctgttgt tataaccaca    1020
tttaagaagg agagtgtaaa gcatccyctt gagggttttg gagtgcttgt accytccsag    1080
gagcaaaaac atggtctgaa gacaytaggc accctcttct cttctatgat gtttccagat    1140
cgtgcaccca acaatgtcta tctctatact acatttgttg gtggaagccg aaatagagaa    1200
ctygcgaaag cctcgaggac tgagctgaaa gagatagtaa cttctgacct taagcagttg    1260
ttgggtgctg agggagagcc aacatatgtg aatcatgtat gctggagtaa agcatttccg    1320
ttgtacgggc ataactatga ttcagtmctc gatgcaattg acaaaatgga gaaaaatctt    1380
cctggattat tctatgcagg taaccacaag ggaggattgt cagttggcaa agcactatct    1440 tctgatgta atgcagcaga tcttgttata tcatatcttg aagccgtttc aacggacwcc    1500
aaaaaccata gctga                                                      1515

<210> SEQ ID NO 29
<211> LENGTH: 504
<212> TYPE: PRT
<213> ORGANISM: Solanum tuberosum

<400> SEQUENCE: 29

Met Ala Pro Ser Ala Gly Glu Asp Lys Gln Asn Cys Pro Lys Arg Val
1               5                   10                  15

Ala Val Ile Gly Ala Gly Val Ser Gly Leu Ala Ala Ala Tyr Lys Leu
            20                  25                  30

Lys Ile His Gly Leu Asp Val Thr Val Phe Glu Ala Glu Gly Arg Ala
        35                  40                  45

Gly Gly Lys Leu Arg Ser Leu Ser Gln Asp Gly Leu Ile Trp Asp Glu
    50                  55                  60

Gly Ala Asn Thr Met Thr Glu Ser Glu Gly Asp Val Thr Phe Leu Leu
65                  70                  75                  80
```

-continued

```
Asp Ser Leu Gly Leu Arg Glu Lys Gln Gln Phe Pro Leu Ser Gln Asn
             85              90              95

Lys Arg Tyr Ile Ala Arg Asn Gly Thr Pro Thr Leu Ile Pro Ser Asn
            100             105             110

Pro Ile Asp Leu Ile Lys Ser Asn Phe Leu Ser Thr Gly Ser Lys Leu
            115             120             125

Gln Met Leu Phe Glu Pro Leu Leu Trp Lys Asn Lys Lys Leu Thr Lys
        130             135             140

Val Ser Asp Glu His Glu Ser Val Ser Gly Phe Phe Gln Arg His Phe
145             150             155             160

Gly Lys Glu Val Val Asp Tyr Leu Ile Asp Pro Phe Val Ala Gly Thr
            165             170             175

Cys Gly Gly Asp Pro Asp Ser Leu Ser Met His Leu Ser Phe Pro Glu
            180             185             190

Leu Trp Asn Leu Glu Lys Arg Phe Gly Ser Val Ile Val Gly Ala Ile
            195             200             205

Arg Ser Lys Leu Ser Pro Ile Lys Glu Lys Lys Gln Gly Pro Pro Lys
        210             215             220

Thr Ser Val Asn Lys Lys Arg Gln Arg Gly Ser Phe Ser Phe Leu Gly
225             230             235             240

Gly Met Gln Thr Leu Thr Asp Ala Ile Cys Asn Asp Leu Lys Glu Asp
            245             250             255

Glu Leu Arg Leu Asn Ser Arg Val Leu Glu Leu Ser Cys Ser Cys Ser
            260             265             270

Gly Asp Ser Ala Thr Asp Ser Trp Ser Ile Phe Ser Ala Ser Pro His
            275             280             285

Lys Arg Gln Ala Glu Glu Asp Ser Phe Asp Ala Val Ile Met Thr Ala
        290             295             300

Pro Leu Cys Asp Val Lys Gly Met Lys Ile Ala Lys Arg Gly Asn Pro
305             310             315             320

Phe Leu Leu Asn Phe Ile Pro Glu Val Asp Tyr Val Pro Leu Ser Val
            325             330             335

Val Ile Thr Thr Phe Lys Lys Glu Ser Val Lys His Pro Leu Glu Gly
            340             345             350

Phe Gly Val Leu Val Pro Ser Glu Glu Gln Lys His Gly Leu Lys Thr
            355             360             365

Leu Gly Thr Leu Phe Ser Ser Met Met Phe Pro Asp Arg Ala Pro Asn
        370             375             380

Asn Val Tyr Leu Tyr Thr Thr Phe Val Gly Gly Ser Arg Asn Arg Glu
385             390             395             400

Leu Ala Lys Ala Ser Arg Thr Glu Leu Lys Glu Ile Val Thr Ser Asp
            405             410             415

Leu Lys Gln Leu Leu Gly Ala Glu Gly Glu Pro Thr Tyr Val Asn His
            420             425             430

Val Cys Trp Ser Lys Ala Phe Pro Leu Tyr Gly His Asn Tyr Asp Ser
            435             440             445

Val Leu Asp Ala Ile Asp Lys Met Glu Lys Asn Leu Pro Gly Leu Phe
        450             455             460

Tyr Ala Gly Asn His Lys Gly Gly Leu Ser Val Gly Lys Ala Leu Ser
465             470             475             480

Ser Gly Cys Asn Ala Ala Asp Leu Val Ile Ser Tyr Leu Glu Ala Val
            485             490             495
```

-continued

Ser Thr Asp Thr Lys Asn His Arg
            500

<210> SEQ ID NO 30
<211> LENGTH: 1608
<212> TYPE: DNA
<213> ORGANISM: Solanum tuberosum

<400> SEQUENCE: 30
atggctccat ctgccggaga agataaacaa aattgtccca agagagttgc agtcattggt      60
gctggcgtca gtggacttgc tgcagcatac aagttgaaaa ttcatggctt ggatgtcaca     120
gtattcgaag cagaagggag agctggaggg aagttacgaa gcctgagtca agatggccta     180
atatgggatg aaggcgcaaa tactatgact gaaagtgaag gtgatgtcac atttttgctt     240
gattcgcttg actccgaga aaaacaacaa tttccacttt cacagaacaa gcgctacatt       300
gccagaaatg gtactcctac tctgatacct tcaaatccaa ttgacctgat caaaagcaat     360
tttctttcca ctggatcaaa gcttcagatg ctttttcgagc cactttttgtg aagaataaa    420 aagcttacaa aggtgtctga cgaacacgaa agtgtcagtg gattcttcca gcgtcatttt     480
ggaaaggagg ttgttgacta tctaattgat cctttttgttg ctggaacatg tggtggtgat     540
cctgactcgc tttcaatgca cctttcgttt ccagagttgt ggaatttaga gaaaaggttt     600
ggctcagtca tagttggggc aattcgatcc aagttatcac ctataaagga aaagaaacaa     660
ggaccaccca aaacttcagt aaataagaag cgccagcggg ggtcctttttc attttttgggc    720 ggaatgcaaa cacttactga cgcaatatgc aatgatctca agaagatga acttaggcta       780 aactctagag ttctggaatt atcttgtagc tgtagtgggg actctgcgac agatagctgg      840 tcaattttttt ctgcctcacc acacaagcgg caagcagaag aagattcatt tgatgctgta    900
attatgacgg cccctctctg tgacgttaag ggtatgaaga ttgctaagag aggaaatcca     960
tttctgctca actttattcc tgaggttgat tatgtaccac tatctgttgt tataaccaca    1020
tttaagaagg agagtgtaaa gcatcctctt gagggttttg gagtgcttgt accttccgag    1080
gagcaaaaac atggtctgaa gacattaggc accctcttct cttctatgat gtttccagat    1140
cgtgcaccca acaatgtcta tctctatact acatttgttg gtggaagccg aaatagagaa    1200
ctcgcgaaag cctcgaggac tgagctgaaa gagatagtaa cttctgacct taagcagttg    1260
ttgggtgctg agggagagcc aacatatgtg aatcatgtat gctggagtaa agcatttccg    1320
ttgtacgggc ataactatga ttcagtcctc gatgcaattg acaaaatgga gaaaaatctt    1380
cctggattat tctatgcagg taaccacaag ggaggattgt cagttggcaa agcactatct    1440
tctggatgta atgcagcaga tcttgttata tcatatcttg aagccgtttc aacggacacc    1500
aaaaaccata ggtgaaatct attctctcat gcagcttgcc gttctttgtt ccacaaaatc    1560
gtttaacttc atgacgagga gcaactttaa cgtgcagcca gtgacgca                   1608

<210> SEQ ID NO 31
<211> LENGTH: 504
<212> TYPE: PRT
<213> ORGANISM: Solanum tuberosum

<400> SEQUENCE: 31

Met Ala Pro Ser Ala Gly Glu Asp Lys Gln Asn Cys Pro Lys Arg Val
1               5                   10                  15

Ala Val Ile Gly Ala Gly Val Ser Gly Leu Ala Ala Ala Tyr Lys Leu
            20                  25                  30

-continued

```
Lys Ile His Gly Leu Asp Val Thr Val Phe Glu Ala Glu Gly Arg Ala
        35              40              45

Gly Gly Lys Leu Arg Ser Leu Ser Gln Asp Gly Leu Ile Trp Asp Glu
    50              55              60

Gly Ala Asn Thr Met Thr Glu Ser Glu Gly Asp Val Thr Phe Leu Leu
65              70              75              80

Asp Ser Leu Gly Leu Arg Glu Lys Gln Gln Phe Pro Leu Ser Gln Asn
                85              90              95

Lys Arg Phe Ile Ala Arg Asn Gly Thr Pro Thr Leu Ile Pro Ser Asn
            100             105             110

Pro Ile Asp Leu Ile Lys Ser Asn Phe Leu Ser Thr Gly Ser Lys Leu
            115             120             125

Gln Met Leu Phe Glu Pro Leu Leu Trp Lys Asn Lys Lys Leu Thr Lys
        130             135             140

Val Ser Asp Glu His Glu Ser Val Ser Gly Phe Phe Gln Arg His Phe
145             150             155             160

Gly Lys Glu Val Val Asp Tyr Leu Ile Asp Pro Phe Val Ala Gly Thr
                165             170             175

Cys Gly Gly Asp Pro Asp Ser Leu Ser Met His Leu Ser Phe Pro Glu
            180             185             190

Leu Trp Asn Leu Glu Lys Arg Phe Gly Ser Val Ile Val Gly Ala Ile
        195             200             205

Arg Ser Lys Leu Ser Pro Ile Lys Glu Lys Lys Gln Gly Pro Pro Lys
        210             215             220

Thr Ser Glu Asn Lys Lys Arg Gln Arg Gly Ser Phe Ser Phe Leu Gly
225             230             235             240

Gly Met Gln Thr Leu Thr Asp Ala Ile Cys Asn Asp Leu Lys Glu Asp
            245             250             255

Glu Leu Arg Leu Asn Ser Arg Val Leu Glu Leu Ser Cys Ser Cys Ser
            260             265             270

Gly Asp Ser Ala Thr Asp Ser Trp Ser Ile Phe Ser Ala Ser Pro His
        275             280             285

Lys Arg Gln Ala Glu Glu Asp Ser Phe Asp Ala Val Ile Met Thr Ala
        290             295             300

Pro Leu Cys Asp Val Lys Gly Met Lys Ile Ala Lys Arg Gly Asn Pro
305             310             315             320

Phe Leu Leu Asn Phe Ile Pro Glu Val Asp Tyr Val Pro Leu Ser Val
            325             330             335

Val Ile Thr Thr Phe Lys Lys Glu Ser Val Lys His Pro Leu Glu Gly
            340             345             350

Phe Gly Val Leu Val Pro Ser Glu Glu Gln Lys His Gly Leu Lys Thr
            355             360             365

Leu Gly Thr Leu Phe Ser Ser Met Met Phe Pro Asp Arg Ala Pro Asn
        370             375             380

Asn Val Tyr Leu Tyr Thr Thr Phe Val Gly Gly Ser Arg Asn Arg Glu
385             390             395             400

Leu Ala Lys Ala Ser Arg Thr Glu Leu Lys Glu Ile Val Thr Ser Asp
            405             410             415

Leu Lys Gln Leu Leu Gly Ala Glu Gly Glu Pro Thr Tyr Val Asn His
        420             425             430

Val Cys Trp Ser Lys Ala Phe Pro Leu Tyr Gly His Asn Tyr Asp Ser
        435             440             445

Val Leu Asp Ala Ile Asp Lys Met Glu Lys Asn Leu Pro Gly Leu Phe
```

-continued

```
          450              455              460

Tyr Ala Gly Asn His Lys Gly Gly Leu Ser Val Gly Lys Ala Leu Ser
465                  470              475              480

Ser Gly Cys Asn Ala Ala Asp Leu Val Ile Ser Tyr Leu Glu Ala Val
                485              490              495

Ser Thr Asp Thr Lys Asn His Arg
            500

<210> SEQ ID NO 32
<211> LENGTH: 1608
<212> TYPE: DNA
<213> ORGANISM: Solanum tuberosum

<400> SEQUENCE: 32
atggctccat ctgccggaga agataaacaa aattgtccca agagagttgc agtcattggt      60
gctggcgtca gtggacttgc tgcagcatac aagttgaaaa ttcatggctt ggatgtcaca     120
gtattcgaag cagaagggag agctggaggg aagttacgaa gcctgagtca agatggccta     180
atatgggatg aaggcgcaaa tactatgact gaaagtgaag gtgatgtcac attttttgctt    240 gattcgcttg gactccgaga aaaacaacaa tttccacttt cacagaacaa gcgcttcatt     300
gccagaaatg gtactcctac tctgatacct tcaaatccaa ttgacctgat caaaagcaat     360
tttctttcca ctggatcaaa gcttcagatg cttttttcgagc cactttttgtg gaagaataaa    420 aagcttacaa aggtgtctga cgaacacgaa agtgtcagtg gattcttcca gcgtcatttt     480
ggaaaggagg ttgttgacta tctaattgat cctttttgttg ctggaacatg tggtggtgat     540
cctgactcgc tttcaatgca cctttttcgttt ccagagttgt ggaatttaga gaaaaggttt    600
ggctcagtca tagttggggc aattcgatcc aagttatcac ctataaagga aaagaaacaa     660
ggaccaccca aaacttcaga aaataagaag cgccagcggg ggtccttttc atttttttgggc    720 ggaatgcaaa cacttactga cgcaatatgc aatgatctca agaagatgat acttaggcta     780
aactctagag ttctggaatt atcttgtagc tgtagtgggg actctgcgac agatagctgg     840 tcaattttttt ctgcctcacc acacaagcgg caagcagaag aagattcatt tgatgctgta     900
attatgacgg cccctctctg tgacgttaag ggtatgaaga ttgctaagag aggaaatcca     960
tttctgctca actttattcc tgaggttgat tatgtaccac tatctgttgt tataaccaca    1020
tttaagaagg agagtgtaaa gcatcctctt gagggttttg gagtgcttgt accttccgag    1080
gagcaaaaac atggtctgaa gacattaggc accctcttct cttctatgat gtttccagat    1140 cgtgcacccca acaatgtcta tctctatact acatttgttg gtggaagccg aaatagagaa    1200
ctcgcgaaag cctcgaggac tgagctgaaa gagatagtaa cttctgacct taagcagttg    1260
ttgggtgctg agggagagcc aacatatgtg aatcatgtat gctggagtaa agcatttccg    1320
ttgtacgggc ataactatga ttcagtcctc gatgcaattg acaaaatgga gaaaaatctt    1380
cctggattat tctatgcagg taaccacaag ggaggattgt cagttggcaa agcactatct    1440
tctggatgta atgcagcaga tcttgttata tcatatcttg aagccgtttc aacggacacc    1500
aaaaaccata ggtgaaatct attctctcat gcagcttgcc gttctttgtt ccacaaaatc    1560
gtttaacttc atgacgagga gcaactttaa cgtgcagcca gtgacgca               1608

<210> SEQ ID NO 33
<211> LENGTH: 535
<212> TYPE: PRT
<213> ORGANISM: Brassica napus
```

<400> SEQUENCE: 33

Met Asp Leu Ser Leu Leu Arg Pro Gln Pro Phe Leu Ser Pro Phe Ser
1               5                   10                  15

Asn Pro Phe Pro Arg Ser Arg Pro Tyr Lys Pro Leu Asn Leu Arg Cys
                20                  25                  30

Ser Val Ser Gly Gly Ser Val Val Ser Ser Thr Ile Glu Gly Gly Gly
            35                  40                  45

Gly Gly Lys Thr Val Thr Ala Asp Cys Val Ile Val Gly Gly Gly Ile
    50                  55                  60

Ser Gly Leu Cys Ile Ala Gln Ala Leu Val Thr Lys His Pro Asp Ala
65                  70                  75                  80

Ala Lys Asn Val Met Val Thr Glu Ala Lys Asp Arg Val Gly Gly Asn
                85                  90                  95

Ile Ile Thr Arg Glu Glu Gln Gly Phe Leu Trp Glu Glu Gly Pro Asn
                100                 105                 110

Ser Phe Gln Pro Ser Asp Pro Met Leu Thr Met Val Val Asp Ser Gly
            115                 120                 125

Leu Lys Asp Asp Leu Val Leu Gly Asp Pro Thr Ala Pro Arg Phe Val
    130                 135                 140

Leu Trp Asn Gly Lys Leu Arg Pro Val Pro Ser Lys Leu Thr Asp Leu
145                 150                 155                 160

Pro Phe Phe Asp Leu Met Ser Ile Gly Gly Lys Ile Arg Ala Gly Phe
                165                 170                 175

Gly Ala Ile Gly Ile Arg Pro Ser Pro Pro Gly Arg Glu Glu Ser Val
            180                 185                 190

Glu Glu Phe Val Arg Arg Asn Leu Gly Asp Glu Val Phe Glu Arg Leu
            195                 200                 205

Ile Glu Pro Phe Cys Ser Gly Val Tyr Ala Gly Asp Pro Ala Lys Leu
    210                 215                 220

Ser Met Lys Ala Ala Phe Gly Lys Val Trp Lys Leu Glu Glu Asn Gly
225                 230                 235                 240

Gly Ser Ile Ile Gly Gly Ala Phe Lys Ala Ile Gln Ala Lys Asn Lys
            245                 250                 255

Ala Pro Lys Thr Thr Arg Asp Pro Arg Leu Pro Lys Pro Lys Gly Gln
            260                 265                 270

Thr Val Gly Ser Phe Arg Lys Gly Leu Thr Met Leu Pro Asp Ala Ile
    275                 280                 285

Ser Ala Arg Leu Gly Asp Lys Val Lys Val Ser Trp Lys Leu Ser Ser
    290                 295                 300

Ile Ser Lys Leu Pro Ser Gly Gly Tyr Ser Leu Thr Tyr Glu Thr Pro
305                 310                 315                 320

Glu Gly Ile Val Thr Val Gln Ser Lys Ser Val Val Met Thr Val Pro
            325                 330                 335

Ser His Val Ala Ser Ser Leu Leu Arg Pro Leu Ser Asp Ser Ala Ala
            340                 345                 350

Glu Ala Leu Ser Lys Leu Tyr Tyr Pro Pro Val Ala Ala Val Ser Ile
            355                 360                 365

Ser Tyr Pro Lys Glu Ala Ile Arg Ser Glu Cys Leu Ile Asp Gly Glu
    370                 375                 380

Leu Lys Gly Phe Gly Gln Leu His Pro Arg Thr Gln Lys Val Glu Thr
385                 390                 395                 400

Leu Gly Thr Ile Tyr Ser Ser Ser Leu Phe Pro Asn Arg Ala Pro Pro
                405                 410                 415

```
Gly Arg Val Leu Leu Leu Asn Tyr Ile Gly Gly Ala Thr Asn Thr Gly
        420                 425                 430

Ile Leu Ser Lys Ser Glu Gly Glu Leu Val Glu Ala Val Asp Arg Asp
        435                 440                 445

Leu Arg Lys Met Leu Ile Lys Pro Ser Ser Thr Asp Pro Leu Val Leu
        450                 455                 460

Gly Val Lys Val Trp Pro Gln Ala Ile Pro Gln Phe Leu Ile Gly His
465                 470                 475                 480

Ile Asp Leu Val Asp Ala Ala Lys Ala Ser Leu Ser Ser Ser Gly His
                485                 490                 495

Glu Gly Leu Phe Leu Gly Gly Asn Tyr Val Ala Gly Val Ala Leu Gly
        500                 505                 510

Arg Cys Val Glu Gly Ala Tyr Glu Thr Ala Thr Gln Val Asn Asp Phe
        515                 520                 525

Met Ser Arg Tyr Ala Tyr Lys
        530                 535

<210> SEQ ID NO 34
<211> LENGTH: 1830
<212> TYPE: DNA
<213> ORGANISM: Brassica napus

<400> SEQUENCE: 34
ttgaacaaag aggctggacc ggtccggaat cccgggata tcgtcgaccc acgcgtccgg      60
tcgacgctga tcggagataa gagtcgacaa aattgaggat tctccttctc gcgggcgatc     120
gccatggatt tatctcttct ccgtccgcag ccattcctat cgccattctc aaatccattt     180
cctcggtcgc gtccctacaa gcctctcaac ctccgttgct ccgtatccgg tggatccgtc     240
gtctcttcta caatcgaagg cggaggagga ggtaaaaccg tcacggcgga ctgcgtgatc     300
gtcggcggag gaatcagcgg cctgtgcatt cgcgaagcgc tcgtgacgaa gcacccagac     360
gctgcaaaga atgtgatggt gacggaggcg aaggaccgtg tgggagggaa tatcatcacg     420
cgagaggagc aagggtttct atgggaagaa ggtcccaata gctttcagcc gtctgatcct     480
atgctcacta tggtggtaga tagtggtttg aaagatgatc tagtcttggg agatcctact     540
gctccgaggt ttgtgttgtg gaatgggaag ctgaggccgg ttccgtcgaa gctaactgac     600
ttgcctttct ttgacttgat gagtattgga gggaagatta gagctgggtt tggtgccatt     660
ggtattcgac cttcacctcc gggtcgtgag gaatcagtgg aagagtttgt aaggcgtaat     720
cttggtgatg aggttttttga gcgcttgatt gaacccttt gctcaggtgt ttatgcggga     780
gatcctgcga aactgagtat gaaagcagct tttgggaagg tttggaagct agaggagaat     840
ggtgggagca tcattggtgg tgcttttaag gcaattcaag cgaaaaataa agctcccaag     900
acaacccgag acccgcgtct gccaaagcca aagggccaaa cagttggttc tttcaggaaa     960
ggactcacaa tgctgccaga cgcaatctct gcaggttgg gtgacaaggt gaaagtttct    1020
tggaagctct caagtatcag taagctgccc agcggaggat atagcttaac ttacgaaact    1080
ccggagggga tagtcactgt acagagcaaa agtgttgtga tgactgtgcc atctcatgtt    1140
gctagtagtc tcttgcgccc tctctctgac tctgcagctg aagcgctctc aaaactctac    1200
tatccaccag ttgcagcagt atctatctca tacccgaaag aagcaatccg aagcgaatgt    1260
ttaatagatg gtgaactaaa agggttcggc cagttgcatc cacgcacgca gaaagtggaa    1320
actcttggaa caatatacag ttcatcgctc tttcctaacc gagcaccacc tggaagagtg    1380
```

-continued

```
ttgctactga actacatcgg tggagctacc aacactggga tcttatcaaa gtcagaaggt      1440
gagttagtgg aagcagtgga tagagacttg aggaagatgc tgataaagcc aagctcgacc      1500
gatccacttg tacttggagt aaaagtttgg cctcaagcca ttcctcagtt tctgataggt      1560
cacattgatt tggtagacgc agcgaaagca tctctctcgt catctggcca tgagggctta      1620
ttcttgggtg gaaattacgt tgccggtgta gcattgggtc ggtgtgtgga aggtgcttat      1680
gaaactgcaa cccaagtgaa cgatttcatg tcgaggtacg cttacaagta atgtaacgca      1740
gcaacggttt gatactaagt tgtagattgc agttttgact ctgtttgtga aaaattcaag      1800
tctatgattg agtaaattta tatgtattaa                                       1830
```

```
<210> SEQ ID NO 35
<211> LENGTH: 537
<212> TYPE: PRT
<213> ORGANISM: Brassica napus

<400> SEQUENCE: 35

Met Asp Leu Ser Leu Leu Arg Pro Gln Pro Phe Leu Ser Pro Phe Ser
1               5                   10                  15

Asn Pro Phe Pro Arg Ser Arg Pro Tyr Lys Pro Leu Asn Leu Arg Cys
            20                  25                  30

Ser Val Ser Gly Gly Ser Val Val Val Gly Ser Ser Thr Ile Glu Gly
        35                  40                  45

Gly Gly Gly Gly Lys Thr Val Ala Ala Asp Cys Val Ile Val Gly Gly
    50                  55                  60

Gly Ile Ser Gly Leu Cys Ile Ala Gln Ala Leu Val Thr Lys His Pro
65                  70                  75                  80

Asp Ala Ala Lys Ser Val Met Val Thr Glu Ala Lys Asp Arg Val Gly
            85                  90                  95

Gly Asn Ile Ile Thr Arg Glu Glu Gln Gly Phe Leu Trp Glu Glu Gly
            100                 105                 110

Pro Asn Ser Phe Gln Pro Ser Asp Pro Met Leu Thr Met Val Val Asp
            115                 120                 125

Ser Gly Leu Lys Asp Asp Leu Val Leu Gly Asp Pro Thr Ala Pro Arg
        130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                165                 170                 175

Gly Phe Gly Ala Ile Gly Ile Arg Pro Ser Pro Pro Gly Arg Glu Glu
            180                 185                 190

Ser Val Glu Glu Phe Val Arg Arg Asn Leu Gly Asp Glu Val Phe Glu
        195                 200                 205

Arg Leu Ile Glu Pro Phe Cys Ser Gly Val Tyr Ala Gly Asp Pro Ala
    210                 215                 220

Lys Leu Ser Met Lys Ala Ala Leu Gly Lys Val Trp Lys Leu Lys Glu
225                 230                 235                 240

Asn Gly Gly Ser Ile Ile Gly Gly Ala Phe Lys Ala Ile Gln Ala Lys
                245                 250                 255

Asn Lys Ala Pro Lys Thr Thr Arg Asp Pro Arg Leu Pro Lys Pro Lys
            260                 265                 270

Gly Gln Thr Val Gly Ser Phe Arg Lys Gly Leu Thr Met Leu Pro Asp
        275                 280                 285

Ala Ile Ser Ala Arg Leu Gly Asp Lys Val Lys Val Ser Trp Lys Leu
```

```
          290               295               300

Ser Ser Ile Ser Lys Leu Pro Ser Gly Gly Tyr Ser Leu Thr Tyr Glu
305               310               315               320

Thr Pro Glu Gly Ile Val Thr Val Gln Ser Lys Ser Val Val Met Thr
                  325               330               335

Val Pro Ser His Val Ala Ser Ser Leu Leu Arg Pro Leu Ser Asp Ser
                  340               345               350

Ala Ala Glu Ala Leu Ser Lys Leu Tyr Tyr Pro Pro Val Ala Ala Val
              355               360               365

Ser Ile Ser Tyr Pro Lys Glu Ala Ile Arg Ser Glu Cys Leu Ile Asp
          370               375               380

Gly Glu Leu Lys Gly Phe Gly Gln Leu His Pro Arg Thr Gln Lys Val
385               390               395               400

Glu Thr Leu Gly Thr Ile Tyr Ser Ser Ser Leu Phe Pro Asn Arg Ala
              405               410               415

Pro Pro Gly Arg Val Leu Leu Leu Asn Tyr Ile Gly Gly Ala Thr Asn
              420               425               430

Thr Gly Ile Leu Ser Lys Ser Glu Gly Glu Leu Val Glu Ala Val Asp
              435               440               445

Arg Asp Leu Arg Lys Met Leu Ile Lys Pro Ser Ser Thr Asp Pro Leu
          450               455               460

Val Leu Gly Val Lys Val Trp Pro Gln Ala Ile Pro Gln Phe Leu Ile
465               470               475               480

Gly His Ile Asp Leu Val Asp Ala Ala Lys Ala Ser Leu Ser Ser Ser
              485               490               495

Gly His Glu Gly Leu Phe Leu Gly Gly Asn Tyr Val Ala Gly Val Ala
              500               505               510

Leu Gly Arg Cys Val Glu Gly Ala Tyr Glu Thr Ala Thr Gln Val Asn
              515               520               525

Asp Phe Met Ser Arg Tyr Ala Tyr Lys
      530               535

<210> SEQ ID NO 36
<211> LENGTH: 1668
<212> TYPE: DNA
<213> ORGANISM: Brassica napus

<400> SEQUENCE: 36
gatcggagat aaggttgacg aaattgagaa tcctcctcct cgcgggccat cgccatggat      60
ttatctcttc tccgtccgca gccattccta tcgccattct caaatccatt tcctcggtcg     120
cgtccctaca agcctctcaa cctccgttgc tccgtatccg gtggatccgt cgtcgtcggc     180
tcgtccacaa tcgaaggcgg aggaggaggt aaaaccgtcg cggcggattg cgtgatcgtc     240
ggcggaggaa tcagcggcct gtgcattgcg caagcgctcg tgacgaagca cccggacgct     300
gcgaagagtg tgatggtgac ggaggcgaag accgcgtgg gagggaatat catcacgcga      360
gaggagcaag ggtttctatg ggaagaaggt cccaacagct ttcagccgtc tgatcctatg     420
ctcactatgg tggtagatag tggtttgaag gatgatctag tcttgggaga tcctactgcg     480
ccgaggttcg tgttgtggaa tgggaagctg aggccggttc cgtcgaagct aactgacttg     540
cctttctttg acttgatgag cattggaggg aagattagag ctgggtttgg tgccattggc     600
attcgaccgt cacctccagg tcgtgaggaa tctgtggaag agtttgtaag gcgtaacctt     660
ggtgatgagg tttttgagcg tttgattgaa ccctttttgtt caggtgttta tgcgggagat     720
```

-continued

```
cctgcgaaac tgagtatgaa agcagctttg gggaaggttt ggaaactaaa ggagaatggt      780
ggaagcatca taggtggtgc tttttaaggca attcaagcga aaaataaagc tcccaagaca      840
acccgagacc cgcgtctgcc aaagccaaag ggccaaacag ttggttcttt caggaaagga      900
ctcacaatgc tgccagacgc aatctctgca aggttgggtg acaaggtgaa agtttcttgg      960
aagctctcaa gtatcagtaa gctgcccagc ggaggatata gcttaactta cgaaactccg     1020
gaggggatag tcactgtaca gagcaaaagt gttgtgatga ctgtgccatc tcatgttgct     1080
agtagtctct tgcgccctct ctctgactct gcagctgaag cgctctcaaa actctactat     1140
ccaccagttg cagcagtatc tatctcatac ccgaaagaag caatccgaag cgaatgttta     1200
atagatggtg aactaaaagg gttcggccag ttgcatccac gcacgcagaa agtggaaact     1260
cttggaacaa tatacagttc atcgctcttt cctaaccgag caccacctgg aagagtgttg     1320
ctactgaact acatcggtgg agctaccaac actgggatct tatcaaagtc agaaggtgag     1380
ttagtggaag cagtggatag agacttgagg aagatgctga taaagccaag ctcgaccgat     1440
ccacttgtac ttggagtaaa agtttggcct caagccattc ctcagtttct gataggtcac     1500
attgatttgg tagacgcagc gaaagcatct ctctcgtcat ctggccatga gggcttattc     1560
ttgggtggaa attacgttgc cggtgtagca ttgggtcggt gtgtggaagg tgcttatgaa     1620
actgcaaccc aagtgaacga tttcatgtcg aggtacgctt acaagtaa                   1668
```

```
<210> SEQ ID NO 37
<211> LENGTH: 212
<212> TYPE: PRT
<213> ORGANISM: Brassica napus

<400> SEQUENCE: 37

Val Thr Val Gln Ser Lys Ser Val Val Met Thr Val Pro Ser His Val
1               5                   10                  15

Ala Ser Ser Leu Leu Arg Pro Leu Ser Asp Ser Ala Ala Glu Ala Leu
                20                  25                  30

Ser Lys Leu Tyr Tyr Pro Pro Val Ala Ala Val Ser Ile Ser Tyr Ala
            35                  40                  45

Lys Glu Ala Ile Arg Ser Glu Cys Leu Ile Asp Gly Glu Leu Lys Gly
        50                  55                  60

Phe Gly Gln Leu His Pro Arg Thr Gln Lys Val Glu Thr Leu Gly Thr
65                  70                  75                  80

Ile Tyr Ser Ser Ser Leu Phe Pro Asn Arg Ala Pro Pro Gly Arg Val
                85                  90                  95

Leu Leu Leu Asn Tyr Ile Gly Gly Ala Thr Asn Thr Gly Ile Leu Ser
                100                 105                 110

Lys Ser Glu Gly Glu Leu Val Glu Ala Val Asp Arg Asp Leu Arg Lys
            115                 120                 125

Met Leu Ile Lys Pro Ser Ser Thr Asp Pro Leu Val Leu Gly Val Lys
        130                 135                 140

Leu Trp Pro Gln Ala Ile Pro Gln Phe Leu Ile Gly His Ile Asp Leu
145                 150                 155                 160

Val Asp Ala Ala Lys Ala Ser Leu Ser Ser Ser Gly His Glu Gly Leu
                165                 170                 175

Phe Leu Gly Gly Asn Tyr Val Ala Gly Val Ala Leu Gly Arg Cys Val
                180                 185                 190

Glu Gly Ala Tyr Glu Thr Ala Thr Gln Val Asn Asp Phe Met Ser Arg
            195                 200                 205
```

-continued

Tyr Ala Tyr Lys
    210

<210> SEQ ID NO 38
<211> LENGTH: 757
<212> TYPE: DNA
<213> ORGANISM: Brassica napus

<400> SEQUENCE: 38

```
tagtcactgt acagagcaaa agtgtagtga tgactgtgcc atctcatgta gctagtagtc      60
tcttgcgccc tctctctgat tctgcagctg aagcgctctc aaaactctac tatccgccag     120
ttgcagccgt atccatctca tacgcgaaag aagcaatccg aagcgaatgc ttaatagatg     180
gtgaactaaa agggttcggc cagttgcatc cacgcacgca aaaagtggaa actcttggaa     240
caatatacag ttcatcgctc tttcccaacc gagcaccgcc tggaagagta ttgctattga     300
actacatcgg tggagctacc aacactggga tcttatcaaa gtcggaaggt gagttagtgg     360
aagcagtaga tagagacttg aggaagatgc tgataaagcc aagctcgacc gatccacttg     420
tacttggagt aaaattatgg cctcaagcca ttcctcagtt tctgataggt cacattgatt     480
tggtagacgc agcgaaagca tcgctctcgt catctggtca tgagggctta ttcttgggtg     540
gaaattacgt tgccggtgta gcattgggtc ggtgtgtgga aggtgcttat gaaactgcaa     600
cccaagtgaa tgatttcatg tcaaggtatg cttacaagta atgtaacgca gcaacgattt     660
gatactaagt agtagatttc gcagttctga ctttaagaac actctgtttg tgaaaaattc     720
aagtctgtga ttgagtaaat ttatgtatta ttactaa                               757
```

<210> SEQ ID NO 39
<211> LENGTH: 536
<212> TYPE: PRT
<213> ORGANISM: Glycine max

<400> SEQUENCE: 39

```
Met Val Ala Ala Ala Ala Met Ala Thr Ala Ala Ser Ala Ala Ala Pro
1               5                   10                  15

Leu Leu Asn Gly Thr Arg Arg Pro Ala Arg Leu Arg Arg Arg Gly Leu
            20                  25                  30

Arg Val Arg Cys Ala Ala Val Ala Gly Gly Ala Ala Glu Ala Pro Ala
        35                  40                  45

Ser Thr Gly Ala Arg Leu Ser Ala Asp Cys Val Val Val Gly Gly Gly
    50                  55                  60

Ile Ser Gly Leu Cys Thr Ala Gln Ala Leu Ala Thr Arg His Gly Val
65                  70                  75                  80

Gly Glu Val Leu Val Thr Glu Ala Arg Ala Arg Pro Gly Gly Asn Ile
            85                  90                  95

Thr Thr Val Glu Arg Pro Glu Glu Gly Tyr Leu Trp Glu Glu Gly Pro
            100                 105                 110

Asn Ser Phe Gln Pro Ser Asp Pro Val Leu Ser Met Ala Val Asp Ser
        115                 120                 125

Gly Leu Lys Asp Asp Leu Val Phe Gly Asp Pro Asn Ala Pro Arg Phe
    130                 135                 140

Val Leu Trp Glu Gly Lys Leu Arg Pro Val Pro Ser Lys Pro Ala Asp
145                 150                 155                 160

Leu Pro Phe Phe Asp Leu Met Ser Ile Pro Gly Lys Leu Arg Ala Gly
            165                 170                 175

Leu Gly Ala Leu Gly Ile Arg Pro Pro Pro Pro Gly Arg Glu Glu Ser
```

```
                180              185              190

Val Glu Glu Phe Val Arg Arg Asn Leu Gly Ala Glu Val Phe Glu Arg
            195              200              205

Leu Ile Glu Pro Phe Cys Ser Gly Val Tyr Ala Gly Asp Pro Ser Lys
            210              215              220

Leu Ser Met Lys Ala Ala Phe Gly Lys Val Trp Arg Leu Glu Glu Ala
225              230              235              240

Gly Gly Ser Ile Ile Gly Gly Thr Ile Lys Thr Ile Gln Glu Arg Gly
                245              250              255

Lys Asn Pro Lys Pro Pro Arg Asp Pro Arg Leu Pro Lys Pro Lys Gly
                260              265              270

Gln Thr Val Ala Ser Phe Arg Lys Gly Leu Ala Met Leu Pro Asn Ala
            275              280              285

Ile Thr Ser Ser Leu Gly Ser Lys Val Lys Leu Ser Trp Lys Leu Thr
            290              295              300

Ser Ile Thr Lys Ser Asp Gly Lys Gly Tyr Val Leu Glu Tyr Glu Thr
305              310              315              320

Pro Glu Gly Val Val Leu Val Gln Ala Lys Ser Val Ile Met Thr Ile
                325              330              335

Pro Ser Tyr Val Ala Ser Asp Ile Leu Arg Pro Leu Ser Gly Asp Ala
            340              345              350

Ala Asp Ala Leu Ser Arg Phe Tyr Tyr Pro Pro Val Ala Ala Val Thr
            355              360              365

Val Ser Tyr Pro Lys Glu Ala Ile Arg Lys Glu Cys Leu Ile Asp Gly
            370              375              380

Glu Leu Gln Gly Phe Gly Gln Leu His Pro Arg Ser Gln Gly Val Glu
385              390              395              400

Thr Leu Gly Thr Ile Tyr Ser Ser Ser Leu Phe Pro Asn Arg Ala Pro
                405              410              415

Ala Gly Arg Val Leu Leu Leu Asn Tyr Ile Gly Gly Ala Thr Asn Thr
                420              425              430

Gly Ile Val Ser Lys Thr Glu Ser Glu Leu Val Glu Ala Val Asp Arg
            435              440              445

Asp Leu Arg Lys Met Leu Ile Asn Ser Thr Ala Val Asp Pro Leu Val
            450              455              460

Leu Gly Val Arg Val Trp Pro Gln Ala Ile Pro Gln Phe Leu Val Gly
465              470              475              480

His Leu Asp Leu Leu Glu Val Ala Lys Ser Ala Leu Asp Gln Gly Gly
                485              490              495

Tyr Asp Gly Leu Phe Leu Gly Gly Asn Tyr Val Ala Gly Val Ala Leu
                500              505              510

Gly Arg Cys Ile Glu Gly Ala Tyr Glu Ser Ala Ala Gln Ile Tyr Asp
            515              520              525

Phe Leu Thr Lys Tyr Ala Tyr Lys
            530              535
```

```
<210> SEQ ID NO 40
<211> LENGTH: 551
<212> TYPE: PRT
<213> ORGANISM: Glycine max

<400> SEQUENCE: 40

Met Val Ser Val Phe Asn Asp Ile Leu Phe Pro Pro Asn Gln Thr Leu
1               5               10              15
```

```
Ser Pro Thr Ser Phe Phe Thr Ser Pro Thr Arg Lys Phe Pro Arg Ser
         20              25              30

Arg Pro Asn Pro Ile Leu Arg Cys Ser Ile Ala Glu Glu Ser Thr Glu
         35              40              45

Ser Arg Pro Lys Thr Gly Asp Ser Pro Pro Pro Leu Met Glu Ala
         50              55              60

Leu Ala Val Trp His Arg Pro Gly Pro Arg His Gln Ala Arg Gln Cys
65               70              75              80

Gln His Cys Trp Gly Asp Ser Arg Ala Arg Asp Arg Val Gly Gly Gly
              85              90              95

Asn Ile Thr Thr Met Glu Ser Gly Gly Tyr Leu Trp Glu Glu Gly Pro
         100             105             110

Asn Ser Phe Gln Pro Ser Asp Pro Met Leu Thr Met Val Val Asp Ser
         115             120             125

Gly Leu Lys Asp Gln Leu Val Leu Gly Asp Pro Asp Ala Pro Arg Phe
         130             135             140

Val Leu Trp Asn Gly Lys Leu Arg Pro Val Pro Gly Lys Pro Thr Asp
145              150             155             160

Leu Pro Phe Phe Asp Leu Met Ser Ile Gly Gly Lys Ile Arg Ala Gly
              165             170             175

Phe Gly Val Leu Gly Ile Arg Pro Pro Pro Val Glu Glu Phe Val
              180             185             190

Arg Arg Asn Leu Gly Asp Asp Val Phe Glu Arg Leu Ile Glu Pro Phe
         195             200             205

Cys Ser Gly Gly Asn Thr Cys Ile Phe Lys Phe Val Gly Ala Leu Leu
         210             215             220

Ile Leu Trp Gly Leu Cys Arg Arg Ser Phe Lys Ile Lys Tyr Glu Ser
225              230             235             240

Ser Ile Trp Glu Ser Leu Glu Ala Gly Lys Asn Gly Gly Ser Ile Ile
              245             250             255

Gly Gly Thr Phe Lys Ala Ile Gln Glu Arg Asn Gly Ala Ser Lys Pro
              260             265             270

Pro Arg Asp Pro Arg Leu Pro Lys Pro Lys Gly Gln Thr Val Gly Ser
         275             280             285

Phe Arg Lys Gly Leu Ile Met Leu Pro Asp Ala Ile Ser Ala Arg Leu
         290             295             300

Gly Asn Lys Val Lys Leu Ser Trp Lys Leu Ser Ser Ile Ser Lys Leu
305              310             315             320

Asp Ser Gly Glu Tyr Ser Leu Thr Tyr Glu Thr Pro Glu Gly Val Val
              325             330             335

Ser Leu Gln Cys Lys Thr Val Val Leu Thr Ile Pro Ser Tyr Val Ala
              340             345             350

Ser Thr Leu Leu Arg Pro Leu Ser Ala Ala Ala Asp Thr Leu Ser
         355             360             365

Lys Phe Tyr Tyr Pro Pro Val Val Ala Val Ser Ile Ser Tyr Pro Lys
         370             375             380

Glu Ala Ile Arg Ser Glu Cys Leu Ile Asp Gly Glu Leu Lys Gly Phe
385              390             395             400

Gly Ala Ile Tyr Ser Ser Ser Leu Phe Ser Asn Arg Ala Pro Pro Gly
              405             410             415

Arg Val Leu Leu Leu Asn Tyr Ile Gly Gly Ala Thr Asn Thr Gly Ile
              420             425             430

Tyr Gln Ser Phe Ser Gly Lys Leu Gln Gly Trp Phe Lys Glu Leu Ile
```

-continued

```
            435                 440                 445
Ile Phe Thr Ser Gly Leu Phe Gly Cys Phe Lys Gln Leu Arg Pro Asn
    450                 455                 460

Gly Leu Val Ser Asn Thr Asp Ser Glu Leu Val Ala Thr Val Asp Arg
465                 470                 475                 480

Asp Leu Arg Lys Ile Leu Ile Asn Pro Asn Ala Gln Asp Pro Phe Val
                485                 490                 495

Val Gly Val Arg Leu Trp Pro Gln Ala Ile Pro Gln Phe Leu Ile Gly
                500                 505                 510

His Leu Asp Leu Leu Asp Val Ala Lys Ala Ser Leu Arg Asn Thr Gly
                515                 520                 525

Phe Glu Gly Leu Phe Leu Gly Gly Asn Tyr Val Ser Gly Val Ala Leu
    530                 535                 540

Gly Arg Trp Val Glu Gly Ala
545                 550

<210> SEQ ID NO 41
<211> LENGTH: 1656
<212> TYPE: DNA
<213> ORGANISM: Glycine max

<400> SEQUENCE: 41
atggtttccg tcttcaacga catcctattc ccgcctaacc aaaccctttc cccaacgtcc       60
ttcttcacct ctcccactcg aaaattccct cgctctcgcc ctaaccctat tctccgctgc      120
tccatcgccg aggagtccac cgagtctcgg cccaaaaccg gagactcccc cccccccgccg     180 ttgatggagg cgttagcggt ctggcatcgc ccaggccctc gccaccaagc acgccaatgc      240
caacactgtt ggggagattc gagggcccga gaccgtgtcg gcggcggcaa catcaccacg      300
atggagagtg gcggatacct ctgggaagaa ggccccaaca gctttcagcc ctctgatcca      360
atgctcacca tggtggtgga cagtggctta aaggatcagc ttgttttggg ggatcctgat      420
gcacctcggt ttgtgttgtg aatgggaag ttgaggccag tgcctgggaa gccgactgat       480
ttgcctttct ttgacttgat gagcatcggt ggcaaaatca gggctggctt tggtgtgctt      540
ggtattcggc ctcctcctcc agttgaagag tttgttcgtc ggaaccttgg tgatgatgtt      600
tttgaacgat tgatagagcc ttttttgttca gggggcaata cttgtatatt taaatttgtg     660
ggagcattac tcatattgtg gggtctatgc aggcgatcct tcaaaattaa gtatgaaagc      720
agcatttggg aaagtttgga ggctggaaaa aatggtggta gcataattgg tggaactttc      780
aaagcaatac aagagagaaa tggagcttca aaaccacctc gagatccacg tctgccaaaa      840
ccaaagggtc agactgttgg atcttttcgg aagggactta tcatgttgcc tgatgcaatt      900
tctgcaagat taggcaacaa agtaaagtta tcttggaagc tttcaagtat tagtaaactg      960
gatagtggag agtacagttt gacatatgaa acacccgaag gagtggtttc tttgcagtgc     1020
aaaaccgttg tcctgaccat tccttcctat gttgctagta cattgctgcg tcctctgtct     1080
gctgctgctg cagatacgct ttcaaagttt tattaccctc agttgttgc agtttccata      1140 tcctatccaa aagaagctat tagatcagaa tgcttgatag atggtgagtt gaagggggtt      1200
ggagctatat acagctcatc actattctcc aatcgagcac cacctggaag ggttctactc     1260
ttgaattaca ttggaggagc tactaatact ggaatttatc aaagtttttc tgggaaactt     1320
caaggatggt ttaaagaact aatcattttc accagcgggt tatttgggtg ttttaaacaa     1380
ctcaggccta atggtcttgt ttcgaatacg gacagtgaac ttgtcgcaac agttgatcga     1440
```

```
gatttgagaa aaatccttat aaacccaaat gcccaggatc catttgtagt gggggtgaga    1500
ctgtggcctc aagctattcc acagttctta attggccatc ttgatcttct agatgttgct    1560
aaagcttctc tcagaaatac tgggtttgaa gggctgttcc ttgggggtaa ctatgtgtct    1620
ggtgttgcct tgggacgatg ggttgaggga gcctga                             1656
```

<210> SEQ ID NO 42
<211> LENGTH: 543
<212> TYPE: PRT
<213> ORGANISM: Glycine max

<400> SEQUENCE: 42

```
Met Val Ser Val Phe Asn Glu Ile Leu Phe Pro Pro Asn Gln Thr Leu
1               5                   10                  15

Leu Arg Pro Ser Leu His Ser Pro Thr Ser Phe Phe Thr Ser Pro Thr
            20                  25                  30

Arg Lys Phe Pro Arg Ser Arg Pro Asn Pro Ile Leu Arg Cys Ser Ile
        35                  40                  45

Ala Glu Glu Ser Thr Ala Ser Pro Pro Lys Thr Arg Asp Ser Ala Pro
    50                  55                  60

Val Asp Cys Val Val Val Gly Gly Gly Val Ser Gly Leu Cys Ile Ala
65                  70                  75                  80

Gln Ala Leu Ala Thr Lys His Ala Asn Ala Asn Val Val Val Thr Glu
                85                  90                  95

Ala Arg Asp Arg Val Gly Gly Asn Ile Thr Thr Met Glu Arg Asp Gly
            100                 105                 110

Tyr Leu Trp Glu Glu Gly Pro Asn Ser Phe Gln Pro Ser Asp Pro Met
            115                 120                 125

Leu Thr Met Val Val Asp Ser Gly Leu Lys Asp Glu Leu Val Leu Gly
        130                 135                 140

Asp Pro Asp Ala Pro Arg Phe Val Leu Trp Asn Arg Lys Leu Arg Pro
145                 150                 155                 160

Val Pro Gly Lys Leu Thr Asp Leu Pro Phe Phe Asp Leu Met Ser Ile
                165                 170                 175

Gly Gly Lys Ile Arg Ala Gly Phe Gly Ala Leu Gly Ile Arg Pro Pro
            180                 185                 190

Pro Pro Gly His Glu Glu Ser Val Glu Glu Phe Val Arg Arg Asn Leu
            195                 200                 205

Gly Asp Glu Val Phe Glu Arg Leu Ile Glu Pro Phe Cys Ser Gly Val
        210                 215                 220

Tyr Ala Gly Asp Pro Ser Lys Leu Ser Met Lys Ala Ala Phe Gly Lys
225                 230                 235                 240

Val Trp Lys Leu Glu Lys Asn Gly Gly Ser Ile Ile Gly Gly Thr Phe
                245                 250                 255

Lys Ala Ile Gln Glu Arg Asn Gly Ala Ser Lys Pro Pro Arg Asp Pro
            260                 265                 270

Arg Leu Pro Lys Pro Lys Gly Gln Thr Val Gly Ser Phe Arg Lys Gly
            275                 280                 285

Leu Thr Met Leu Pro Asp Ala Ile Ser Ala Arg Leu Gly Asn Lys Val
        290                 295                 300

Lys Leu Ser Trp Lys Leu Ser Ser Ile Ser Lys Leu Asp Ser Gly Glu
305                 310                 315                 320

Tyr Ser Leu Thr Tyr Glu Thr Pro Glu Gly Val Val Ser Leu Gln Cys
                325                 330                 335
```

-continued

```
Lys Thr Val Val Leu Thr Ile Pro Ser Tyr Val Ala Ser Thr Leu Leu
            340                 345                 350

Arg Pro Leu Ser Ala Ala Ala Ala Asp Ala Leu Ser Lys Phe Tyr Tyr
            355                 360                 365

Pro Pro Val Ala Ala Val Ser Ile Ser Tyr Pro Lys Glu Ala Ile Arg
            370                 375                 380

Ser Glu Cys Leu Ile Asp Gly Glu Leu Lys Gly Phe Gly Gln Leu His
385                 390                 395                 400

Pro Arg Ser Gln Gly Val Glu Thr Leu Gly Thr Ile Tyr Ser Ser Ser
                405                 410                 415

Leu Phe Pro Asn Arg Ala Pro Pro Gly Arg Val Leu Leu Leu Asn Tyr
                420                 425                 430

Ile Gly Gly Ala Thr Asn Thr Gly Ile Leu Ser Lys Thr Asp Ser Glu
            435                 440                 445

Leu Val Glu Thr Val Asp Arg Asp Leu Arg Lys Ile Leu Ile Asn Pro
            450                 455                 460

Asn Ala Gln Asp Pro Phe Val Val Gly Val Arg Leu Trp Pro Gln Ala
465                 470                 475                 480

Ile Pro Gln Phe Leu Val Gly His Leu Asp Leu Leu Asp Val Ala Lys
                485                 490                 495

Ala Ser Ile Arg Asn Thr Gly Phe Glu Gly Leu Phe Leu Gly Gly Asn
            500                 505                 510

Tyr Val Ser Gly Val Ala Leu Gly Arg Cys Val Glu Gly Ala Tyr Glu
            515                 520                 525

Val Ala Ala Glu Val Asn Asp Phe Leu Thr Asn Arg Val Tyr Lys
            530                 535                 540

<210> SEQ ID NO 43
<211> LENGTH: 1632
<212> TYPE: DNA
<213> ORGANISM: Glycine max

<400> SEQUENCE: 43
atggtttccg tcttcaacga gatcctattc ccgccgaacc aaacccttct tcgcccctcc      60
ctccattccc caacctcttt cttcacctct cccactcgaa aattccctcg ctctcgccct     120
aaccctattc tacgctgctc cattgcggag gaatccaccg cgtctccgcc caaaaccaga     180
gactccgccc ccgtggactg cgtcgtcgtc ggcggaggcg tcagcggcct ctgcatcgcc     240
caggccctcg ccaccaaaca cgccaatgcc aacgtcgtcg tcacggaggc ccgagaccgc     300
gtcggcggca acatcaccac gatggagagg gacggatacc tctgggaaga aggccccaac     360
agcttccagc cttctgatcc aatgctcacc atggtggtgg acagtggttt aaaggatgag     420
cttgttttgg gggatcctga tgcacctcgg tttgtgttgt ggaacaggaa gttgaggccg     480
gtgcccggga agctgactga tttgcctttc tttgacttga tgagcattgg tggcaaaatc     540
agggctggct ttggtgcgct tggaattcgg cctcctcctc caggtcatga ggaatcggtt     600
gaagagtttg ttcgtcggaa ccttggtgat gaggtttttg aacggttgat agagcctttt     660
tgttcagggg tctatgcagg cgatccttca aaattaagta tgaaagcagc attcgggaaa     720
gtttggaagc tggaaaaaaa tggtggtagc attattggtg aactttcaa agcaatacaa     780 gagagaaatg gagcttcaaa accacctcga gatccgcgtc tgccaaaacc aaaaggtcag     840
actgttggat ctttccggaa gggacttacc atgttgcctg atgcaatttc tgccagacta     900
ggcaacaaag taaagttatc ttggaagctt tcaagtatta gtaaactgga tagtggagag     960
```

-continued

```
tacagtttga catatgaaac accagaagga gtggtttctt tgcagtgcaa aactgttgtc    1020
ctgaccattc cttcctatgt tgctagtaca ttgctgcgtc ctctgtctgc tgctgctgca    1080
gatgcacttt caaagtttta ttaccctcca gttgctgcag tttccatatc ctatccaaaa    1140
gaagctatta gatcagaatg cttgatagat ggtgagttga aggggtttgg tcaattgcat    1200
ccacgtagcc aaggagtgga aacattagga actatataca gctcatcact attccccaac    1260
cgagcaccac ctggaagggt tctactcttg aattacattg gaggagcaac taatactgga    1320
attttatcga agacggacag tgaacttgtg gaaacagttg atcgagattt gaggaaaatc    1380
cttataaacc caaatgccca ggatccattt gtagtggggg tgagactgtg gcctcaagct    1440
attccacagt tcttagttgg ccatcttgat cttctagatg ttgctaaagc ttctatcaga    1500
aatactgggt ttgaagggct cttccttggg ggtaattatg tgtctggtgt tgccttggga    1560
cgatgcgttg agggagccta tgaggtagca gctgaagtaa acgattttct cacaaataga    1620
gtgtacaaat ag                                                        1632
```

<210> SEQ ID NO 44
<211> LENGTH: 515
<212> TYPE: PRT
<213> ORGANISM: Glycine max

<400> SEQUENCE: 44

```
Met Ala Ser Ser Ala Thr Asp Asp Asn Pro Arg Ser Val Lys Arg Val
1               5                   10                  15

Ala Val Val Gly Ala Gly Val Ser Gly Leu Ala Ala Ala Tyr Lys Leu
            20                  25                  30

Lys Ser His Gly Leu Asp Val Thr Val Phe Glu Ala Glu Gly Arg Ala
        35                  40                  45

Gly Gly Arg Leu Arg Ser Val Ser Gln Asp Gly Leu Ile Trp Asp Glu
    50                  55                  60

Gly Ala Asn Thr Met Thr Glu Ser Glu Ile Glu Val Lys Gly Leu Ile
65                  70                  75                  80

Asp Ala Leu Gly Leu Gln Glu Lys Gln Gln Phe Pro Ile Ser Gln His
            85                  90                  95

Lys Arg Tyr Ile Val Lys Asn Gly Ala Pro Leu Leu Val Pro Thr Asn
            100                 105                 110

Pro Ala Ala Leu Leu Lys Ser Lys Leu Leu Ser Ala Gln Ser Lys Ile
        115                 120                 125

His Leu Ile Phe Glu Pro Phe Met Trp Lys Arg Ser Asp Pro Ser Asn
    130                 135                 140

Val Cys Asp Glu Asn Ser Val Glu Ser Val Gly Arg Phe Phe Glu Arg
145                 150                 155                 160

His Phe Gly Lys Glu Val Val Asp Tyr Leu Ile Asp Pro Phe Val Gly
            165                 170                 175

Gly Thr Ser Ala Ala Asp Pro Glu Ser Leu Ser Met Arg His Ser Phe
            180                 185                 190

Pro Glu Leu Trp Asn Leu Glu Lys Arg Phe Gly Ser Ile Ile Ala Gly
        195                 200                 205

Ala Leu Gln Ser Lys Leu Phe Ala Lys Arg Glu Lys Thr Gly Glu Asn
    210                 215                 220

Arg Thr Ala Leu Arg Lys Asn Lys His Lys Arg Gly Ser Phe Ser Phe
225                 230                 235                 240

Gln Gly Gly Met Gln Thr Leu Thr Asp Thr Leu Cys Lys Glu Leu Gly
            245                 250                 255
```

```
Lys Asp Asp Leu Lys Leu Asn Glu Lys Val Leu Thr Leu Ala Tyr Gly
         260               265               270

His Asp Gly Ser Ser Ser Ser Gln Asn Trp Ser Ile Thr Ser Ala Ser
         275               280               285

Asn Gln Ser Thr Gln Asp Val Asp Ala Val Ile Met Thr Asn Leu His
         290               295               300

Tyr Leu Lys His Ser Leu His Asn Gly Gln Ala Pro Leu Tyr Asn Val
305               310               315               320

Lys Asp Ile Lys Ile Thr Lys Arg Gly Thr Pro Phe Pro Leu Asn Phe
             325               330               335

Leu Pro Glu Val Ser Tyr Val Pro Ile Ser Val Met Ile Thr Thr Phe
         340               345               350

Lys Lys Glu Asn Val Lys Arg Pro Leu Glu Gly Phe Gly Val Leu Val
         355               360               365

Pro Ser Lys Glu Gln Lys Asn Gly Leu Lys Thr Leu Gly Thr Leu Phe
         370               375               380

Ser Ser Met Met Phe Pro Asp Arg Ala Pro Ser Asp Leu Tyr Leu Tyr
385               390               395               400

Thr Thr Phe Ile Gly Gly Thr Gln Asn Arg Glu Leu Ala Gln Ala Ser
             405               410               415

Thr Asp Glu Leu Arg Lys Ile Val Thr Ser Asp Leu Arg Lys Leu Leu
         420               425               430

Gly Ala Glu Gly Glu Pro Thr Phe Val Asn His Phe Tyr Trp Ser Lys
         435               440               445

Gly Phe Pro Leu Tyr Gly Arg Asn Tyr Gly Ser Val Leu Gln Ala Ile
         450               455               460

Asp Lys Ile Glu Lys Asp Leu Pro Gly Phe Phe Phe Ala Gly Asn Tyr
465               470               475               480

Lys Gly Gly Leu Ser Val Gly Lys Ala Ile Ala Ser Gly Cys Lys Ala
             485               490               495

Ala Asp Leu Val Ile Ser Tyr Leu Asn Ser Ala Ser Asp Asn Thr Val
             500               505               510

Pro Asp Lys
         515

<210> SEQ ID NO 45
<211> LENGTH: 1548
<212> TYPE: DNA
<213> ORGANISM: Glycine max

<400> SEQUENCE: 45
atggcttcct ctgcaacaga cgataaccca agatctgtaa aaagagtagc tgttgttggt        60
gctggggtaa gtgggcttgc tgcggcttac aaattgaaat cacatggtct ggatgtcact       120
gtatttgaag ctgagggaag agctggaggg aggttgagaa gtgtttctca ggatggtcta       180
atttgggatg agggagctaa tacaatgact gaaagtgaaa ttgaggttaa aggtttgatt       240
gatgctcttg gacttcaaga aaagcagcag tttccaatat cacagcataa gcgctatatt       300
gtgaaaaatg gggcaccact tctggtaccc acaaatcctg ctgcactact gaagagtaaa       360
ctgctttctg cacaatcaaa gatccatctc atttttgaac catttatgtg gaaaagaagt       420
gacccctcta atgtgtgtga tgaaaattct gtggaaagtg taggcaggtt ctttgaacgt       480
cattttggaa aagaggttgt ggactatctg attgatcctt ttgttggggg cactagtgca       540
gcagatcctg aatctctctc tatgcgccat tctttcccag agctatggaa tttggagaaa       600
```

-continued

```
aggtttggct ccattatagc cggggcattg caatctaagt tattcgccaa aagggaaaaa      660
actggagaaa ataggactgc actaagaaaa aacaaacaca agcgtggttc gttttctttc      720
cagggtggga tgcagacact gacagataca ttgtgcaaag agcttggcaa agacgacctt      780
aaattaaatg aaaaggtttt gacattagct tatggtcatg atggaagttc ctcttcacaa      840
aactggtcta ttactagtgc ttctaaccaa agtacacaag atgttgatgc agtaatcatg      900
acgaatctgc attatttaaa gcattcgttg cataatggtc aagctcctct atataatgtc      960
aaggacatca agatcacaaa aaggggaact ccctttccac ttaattttct tcccgaggta     1020
agctacgtgc caatctcagt catgattact accttcaaaa aggagaatgt aaagagacct     1080
ttggagggat ttggagttct tgttccttct aaagagcaaa aaaatggttt aaaaaccctt     1140
ggtacacttt tttcctctat gatgttccca gatcgtgcac ctagtgattt atatctctat     1200
accaccttca ttggcggaac tcaaaacagg gaacttgctc aagcttcaac tgacgagctt     1260
aggaaaattg ttacttctga cctgagaaag ttgttgggag cagaggggga accaacattt     1320
gttaaccatt tctattggag taaaggcttt cctttgtatg gacgtaacta tgggtcagtt     1380
cttcaagcaa ttgataagat agaaaaagat cttcccggat ttttctttgc aggtaactac     1440
aaaggtggac tctcagttgg caaagcaata gcctcaggct gcaaagcagc tgatcttgtg     1500
atatcctacc tcaactctgc ttcagacaac acagtgcctg ataaatga                 1548
```

```
<210> SEQ ID NO 46
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gttgggagat cctgatgcgc cttgctttgt cttgtggaag gataaacc                  48

<210> SEQ ID NO 47
<211> LENGTH: 48
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
gtttatcctt ccacaagaca aagcaaggcg catcaggatc tcccaacc                  48

<210> SEQ ID NO 48
<211> LENGTH: 43
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
catcatttta caggtgttta caccggtgac ccctcaaaat tgc                       43

<210> SEQ ID NO 49
<211> LENGTH: 43
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 49
caattttgag gggtcaccgg tgtaaacacc tgtaaaatga tgc                          43

<210> SEQ ID NO 50
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Val Pro Met Leu Lys
1               5

<210> SEQ ID NO 51
<211> LENGTH: 404
<212> TYPE: PRT
<213> ORGANISM: Solanum tuberosum

<400> SEQUENCE: 51

Met Ala Pro Ser Ala Gly Glu Asp Lys Gln Asn Cys Pro Lys Arg Val
1               5                   10                  15

Ala Val Ile Gly Ala Gly Val Ser Gly Leu Ala Ala Ala Tyr Lys Leu
                20                  25                  30

Lys Ile His Gly Leu Asn Val Thr Val Phe Glu Ala Glu Gly Arg Ala
            35                  40                  45

Gly Gly Lys Leu Arg Ser Leu Ser Gln Asp Gly Leu Ile Trp Asp Glu
        50                  55                  60

Gly Ala Asn Thr Met Thr Glu Ser Glu Gly Asp Val Thr Phe Leu Leu
65                  70                  75                  80

Asp Ser Leu Gly Leu Arg Glu Lys Gln Gln Phe Pro Leu Ser Gln Asn
                85                  90                  95

Lys Arg Tyr Ile Ala Arg Asn Gly Thr Pro Thr Leu Ile Pro Ser Asn
                100                 105                 110

Pro Ile Asp Leu Ile Lys Ser Asn Phe Leu Ser Thr Gly Ser Lys Leu
            115                 120                 125

Gln Met Leu Phe Glu Pro Leu Leu Trp Lys Asn Asn Lys Leu Thr Lys
        130                 135                 140

Val Ser Asp Glu His Glu Ser Val Ser Gly Phe Phe Gln Arg His Phe
145                 150                 155                 160

Gly Lys Glu Val Val Asp Tyr Leu Ile Asp Pro Phe Val Ala Gly Thr
                165                 170                 175

Cys Gly Gly Asp Pro Asp Ser Leu Ser Met His Leu Ser Phe Pro Glu
            180                 185                 190

Leu Trp Asn Leu Glu Lys Arg Phe Gly Ser Val Ile Val Gly Ala Ile
            195                 200                 205

Arg Ser Lys Leu Ser Pro Ile Lys Glu Lys Lys Gln Gly Pro Pro Lys
        210                 215                 220

Thr Ser Val Asn Lys Lys Arg Gln Arg Gly Ser Phe Ser Phe Leu Gly
225                 230                 235                 240

Gly Met Gln Thr Leu Thr Asp Ala Ile Cys Lys Asp Leu Lys Glu Asp
                245                 250                 255

Glu Leu Arg Leu Asn Ser Arg Val Leu Glu Leu Ser Cys Ser Cys Ser
                260                 265                 270

-continued

```
Gly Asp Ser Ala Ile Asp Ser Trp Ser Ile Phe Ser Ala Ser Pro His
        275                 280                 285

Lys Arg Gln Ala Glu Glu Glu Ser Phe Asp Ala Val Ile Met Thr Ala
        290                 295                 300

Pro Leu Cys Asp Val Lys Ser Met Lys Ile Ala Lys Arg Gly Asn Pro
305                 310                 315                 320

Phe Leu Leu Asn Phe Ile Pro Glu Val Asp Tyr Val Pro Leu Ser Val
                325                 330                 335

Val Ile Thr Thr Phe Lys Lys Glu Ser Val Lys His Pro Leu Glu Gly
                340                 345                 350

Phe Gly Val Leu Val Pro Ser Gln Glu Gln Lys His Gly Leu Lys Thr
                355                 360                 365

Leu Gly Thr Leu Phe Ser Ser Met Met Phe Pro Asp Arg Ala Pro Asn
        370                 375                 380

Asn Val Tyr Leu Tyr Thr Thr Phe Val Gly Gly Ser Arg Asn Arg Glu
385                 390                 395                 400

Leu Ala Lys Ala

<210> SEQ ID NO 52
<211> LENGTH: 533
<212> TYPE: PRT
<213> ORGANISM: Amaranthus tuberculatus

<400> SEQUENCE: 52

Met Val Ile Gln Ser Ile Thr His Leu Ser Pro Asn Leu Ala Leu Pro
1               5                   10                  15

Ser Pro Leu Ser Val Ser Thr Lys Asn Tyr Pro Val Ala Val Met Gly
                20                  25                  30

Asn Ile Ser Glu Arg Glu Glu Pro Thr Ser Ala Lys Arg Val Ala Val
                35                  40                  45

Val Gly Ala Gly Val Ser Gly Leu Ala Ala Ala Tyr Lys Leu Lys Ser
        50                  55                  60

His Gly Leu Ser Val Thr Leu Phe Glu Ala Asp Ser Arg Ala Gly Gly
65                  70                  75                  80

Lys Leu Lys Thr Val Lys Lys Asp Gly Phe Ile Trp Asp Glu Gly Ala
                85                  90                  95

Asn Thr Met Thr Glu Ser Glu Ala Glu Val Ser Ser Leu Ile Asp Asp
                100                 105                 110

Leu Gly Leu Arg Glu Lys Gln Gln Leu Pro Ile Ser Gln Asn Lys Arg
        115                 120                 125

Tyr Ile Ala Arg Asp Gly Leu Pro Val Leu Leu Pro Ser Asn Pro Ala
        130                 135                 140

Ala Leu Leu Thr Ser Asn Ile Leu Ser Ala Lys Ser Lys Leu Gln Ile
145                 150                 155                 160

Met Leu Glu Pro Phe Leu Trp Arg Lys His Asn Ala Thr Glu Leu Ser
                165                 170                 175

Asp Glu His Val Gln Glu Ser Val Gly Glu Phe Phe Glu Arg His Phe
                180                 185                 190

Gly Lys Glu Phe Val Asp Tyr Val Ile Asp Pro Phe Val Ala Gly Thr
        195                 200                 205

Cys Gly Asp Pro Gln Ser Leu Ser Met His His Thr Phe Pro Glu Val
        210                 215                 220

Trp Asn Ile Glu Lys Arg Phe Gly Ser Val Phe Ala Gly Leu Ile Gln
225                 230                 235                 240
```

-continued

```
Ser Thr Leu Leu Ser Lys Lys Glu Lys Gly Gly Glu Asn Ala Ser Ile
                245                 250                 255

Lys Lys Pro Arg Val Arg Gly Ser Phe Ser Phe Gln Gly Gly Met Gln
            260                 265                 270

Thr Leu Val Asp Thr Met Cys Lys Gln Leu Gly Glu Asp Glu Leu Lys
        275                 280                 285

Leu Gln Cys Glu Val Leu Ser Leu Ser Tyr Asn Gln Lys Gly Ile Pro
    290                 295                 300

Ser Leu Gly Asn Trp Ser Val Ser Ser Met Ser Asn Asn Thr Ser Glu
305                 310                 315                 320

Asp Gln Ser Tyr Asp Ala Val Val Val Thr Ala Pro Ile Arg Asn Val
                325                 330                 335

Lys Glu Met Lys Ile Met Lys Phe Gly Asn Pro Phe Ser Leu Asp Phe
            340                 345                 350

Ile Pro Glu Val Thr Tyr Val Pro Leu Ser Val Met Ile Thr Ala Phe
            355                 360                 365

Lys Lys Asp Lys Val Lys Arg Pro Leu Glu Gly Phe Gly Val Leu Ile
    370                 375                 380

Pro Ser Lys Glu Gln His Asn Gly Leu Lys Thr Leu Gly Thr Leu Phe
385                 390                 395                 400

Ser Ser Met Met Phe Pro Asp Arg Ala Pro Ser Asp Met Cys Leu Phe
                405                 410                 415

Thr Thr Phe Val Gly Gly Ser Arg Asn Arg Lys Leu Ala Asn Ala Ser
            420                 425                 430

Thr Asp Glu Leu Lys Gln Ile Val Ser Ser Asp Leu Gln Gln Leu Leu
            435                 440                 445

Gly Thr Glu Asp Glu Pro Ser Phe Val Asn His Leu Phe Trp Ser Asn
    450                 455                 460

Ala Phe Pro Leu Tyr Gly His Asn Tyr Asp Cys Val Leu Arg Ala Ile
465                 470                 475                 480

Asp Lys Met Glu Lys Asp Leu Pro Gly Phe Phe Tyr Ala Gly Asn His
                485                 490                 495

Lys Gly Gly Leu Ser Val Gly Lys Ala Met Ala Ser Gly Cys Lys Ala
            500                 505                 510

Ala Glu Leu Val Ile Ser Tyr Leu Asp Ser His Ile Tyr Val Lys Met
        515                 520                 525

Asp Glu Lys Thr Ala
    530
```

```
<210> SEQ ID NO 53
<211> LENGTH: 584
<212> TYPE: PRT
<213> ORGANISM: Unknown
<220> FEATURE:
<223> OTHER INFORMATION: Pt0014S10720 PPX protein

<400> SEQUENCE: 53
```

```
Met Thr Val Lys Gln Ser Ser Val Ala Arg Ile Lys Gly Leu Ile Asn
1               5                   10                  15

Pro Ser Ser Ser Gln Ile Thr Ser Leu Gln Gly Ser Gly Ser Phe Ala
            20                  25                  30

Cys Gln Thr Glu Ser Glu Pro Ala Met Thr Ser Thr Phe Thr Asp Leu
        35                  40                  45

Ser Leu Leu Arg Pro Thr Ile Pro Ser Leu Ile Pro Ser Ser Phe Ser
    50                  55                  60
```

```
Lys Phe Thr Thr His Arg Pro Leu Lys Leu Arg Cys Ser Leu Thr Glu
65              70                  75                  80

Asp Ser Thr Thr Phe Ile Pro Phe Lys Leu Asn Gly Glu Ala Gln Ser
                85                  90                  95

Ser Ala Gly His Ser Ala Thr Ala Asp Cys Val Ile Val Gly Gly Gly
            100                 105                 110

Ile Ser Gly Leu Cys Ile Ala Gln Ala Leu Ala Thr Lys His Trp Asp
            115                 120                 125

Val Ala Pro Asn Val Ile Val Thr Glu Ala Arg Asp Arg Val Gly Gly
            130                 135                 140

Asn Ile Thr Thr Leu Glu Arg Asp Gly Tyr Leu Trp Glu Glu Gly Pro
145                 150                 155                 160

Asn Ser Glu Gln Pro Ser Asp Pro Met Leu Thr Met Val Val Asp Ser
                165                 170                 175

Gly Leu Lys Glu Asp Leu Val Leu Gly Asp Pro Asn Ala Pro Arg Phe
            180                 185                 190

Val Leu Trp Asp Gly Thr Leu Arg Pro Val Pro Gly Lys Pro Thr Asp
            195                 200                 205

Leu Pro Phe Phe Asp Leu Met Ser Ile Gly Gly Lys Leu Arg Ala Gly
    210                 215                 220

Phe Gly Ala Leu Gly Leu Arg Pro Pro Pro Gly His Glu Glu Ser
225                 230                 235                 240

Val Glu Glu Phe Val Arg Arg Asn Leu Gly Asp Glu Val Phe Glu Arg
                245                 250                 255

Leu Ile Glu Pro Phe Cys Ser Gly Val Tyr Ala Gly Asp Pro Ser Lys
            260                 265                 270

Leu Ser Met Lys Ala Ala Phe Gly Lys Val Trp Asn Leu Glu Gln Thr
            275                 280                 285

Gly Gly Ser Ile Phe Gly Gly Thr Phe Lys Thr Ile Gln Glu Arg Ser
    290                 295                 300

Lys Asn Pro Lys Pro Pro Arg Asp Pro His Leu Pro Thr Pro Lys Gly
305                 310                 315                 320

Gln Thr Val Gly Ser Phe Arg Lys Gly Leu Ala Met Leu Pro Asp Ala
                325                 330                 335

Ile Ala Thr Arg Leu Gly Ser Asn Val Lys Leu Ser Trp Lys Leu Ser
            340                 345                 350

Ser Ile Ile Lys Leu Glu Asn Gly Gly Tyr Ser Leu Thr Tyr Glu Thr
            355                 360                 365

Pro Glu Gly Leu Val Ser Leu Leu Ser Lys Ser Val Val Phe Thr Ile
    370                 375                 380

Pro Ser His Ile Ala Ser Thr Leu Leu Arg Pro Leu Ser Ala Thr Ala
385                 390                 395                 400

Ala Asp Ala Leu Ser Lys Phe Tyr Tyr Pro Pro Val Ala Ala Val Ser
            405                 410                 415

Ile Ser Tyr Pro Lys Glu Ala Ile Arg Pro Glu Arg Leu Ile Asp Gly
            420                 425                 430

Glu Leu Lys Gly Phe Gly Gln Leu His Pro Arg Ser Gln Gly Val Glu
            435                 440                 445

Thr Leu Gly Thr Ile Tyr Ser Ser Ser Leu Phe Pro Asn Arg Ala Pro
    450                 455                 460

Ala Gly Arg Ile Leu Leu Leu Asn Tyr Ile Gly Gly Ala Thr Asn Arg
465                 470                 475                 480

Gly Ile Val Ser Lys Thr Glu Ser Glu Leu Val Glu Ala Val Asp Arg
```

```
                        485                 490                 495
Asp Leu Arg Lys Leu Leu Ile Asn Pro Asn Ala Thr Asp Pro Leu Val
            500                 505                 510

Leu Gly Val Arg Val Trp Pro Gln Ala Ile Pro Gln Phe Leu Ile Gly
            515                 520                 525

His Phe Asp Ile Leu Asp Ala Ala Arg Asp Ala Leu Lys Ala Lys Gly
        530                 535                 540

Leu Gln Gly Leu Phe Leu Gly Gly Asn Phe Val Ser Gly Val Ala Leu
545                 550                 555                 560

Gly Arg Cys Val Glu Gly Ala Tyr Glu Val Ala Ser Glu Val Thr Asp
                565                 570                 575

Phe Leu Ser Gln Tyr Ala Tyr Lys
            580

<210> SEQ ID NO 54
<211> LENGTH: 543
<212> TYPE: PRT
<213> ORGANISM: Unknown
<220> FEATURE:
<223> OTHER INFORMATION: Pt0002S18740 PPX protein

<400> SEQUENCE: 54

Met Thr Thr Phe Ile Asp Phe Ser Leu Leu Arg Pro Thr Thr Pro Ser
1               5                   10                  15

Leu Ile Pro Ser Ser Phe Ser Lys Phe Ser Thr Pro Arg Pro Phe Lys
            20                  25                  30

Leu Arg Cys Ser Leu Thr Glu Glu Ser Ala Thr Ile Thr Pro Ser Lys
        35                  40                  45

Leu Asn Gly Glu Ala Gln Ser Asn Gly Gly His Ser Ala Ala Ala Asp
    50                  55                  60

Cys Val Ile Val Gly Gly Gly Ile Ser Gly Leu Cys Ile Ala Gln Ala
65                  70                  75                  80

Leu Ala Thr Lys His Arg Asp Val Ala Pro Asn Val Ile Val Thr Glu
                85                  90                  95

Ala Arg Asp Arg Val Gly Gly Asn Ile Thr Thr Leu Glu Arg Asp Gly
            100                 105                 110

Tyr Leu Trp Glu Glu Gly Pro Asn Ser Glu Gln Pro Ser Asp Pro Met
        115                 120                 125

Leu Thr Met Val Val Asp Ser Gly Leu Lys Glu Asp Leu Val Leu Gly
    130                 135                 140

Asp Pro Asn Ala Pro Arg Phe Val Leu Trp Asn Gly Lys Leu Arg Pro
145                 150                 155                 160

Val Pro Gly Lys Pro Thr Asp Leu Pro Phe Phe Asp Leu Met Ser Ile
                165                 170                 175

Gly Gly Lys Leu Arg Ala Gly Phe Gly Ala Leu Gly Leu Arg Pro Pro
            180                 185                 190

Pro Pro Gly His Glu Glu Ser Val Glu Glu Phe Val Arg Arg Asn Leu
        195                 200                 205

Gly Asp Glu Val Phe Glu Arg Leu Ile Glu Pro Phe Cys Ser Gly Val
    210                 215                 220

Tyr Ala Gly Asp Pro Ser Lys Leu Ser Met Lys Ala Ala Phe Gly Lys
225                 230                 235                 240

Val Trp Asn Leu Glu Gln Thr Gly Gly Ser Ile Ile Gly Gly Thr Phe
                245                 250                 255

Lys Thr Ile Gln Glu Arg Arg Lys Asn Pro Lys Pro Pro Arg Asp Pro
```

-continued

```
           260             265             270
Arg Leu Pro Thr Pro Lys Gly Gln Thr Val Gly Ser Phe Arg Lys Gly
        275             280             285
Leu Ala Met Leu Pro Asp Ala Ile Ala Thr Arg Leu Gly Ser Asn Val
        290             295             300
Lys Leu Ser Trp Lys Leu Ala Ser Val Ile Lys Leu Asp Ser Gly Gly
305             310             315             320
Tyr Ser Leu Thr Tyr Glu Thr Pro Glu Gly Leu Val Ser Leu Leu Ser
            325             330             335
Lys Ser Val Val Phe Thr Ile Pro Ser His Ile Ala Ser Thr Leu Leu
        340             345             350
Arg Pro Leu Ser Ala Thr Ala Ala Asp Ala Leu Ser Lys Phe Tyr Tyr
        355             360             365
Pro Pro Val Ala Ala Val Ser Val Ser Tyr Pro Lys Glu Ala Ile Arg
        370             375             380
Pro Glu Arg Leu Ile Asp Gly Glu Leu Lys Gly Phe Gly Gln Leu His
385             390             395             400
Pro Arg Ser Gln Gly Val Glu Thr Leu Gly Thr Ile Tyr Ser Ser Ser
            405             410             415
Leu Phe Pro Asn Arg Ala Pro Thr Gly Arg Ile Leu Leu Leu Asn Tyr
        420             425             430
Ile Gly Gly Thr Thr Asn Pro Gly Ile Val Ser Lys Thr Glu Ser Glu
        435             440             445
Leu Val Glu Ala Val Asp Arg Asp Leu Arg Lys Met Leu Ile Asn Pro
        450             455             460
Asn Ala Thr Asp Pro Leu Val Leu Gly Val Arg Val Trp Pro Gln Ala
465             470             475             480
Ile Pro Gln Phe Leu Ile Gly His Phe Asp Ile Leu Asp Ala Ala Arg
            485             490             495
Asp Ala Leu Lys Ala Lys Gly Leu Gln Gly Leu Phe Leu Gly Gly Asn
        500             505             510
Tyr Val Ser Gly Val Ala Leu Gly Arg Cys Val Glu Gly Ala Tyr Glu
        515             520             525
Val Ala Ala Glu Val Thr Asp Phe Leu Ser Gln Tyr Ala Asn Lys
        530             535             540
```

<210> SEQ ID NO 55
<211> LENGTH: 536
<212> TYPE: PRT
<213> ORGANISM: Sorghum bicolor

<400> SEQUENCE: 55

```
Met Val Ala Ala Ala Ala Met Ala Thr Ala Ala Ser Ala Ala Ala Pro
1               5               10              15
Leu Leu Asn Gly Thr Arg Arg Pro Ala Arg Leu Arg Arg Arg Gly Leu
            20              25              30
Arg Val Arg Cys Ala Ala Val Ala Gly Gly Ala Ala Glu Ala Pro Ala
        35              40              45
Ser Thr Gly Ala Arg Leu Ser Ala Asp Cys Val Val Val Gly Gly Gly
        50              55              60
Ile Ser Gly Leu Cys Thr Ala Gln Ala Leu Ala Thr Arg His Gly Val
65              70              75              80
Gly Glu Val Leu Val Thr Glu Ala Arg Ala Arg Pro Gly Gly Asn Ile
            85              90              95
```

-continued

```
Thr Thr Val Glu Arg Pro Glu Glu Gly Tyr Leu Trp Glu Glu Gly Pro
            100             105             110

Asn Ser Phe Gln Pro Ser Asp Pro Val Leu Ser Met Ala Val Asp Ser
            115             120             125

Gly Leu Lys Asp Asp Leu Val Phe Gly Asp Pro Asn Ala Pro Arg Phe
        130             135             140

Val Leu Trp Glu Gly Lys Leu Arg Pro Val Pro Ser Lys Pro Ala Asp
145             150             155             160

Leu Pro Phe Phe Asp Leu Met Ser Ile Pro Gly Lys Leu Arg Ala Gly
                165             170             175

Leu Gly Ala Leu Gly Ile Arg Pro Pro Pro Gly Arg Glu Glu Ser
            180             185             190

Val Glu Glu Phe Val Arg Arg Asn Leu Gly Ala Glu Val Phe Glu Arg
            195             200             205

Leu Ile Glu Pro Phe Cys Ser Gly Val Tyr Ala Gly Asp Pro Ser Lys
        210             215             220

Leu Ser Met Lys Ala Ala Phe Gly Lys Val Trp Arg Leu Glu Glu Ala
225             230             235             240

Gly Gly Ser Ile Ile Gly Gly Thr Ile Lys Thr Ile Gln Glu Arg Gly
                245             250             255

Lys Asn Pro Lys Pro Pro Arg Asp Pro Arg Leu Pro Lys Pro Lys Gly
            260             265             270

Gln Thr Val Ala Ser Phe Arg Lys Gly Leu Ala Met Leu Pro Asn Ala
            275             280             285

Ile Thr Ser Ser Leu Gly Ser Lys Val Lys Leu Ser Trp Lys Leu Thr
        290             295             300

Ser Ile Thr Lys Ser Asp Gly Lys Gly Tyr Val Leu Glu Tyr Glu Thr
305             310             315             320

Pro Glu Gly Val Val Leu Val Gln Ala Lys Ser Val Ile Met Thr Ile
                325             330             335

Pro Ser Tyr Val Ala Ser Asp Ile Leu Arg Pro Leu Ser Gly Asp Ala
            340             345             350

Ala Asp Ala Leu Ser Arg Phe Tyr Tyr Pro Pro Val Ala Ala Val Thr
            355             360             365

Val Ser Tyr Pro Lys Glu Ala Ile Arg Lys Glu Cys Leu Ile Asp Gly
        370             375             380

Glu Leu Gln Gly Phe Gly Gln Leu His Pro Arg Ser Gln Gly Val Glu
385             390             395             400

Thr Leu Gly Thr Ile Tyr Ser Ser Ser Leu Phe Pro Asn Arg Ala Pro
                405             410             415

Ala Gly Arg Val Leu Leu Leu Asn Tyr Ile Gly Gly Ala Thr Asn Thr
            420             425             430

Gly Ile Val Ser Lys Thr Glu Ser Glu Leu Val Glu Ala Val Asp Arg
            435             440             445

Asp Leu Arg Lys Met Leu Ile Asn Ser Thr Ala Val Asp Pro Leu Val
        450             455             460

Leu Gly Val Arg Val Trp Pro Gln Ala Ile Pro Gln Phe Leu Val Gly
465             470             475             480

His Leu Asp Leu Leu Glu Val Ala Lys Ser Ala Leu Asp Gln Gly Gly
                485             490             495

Tyr Asp Gly Leu Phe Leu Gly Gly Asn Tyr Val Ala Gly Val Ala Leu
            500             505             510

Gly Arg Cys Ile Glu Gly Ala Tyr Glu Ser Ala Ala Gln Ile Tyr Asp
```

-continued

```
                515                 520                 525

Phe Leu Thr Lys Tyr Ala Tyr Lys
    530                 535

<210> SEQ ID NO 56
<211> LENGTH: 539
<212> TYPE: PRT
<213> ORGANISM: Unknown
<220> FEATURE:
<223> OTHER INFORMATION: CP0057G0026 PPX protein

<400> SEQUENCE: 56

Met Ala Ala Leu Met Glu Leu Ser Val Leu Arg Pro Thr Gly His Ser
1               5                   10                  15

Leu Phe Pro Ser Ile Ser Thr Ser Asn Leu Arg Val Lys Thr Asn Ser
                20                  25                  30

Ser Leu Arg Leu Gln Cys Ser Ile Ala Glu Gly Ser Thr Ile Ser Pro
        35                  40                  45

Ser Asn Ile Asp Asp Gly Gly Ile Pro Thr Ala Asp Cys Val Ile Val
    50                  55                  60

Gly Gly Gly Ile Ser Gly Leu Cys Ile Ala Gln Ala Leu Ala Thr Lys
65                  70                  75                  80

His Arg Asp Val Ala Ser Asn Val Ile Val Thr Glu Ala Arg Asp Arg
                85                  90                  95

Val Gly Gly Asn Ile Thr Thr Val Glu Arg Asp Gly Tyr Leu Trp Glu
                100                 105                 110

Glu Gly Pro Asn Ser Glu Gln Pro Ser Asp Pro Ile Leu Thr Met Val
        115                 120                 125

Val Asp Ser Gly Leu Lys Asp Asp Leu Val Leu Gly Asp Pro Asn Ala
    130                 135                 140

Pro Arg Phe Val Phe Trp Asn Gly Lys Leu Arg Pro Val Pro Ala Lys
145                 150                 155                 160

Pro Thr Asp Leu Pro Phe Phe Asp Leu Met Ser Phe Gly Gly Lys Leu
                165                 170                 175

Arg Ala Gly Phe Gly Ala Ile Gly Ile Arg Pro Ala Pro Pro Gly His
                180                 185                 190

Glu Glu Ser Val Glu Glu Phe Val Arg Arg Asn Leu Gly Asp Glu Val
        195                 200                 205

Phe Glu Arg Leu Ile Glu Pro Phe Cys Ser Gly Val Tyr Ala Gly Asp
    210                 215                 220

Pro Ser Lys Leu Ser Met Lys Ala Ala Phe Gly Lys Val Trp Arg Leu
225                 230                 235                 240

Glu Gln Leu Gly Gly Ser Ile Ile Gly Gly Ala Phe Lys Ala Ile Gln
                245                 250                 255

Glu Arg Asn Asn Thr Val Lys Pro Pro Arg Asp Pro Arg Leu Pro Lys
                260                 265                 270

Pro Lys Gly Gln Thr Val Gly Ser Phe Arg Lys Gly Leu Thr Met Leu
        275                 280                 285

Pro Glu Ala Ile Ser Ala Arg Leu Gly Ser Lys Val Lys Leu Ser Trp
    290                 295                 300

Lys Leu Ser Ser Ile Ile Lys Leu Asn Asn Arg Gly Tyr Cys Leu Thr
305                 310                 315                 320

Tyr Glu Thr Pro Glu Gly Leu Val Ser Leu Gln Ser Lys Ser Val Val
                325                 330                 335

Met Thr Val Pro Ser His Val Ala Ser Ser Leu Leu Arg Pro Leu Ser
```

-continued

```
                340                 345                 350

Asp Pro Ala Ala Asp Ala Leu Ser Lys Phe Tyr Tyr Pro Pro Val Ala
        355                 360                 365

Ala Val Ser Ile Ser Tyr Pro Lys Glu Ala Ile Arg Thr Glu Cys Leu
        370                 375                 380

Ile Asp Gly Glu Leu Lys Gly Phe Gly Gln Leu His Pro Arg Ser Gln
385                 390                 395                 400

Gly Val Glu Thr Leu Gly Thr Ile Tyr Ser Ser Ser Leu Phe Pro Asn
                405                 410                 415

Arg Ala Pro Ala Gly Arg Val Leu Leu Leu Asn Tyr Ile Gly Gly Ala
                420                 425                 430

Thr Asn Arg Gly Ile Leu Ser Lys Thr Glu Ala Lys Leu Val Glu Val
        435                 440                 445

Val Asp Arg Asp Leu Arg Lys Met Leu Ile Asn Pro Ser Ala Lys Asp
        450                 455                 460

Pro Glu Val Leu Gly Val Arg Val Trp Pro Gln Ala Ile Pro Gln Phe
465                 470                 475                 480

Leu Val Gly His Leu Asp Val Leu Asp Ala Ala Lys Ser Ala Leu Asn
                485                 490                 495

Ser Gly Gly Phe Glu Gly Leu Phe Leu Gly Gly Asn Tyr Val Ser Gly
                500                 505                 510

Val Ala Leu Gly Arg Cys Val Glu Gly Ala Tyr Glu Val Ala Ala Glu
        515                 520                 525

Val Asn Ser Phe Leu Ser Gln Tyr Thr Tyr Asn
        530                 535
```

```
<210> SEQ ID NO 57
<211> LENGTH: 548
<212> TYPE: PRT
<213> ORGANISM: Unknown
<220> FEATURE:
<223> OTHER INFORMATION: W7G0627 PPX protein

<400> SEQUENCE: 57

Met Pro Thr Leu Thr Leu Ala Asp Pro Pro Thr Leu Arg Leu Leu Ser
1               5                   10                  15

Pro Val Asn Leu Arg Arg Ser Thr Ser Ile Ser Ser Pro Phe Phe Cys
            20                  25                  30

Arg Ser Arg Asn Asn Cys Thr Gly Pro Trp Arg Val Arg Cys Ala Val
        35                  40                  45

Ala Gly Glu Ser Thr Ile Ser Ser Ser Lys Val Gly Asp Gly Asn Asn
        50                  55                  60

Tyr Ser Pro Val Asp Cys Val Ile Val Gly Ala Gly Ile Ser Gly Leu
65                  70                  75                  80

Cys Ile Ala Gln Ala Leu Ala Thr Lys His Gly Asp Val Gly Ser Asn
                85                  90                  95

Val Ile Val Thr Glu Ala Arg Asp Arg Val Gly Gly Asn Ile Thr Thr
            100                 105                 110

Met Glu Gly Asp Gly Tyr Leu Trp Glu Glu Gly Pro Asn Ser Glu Gln
        115                 120                 125

Pro Ser Asp Ser Met Leu Thr Met Ala Val Asp Ser Gly Leu Lys Asp
        130                 135                 140

Asp Leu Val Leu Gly Asp Pro Asn Ala Pro Arg Phe Val Leu Trp Asn
145                 150                 155                 160

Gly Lys Leu Arg Pro Val Pro Ser Lys Pro Thr Asp Leu Pro Phe Phe
```

```
                    165                    170                    175

Asp Leu Met Ser Phe Pro Gly Lys Leu Arg Ala Gly Phe Gly Ala Leu
            180                    185                    190

Gly Ile Arg Pro Pro Pro Asp His Glu Glu Ser Val Glu Glu Phe
            195                    200                    205

Val Arg Arg Asn Leu Gly Asp Glu Val Phe Glu Arg Leu Ile Glu Pro
    210                    215                    220

Phe Cys Ser Gly Val Tyr Ala Gly Asp Pro Ser Lys Leu Ser Met Lys
225                    230                    235                    240

Ala Ala Phe Gly Lys Val Trp Lys Leu Glu Gln Lys Gly Gly Ser Ile
            245                    250                    255

Ile Gly Gly Thr Phe Lys Ala Ile Gln Glu Lys Asn Asn Thr Pro Lys
            260                    265                    270

Pro Leu Arg Asp Pro Arg Leu Pro Lys Pro Lys Gly Gln Thr Val Gly
            275                    280                    285

Ser Phe Arg Lys Gly Leu Ile Met Leu Pro Glu Ala Ile Ser Lys Arg
    290                    295                    300

Leu Gly Gly Lys Val Lys Leu Ser Trp Lys Leu Ser Ser Ile Ile Arg
305                    310                    315                    320

Leu Asp Asp Gly Gly Tyr Ser Leu Thr Tyr Glu Thr Pro Glu Gly Leu
            325                    330                    335

Val Ser Leu Gln Ser Arg Ser Val Val Met Thr Val Pro Ser Arg Val
            340                    345                    350

Ala Ser Ser Leu Leu Arg Pro Leu Ser Ala Val Ala Ala Asp Ala Leu
            355                    360                    365

Ser Lys Phe Tyr Tyr Pro Pro Val Ala Ala Val Ser Ile Ser Tyr Pro
    370                    375                    380

Lys Glu Ala Ile Arg Thr Glu Cys Leu Ile Glu Gly Glu Leu Lys Gly
385                    390                    395                    400

Phe Gly Gln Leu His Pro Arg Ser Gln Gly Val Glu Thr Leu Gly Thr
            405                    410                    415

Ile Tyr Ser Ser Ser Leu Phe Pro Asn Arg Ala Pro Pro Gly Arg Ile
            420                    425                    430

Leu Leu Leu Asn Tyr Ile Gly Gly Ala Thr Asn Pro Gly Ile Leu Ser
            435                    440                    445

Lys Thr Glu Ser Glu Leu Val Glu Ala Val Asp Arg Asp Leu Arg Lys
    450                    455                    460

Met Leu Ile Asn Pro Asn Ala Lys Asp Pro Leu Val Leu Gly Val Arg
465                    470                    475                    480

Val Trp Pro Gln Ala Ile Pro Gln Phe Leu Ile Gly His Leu Asp Val
            485                    490                    495

Leu Asp Ala Ala Lys Ser Ala Leu Arg Asp Gly Gly Phe Gln Gly Met
            500                    505                    510

Phe Leu Gly Gly Asn Tyr Val Ser Gly Val Ala Leu Gly Arg Cys Val
            515                    520                    525

Glu Gly Ala Tyr Glu Val Ala Ala Glu Val Ala Asp Phe Leu Ser Gln
    530                    535                    540

Tyr Val Tyr Lys
545
```

```
<210> SEQ ID NO 58
<211> LENGTH: 420
<212> TYPE: PRT
<213> ORGANISM: Artificial Sequence
```

<220> FEATURE:
<223> OTHER INFORMATION: Consensus sequence

<400> SEQUENCE: 58

```
Leu Leu Arg Cys Ser Ala Val Val Val Gly Ala Gly Ile Ser Gly Leu
1               5                   10                  15

Cys Ala Leu Thr Lys His Val Val Thr Glu Ala Arg Asp Arg Gly Gly
            20                  25                  30

Asn Ile Thr Val Glu Asp Gly Tyr Leu Trp Glu Glu Gly Pro Asn Ser
            35                  40                  45

Glu Gln Pro Ser Asp Pro Ile Leu Thr Met Val Val Asp Ser Gly Leu
    50                  55                  60

Lys Asp Asp Leu Val Leu Gly Asp Pro Asn Ala Pro Arg Phe Val Phe
65                  70                  75                  80

Trp Asn Gly Lys Leu Arg Pro Val Pro Ala Lys Pro Thr Asp Leu Pro
                85                  90                  95

Phe Phe Asp Leu Met Ser Gly Lys Leu Arg Ala Gly Phe Gly Ala Leu
            100                 105                 110

Gly Ile Arg Pro Pro Pro Glu Glu Ser Val Glu Glu Phe Val Arg Arg
            115                 120                 125

Asn Leu Gly Glu Val Phe Glu Arg Leu Ile Glu Pro Phe Cys Ser Gly
            130                 135                 140

Val Tyr Ala Gly Asp Pro Ser Lys Leu Ser Met Lys Ala Ala Phe Gly
145                 150                 155                 160

Lys Val Trp Asn Leu Glu Gly Gly Ser Ile Ile Gly Gly Ile Lys Ser
                165                 170                 175

Ile Gln Arg Lys Pro Arg Asp Pro Arg Leu Pro Lys Pro Lys Gly Gln
            180                 185                 190

Thr Val Gly Ser Phe Arg Lys Gly Leu Met Leu Pro Asp Ala Ile Leu
            195                 200                 205

Gly Val Lys Leu Ser Trp Lys Leu Ser Ser Ile Ser Lys Gly Gly Tyr
    210                 215                 220

Ser Leu Thr Tyr Glu Thr Pro Glu Gly Val Val Ser Leu Gln Lys Ser
225                 230                 235                 240

Val Val Met Thr Ile Pro Ser His Val Ala Ser Val Leu Arg Pro Leu
                245                 250                 255

Ser Ala Ala Asp Ala Leu Ser Lys Tyr Tyr Pro Pro Val Ala Ala Val
            260                 265                 270

Ser Ile Ser Tyr Pro Lys Glu Ala Ile Arg Lys Glu Leu Ile Asp Gly
            275                 280                 285

Glu Leu Gly Phe Gly Gln Leu His Pro Arg Ser Gln Val Glu Thr Leu
    290                 295                 300

Gly Thr Ile Tyr Ser Ser Ser Leu Phe Pro Asn Arg Ala Pro Gly Arg
305                 310                 315                 320

Val Leu Leu Leu Asn Tyr Ile Gly Gly Ala Thr Asn Gly Ile Leu Ser
                325                 330                 335

Lys Ser Glu Ser Glu Leu Val Glu Val Asp Arg Asp Leu Arg Lys Met
            340                 345                 350

Leu Ile Ala Asp Pro Val Leu Gly Val Arg Val Trp Pro Gln Ala Ile
            355                 360                 365

Pro Gln Phe Leu Ile Gly His Asp Val Leu Asp Ala Ala Lys Ala Leu
    370                 375                 380

Lys Gly Leu Gly Leu Phe Leu Gly Gly Asn Tyr Val Ala Gly Val Ala
385                 390                 395                 400
```

-continued

```
Leu Gly Arg Cys Val Glu Gly Ala Tyr Glu Ala Ala Val Phe Leu Ser
            405                 410                 415

Tyr Ala Tyr Lys
            420
```